US010328139B2

(12) United States Patent
Chopra et al.

(10) Patent No.: US 10,328,139 B2
(45) Date of Patent: Jun. 25, 2019

(54) LIVE-ATTENUATED VACCINE AGAINST PLAGUE

(71) Applicants: Ashok K. Chopra, League City, TX (US); Jian Sha, League City, TX (US)

(72) Inventors: Ashok K. Chopra, League City, TX (US); Jian Sha, League City, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/995,743

(22) Filed: Jan. 14, 2016

(65) Prior Publication Data

US 2016/0199475 A1 Jul. 14, 2016

Related U.S. Application Data

(60) Provisional application No. 62/103,432, filed on Jan. 14, 2015, provisional application No. 62/121,760, filed on Feb. 27, 2015.

(51) Int. Cl.
| | |
|---|---|
| *C12N 13/00* | (2006.01) |
| *A61K 39/02* | (2006.01) |
| *A61K 45/06* | (2006.01) |
| *A61K 39/00* | (2006.01) |

(52) U.S. Cl.
CPC .......... *A61K 39/0291* (2013.01); *A61K 45/06* (2013.01); *A61K 2039/522* (2013.01); *A61K 2039/572* (2013.01)

(58) Field of Classification Search
None
See application file for complete search history.

(56) References Cited

PUBLICATIONS

Tiner et al. Jan. 20, 2015. Infect. Immun., 83:1318-1338.*
Achtman et al., "*Yersinia pestis*, the cause of plague, is a recently emerged clone of *Yersinia pseudotuberculosis*," *Proc Natl Acad Sci U S A*, 1999; 96:14043-14048.
Achtman et al., "Microevolution and history of the plague bacillus, *Yersinia pestis*," *Proc Natl Acad Sci U S A*, 2004; 101:17837-17842.
"African Green monkey (*Chlorocebus aethiops*) animal model development to evaluate treatment of pneumonic plague," Food and Drug Administration (FDA) Anti-Infective Drugs Advisory Committee Meeting, Apr. 3, 2012, Silver Spring, MD; 68 pages.
Agar et al., "Characterization of a mouse model of plague after aerosolization of Yersinia pestis CO92," *Microbiology*, Jul. 2008; 154(Pt. 7):1939-1948.
Agar et al., "Deletion of Braun lipoprotein gene (lpp) and curing of plasmid pPCP1 dramatically alter the virulence of *Yersinia pestis* CO92 in a mouse model of pneumonic plague," *Microbiology*, 2009; 155:3247-3259.
Agar et al., "Characterization of the rat pneumonic plague model: infection kinetics following aerosolization of *Yersinia pestis* CO92," *Microbes Infect*, 2009; 11:205-214.
Agarkov et al., "Substrate specificity and screening of the integral membrane protease Pla," *Bioorg Med Chem Lett.*, 2008; 18:427-431.
Aliprantis et al., "Cell activation and apoptosis by bacterial lipoproteins through toll-like receptor-2," *Science*, 1999; 285:736-739.
Alvarez et al., "Prevention of bubonic and pneumonic plague using plant-derived vaccines," *Biotechnol Adv.*, 2010; 28:184-196.
Anisimov et al., "Effect of deletion of the 1pxM gene on virulence and vaccine potential of *Yersinia pestis* in mice," *J Med Microbiol.*, 2007; 56:443-453.
Anisimov et al., "Variability of the protein sequences of lcrV between epidemic and atypical rhamnose-positive strains of *Yersinia pestis*," *Adv Exp Med Biol.*, 2007; 603:23-27.
Anisimov et al., "Amino acid and structural variability of *Yersinia pestis* LcrV protein," *Infect Genet Evol.*, 2010; 10:137-145.
Anonymous, "Plague manual—epidemiology, distribution, surveillance and control," *Wkly Epidemiol Rec.*, 1999; 74(51/52):447.
Anonymous, "Fatal laboratory-acquired infection with an attenuated *Yersinia pestis* Strain—Chicago, Illinois, 2009," *CDC MMWR Morb Mortal Wkly Rep.*, Feb. 25, 2011; 60(7):201-205.
Barroga et al., "The proteins encoded by the rbs operon of *Escherichia coli*: I. Overproduction, purification, characterization, and functional analysis of RbsA," *Protein Sci.*, 1996; 5:1093-1099.
Bartra et al., "Resistance of *Yersinia pestis* to complement-dependent killing is mediated by the Ail outer membrane protein," *Infect Immun.*, 2008; 76:612-622.
Bashir et al., "Lipopolysaccharide, mediator of sepsis enigma: recognition and signaling," *Int. J. Biochem. Res. Rev.*, 2011; 1:1-13.
Ben-Gurion et al., "Bacteriocin-like material produced by *Pasteurella pestis*," *J Gen Microbiol.*, 1958; 19:289-297.
Biedzka-Sarek et al., "Characterization of complement factor H binding to *Yersinia enterocolitica* serotype O:3," *Infect Immun.*, 2008; 76:4100-4109.
Biedzka-Sarek et al., "Functional mapping of YadA- and Ail-mediated binding of human factor H to *Yersinia enterocolitica* serotype O:3," Infect Immun., 2008; 76:5016-5027.
Bladergroen et al., "Infection-blocking genes of a symbiotic *Rhizobium leguminosarum* strain that are involved in temperature-dependent protein secretion," *Mol Plant Microbe Interact.*, 2003; 16:53-64.

(Continued)

*Primary Examiner* — Jennifer E Graser
(74) *Attorney, Agent, or Firm* — Mueting, Raasch & Gebhardt, P.A.

(57) ABSTRACT

Provided herein is a genetically modified *Y. pestis* that includes three alterations compared to a control *Y. pestis*. Two alterations include decreased mRNA, decreased protein, or a combination thereof, encoded by a lpp coding region and encoded by a msbB coding region. The third alteration is selected from an alteration of an intergenic region between the coding regions ypo1119 and ypo1120, and decreased mRNA, decreased protein, or a combination thereof, encoded by a coding region selected from pla, ypo1717, ypmt1.80c, rbsA (ypo2500), ypo0498, vasK (ypo3603), ypo3164, hxuB (ypo3248), ypo1616, ypo1119, ypo1120, and ail. Also provided are compositions that include the genetically modified *Y. pestis*, and methods of using the genetically modified *Y. pestis*.

19 Claims, 34 Drawing Sheets
Specification includes a Sequence Listing.

(56) References Cited

PUBLICATIONS

Boland et al., "Role of YopP in suppression of tumor necrosis factor alpha release by macrophages during *Yersinia* infection," *Infect Immun.*, 1998; 66:1878-1884.

Bonacorsi et al., "Assessment of a fluoroquinolone, three beta-lactams, two aminoglycosides, and a cycline in treatment of murine *Yersinia pestis* infection," *Antimicrob Agents Chemother.*, 1994; 38:481-486.

Boyer et al., "Dissecting the bacterial type VI secretion system by a genome wide in silico analysis: what can be learned from available microbial genomic resources?" *BMC Genomics*, 2009; 10:104.

Braun et al., "Biochemistry of bacterial cell envelopes," *Annu Rev Biochem.*, 1974; 43:89-121.

Bubeck et al., "Delayed inflammatory response to primary pneumonic plague occurs in both outbred and inbred mice," *Infect. Immun.*, 2007; 75:697-705.

Caulfield et al., "The Pla protease of *Yersinia pestis* degrades fas ligand to manipulate host cell death and inflammation," *Cell Host & Microbe*, 2014; 15:424-434.

Centers for Disease Control and Prevention. "CDC Select Agent Program—Protecting the American public by ensuring safe and secure possession, use, and transfer of select agents and toxins that pose a threat to public health." Nov. 17, 2008, posting date. Available on the Internet:<URL: https://stacks.cdc.gov/view/cdc/12314>; Centers for Disease Control and Prevention, Atlanta, GA.

Centers for Disease Control and Prevention, Department of Health and Human Services, "Possession, use, and transfer of select agents and toxins; biennial review," Final rule. *Federal Register.*, 2012; 77(194):61083-61115.

Chauvaux et al., "Transcriptome analysis of *Yersinia pestis* in human plasma: an approach for discovering bacterial genes involved in septicaemic plague," *Microbiology*, 2007; 153:3112-3124.

Cheng et al., "*Yersinia enterocolitica* TyeA, an intracellular regulator of the type III machinery, is required for specific targeting of YopE, YopH, YopM, and YopN into the cytosol of eukaryotic cells," *J Bacteriol.*, 2000; 182:3183-3190.

Choi et al., "A Tn7-based broad-range bacterial cloning and expression system," *Nat Methods*, 2005; 2:443-448.

Choi et al., "An improved method for rapid generation of unmarked Pseudomonas aeruginosa deletion mutants," *BMC Microbiol.*, 2005; 5:30.

Chopra, Ashok, "Identification of New Antigens for a Plague Vaccine," Grant Abstract, Grant No. 5R01AI064389-10 [online]. National Institute of Allergy and Infectious Diseases, National Institutes of Health, project dates Feb. 1, 2005 to Apr. 30, 2016 [retrieved on Oct. 19, 2016]. Retrieved from the Internet:<URL: https://projectreporter.nih.gov/project_info_description.cfm?aid=8645584&icde=31584578&ddparam=&ddvalue=&ddsub=&cr=1&csb=default&cs=ASC>; 2 pgs.

Chromy et al., "Proteomic characterization of *Yersinia pestis* virulence," *J Bacteriol.*, 2005; 187:8172-8180.

Clementz et al., "Function of the htrB high temperature requirement gene of *Escherchia coli* in the acylation of lipid A: HtrB catalyzed incorporation of laurate," *J Biol Chem.*, 1996; 271:12095-12102.

Clementz et al., "Function of the *Escherichia coli* msbB gene, a multicopy suppressor of htrB knockouts, in the acylation of lipid A. Acylation by MsbB follows laurate incorporation by HtrB," *J Biol Chem.*, 1997; 272:10353-10360.

Combadiere et al., "Transcutaneous and intradermal vaccination," *Hum Vaccin.*, 2011; 7:811-827.

Cornelis, "*Yersinia* type III secretion: send in the effectors," *J Cell Biol.*, 2002; 158:401-408.

Cowan et al., "Invasion of epithelial cells by *Yersinia pestis*: evidence for a *Y. pestis*-specific invasin," *Infect Immun.*, 2000; 68:4523-4530.

Craig, "Transposon Tn7," *Curr Top Microbiol Immunol.*, 1996; 204:27-48.

Cui et al., "Genetic variations of live attenuated plague vaccine strains (*Yersinia pestis* EV76 lineage) during laboratory passages in different countries," *Infect Genet Evol.*, 2014; 26:172-179.

Darwin et al., "Identification of *Yersinia enterocolitica* genes affecting survival in an animal host using signature-tagged transposon mutagenesis," *Mol Microbiol.*, 1999; 32:51-62.

Datsenko et al., "One-step inactivation of chromosomal genes in *Escherichia coli* K-12 using PCR products," *Proc Natl Acad Sci U S A*, 2000; 97:6640-6645.

Davidson et al., "Structure, function, and evolution of bacterial ATP-binding cassette systems," *Microbiol Mol Biol Rev.*, 2008; 72:317-364.

DeBord et al., "Roles of LcrG and LcrV during type III targeting of effector Yops by *Yersinia enterocolitica*." J Bacteriol., 2001; 183:4588-4598.

Deng et al., "Genome sequence of *Yersinia pestis* KIM," *J Bacteriol.*, 2002; 184:4601-4611.

Du et al., "Role of fraction 1 antigen of *Yersinia pestis* in inhibition of phagocytosis," *Infect Immun.*, 2002; 70:1453-1460.

Eddy et al., "Production of outer membrane vesicles by the plague pathogen *Yersinia pestis*," *PLoS One*, 2014; 9:e107002.

Edwards et al., "Improved allelic exchange vectors and their use to analyze 987P fimbria gene expression," *Gene*, 1998; 207:149-157.

Elvin et al., "Evolutionary genetics: Ambiguous role of CCR5 in *Y. pestis* infection," *Nature*, 2004; 430:417.

Erova et al., "Evaluation of protective potential of *Yersinia pestis* outer membrane protein antigens as possible candidates for a new-generation recombinant plague vaccine," *Clin Vaccine Immunol.*, 2013; 20:227-238.

Felek et al., "The *Yersinia pestis* Ail protein mediates binding and Yop delivery to host cells required for plague virulence," *Infect Immun.*, 2009; 77:825-836.

Felek et al., "Three *Yersinia pestis* adhesins facilitate Yop delivery to eukaryotic cells and contribute to plague virulence," *Infect Immun.*, 2010; 78:4134-4150.

Fellows et al., "Characterization of a *Cynomolgus Macaque* Model of Pneumonic Plague for Evaluation of Vaccine Efficacy," *Clin Vaccine Immunol.*, 2015; 22 : 1070-1078.

Feodorova et al., "Plague vaccines: current developments and future perspectives," *Emerg Microbes & Infect.*, 2012; 1: p. e36.

Feodorova et al., "Russian vaccines against especially dangerous bacterial pathogens," *Emerg Microbes Infect.*, 2014; 3:e86.

Fernando et al., "The pro inflammatory cytokine, interleukin-6, enhances the polarization of alternatively activated macrophages," *PLoS One*, 2014; 9:e94188.

Flashner et al., "Generation of *Yersinia pestis* attenuated strains by signature-tagged mutagenesis in search of novel vaccine candidates," *Infect Immun.*, 2004; 72:908-915.

Galindo et al., "Comparative global gene expression profiles of wild-type *Yersinia pestis* CO92 and its Braun lipoprotein mutant at flea and human body temperatures," *Comp Funct Genomics*, 2010; 2010:342168.

Galindo et al., "Pathogenesis of *Y. enterocolitica* and *Y. pseudotuberculosis* in human yersiniosis," *J Pathog.*, 2011; vol. 2011, Article ID 182051; 16 pages.

Glauser et al., "Septic shock: pathogenesis," *Lancet*, 1991; 338:732-736.

Gonzalez et al., "Comparison of Models for Bubonic Plague Reveals Unique Pathogen Adaptations to the Dermis," *Infect Immun.*, 2015; 83 :2855-2861.

Grant Abstract, "In Vitro and Animal Models for Emerging Infectious Diseases and Biodefense," Grant No. N01AI30065 [online]. National Institute of Allergy and Infectious Diseases, National Institutes of Health, project dates Sep. 30, 2003 to Sep. 29, 2010 [retrieved on Oct. 19, 2016]. Retrieved from the Internet:URL:https://projectreporter.nih.gov/project_info_description.cfm?aid=7694899&icde=31584879; 2 pgs.

Grim et al., "Functional genomic characterization of virulence factors from necrotizing fasciitis-causing strains of *Aeromonas hydrophila*," *Appl Environ Microbiol.*, 2014; 80:4162-4183.

Groswasser et al., "Needle length and injection technique for efficient intramuscular vaccine delivery in infants and children evaluated through an ultrasonographic determination of subcutaneous and muscle layer thickness," *Pediatrics*, 1997; 100:400-403.

(56) References Cited

PUBLICATIONS

Hallett et al., "Pathogenicity and immunogenic efficacy of a live attentuated plaque vaccine in vervet monkeys," *Infect Immun.*, 1973; 8:876-881.

Hantke et al., "Covalent binding of lipid to protein. Diglyceride and amide linked fatty acid at the N-terminal end of the murein-lipoprotein of the *Escherichia coli* outer membrane," *Eur J Biochem.*, 1973; 34:284-296.

Hensel et al., "Simultaneous identification of bacterial virulence genes by negative selection," *Science*, 1995; 269:400-403.

Hinnebusch et al., "Role of the *Yersinia pestis* Ail protein in preventing a protective polymorphonuclear leukocyte response during bubonic plague," *Infect Immun.*, 2011; 79:4984-4989.

Ho et al., "Functional recruitment of the human complement inhibitor C4BP to *Yersinia pseudotuberculosis* outer membrane protein Ail," *J Immunol.*, 2012; 188:4450-4459.

Ho et al., "The *Yersinia pseudotuberculosis* outer membrane protein Ail recruits the human complement regulatory protein factor H," *J Immunol.*, 2012; 189:3593-3599.

Ho et al., "*Yersinia pestis* Ail recruitment of C4b binding protein leads to factor I-mediated inactivation of covalently and noncovalently bound C4b," *Eur J Immunol.*, 2014; 44:742-751.

Horazdovsky et al., "High-affinity L-arabinose transport operon. Gene product expression and mRNAs," *J Mol Biol.*, 1987; 197:27-35.

Houppert et al., "Identification of chromosomal genes in *Yersinia pestis* that influence type III secretion and delivery of Yops into target cells," *PLoS One*, 2012; 7:e34039.

Huang et al., "Current trends in plague research: from genomics to virulence," *Clin Med Res.*, 2006; 4:189-199.

Inglesby et al., "Plague as a biological weapon: medical and public health management," Working Group on Civilian Biodefense, *JAMA*, 2000; 283:2281-2290.

Jacob et al., "The role of the complement cascade in endotoxin-induced septic encephalopathy," *Lab Invest.*, 2007; 87:1186-1194.

Karlyshev et al., "Application of high-density array-based signature-tagged mutagenesis to discover novel *Yersinia* virulence-associated genes," *Infect Immun.*, 2001; 69:7810-7819.

Karow et al., "Isolation and characterization of the *Escherichia coli* msbB gene, a multicopy suppressor of null mutations in the high-temperature requirement gene htrB," *J Bacteriol.*, 1992; 174:702-710.

Kawahara et al., "Modification of the structure and activity of lipid A in *Yersinia pestis* lipopolysaccharide by growth temperature," *Infect Immun.*, 2002; 70:4092-4098.

Kirjavainen et al., "*Yersinia enterocolitica* serum resistance proteins YadA and ail bind the complement regulator C4b-binding protein," *PLoS Pathog.*, 2008; 4:e1000140.

Knirel et al., "Temperature-dependent variations and intraspecies diversity of the structure of the lipopolysaccharide of *Yersinia pestis*," *Biochemistry*, 2005; 44:1731-1743.

Kolodziejek et al., "Phenotypic characterization of OmpX, an Ail homologue of *Yersinia pestis* KIM," *Microbiology*, 2007; 153:2941-2951.

Kolodziejek et al., "Outer membrane protein X (Ail) contributes to *Yersinia pestis* virulence in pneumonic plague and its activity is dependent on the lipopolysaccharide core length," *Infect Immun.*, 2010; 78:5233-5243.

Korhonen et al., "Fibrinolytic and coagulative activities of *Yersinia pestis*," *Front Cell Infect Microbiol.*, 2013; 3:35.

Kovacs-Simon et al., "Lipoproteins of bacterial pathogens," *Infect Immun.*, 2011; 79:548-561.

Kroger et al., "General Recommendations on Immunization: Recommendations of the Advisory Committee on Immunization Practices (ACIP)," *CDC MMWR*, Jan. 28, 2011, 60(2):1-64.

Kumar et al., "Biothreats-bacterial warfare agents," J Bioterrorism & Biodefense, 2011; 2:112.

Kumar et al., "Th17 cell based vaccines in mucosal immunity," *Curr Opin Immunol.*, 2013; 25:373-380.

Lathem et al., "Progression of primary pneumonic plague: a mouse model of infection, pathology, and bacterial transcriptional activity," *Proc Natl Acad Sci U S A*, 2005; 102:17786-17791.

Lathem et al., "A plasminogen-activating protease specifically controls the development of primary pneumonic plague," *Science*, 2007; 315:509-513.

Layton et al.,. "Levofloxacin cures experimental pneumonic plague in African green monkeys," *PLoS Negl Trop Dis.*, 2011; 5:e959.

Lee et al., "Targeting of *Yersinia* Yop proteins into the cytosol of HeLa cells: one-step translocation of YopE across bacterial and eukaryotic membranes is dependent on SycE chaperone," *Mol Microbiol.*, 1998; 28:593-601.

Leigh et al., "Unexpected results from the application of signature-tagged mutagenesis to identify *Yersinia pestis* genes required for adherence and invasion," *Microb Pathog.*, 2005; 38:259-266.

Li et al., "Interaction between *Yersinia pestis* and the host immune system," *Infect Immun.*, 2008; 76:1804-1811.

Lin et al., "IL-17 contributes to cell-mediated defense against pulmonary *Yersinia pestis* infection,"*J Immunol.*, 2011; 186:1675-1684.

Liu et al., "Effects of Psa and F1 on the adhesive and invasive interactions of *Yersinia pestis* with human respiratory tract epithelial cells," *Infect Immun.*, 2006; 74:5636-5644.

Liu et al., "Deletion of Braun lipoprotein gene (lpp) attenuates *Yersinia pestis* KIM/D27 strain: role of Lpp in modulating host immune response, NF-kappaB activation and cell death," *Microb Pathog.*, 2010; 48:42-52.

Mazurkiewicz et al., "Signature-tagged mutagenesis: barcoding mutants for genome-wide screens," *Nat Rev Genet.*, 2006; 7:929-939.

Mecsas et al., "Identification of attenuated *Yersinia pseudotuberculosis* strains and characterization of an orogastric infection in BALB/c mice on day 5 postinfection by signature-tagged mutagenesis," *Infect Immun.*, 2001; 69:2779-2787.

Mei et al., "Identification of *Staphylococcus aureus* virulence genes in a murine model of bacteraemia using signature-tagged mutagenesis," *Mol Microbiol.*, 1997; 26:399-407.

Meyer et al., "Plague immunization. I. Past and present trends," *J Infect Dis.*, 1974; 129:Suppl:S13-18.

Meyer et al., "Live, attenuated *Yersinia pestis* vaccine: virulent in nonhuman primates, harmless to guinea pigs," *J Infect Dis.*, 1974; 129:Suppl:S85-12.

Miller et al., "Identification of regions of Ail required for the invasion and serum resistance phenotypes," *Mol Microbiol.*, 2001; 41:1053-1062.

Montminy et al., "Virulence factors of *Yersinia pestis* are overcome by a strong lipopolysaccharide response," *Nat Immunol.*, 2006; 7:1066-1073.

Myers-Morales et al., "A surface-focused biotinylation procedure identifies the *Yersinia pestis* catalase KatY as a membrane-associated but non-surface-located protein," *Appl Environ Microbiol.*, 2007; 73:5750-5759.

Nakajima et al., "Association between virulence of *Yersinia pestis* and suppression of gamma interferon and tumor necrosis factor alpha," *Infect Immun.*, 1993; 61:23-31.

Neilsen et al., "*Escherichia coli* Braun lipoprotein induces a lipopolysaccharide-like endotoxic response from primary human endothelial cells," *J Immunol.*, 2001; 167:5231-5239.

Nicolas et al., "Intradermal, epidermal and transcutaneous vaccination: from immunology to clinical practice," *Expert Rev Vaccines*, 2008; 7:1201-1214.

Oyston et al., "Expression of heterologous O-antigen in *Yersinia pestis* KIM does not affect virulence by the intravenous route," *J Med Microbiol.*, 2003; 52:289-294.

Paczosa et al., "*Yersinia pseudotuberculosis* uses Ail and YadA to circumvent neutrophils by directing Yop translocation during lung infection," *Cell Microbiol.*, 2014; 16:247-268.
Palace et al., "Genome-wide mutant fitness profiling identifies nutritional requirements for optimal growth of *Yersinia pestis* in deep tissue," *mBio*, 2014; 5:e01385-14.
Park et al., "Molecular interactions in ribose transport: the binding protein module symmetrically associates with the homodimeric membrane transporter," *Embo J.*, 1999; 18:4149-4156.

(56) References Cited

PUBLICATIONS

Park et al., "Topology of RbsC, a membrane component of the ribose transporter, belonging to the AraH superfamily," *J Bacteriol.*, 1999; 181:1039-1042.

Parkhill et al., "Genome sequence of Yersinia pestis, the causative agent of plague," *Nature*, 2001; 413:523-527.

Pearson et al., "Biological Weapons Proliferation: Reasons for Concern, Courses of Action," The Henry L. Stimson Center, Washington DC, Jan. 1998; 141 pages.

Perez-Gutierrez et al., "Role of lipid A acylation in *Yersinia enterocolitica* virulence," *Infect Immun.*, 2010; 78:2768-2781.

Pernerstorfer et al., "Endotoxin-induced activation of the coagulation cascade in humans: effect of acetylsalicylic acid and acetaminophen," *Arterioscler Thromb Vasc Biol.*, 1999; 19:2517-2523.

Perry et al., "*Yersinia pestis*—etiologic agent of plague," *Clin Microbiol Rev.*, 1997; 10:35-66.

Peters et al., "Tn 7: smarter than we thought," *Nat Rev Mol Cell Biol.*, 2001; 2:806-814.

Peterson et al., "Protection Afforded by Fluoroquinolones in Animal Models of Respiratory Infections with *Bacillus anthracis*, *Yersinia pestis*, and *Francisella tularensis*," *Open Microbiol J.*, 2010; 4:34-46.

Pieper et al., "Temperature and growth phase influence the outer-membrane proteome and the expression of a type VI secretion system in *Yersinia pestis*," *Microbiology*, 2009; 155:498-512.

Pieper et al., "Integral and peripheral association of proteins and protein complexes with *Yersinia pestis* inner and outer membranes," *Proteome Sci.*, 2009; 7:5.

Pillay et al., "In vivo labeling with 2H2O reveals a human neutrophil lifespan of 5.4 days," *Blood*, 2010; 116:625-627.

Poland et al., "Determination of deltoid fat pad thickness. Implications for needle length in adult immunization," *JAMA*, 1997; 277:1709-1711.

Ponnusamy et al., "High-throughput, signature-tagged mutagenic approach to identify novel virulence factors of Yersinia pestis CO92 in a mouse model of infection," *Infect Immun.*, May 2015; 83(5):2065-2081.

Prentice et al., "Plague," *Lancet*, 2007; 369:1196-1207.

Price et al., "Pulmonary infection by *Yersinia pestis* rapidly establishes a permissive environment for microbial proliferation," *Proc Natl Acad Sci U S A*, 2012; 109:3083-3088.

Pujol et al., "The ability to replicate in macrophages is conserved between *Yersinia pestis* and *Yersinia pseudotuberculosis*," *Infect Immun.*, 2003; 71:5892-5899.

Pukatzki et al., "The type VI secretion system: translocation of effectors and effector-domains," *Curr Opin Microbiol.*, 2009; 12:11-17.

Qi et al., "Comparison of mouse, guinea pig and rabbit models for evaluation of plague subunit vaccine F1+rV270," *Vaccine*, 2010; 28:1655-1660.

Quenee et al., "*Yersinia pestis* caf1 variants and the limits of plague vaccine protection," *Infect Immun.*, 2008; 76:2025-2036.

Quenee et al., "Plague in Guinea pigs and its prevention by subunit vaccines," *Am J Pathol.*, 2011; 178:1689-1700.

Quenee et al., "Prevention of pneumonic plague in mice, rats, guinea pigs and non-human primates with clinical grade rV10, rV10-2 or F1-V vaccines," *Vaccine*, 2011; 29:6572-6583.

Quenee et al., "Hereditary hemochromatosis restores the virulence of plague vaccine strains," *J Infect Dis.*, 2012; 206:1050-1058.

Rebeil et al., "Variation in lipid A structure in the pathogenic yersiniae," *Mol Microbiol.*, 2004; 52:1363-1373.

Rebeil et al., Characterization of late acyltransferase genes of *Yersinia pestis* and their role in temperature-dependent lipid A variation, *J Bacteriol.*, 2006; 188:1381-1388.

Robinson et al., "Evaluation of a *Yersinia pestis* mutant impaired in a thermoregulated type VI-like secretion system in flea, macrophage and murine models," *Microb Pathog.*, 2009; 47:243-251.

Rollins et al., "*Yersinia pestis* and the plague," *Am J Clin Pathol.*, 2003; 119 Suppl:S78-85.

Rosenzweig et al., "Cethromycin-mediated protection against the plague pathogen *Yersinia pestis* in a rat model of infection and comparison with levofloxacin," *Antimicrob Agents Chemother .*, 2011; 55:5034-5042.

Rosenzweig et al., "Progress on plague vaccine development," *Appl Microbiol Biotechnol.*, 2011; 91:265-286.

Rothe, Eric, "Evaluation and Production of a Multivalent Adenoviral Plague Vaccine," Grant Abstract, Grant No. 5R44AI071634-05 [online]. National Institute of Allergy and Infectious Diseases, National Institutes of Health, project dates Jul. 1, 2006 to Jun. 30, 2016 [retrieved on Oct. 19, 2016]. Retrieved from the Internet:<URL:https://projectreporter.nih.gov/project_info_description.cfm?aid=8690739&icde=31584656>; 2 pgs.

Russell et al., "A comparison of Plague vaccine, USP and EV76 vaccine induced protection against *Yersinia pestis* in a murine model," *Vaccine*, 1995; 13:1551-1556.

Sebbane et al., "Adaptive response of *Yersinia pestis* to extracellular effectors of innate immunity during bubonic plague," *Proc Natl Acad Sci U S A*, 2006; 103:11766-11771.

Sha et al., "Braun lipoprotein (Lpp) contributes to virulence of yersiniae: potential role of Lpp in inducing bubonic and pneumonic plague," *Infect Immun.*, 2008; 76:1390-1409.

Sha et al., "Characterization of an F1 deletion mutant of *Yersinia pestis* CO92, pathogenic role of F1 antigen in bubonic and pneumonic plague, and evaluation of sensitivity and specificity of F1 antigen capture-based dipsticks," *J Clin Microbiol.*, 2011; 49:1708-1715.

Sha et al., "Deletion of the Braun lipoprotein-encoding gene and altering the function of lipopolysaccharide attenuate the plague bacterium," *Infect Immun.*, 2013; 81:815-828.

Sha et al., "A non-invasive in vivo imaging system to study dissemination of bioluminescent *Yersinia pestis* CO92 in a mouse model of pneumonic plague," *Microb Pathog.*, 2013; 55:39-50.

Shaw et al., "Effect of anatomic injection site, age and smoking on the immune response to hepatitis B vaccination," *Vaccine*, 1989; 7:425-430.

Shayan et al., "Lymphatic vessels in cancer metastasis: bridging the gaps," *Carcinogenesis*, 2006; 27:1729-1738.

Silver et al., "Identification of *Aeromonas veronii* genes required for colonization of the medicinal leech, *Hirudo verbena*," *J Bacteriol.*, 2007; 189:6763-6772.

Silver et al., "Interaction between innate immune cells and a bacterial type III secretion system in mutualistic and pathogenic associations," *Proc Natl Acad Sci U S A*, 2007; 104:9481-9486.

Sing et al., "*Yersinia* V-antigen exploits toll-like receptor 2 and CD14 for interleukin 10-mediated immunosuppression," *J Exp Med.*, 2002; 196:1017-1024.

Skurnik et al., "Characterization of the O-antigen gene clusters of *Yersinia pseudotuberculosis* and the cryptic O-antigen gene cluster of *Yersinia pestis* shows that the plague bacillus is most closely related to and has evolved from *Y. pseudotuberculosis* serotype O:1b," *Mol Microbiol.*, 2000; 37:316-330.

Smiley, "Cell-mediated defense against *Yersinia pestis* infection," Chapter 35 in *Adv Exp Med Biol.*, 2007; vol. 603 The Genus *Yersinia*, pp. 376-386.

Smiley, "Current challenges in the development of vaccines for pneumonic plague," *Expert Rev Vaccines*, 2008; 7:209-221.

Smiley, "Immune defense against pneumonic plague," *Immunol Rev.*, 2008; 225:256-271.

Sodeinde et al., "A surface protease and the invasive character of plague," *Science*, 1992, 258:1004-1007.

Somerville et al., "A novel *Escherichia coli* lipid A mutant that produces an antiinflammatory lipopolysaccharide," *J Clin Invest.*, 1996; 97:359-365.

Straley, "The plasmid-encoded outer-membrane proteins of *Yersinia pestis*," *Rev Infect Dis.*, 1998; 10 Suppl 2:S323-326.

Suarez et al., Molecular characterization of a functional type VI secretion system from a clinical isolate of *Aeromonas hydrophila*, *Microb Pathog.*, 2008; 44:344-361.

Suarez et al., "Role of Hcp, a type 6 secretion system effector, of *Aeromonas hydrophila* in modulating activation of host immune cells," *Microbiology*, 2010; 156:3678-3688.

Sun et al., "Developing live vaccines against plague," *J Infect Dev Ctries*, 2011; 5:614-627.

(56) References Cited

PUBLICATIONS

Suomalainen et al., "Temperature-induced changes in the lipopolysaccharide of *Yersinia pestis* affect plasminogen activation by the Pla surface protease," *Infect Immun.*, 2010; 78:2644-2652.

Szaba et al., "D27-pLpxL, an avirulent strain of *Yersinia pestis*, primes T cells that protect against pneumonic plague," *Infect Immun.*, 2009; 77:4295-4304.

Tao et al., "Mutated and bacteriophage T4 nanoparticle arrayed F1-V immunogens from *Yersinia pestis* as next generation plague vaccines," *PLoS Pathog.*, 2013; 9:e1003495.

Tatusova et al., "BLAST 2 Sequences, a new tool for comparing protein and nucleotide sequences," *FEMS Microbiol Lett.*, May 1999; 174(2):247-250.

Teunissen et al., "Insight into the immunobiology of human skin and functional specialization of skin dendritic cell subsets to innovate intradermal vaccination design," *Curr Top Microbiol Immunol.*, 2012; 351:25-76.

Tiner et al., "Combinational Deletion of Three Membrane Protein-Encoding Genes Highly Attenuates *Yersinia pestis* while Retaining Immunogenicity in a Mouse Model of Pneumonic Plague," *Infect Immun.*, 2015; 83:1318-1338.

Tiner et al., "Intramuscular immunization of mice with a live-attenuated triple mutant of *Yersina pestis* CO92 induces robust humoral and cell-mediated immunity to completely protect animals against pneumonic plague," *Clin Vaccine Immunol*, Dec. 2015; 22(12):1255-1268.

Tsang et al., "Ail binding to fibronectin facilitates *Yersinia pestis* binding to host cells and Yop delivery," *Infect Immun.*, 2010; 78:3358-3368.

Tsang et al., "Ail protein binds ninth type III fibronectin repeat (9FNIII) within central 120-kDa region of fibronectin to facilitate cell binding by *Yersinia pestis*," *J Biol Chem.*, 2012; 287:16759-16767.

Tsang et al., "Ail proteins of *Yersinia pestis* and *Y. pseudotuberculosis* have different cell binding and invasion activities," *PLoS One*, 2013; 8:e83621.

Une et al., "In vivo comparison of avirulent Vwa- and Pgm- or Pstr phenotypes of *yersiniae*," *Infect Immun.*, 1984; 43:895-900.

Vadyvaloo et al., "Transit through the flea vector induces a pretransmission innate immunity resistance phenotype in *Yersinia pestis*," *PLoS Pathog.*, 2010; 6:e1000783.

Van Lier et al., "Deletion of Braun lipoprotein and plasminogen-activating protease-encoding genes attenuates *Yersinia pestis* in mouse models of bubonic and pneumonic plague," *Infect Immun.*, 2014; 82:2485-2503.

Walker et al., "Studies on immunization against plague. V. Multiplication and persistence of virulent and avirulent *Pasteurella pestis* in mice and guinea pigs," *J Immunol.*, 1953; 70:245-252.

Wang et al., "Long-term observation of subunit vaccine F 1-rV270 against *Yersinia pestis* in mice," *Clin Vaccine Immunol.*, 2010; 17:199-201.

Williams et al., "Potency of killed plague vaccines prepared from avirulent *Yersinia pestis*," *Bull World Health Organ.*, 1980; 58:753-756.

Williams et al., "*Vibrio cholerae* Hcp, a secreted protein coregulated with HlyA," *Infect Immun.*, 1996; 64:283-289.

Williamson et al., "Recombinant (F1+V) vaccine protects *cynomolgus macaques* against pneumonic plague," *Vaccine*, 2011; 29:4771-4777.

Yamashita et al., "Structural insights into Ail-mediated adhesion in *Yersinia pestis*," *Structure*, 2011; 19:1672-1682.

Yang et al., "Omics strategies for revealing *Yersinia pestis* virulence," *Front Cell Infect Microbiol.*, 2012; vol. 2, Article 157; 16 pages.

You et al., "Comparative genomic analysis of gene variations of two Chinese *Yersinia pestis* isolates from vaccine strain EV76," *Biomed Environ Sci.*, 2012; 25:440-448.

Zaitseva et al., "The proteins encoded by the rbs operon of *Escherichia coli*: II. Use of chimeric protein constructs to isolate and characterize RbsC," *Protein Sci.*, 1996; 5:1100-1107.

Zhang et al., "Kinetics of memory B cell and plasma cell responses in the mice immunized with plague vaccines," *Scand J Immunol.*, 2014; 79:157-162.

Zhao et al., "Identification of protease and rpoN-associated genes of uropathogenic *Proteus mirabilis* by negative selection in a mouse model of ascending urinary tract infection," *Microbiology*, 1999; 145:185-195.

\* cited by examiner

Figure 1.
A
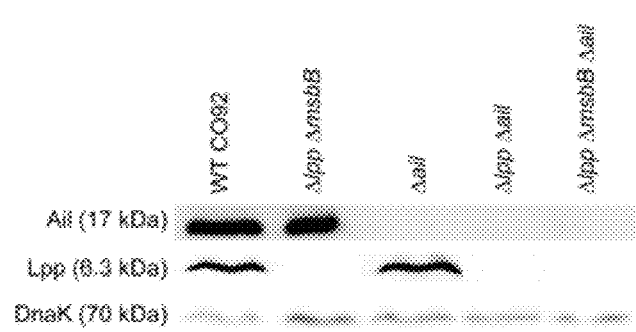
B
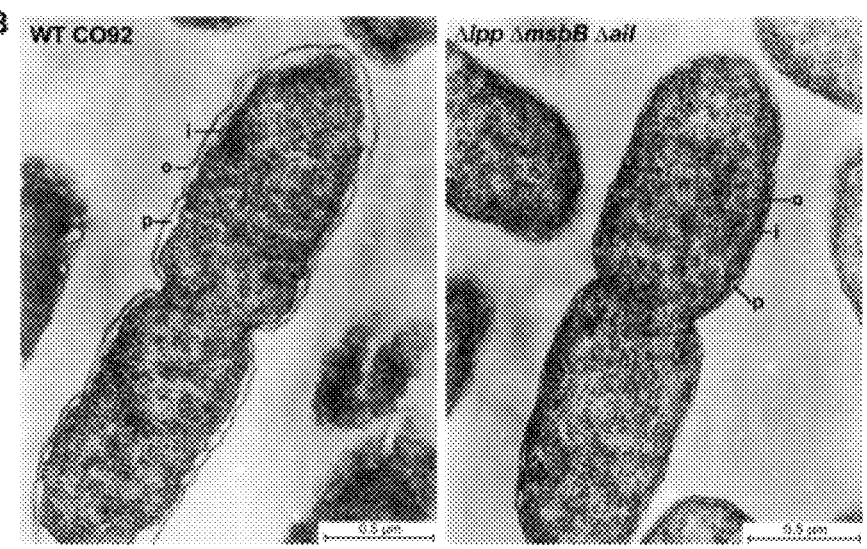

Figure 4.
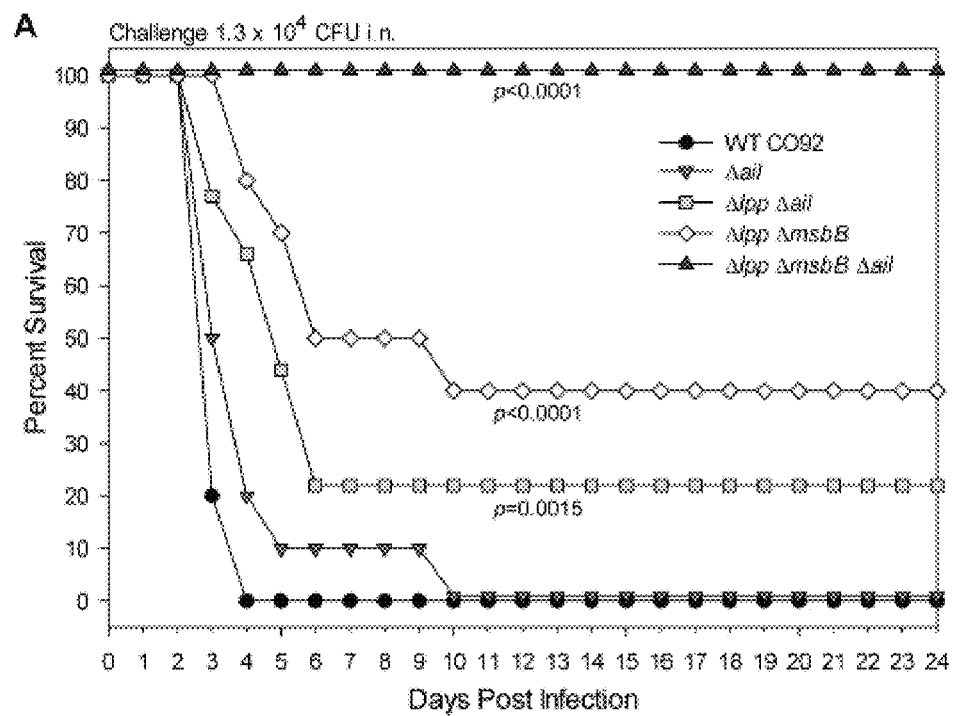
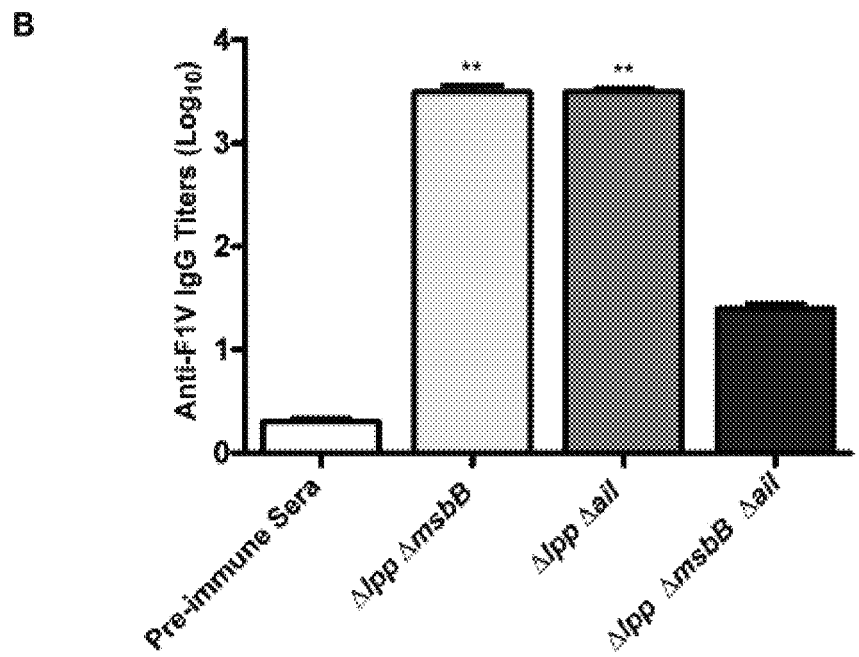

Figure 6.

Figure 13.
A. MH-S Alveolar Murine Macrophages
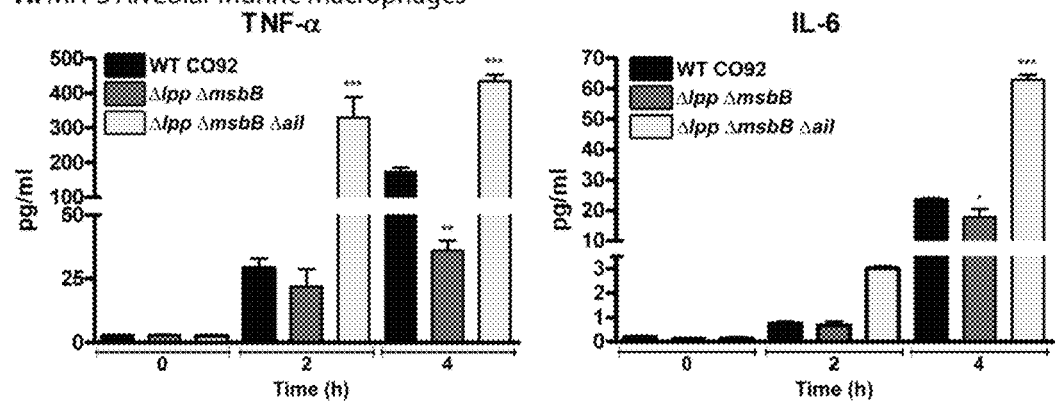
B. Human Monocyte Derived Macrophages
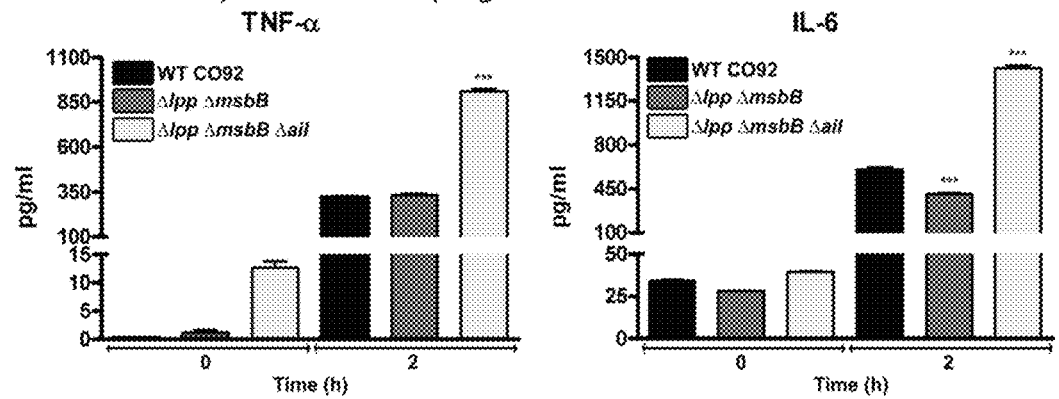

TTTTCCTTGAGCACAATCCTACCTATGGGCCATCCGGCCCATAATTATTTTCGTTCTATTCTCGCAAGTGATTCCAAA
GCTCAACGCTCTTCAGTATAGTGTGTTCGTTAATTGCATTACTGGGAAGTAGA (SEQ ID NO:1)

SEQUENCE LISTING

```
<160> NUMBER OF SEQ ID NOS: 62

<210> SEQ ID NO 1
<211> LENGTH: 131
<212> TYPE: DNA
<213> ORGANISM: Yersinia pestis

<400> SEQUENCE: 1
ttttccttga gcacaatcct acctatgggc catccggccc ataattattt tcgttctatt      60
ctcgcaagtg attccaaagc tcaacgctct tcagtatagt gtgttcgtta attgcattac     120
tgggaagtag a                                                         131

<210> SEQ ID NO 2
<211> LENGTH: 24
<212> TYPE: PRT
```

<213> ORGANISM: Yersinia pestis

<400> SEQUENCE: 2

```
Met Gly His Pro Ala His Asn Tyr Phe Arg Ser Ile Leu Ala Ser Asp
1               5                   10                  15

Ser Lys Ala Gln Arg Ser Ser Val
            20
```

<210> SEQ ID NO 3
<211> LENGTH: 29
<212> TYPE: DNA
<213> ORGANISM: artificial
<220> FEATURE:
<223> OTHER INFORMATION: primer

<400> SEQUENCE: 3
tatgagctca cgacgcacaa gactctggc 29

<210> SEQ ID NO 4
<211> LENGTH: 28
<212> TYPE: DNA
<213> ORGANISM: artificial
<220> FEATURE:
<223> OTHER INFORMATION: primer

<400> SEQUENCE: 4
aacggatccc catccagatt gttataac 28

<210> SEQ ID NO 5
<211> LENGTH: 30
<212> TYPE: DNA
<213> ORGANISM: artificial
<220> FEATURE:
<223> OTHER INFORMATION: primer

<400> SEQUENCE: 5
atgaagcttc ctaacgtcct cctaaccatg 30

<210> SEQ ID NO 6
<211> LENGTH: 20
<212> TYPE: DNA
<213> ORGANISM: artificial
<220> FEATURE:
<223> OTHER INFORMATION: primer

<400> SEQUENCE: 6
gcatccgtca atggtaccag 20

<210> SEQ ID NO 7
<211> LENGTH: 20
<212> TYPE: DNA
<213> ORGANISM: artificial
<220> FEATURE:
<223> OTHER INFORMATION: primer

<400> SEQUENCE: 7
attccgggga tccgtcgacc 20

<210> SEQ ID NO 8
<211> LENGTH: 29
<212> TYPE: DNA
<213> ORGANISM: artificial
<220> FEATURE:
<223> OTHER INFORMATION: primer

<400> SEQUENCE: 8
cttaagcttg tgtaggctgg agctgcttc                                        29

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9
atgcccacat cgttaccacc                                                  20

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10
ccgtaatcca tggtgatctg                                                  20

<210> SEQ ID NO 11
<211> LENGTH: 19
<212> TYPE: DNA
<213> ORGANISM: artificial
<220> FEATURE:
<223> OTHER INFORMATION: primer

<400> SEQUENCE: 11
taatgtgtat gccgaaggc                                                   19

<210> SEQ ID NO 12
<211> LENGTH: 20
<212> TYPE: DNA
<213> ORGANISM: artificial
<220> FEATURE:
<223> OTHER INFORMATION: primer

<400> SEQUENCE: 12
ttggagtatt catatgaagc                                                  20

<210> SEQ ID NO 13
<211> LENGTH: 30
<212> TYPE: DNA
<213> ORGANISM: artificial
<220> FEATURE:
<223> OTHER INFORMATION: primer

<400> SEQUENCE: 13
cgggatcccg caaggtcaat ggggctattg                                       30

<210> SEQ ID NO 14
<211> LENGTH: 30
<212> TYPE: DNA
<213> ORGANISM: artificial
<220> FEATURE:
<223> OTHER INFORMATION: primer

<400> SEQUENCE: 14
acgcgtcgac ttagaaccgg taacccgcgc                                       30

<210> SEQ ID NO 15
<211> LENGTH: 20
<212> TYPE: DNA

```
<213> ORGANISM: artificial
<220> FEATURE:
<223> OTHER INFORMATION: primer

<400> SEQUENCE: 15
ggaatactgt acgaatatcc                                                    20

<210> SEQ ID NO 16
<211> LENGTH: 29
<212> TYPE: DNA
<213> ORGANISM: artificial
<220> FEATURE:
<223> OTHER INFORMATION: primer

<400> SEQUENCE: 16
tatgagctca cgacgcacaa gactctggc                                          29

<210> SEQ ID NO 17
<211> LENGTH: 40
<212> TYPE: DNA
<213> ORGANISM: artificial
<220> FEATURE:
<223> OTHER INFORMATION: primer

<400> SEQUENCE: 17
tagtacttag cagcaccagc aataagtgcg aatccgtcaa                               40

<210> SEQ ID NO 18
<211> LENGTH: 40
<212> TYPE: DNA
<213> ORGANISM: artificial
<220> FEATURE:
<223> OTHER INFORMATION: primer

<400> SEQUENCE: 18
ttgacggatt cgcacttatt gctggtgctg ctaagtacta                               40

<210> SEQ ID NO 19
<211> LENGTH: 20
<212> TYPE: DNA
<213> ORGANISM: artificial
<220> FEATURE:
<223> OTHER INFORMATION: primer

<400> SEQUENCE: 19
gcatccgtca atggtaccag                                                    20

<210> SEQ ID NO 20
<211> LENGTH: 29
<212> TYPE: DNA
<213> ORGANISM: artificial
<220> FEATURE:
<223> OTHER INFORMATION: primer

<400> SEQUENCE: 20
tatgagctca cgacgcacaa gactctggc                                          29

<210> SEQ ID NO 21
<211> LENGTH: 20
<212> TYPE: DNA
<213> ORGANISM: artificial
<220> FEATURE:
<223> OTHER INFORMATION: primer

<400> SEQUENCE: 21
gcatccgtca atggtaccag                                                    20
```

```
<210> SEQ ID NO 22
<211> LENGTH: 20
<212> TYPE: DNA
<213> ORGANISM: artificial
<220> FEATURE:
<223> OTHER INFORMATION: primer

<400> SEQUENCE: 22
atgcccacat cgttaccacc                                               20

<210> SEQ ID NO 23
<211> LENGTH: 20
<212> TYPE: DNA
<213> ORGANISM: artificial
<220> FEATURE:
<223> OTHER INFORMATION: primer

<400> SEQUENCE: 23
ccgtaatcca tggtgatctg                                               20

<210> SEQ ID NO 24
<211> LENGTH: 20
<212> TYPE: DNA
<213> ORGANISM: artificial
<220> FEATURE:
<223> OTHER INFORMATION: primer

<400> SEQUENCE: 24
ggtggcaccg aacaatgaat                                               20

<210> SEQ ID NO 25
<211> LENGTH: 20
<212> TYPE: DNA
<213> ORGANISM: artificial
<220> FEATURE:
<223> OTHER INFORMATION: primer

<400> SEQUENCE: 25
cattacgctg acttgacggg                                               20

<210> SEQ ID NO 26
<211> LENGTH: 20
<212> TYPE: DNA
<213> ORGANISM: artificial
<220> FEATURE:
<223> OTHER INFORMATION: primer

<400> SEQUENCE: 26
ggaatactgt acgaatatcc                                               20

<210> SEQ ID NO 27
<211> LENGTH: 18
<212> TYPE: DNA
<213> ORGANISM: artificial
<220> FEATURE:
<223> OTHER INFORMATION: primer

<400> SEQUENCE: 27
tacctacaac ctcaagct                                                 18

<210> SEQ ID NO 28
<211> LENGTH: 18
<212> TYPE: DNA
<213> ORGANISM: artificial
<220> FEATURE:
```

<223> OTHER INFORMATION: primer

<400> SEQUENCE: 28
tacccattct aaccaagc                                                    18

<210> SEQ ID NO 29
<211> LENGTH: 19
<212> TYPE: DNA
<213> ORGANISM: artificial
<220> FEATURE:
<223> OTHER INFORMATION: primer

<400> SEQUENCE: 29
gcgcaacgga acattcatc                                                   19

<210> SEQ ID NO 30
<211> LENGTH: 20
<212> TYPE: DNA
<213> ORGANISM: artificial
<220> FEATURE:
<223> OTHER INFORMATION: primer

<400> SEQUENCE: 30
gcaagcttcg gccgcctagg                                                  20

<210> SEQ ID NO 31
<211> LENGTH: 20
<212> TYPE: DNA
<213> ORGANISM: artificial
<220> FEATURE:
<223> OTHER INFORMATION: primer

<400> SEQUENCE: 31
agggtcagcc tgaatacgcg                                                  20

<210> SEQ ID NO 32
<211> LENGTH: 21
<212> TYPE: DNA
<213> ORGANISM: artificial
<220> FEATURE:
<223> OTHER INFORMATION: primer

<400> SEQUENCE: 32
ctgactctta tacacaagtg c                                                21

<210> SEQ ID NO 33
<211> LENGTH: 70
<212> TYPE: DNA
<213> ORGANISM: artificial
<220> FEATURE:
<223> OTHER INFORMATION: primer

<400> SEQUENCE: 33
ttagctggta agcgtgtcaa ttctcgctct gctcaggcag agcgataacc gtgtaggctg      60
gagctgcttc                                                             70

<210> SEQ ID NO 34
<211> LENGTH: 70
<212> TYPE: DNA
<213> ORGANISM: artificial
<220> FEATURE:
<223> OTHER INFORMATION: primer

<400> SEQUENCE: 34
taatgcactc cctgttgcgt gaagcatgat gttattagat tcaatttcat attccgggga      60

```
tccgtcgacc                                                           70

<210> SEQ ID NO 35
<211> LENGTH: 25
<212> TYPE: DNA
<213> ORGANISM: artificial
<220> FEATURE:
<223> OTHER INFORMATION: primer

<400> SEQUENCE: 35
cgtattgcac tgggtatcgc gttgg                                          25

<210> SEQ ID NO 36
<211> LENGTH: 25
<212> TYPE: DNA
<213> ORGANISM: artificial
<220> FEATURE:
<223> OTHER INFORMATION: primer

<400> SEQUENCE: 36
gtcatttaac ccgctcatta agaca                                          25

<210> SEQ ID NO 37
<211> LENGTH: 30
<212> TYPE: DNA
<213> ORGANISM: artificial
<220> FEATURE:
<223> OTHER INFORMATION: primer

<400> SEQUENCE: 37
cgggatccgg ttagcgtaga cggccaacca                                     30

<210> SEQ ID NO 38
<211> LENGTH: 30
<212> TYPE: DNA
<213> ORGANISM: artificial
<220> FEATURE:
<223> OTHER INFORMATION: primer

<400> SEQUENCE: 38
acgcgtcgac tcataatgca ctccctgttg                                     30

<210> SEQ ID NO 39
<211> LENGTH: 70
<212> TYPE: DNA
<213> ORGANISM: artificial
<220> FEATURE:
<223> OTHER INFORMATION: primer

<400> SEQUENCE: 39
gacaactcaa accatgatcg ccatggaatg ccacaggagc gttagcgcat gtgtaggctg    60
gagctgcttc                                                           70

<210> SEQ ID NO 40
<211> LENGTH: 70
<212> TYPE: DNA
<213> ORGANISM: artificial
<220> FEATURE:
<223> OTHER INFORMATION: primer

<400> SEQUENCE: 40
tgcgatctgt ctcaatacaa tcgtgtgtct caatacagag tgtctggcag attccgggga    60
tccgtcgacc                                                           70
```

```
<210> SEQ ID NO 41
<211> LENGTH: 25
<212> TYPE: DNA
<213> ORGANISM: artificial
<220> FEATURE:
<223> OTHER INFORMATION: primer

<400> SEQUENCE: 41
taaaccggca accacagcaa tccga                                         25

<210> SEQ ID NO 42
<211> LENGTH: 25
<212> TYPE: DNA
<213> ORGANISM: artificial
<220> FEATURE:
<223> OTHER INFORMATION: primer

<400> SEQUENCE: 42
ttgacctctg gccgtgccgg gtggt                                         25

<210> SEQ ID NO 43
<211> LENGTH: 30
<212> TYPE: DNA
<213> ORGANISM: artificial
<220> FEATURE:
<223> OTHER INFORMATION: primer

<400> SEQUENCE: 43
ctagctagcc tacagatgat aaaccggcaa                                    30

<210> SEQ ID NO 44
<211> LENGTH: 30
<212> TYPE: DNA
<213> ORGANISM: artificial
<220> FEATURE:
<223> OTHER INFORMATION: primer

<400> SEQUENCE: 44
acgcgtcgac tcaatacaga gtgtctggca                                    30

<210> SEQ ID NO 45
<211> LENGTH: 70
<212> TYPE: DNA
<213> ORGANISM: artificial
<220> FEATURE:
<223> OTHER INFORMATION: primer

<400> SEQUENCE: 45
accattagca cgatgacgtg gatgaatagc caaaataaga ggacatagat gtgtaggctg    60
gagctgcttc                                                          70

<210> SEQ ID NO 46
<211> LENGTH: 70
<212> TYPE: DNA
<213> ORGANISM: artificial
<220> FEATURE:
<223> OTHER INFORMATION: primer

<400> SEQUENCE: 46
tacctcttaa tctccagaga ttttagatcc tttgcgtgtc agataggaca attccgggga    60
tccgtcgacc                                                          70

<210> SEQ ID NO 47
<211> LENGTH: 20
```

-continued

```
<212> TYPE: DNA
<213> ORGANISM: artificial
<220> FEATURE:
<223> OTHER INFORMATION: primer

<400> SEQUENCE: 47
gctattcgct ggttgaggct                                                 20

<210> SEQ ID NO 48
<211> LENGTH: 20
<212> TYPE: DNA
<213> ORGANISM: artificial
<220> FEATURE:
<223> OTHER INFORMATION: primer

<400> SEQUENCE: 48
aacgctggca gagagatgag                                                 20

<210> SEQ ID NO 49
<211> LENGTH: 78
<212> TYPE: PRT
<213> ORGANISM: Yersinia pestis

<400> SEQUENCE: 49

Met Asn Arg Thr Lys Leu Val Leu Gly Ala Val Ile Leu Ala Ser Thr
  1               5                  10                  15

Met Leu Ala Gly Cys Ser Ser Asn Ala Lys Ile Asp Gln Leu Ser Ser
                 20                  25                  30

Asp Val Gln Thr Leu Asn Ala Lys Val Asp Gln Leu Ser Asn Asp Val
             35                  40                  45

Asn Ala Val Arg Ala Asp Val Gln Ala Lys Asp Asp Ala Ala Arg
         50                  55                  60

Ala Asn Gln Arg Leu Asp Asn Gln Ala Gln Ala Tyr Lys Lys
 65                  70                  75

<210> SEQ ID NO 50
<211> LENGTH: 320
<212> TYPE: PRT
<213> ORGANISM: Yersinia pestis

<400> SEQUENCE: 50

Met His Lys Glu Lys Asn Asp Ala Thr Gly Phe Ile Pro Val Phe Gln
  1               5                  10                  15

Lys Thr Phe Leu His Pro Arg Phe Trp Gly Val Trp Leu Gly Ala Gly
                 20                  25                  30

Ala Ile Ala Ala Leu Ala Tyr Ile Pro Pro Lys Phe Arg Asp Pro Leu
             35                  40                  45

Leu Ala Gly Ile Gly Arg Leu Ala Gly Lys Phe Ala Lys Ser Ala Arg
         50                  55                  60

Arg Arg Ala Arg Ile Asn Leu Leu Tyr Cys Met Pro Glu Leu Pro Glu
 65                  70                  75                  80

Ser Glu Arg Glu His Ile Ile Asp Gln Met Phe Ala Thr Ala Ala Gln
                 85                  90                  95

Pro Leu Met Met Met Ala Glu Leu Cys Phe Arg Asp Pro Lys Lys Val
                100                 105                 110

Leu Thr Arg Val His Trp His Gly Gln Glu Ile Leu Asp Glu Leu Gln
            115                 120                 125

Gln Gln Glu Arg Asn Val Ile Leu Leu Val Pro His Ala Trp Ser Ile
        130                 135                 140
```

```
Asp Ile Pro Ala Met Leu Ala Glu Gln Gly Lys Pro Val Ala Gly
145                 150                 155                 160

Met Phe His His Gln Arg Asn Pro Leu Val Asp Tyr Leu Trp Asn Ser
            165                 170                 175

Ala Arg Leu His Phe Gly Gly Arg Ile His Ala Arg Glu Ser Gly Ile
        180                 185                 190

Lys Pro Phe Ile Ser Ser Val Arg Gln Gly Phe Trp Gly Tyr Tyr Leu
    195                 200                 205

Pro Asp Glu Asp Tyr Gly Pro Glu Gln Ser Glu Phe Val Asp Phe Phe
210                 215                 220

Ala Thr Tyr Lys Ala Thr Leu Pro Ala Ile Gly Arg Leu Met Lys Val
225                 230                 235                 240

Cys Arg Ala Ala Ile Val Pro Met Phe Pro Val Tyr Asn Tyr Arg Glu
                245                 250                 255

His Arg Leu Asp Ile Tyr Ile Arg Pro Pro Met Asp Asp Leu Ala Asp
            260                 265                 270

Ala Asp Asp Ala Tyr Ile Ala Arg Arg Met Asn Glu Glu Val Glu Leu
        275                 280                 285

Leu Val Lys Pro Asn Pro Glu Gln Tyr Thr Trp Ile Leu Lys Leu Leu
    290                 295                 300

Lys Thr Arg Lys Glu Gly Glu Thr Glu Pro Tyr Val Arg Lys Asp Leu
305                 310                 315                 320

<210> SEQ ID NO 51
<211> LENGTH: 312
<212> TYPE: PRT
<213> ORGANISM: Yersinia pestis

<400> SEQUENCE: 51

Met Lys Lys Ser Ser Ile Val Ala Thr Ile Ile Thr Ile Leu Ser Gly
1               5                   10                  15

Ser Ala Asn Ala Ala Ser Ser Gln Leu Ile Pro Asn Ile Ser Pro Asp
            20                  25                  30

Ser Phe Thr Val Ala Ala Ser Thr Gly Met Leu Ser Gly Lys Ser His
        35                  40                  45

Glu Met Leu Tyr Asp Ala Glu Thr Gly Arg Lys Ile Ser Gln Leu Asp
    50                  55                  60

Trp Lys Ile Lys Asn Val Ala Ile Leu Lys Gly Asp Ile Ser Trp Asp
65                  70                  75                  80

Pro Tyr Ser Phe Leu Thr Leu Asn Ala Arg Gly Trp Thr Ser Leu Ala
                85                  90                  95

Ser Gly Ser Gly Asn Met Asp Asp Tyr Asp Trp Met Asn Glu Asn Gln
            100                 105                 110

Ser Glu Trp Thr Asp His Ser His Pro Ala Thr Asn Val Asn His
        115                 120                 125

Ala Asn Glu Tyr Asp Leu Asn Val Lys Gly Trp Leu Leu Gln Asp Glu
    130                 135                 140

Asn Tyr Lys Ala Gly Ile Thr Ala Gly Tyr Gln Glu Thr Arg Phe Ser
145                 150                 155                 160

Trp Thr Ala Thr Gly Gly Ser Tyr Ser Tyr Asn Asn Gly Ala Tyr Thr
                165                 170                 175

Gly Asn Phe Pro Lys Gly Val Arg Val Ile Gly Tyr Asn Gln Arg Phe
            180                 185                 190

Ser Met Pro Tyr Ile Gly Leu Ala Gly Gln Tyr Arg Ile Asn Asp Phe
        195                 200                 205
```

```
Glu Leu Asn Ala Leu Phe Lys Phe Ser Asp Trp Val Arg Ala His Asp
    210                 215                 220

Asn Asp Glu His Tyr Met Arg Asp Leu Thr Phe Arg Glu Lys Thr Ser
225                 230                 235                 240

Gly Ser Arg Tyr Tyr Gly Thr Val Ile Asn Ala Gly Tyr Tyr Val Thr
                245                 250                 255

Pro Asn Ala Lys Val Phe Ala Glu Phe Thr Tyr Ser Lys Tyr Asp Glu
                260                 265                 270

Gly Lys Gly Gly Thr Gln Thr Ile Asp Lys Asn Ser Gly Asp Ser Val
                275                 280                 285

Ser Ile Gly Gly Asp Ala Ala Gly Ile Ser Asn Lys Asn Tyr Thr Val
    290                 295                 300

Thr Ala Gly Leu Gln Tyr Arg Phe
305                 310

<210> SEQ ID NO 52
<211> LENGTH: 182
<212> TYPE: PRT
<213> ORGANISM: Yersinia pestis

<400> SEQUENCE: 52

Met Thr Gly Glu Gly His Leu Ile Phe Ser Val Ala Cys Val Ile Leu
1               5                   10                  15

Ala Lys Lys Val Gly Leu Thr Pro Glu Leu Ala His Gly Asp Trp Trp
                20                  25                  30

His Ile Ile Pro Gly Ala Leu Leu Thr Ser Leu Leu Pro Asp Ile Asp
            35                  40                  45

His Pro Lys Ser Ile Leu Gly Gln Arg Leu Lys Trp Val Ser Val Pro
    50                  55                  60

Ile Ala Arg Val Phe Gly His Arg Gly Phe Thr His Ser Leu Leu Ala
65                  70                  75                  80

Val Ile Ala Gly Ile Ala Leu Phe Gln Val Asp Ala Pro Leu Asn Gly
                85                  90                  95

Val Leu Pro Pro Asp Val Phe His Ala Met Ile Ile Gly Tyr Phe Ser
                100                 105                 110

His Leu Leu Ala Asp Met Ile Thr Pro Ala Gly Val Pro Leu Leu Trp
            115                 120                 125

Pro Cys Arg Trp Arg Phe Ser Ile Pro Leu Leu Arg Pro Gln Lys Gly
    130                 135                 140

Asn Gln Leu Glu Arg Val Leu Cys Val Leu Leu Val Cys Phe Ser Val
145                 150                 155                 160

Tyr Trp Gln Thr Asp Thr Thr Ile Pro Leu Leu Tyr Tyr Met Glu Gln
                165                 170                 175

Leu Lys Ser Phe Arg Leu
                180

<210> SEQ ID NO 53
<211> LENGTH: 402
<212> TYPE: PRT
<213> ORGANISM: Yersinia pestis

<400> SEQUENCE: 53

Met Asp Glu Lys Lys Leu Lys Ala Leu Ala Ala Glu Leu Ala Lys Gly
1               5                   10                  15

Leu Lys Thr Glu Ala Asp Leu Asn Ala Phe Ser Arg Met Leu Thr Lys
                20                  25                  30
```

-continued

```
Leu Thr Val Glu Thr Ala Leu Asn Ala Glu Leu Thr Glu His Leu Gly
             35                  40                  45

His Glu Lys Asn Thr Pro Lys Ser Gly Ser Asn Thr Arg Asn Gly Tyr
 50                  55                  60

Ser Ser Lys Thr Leu Leu Cys Asp Asp Gly Ile Glu Leu Asn Thr
 65                  70                  75                  80

Pro Arg Asp Arg Glu Asn Thr Phe Glu Pro Gln Leu Ile Lys Lys Asn
                 85                  90                  95

Gln Thr Arg Ile Thr Gln Met Asp Ser Gln Ile Leu Ser Leu Tyr Ala
                100                 105                 110

Lys Gly Met Thr Thr Arg Glu Ile Val Ala Thr Phe Lys Glu Met Tyr
                115                 120                 125

Asp Ala Asp Val Ser Pro Thr Leu Ile Ser Lys Val Thr Asp Ala Val
            130                 135                 140

Lys Glu Gln Val Ala Glu Trp Gln Asn Arg Gln Leu Asp Ala Leu Tyr
145                 150                 155                 160

Pro Ile Val Tyr Met Asp Cys Ile Val Lys Val Arg Gln Asn Gly
                165                 170                 175

Ser Val Ile Asn Lys Ala Val Phe Leu Ala Leu Gly Ile Asn Thr Glu
            180                 185                 190

Gly Gln Lys Glu Leu Leu Gly Met Trp Leu Ala Glu Asn Glu Gly Ala
        195                 200                 205

Lys Phe Trp Leu Ser Val Leu Thr Glu Leu Lys Asn Arg Gly Leu Gln
210                 215                 220

Asp Ile Leu Ile Ala Cys Val Asp Gly Leu Lys Gly Phe Pro Asp Ala
225                 230                 235                 240

Ile Asn Ser Val Tyr Pro Gln Thr His Ile Gln Leu Cys Ile Ile His
                245                 250                 255

Met Val Arg Asn Ser Leu Lys Tyr Val Ser Trp Lys Asp Tyr Lys Ala
            260                 265                 270

Val Thr Ser Gly Leu Lys Met Val Tyr Gln Ala Pro Thr Glu Glu Ala
        275                 280                 285

Ala Leu Met Ala Leu Asp Lys Phe Ala Glu Ala Trp Asp Asp Lys Tyr
    290                 295                 300

Pro Gln Ile Ser Lys Ser Trp Arg Thr His Trp Glu Asn Leu Asn Thr
305                 310                 315                 320

Phe Phe Gly Tyr Pro Pro Asp Ile Arg Lys Ala Ile Tyr Thr Thr Asn
                325                 330                 335

Ala Ile Glu Ser Val Asn Ser Val Ile Arg Ala Ala Ile Lys Lys Arg
            340                 345                 350

Lys Val Phe Pro Thr Asp Ser Val Arg Lys Val Val Tyr Leu Ala
        355                 360                 365

Ile Lys Asp Ala Ser Lys Lys Trp Ser Met Pro Ile Gln Asn Trp Arg
    370                 375                 380

Leu Ala Met Ser Arg Phe Ile Ile Glu Phe Gly Asp Arg Leu Ser Asp
385                 390                 395                 400

His Leu

<210> SEQ ID NO 54
<211> LENGTH: 496
<212> TYPE: PRT
<213> ORGANISM: Yersinia pestis

<400> SEQUENCE: 54
```

-continued

```
Met Thr Pro Leu Leu Glu Leu Lys Gln Ile Lys Lys Ser Phe Pro Gly
1               5                   10                  15

Val Lys Ala Leu Asp Gly Ile Asp Leu Thr Ile Gln Arg Gly Glu Val
            20                  25                  30

His Ala Leu Leu Gly Glu Asn Gly Ala Gly Lys Ser Thr Leu Val Lys
                35                  40                  45

Ile Met Cys Gly Ile Tyr Gln Pro Asp Ser Gly Gly Ile Phe Leu Glu
        50                  55                  60

Gly Gln Arg Cys Arg Phe Ala Asn Tyr Arg Asp Ala Ile Asp Ala Gly
65                  70                  75                  80

Ile Gly Ile Ile Phe Gln Glu Phe Ser Leu Ile Pro Tyr Met Asn Thr
                85                  90                  95

Ile Asp Asn Ile Phe Leu Asn Arg Glu Ile Lys Asn Arg Trp Gly Leu
            100                 105                 110

Leu Asp Arg Arg Glu Met Arg Arg Lys Ala Arg Ala Ile Phe Lys Arg
        115                 120                 125

Leu Thr Val Asp Ile Asp Leu Asp Cys Pro Val Glu Gln Leu Ser Val
130                 135                 140

Ala Gln Gln Phe Val Glu Ile Ala Lys Ala Leu Ser Leu Asp Ala
145                 150                 155                 160

Arg Ile Leu Val Leu Asp Glu Pro Thr Ala Thr Leu Thr Pro Gly Glu
                165                 170                 175

Ala Glu His Leu Phe Ser Ile Met His Asp Leu Lys Leu Leu Gly Val
            180                 185                 190

Gly Met Val Phe Ile Ser His His Leu Asp Glu Ile Phe Thr Ile Cys
        195                 200                 205

Asp Gln Ile Thr Val Leu Arg Asp Gly Ala Tyr Ile Gln Thr Leu Pro
210                 215                 220

Ala Ala Glu Thr Asn Val Glu Glu Leu Val Lys Leu Met Val Gly Arg
225                 230                 235                 240

Lys Ile Glu Asn Thr Phe Pro Val Lys Ser His Pro Val Asp Thr Ser
                245                 250                 255

Val Arg Val Leu Glu Ala Thr Val Gln His Thr Lys His Val Met Glu
            260                 265                 270

Asn Ser Phe His Leu Tyr Lys Gly Glu Ile Leu Gly Phe Ala Gly Leu
        275                 280                 285

Val Gly Ser Gly Arg Thr Glu Leu Met Ser Ala Leu Ile Gly Ala Arg
290                 295                 300

Ser Cys Tyr Gln Lys Ser Val Ser Leu Asn Gly Gln Pro Thr Val Leu
305                 310                 315                 320

Arg Asn Pro Ala Gln Ala Leu Asp His Gly Ile Gly Leu Leu Pro Glu
                325                 330                 335

Ser Arg Lys Thr Glu Gly Leu Val Leu Pro Phe Ser Val Ala Gln Asn
            340                 345                 350

Ile Thr Leu Asn Arg His Glu Lys Arg Gly Lys Ile Phe Val Asn Ala
        355                 360                 365

Gly Lys Glu His Asp Ile Val Gln Arg Leu Ile Arg Ala Val Gly Val
370                 375                 380

Lys Thr Pro Asp Ala Asp Thr Ala Val Ser Thr Leu Ser Gly Gly Asn
385                 390                 395                 400

Gln Gln Lys Val Val Ile Ala Arg Trp Leu Asn Asn Asp Cys Asp Ile
                405                 410                 415
```

```
Leu Ile Phe Asp Glu Pro Thr Arg Gly Ile Asp Val Gly Ala Lys Ser
                420             425             430

Glu Ile Tyr Gln Leu Met Gln Gln Leu Thr Gln Lys Gly Ile Ser Ile
            435             440             445

Ile Met Ile Ser Ser Glu Leu Pro Glu Ile Ile Gly Val Cys Asp Arg
        450             455             460

Val Leu Val Phe Arg Gly Gly His Ile Val Ala Glu Leu Ala Gly Asp
465             470             475             480

Glu Ile Glu Ser Asn Asn Ile Met Leu His Ala Thr Gly Ser Ala Leu
            485             490             495
```

<210> SEQ ID NO 55
<211> LENGTH: 247
<212> TYPE: PRT
<213> ORGANISM: Yersinia pestis

<400> SEQUENCE: 55

```
Met Arg Lys Lys Leu Tyr Asn Asp Phe Ala Trp Glu Cys Leu Arg Arg
1               5                   10                  15

Asn Pro Gln Tyr Ile Ser Asp Trp Glu Leu Phe Met Lys Asn Thr Leu
                20                  25                  30

Thr Asn Gly Gly Gly Ile Pro Asp Asp Ser Glu Leu Ile Gln Ser Glu
            35                  40                  45

Leu Asp Leu Asn Ala Glu Lys Lys Trp Gly Val Met Lys Tyr Ile Asp
    50                  55                  60

Pro Tyr Asn Ser Asp Pro Thr Asn Val Phe Trp Ser Leu Lys Leu Ser
65                  70                  75                  80

Asn Arg Ser Val Arg Val Lys Leu Ser Asn Thr Gly Asn Val Lys Gly
                85                  90                  95

Gly Tyr Thr Trp Gly Asp Met Ser Asn Leu Pro Gly Val Lys His Gln
            100                 105                 110

Arg Leu Leu Met His Asp Asn Thr Leu Cys Val Lys Ile Phe Ser Gln
        115                 120                 125

Asn Gly Tyr Phe Gln Leu Phe Ile Glu Ser Ala Asp Ala Leu Lys Asp
    130                 135                 140

Asp Ser Asn Leu Tyr Ile Tyr Ile Pro Leu Asn Leu Glu Ser Asp Val
145                 150                 155                 160

Phe Ala Lys Asn Ile Glu Leu Leu Gln Ser Ile Val Asn His Lys Ile
                165                 170                 175

Glu Val Glu Cys Lys Glu Glu Gln Tyr Leu Gly Leu Leu Lys Thr Ile
            180                 185                 190

Asp Asp Arg Lys Gln Gly Phe Ser His Arg Asp Ile Ala Ser Glu Ile
        195                 200                 205

Phe Gly Lys Glu Leu Val Lys Asn Glu Trp Ser Ala Asp Ser Trp Val
    210                 215                 220

Arg Ala Lys Ile Arg Tyr Arg Ile Lys Lys Ala Asn Ala Leu Ile Asn
225                 230                 235                 240

Tyr Gly Tyr Leu Asn Phe Leu
                245
```

<210> SEQ ID NO 56
<211> LENGTH: 1177
<212> TYPE: PRT
<213> ORGANISM: Yersinia pestis

<400> SEQUENCE: 56

```
Met Lys Leu Pro Phe Phe Ile Arg Ile Ala Lys Pro Ala Ile Pro Arg
1               5                   10                  15

Leu Lys Ala Ser Ile Pro Val Val Leu Ala Leu Met Ala Cys Ala Ala
            20                  25                  30

Leu Ile Trp Val Trp Ile Tyr Gly Pro Glu Trp Gln Leu Gly Glu Asn
        35                  40                  45

Tyr Pro Phe Glu Thr Leu Leu Ser Arg Trp Leu Val Thr Ala Val Phe
    50                  55                  60

Val Leu Val Ala Val Cys Trp Leu Ser Leu Lys Val Met Arg Arg Val
65              70                  75                  80

Gln His Leu Glu Lys Leu Gln Leu Gln Thr Lys Ile Gln Leu Asp Asp
                85                  90                  95

Pro Val Ser Ala Asp Ile Glu Gln Gln Asn His Tyr Leu Asn Gly Trp
            100                 105                 110

Lys His Gln Leu Gln Arg His Leu Asn Thr Pro Glu Tyr Leu Tyr Arg
            115                 120                 125

Leu Pro Trp Tyr Met Val Ile Gly Ala Arg Asn Ser Gly Lys Ser Thr
        130                 135                 140

Leu Ile Lys Glu Gly Tyr Lys Leu Thr Glu Ile Ser Ala Ser Glu Arg
145                 150                 155                 160

Leu His Ala Glu Asp Ala Ala Asp Leu Arg Val Arg Cys Trp Leu Gly
                165                 170                 175

Glu Gln Ala Val Ile Ile Asp Pro Ala Gly Val Leu Ile Glu Gln Pro
            180                 185                 190

Thr Thr Pro Ile Ala Gly Lys Ala Ser Leu Asn Ser Arg Leu Trp Gln
        195                 200                 205

Ser Leu Leu Ser Trp Leu Ile Glu Gln Arg Gln Arg Gln Pro Leu Asn
    210                 215                 220

Gly Ile Ile Leu Thr Val Asp Leu His Gln Met Met Thr Ala Asn Lys
225                 230                 235                 240

Ala Gln Arg Glu Thr Tyr Val Ala Asp Ile His Gln Arg Leu Gln Glu
                245                 250                 255

Ile Arg Leu Ser Leu His Ser Gln Val Pro Leu Tyr Val Val Phe Thr
            260                 265                 270

Lys Met Asp Leu Leu Tyr Gly Phe Glu Ala Met Tyr Gln Ser Leu Asp
        275                 280                 285

Lys Ala Glu Arg Glu Ala Val Leu Gly Val Thr Phe Ser Leu Asn Ala
    290                 295                 300

Ala Asp Pro Asp Val Trp Arg Thr Glu Leu Lys Gln Phe Trp Gln Gln
305                 310                 315                 320

Trp Val Ala Gln Leu Asn Gly Ala Met Pro Asp Met Met Leu Asn Ser
                325                 330                 335

Val Asp Ala Gly Gln Arg Ser Gln Leu Phe Ser Phe Thr Arg Gln Met
            340                 345                 350

Gln Gly Leu His Asp Tyr Val Gln Leu Leu Glu Gly Ile Leu Tyr
        355                 360                 365

Arg Gly Glu His Ala Gln Pro Leu Leu Arg Gly Val Tyr Leu Thr Ser
    370                 375                 380

Ala Gln Gln Arg Gly Gln Met Asp Asp Ile Phe Thr Gln Ser Ala Ala
385                 390                 395                 400

Val Gln Tyr His Leu Ala Pro Gln Ala Phe Pro Thr Trp Pro Val Ser
                405                 410                 415

Asp Thr Thr Pro Tyr Phe Thr Lys Ala Leu Phe Asn Gln Val Leu Leu
```

-continued

```
            420                 425                 430
Ala Glu Pro Asn Leu Ala Gly Glu Asn Gly Ile Trp Leu Gln Lys Thr
            435                 440                 445
Arg Lys Arg Met Phe Ile Phe Ser Gly Val Gly Ala Leu Ala Ala Leu
            450                 455                 460
Thr Leu Trp Gly Tyr Trp His Tyr Tyr His Gln Leu Asn Tyr Arg Ala
465                 470                 475                 480
Gly Glu Glu Val Leu Thr Gln Ala Lys Thr Phe Leu Ser Ile Pro Pro
                    485                 490                 495
Pro Glu Gly Asp Asp Arg Tyr Gly Asn Leu Gln Leu Pro Leu Leu Asn
            500                 505                 510
Pro Ile Arg Asp Ala Thr Leu Ala Tyr Gly Asn Tyr His Glu Arg Ser
            515                 520                 525
Pro Phe Leu Ala Asp Met Gly Leu Tyr Gln Gly Asn Asn Ile Gly Pro
            530                 535                 540
Tyr Val Glu Ser Thr Tyr Leu Gln Leu Leu Gln Gln Arg Phe Val Pro
545                 550                 555                 560
Ala Leu Met Ser Gly Leu Leu Glu Gln Leu Asn Ala Ala Pro Lys Gly
                    565                 570                 575
Ser Glu Glu Lys Leu Glu Ile Leu Arg Val Met Arg Met Leu Glu Asp
            580                 585                 590
Gly Ser Gly Arg Asn Ala Ala Leu Val Glu Gln Tyr Met Ser His Arg
            595                 600                 605
Trp Ser Gln Gln Phe Asn Gly Gln Arg Glu Leu Gln Glu Gln Leu Ser
            610                 615                 620
Ser His Leu Asn Tyr Ala Leu Lys His Thr Asp Trp His Gly Ala Arg
625                 630                 635                 640
Glu Ser Gly Asp Gln Tyr Ala Ile Lys Ser Phe Val Pro Tyr Leu Arg
                    645                 650                 655
Pro Ile Gln Ser Ala Gln Gln Glu Leu Ser Lys Leu Ser Ile Tyr Gln
            660                 665                 670
Arg Val Tyr Gln Asn Leu Arg Ile Lys Ala Gln Asp Ala Leu Pro Pro
            675                 680                 685
Ala Leu Asp Leu Arg Asp Gln Ile Gly Ala Ser Phe Asp Asp Ile Phe
            690                 695                 700
Val Ser Gly Asn Asp Arg Leu Leu Val Ile Pro Gln Phe Leu Thr Arg
705                 710                 715                 720
Ser Gly Leu Gln Ser Tyr Phe Ile Lys Gln Asn Asp Gln Leu Val Asp
                    725                 730                 735
Leu Thr Val Met Asp Ser Trp Val Leu Asn Leu Thr Lys Asn Val Glu
            740                 745                 750
Tyr Ser Glu Ala Asp Arg Lys Glu Ile His Arg Gln Val Thr Glu Gln
            755                 760                 765
Tyr Leu Gly Asp Tyr Thr Ala Thr Trp Arg Ala Met Asn Asn Leu
            770                 775                 780
Ser Val Ser Asp Phe Glu Gly Leu Pro Gln Ala Ile Ser Ala Ile Glu
785                 790                 795                 800
Gln Val Ile Ser Gly Glu Gln Pro Phe Arg Arg Ala Leu Gln Thr Leu
                    805                 810                 815
Ser Asp Asn Thr Arg Leu Pro Val Ile Ser Asp Leu Ile Pro Ala Lys
            820                 825                 830
Glu Gln Gln Glu Leu Leu Gln Lys Pro Asp Tyr Leu Leu Leu Thr Arg
            835                 840                 845
```

Ile Asn Arg Glu Phe Ser Pro Glu Thr Ala Val Leu Val Glu Asn Gly
    850                 855                 860

Asp Lys Gly Ser Val Ile Gln Ser Val Tyr Gln Lys Leu Thr Glu Leu
865                 870                 875                 880

His Arg Tyr Leu Leu Ala Ile Gln Asn Ser Pro Ala Pro Gly Lys Ala
                885                 890                 895

Ala Leu Lys Ala Val Gln Leu Arg Leu Asp Gln Asn Asn Ser Asp Pro
            900                 905                 910

Ile Phe Glu Val Gln Gln Leu Ala Lys Asn Leu Pro Glu Pro Leu Asn
        915                 920                 925

Arg Trp Val Gly Glu Leu Ala Glu Gln Ala Trp Arg Val Val Met Met
    930                 935                 940

Glu Ala Ile Gln Ser Leu Glu Val Glu Trp Asn Glu Thr Val Ile Lys
945                 950                 955                 960

Gln Tyr Gln Thr Tyr Leu Ala Gly Arg Tyr Pro Phe Asp Pro His Ala
                965                 970                 975

Lys Gln Asp Val Pro Leu Ser Glu Phe Glu Arg Phe Gly Pro Lys
            980                 985                 990

Gly Thr Leu Asp Ala Phe Tyr Gln Gln Asn Leu Lys Pro Phe Val Glu
        995                 1000                1005

Asn Asn Leu Thr Gly Gly Ser Asp Gly Glu Leu Leu Ile Arg Pro
    1010                1015                1020

Asp Val Leu Gln Gln Leu Ala Gln Ala Arg Lys Ile Arg Asp Thr
    1025                1030                1035

Phe Phe Ser Ala Gln Asn Gly Leu Gly Thr Gln Phe Ala Ile Glu
    1040                1045                1050

Pro Val Leu Leu Ser Gly Asn Lys Arg Arg Ser Val Leu Asn Leu
    1055                1060                1065

Asp Gly Gln Leu Leu Asp Tyr Ala His Gly Arg Ser Gly Val Val
    1070                1075                1080

His Leu Val Trp Pro Asn Ser Met Arg Ala Gly Val Glu Ser Lys
    1085                1090                1095

Leu Thr Leu Val Pro Asp Glu Ser Gly Lys Ser Pro Arg Thr Leu
    1100                1105                1110

Ser Phe Ser Gly Pro Trp Ala Gln Leu Arg Leu Ile Asn Ala Gly
    1115                1120                1125

Glu Leu Thr Asn Val Gly Thr Asn Ser Phe Asp Val Arg Phe Lys
    1130                1135                1140

Val Asp Gly Gly Glu Met Thr Tyr Arg Ile Phe Val Asp Glu Ser
    1145                1150                1155

Asp Asn Pro Phe Ala Gly Gly Leu Phe Ser Lys Phe Ser Leu Pro
    1160                1165                1170

Asp Thr Leu Tyr
    1175

<210> SEQ ID NO 57
<211> LENGTH: 318
<212> TYPE: PRT
<213> ORGANISM: Yersinia pestis

<400> SEQUENCE: 57

Met Arg Leu Lys Lys Tyr Ile Lys Asn Met Gly Ile Leu Ser Leu Phe
1               5                   10                  15

Ala Ala Thr Val Met Leu Ser Gly Cys Asn Met Val Leu Met Asn Pro

```
            20                  25                  30
Lys Gly Ala Ile Gly Val Glu Gln Lys Thr Leu Ile Leu Thr Ala Ile
            35                  40                  45

Gly Leu Met Leu Ile Val Val Ile Pro Val Ile Phe Met Ala Phe Ala
            50                  55                  60

Phe Ala Trp Lys Phe Arg Ala Ser Asn Lys Ser Ala Thr Tyr Thr Pro
65                  70                  75                  80

Asn Trp Ser His Ser Asn Lys Ile Glu Leu Val Val Trp Ala Val Pro
                85                  90                  95

Ile Ile Ile Ile Ala Ile Leu Ala Thr Ile Thr Trp Lys Thr Thr His
                100                 105                 110

Glu Leu Asp Pro Phe Lys Pro Ile Val Val Ala Gly Lys Asp Pro Ile
            115                 120                 125

Thr Ile Glu Val Val Ser Leu Asp Trp Lys Trp Leu Phe Ile Tyr Pro
            130                 135                 140

Glu Gln Gly Ile Ala Thr Val Asn Glu Leu Ala Phe Pro Thr Gly Val
145                 150                 155                 160

Pro Val Asn Phe Lys Ile Thr Ser Asn Ser Val Met Asn Ser Phe Phe
                165                 170                 175

Ile Pro Gln Leu Gly Gly Gln Ile Tyr Ala Met Ala Gly Met Gln Thr
                180                 185                 190

Lys Leu His Leu Ile Ala Asn Glu Pro Gly Lys Tyr Asn Gly Ile Ser
            195                 200                 205

Gly Ser Phe Ser Gly Gln Gly Phe Ser Gly Met Lys Phe Thr Ala Ile
            210                 215                 220

Ala Thr Pro Thr Gln Glu Asp Phe Asn Gln Trp Val Glu Gln Val Lys
225                 230                 235                 240

Lys Ser Pro Asn Thr Leu Asn Thr Thr Asn Asp Phe Glu Lys Leu Ala
                245                 250                 255

Lys Pro Ser Glu Asn Asn Pro Val Glu Tyr Phe Ser Ser Ile Lys Pro
                260                 265                 270

Ala Leu Phe Lys Gly Ile Ile Gly Lys Phe Met Gly Asp Met Asn Met
            275                 280                 285

Pro Lys Asn Gly His Asp Met Pro Lys Gly Met Asp Met Ser Gln Gly
            290                 295                 300

Met Glu Met Gly Glu His Thr Ala His Ala Gly Ala Glu Glu Glu
305                 310                 315

<210> SEQ ID NO 58
<211> LENGTH: 596
<212> TYPE: PRT
<213> ORGANISM: Yersinia pestis

<400> SEQUENCE: 58

Met Arg Asp Cys Tyr Cys His Gly Met Leu Trp Phe Pro Leu Lys Phe
1               5                   10                  15

Ser Leu Leu Ala Leu Phe Ser Leu Ser Cys Ser Pro Leu Ile Ala Thr
            20                  25                  30

Pro Gln Val Leu Asn Val Pro Asn Ala Gly Ala Ile Ser Asn Glu Ile
            35                  40                  45

Arg Gln Thr Thr Ile Glu Pro Leu Asn Ala Pro Glu Glu Thr Asp Ile
            50                  55                  60

Lys Leu Pro Gln Leu Asn Lys Pro Thr Pro Pro Glu Gly Gly Leu Ala
65                  70                  75                  80
```

```
Thr Glu Arg Ile Thr Leu His Arg Val Arg Phe Glu Gly Asp Val Ser
                85                  90                  95
Leu Phe Gln Pro Gly Ile Thr Ala Asp Asn Lys Asp Leu Gln Ala Leu
            100                 105                 110
Ile Thr Pro Trp Leu Asn Arg Ser Leu Thr Phe Asn Asp Leu Gln Ala
            115                 120                 125
Met Thr Phe Ala Val Thr Arg Phe Tyr Arg Lys Lys Gly Trp Val Ala
            130                 135                 140
Ala Gln Ala Ile Leu Pro Pro Gln Thr Ile Arg Asp Gly Ile Ile Val
145                 150                 155                 160
Val Arg Val Ile Ala Gly Arg Leu Asp Lys Pro Gln Ile Asn Asn Gln
                165                 170                 175
Ser Ser Leu Asn Ser His Phe Ile Thr Thr Val Ile Glu Ser Asn Ser
            180                 185                 190
Cys Ser Lys Lys Asn Gly Ile Phe Gly Asp Lys Asp Cys Ala Ala Ser
            195                 200                 205
Pro Val Glu Leu Ser Arg Leu Glu Arg Thr Ala Leu Ile Leu Asn Glu
            210                 215                 220
Ile Pro Gly Val Glu Ala Ser Leu Ala Leu Lys Pro Gly Thr Gln Ser
225                 230                 235                 240
Gly Met Thr Arg Ile Tyr Ala Asp Val Thr Pro Gly Lys Lys Met Met
                245                 250                 255
Ala Tyr Leu Ala Ala Asp Asn Gln Gly Asn Asp Tyr Ser Gly His Asn
            260                 265                 270
Arg Leu Leu Thr Gly Gly Val Leu Asn Asn Leu Thr Gly Trp Gly Asp
            275                 280                 285
Gln Leu Arg Ala Asp Leu Ile Leu Ser Ser Ser Ala Asp Val Phe Asn
            290                 295                 300
Gly Leu Leu Asp Tyr Asn Phe Pro Ile Asn Ser Tyr Gly Thr Arg Ala
305                 310                 315                 320
Ala Leu Asn Tyr Ser Tyr Leu Asp Tyr Thr Leu Thr Gly Pro Phe Ser
                325                 330                 335
Val Leu Asp Ala Arg Gly His Ser Thr Thr Trp Gly Ile Asn Leu Arg
            340                 345                 350
His Pro Trp Ile Arg Thr Ser Ala Ala Arg Ile Asp Val Asn Ala Gly
            355                 360                 365
Tyr Tyr Gln Ala Arg Met Arg Asp Ala Leu Ile Leu Leu Pro Glu Gln
            370                 375                 380
Lys Arg Asn Leu Asn Ala Gly Glu Phe Gly Ile Ser Gly Thr Phe Thr
385                 390                 395                 400
Ala Leu Pro Arg Gly Leu Ser Asn Phe Asn Leu Leu Gly Thr Ala Gly
                405                 410                 415
Asp Leu Ala Leu Asp Asp Glu Tyr Ser Gln Ser Ile Asn Thr Leu Thr
            420                 425                 430
His Val Ser Gly Asn Phe Ser Arg Phe Asn Tyr Arg Val Gly His Asp
            435                 440                 445
Gln Gly Ile Gly Ser His Val Ser Phe Phe Asn Gln Phe Thr Gly Gln
            450                 455                 460
Met Ala Ser Lys Asn Leu Asp Ser Ser Gln Lys Leu Leu Leu Gly Gly
465                 470                 475                 480
Pro Leu Ala Val Arg Ala Tyr Gly Ile Gly Asp Gly Ser Val Asp Lys
                485                 490                 495
Gly Thr Ile Phe Thr Thr Glu Leu Arg Thr Arg Trp Gln Pro Asp Phe
```

```
            500                 505                 510
Pro Asp Trp Ala Gly Tyr Gly His Gln Ile Thr Val Ala Ala Phe Phe
        515                 520                 525

Asp Gln Gly Trp Gly Ala Tyr Tyr Arg Gln Pro Ile Val Gly Leu Ser
        530                 535                 540

Glu Asn Asn Ile Asn Ile Ser Gly Phe Gly Ser Tyr Ile Thr Phe Ala
545                 550                 555                 560

Arg Pro Ala Asp Tyr Phe Leu Asn Leu Thr Trp Ala His Arg Thr Gly
                565                 570                 575

Gln Ala Val Thr Arg His Gln Asp Asn Asp Gln Leu Trp Leu Ser Ala
            580                 585                 590

Tyr Lys Met Phe
            595
```

<210> SEQ ID NO 59
<211> LENGTH: 180
<212> TYPE: PRT
<213> ORGANISM: Yersinia pestis

<400> SEQUENCE: 59

```
Met Ile Val Tyr Leu His Gly Phe Asp Ser Asn Ser Pro Gly Asn His
1               5                   10                  15

Glu Lys Val Leu Gln Leu Gln Phe Ile Asp Pro Asp Val Arg Phe Ile
            20                  25                  30

Ser Tyr Ser Thr Leu His Pro Arg His Asp Met Gln Tyr Leu Leu Lys
        35                  40                  45

Glu Val Asp Lys Ala Ile Gln Gln Gly Gly Asp Glu Lys Ser Leu Ile
    50                  55                  60

Cys Gly Val Gly Leu Gly Gly Phe Trp Ala Glu Arg Ile Gly Phe Leu
65                  70                  75                  80

Cys Gly Ile Arg Gln Val Ala Phe Asn Pro Asn Leu Tyr Pro Gln Glu
                85                  90                  95

Asn Met Ser Gly Lys Ile Asp Arg Pro Glu Glu Tyr Ile Asp Ile Ala
            100                 105                 110

Ser Lys Cys Ile Asp Gly Phe Arg Glu Lys Asn Arg Asp Arg Cys Leu
        115                 120                 125

Val Val Leu Ser Arg His Asp Glu Met Leu Asp Ser Gln Arg Thr Ala
    130                 135                 140

Gly Asp Leu His Pro Tyr Tyr Glu Ile Val Trp Asp Lys Gln Asn
145                 150                 155                 160

His Lys Phe Lys Asp Leu Ser Pro His Leu Gln Arg Ile Lys Ala Phe
                165                 170                 175

Lys Thr Leu Gly
            180
```

<210> SEQ ID NO 60
<211> LENGTH: 110
<212> TYPE: PRT
<213> ORGANISM: Yersinia pestis

<400> SEQUENCE: 60

```
Met Lys Pro Thr Gln Gln Leu Lys Pro Leu Thr Met Ala Thr Thr Met
1               5                   10                  15

Leu Ser Asp Lys Leu Tyr Glu Leu Met Asp Lys Gly Pro Leu Arg Ala
            20                  25                  30

Leu Ser Leu Val Leu Ala Phe Ala Leu Ala Phe Cys Val Phe Trp Asp
```

```
                35                  40                  45
Pro Thr Arg Phe Ala Ala Thr Ser Ser Leu Glu Val Trp Gln Glu
 50                  55                  60

Val Phe Ile Val Trp Ala Val Cys Thr Gly Val Ile His Gly Val Gly
 65                  70                  75                  80

Phe Arg Pro Lys Gln Val Trp Leu Arg Ala Phe Phe Ala Pro Leu Pro
                 85                  90                  95

Ala Ile Val Ile Leu Ala Thr Gly Leu Phe Tyr Phe Phe Ala
            100                 105                 110

<210> SEQ ID NO 61
<211> LENGTH: 133
<212> TYPE: PRT
<213> ORGANISM: Yersinia pestis

<400> SEQUENCE: 61

Met Ser Asn Thr Leu Phe Arg Trp Pro Val Arg Val Tyr Phe Glu Asp
 1               5                  10                  15

Thr Asp Ala Gly Gly Met Val Tyr His Ala Arg Tyr Val Ala Phe Tyr
                20                  25                  30

Glu Arg Ala Arg Thr Glu Met Leu Arg Gln Arg Asn Phe His Gln Gln
            35                  40                  45

Gln Leu Leu Ser Glu His Val Ala Phe Ala Val Arg Ser Met Thr Val
 50                  55                  60

Glu Tyr Leu Ala Pro Ala Arg Leu Asp Asp Met Leu Glu Val Gln Ser
 65                  70                  75                  80

Glu Val Thr Ala Met Arg Gly Ala Ser Leu Thr Phe Ala Gln Arg Ile
                85                  90                  95

Leu Asp Ser His Gly Asn Leu Leu Ser Ser Ala Glu Val Leu Ile Ala
            100                 105                 110

Cys Ile Asp Pro His Gln Met Lys Pro Arg Ala Leu Pro Lys Ser Ile
        115                 120                 125

Val Ala Glu Phe Lys
    130

<210> SEQ ID NO 62
<211> LENGTH: 183
<212> TYPE: PRT
<213> ORGANISM: Yersinia pestis

<400> SEQUENCE: 62

Met Lys Asn Lys Thr Thr Leu Ala Ala Phe Ile Thr Ala Ile Leu Leu
 1               5                  10                  15

Ser Ser Ser Ala Ala Tyr Ala Ala Gly Asp Arg Thr Ile Ser Leu Gly
                20                  25                  30

Tyr Ala Gln Gly Asp Val Arg Leu Gly Asp Gly Asn Arg Lys Asp Ile
            35                  40                  45

Arg Leu Asp Asp Asp Leu Lys Gly Ile Asn Val Lys Tyr Leu His Lys
 50                  55                  60

Leu Ser Glu Met Phe Gly Ala Ile Gly Ser Phe Thr Tyr Thr Asp Leu
 65                  70                  75                  80

Asn Tyr Asp Tyr Leu Asn Asn Val Lys Ile Gly Asp Ala Ser Phe
                85                  90                  95

Asp Tyr Tyr Ser Leu Met Val Gly Pro Ser Val His Phe Asn Glu Phe
            100                 105                 110

Phe Ser Met Tyr Ala Leu Leu Gly Ile Gly His Gly Asn Ala Lys Ala
```

```
              115                 120                 125
Ser Val Leu Gly Tyr Gly Lys Lys Glu Glu Gln Asp Ser Leu Ala Tyr
    130                 135                 140

Gly Val Gly Met Gln Phe Asn Pro Leu Asn Asn Ile Ala Ile Asp Ala
145                 150                 155                 160

Ser Tyr Glu Tyr Thr Lys Leu Lys Asp Ala Asn Ile Gly Thr Trp Val
                165                 170                 175

Leu Gly Ile Gly Tyr Arg Phe
                180
```

LIVE-ATTENUATED VACCINE AGAINST PLAGUE

CROSS-REFERENCE TO RELATED APPLICATIONS

This application claims the benefit of U.S. Provisional Application Ser. No. 62/103,432, filed Jan. 14, 2015, and 62/121,760, filed Feb. 27, 2015, each of which is incorporated by reference herein.

GOVERNMENT FUNDING

This invention was made with government support under AI064389 and AI071634, awarded by the National Institutes of Health. The government has certain rights in the invention.

SEQUENCE LISTING

This application contains a Sequence Listing electronically submitted via EFS-Web to the U.S. Patent and Trademark Office as an ASCII text file entitled "265-00890101-2nd-SubstSequence Listing ST25" having a size of 50 kilobytes and created on Aug. 7, 2018. The information contained in the Sequence Listing is incorporated by reference herein.

SUMMARY OF THE APPLICATION

Provided herein are genetically modified *Y. pestis*. In one embodiment, a genetically modified *Y. pestis* includes three alterations compared to a control *Y. pestis*. The first alteration includes decreased mRNA, decreased protein, or a combination thereof, encoded by a lpp coding region. The second alteration includes decreased mRNA, decreased protein, or a combination thereof, encoded by a msbB coding region. The third alteration is selected from an alteration of an intergenic region and decreased mRNA, decreased protein, or a combination thereof, encoded by a coding region. The alteration of an intergenic region includes the intergenic region between the coding regions ypo1119 and ypo1120. The decreased mRNA, protein, or a combination thereof, is encoded by a coding region selected from pla, ypo1717, ypmt1.80c, rbsA (ypo2500), ypo0498, vasK (ypo3603), ypo3164, hxuB (ypo3248), ypo1616, ypo1119, ypo1120, and ail.

In one embodiment, the genetically modified *Y. pestis* includes decreased mRNA, decreased protein, or a combination thereof, encoded by the coding regions lpp, msbB, and ail. In one embodiment, the genetically modified *Y. pestis* includes decreased mRNA, decreased protein, or a combination thereof, encoded by the coding regions lpp, msbB, and rbsA (ypo2500). In one embodiment, the genetically modified *Y. pestis* includes decreased mRNA, decreased protein, or a combination thereof, encoded by the coding regions lpp, msbB, and vasK (ypo3603). In one embodiment, the genetically modified *Y. pestis* includes decreased mRNA, decreased protein, or a combination thereof, encoded by the coding regions lpp and msbB, and an alteration of the intergenic region between the coding regions ypo1119 and ypo1120.

In one embodiment, the decreased mRNA or decreased protein is a decrease of at least 0.1% compared to the mRNA or the protein in the control *Y. pestis*. In one embodiment, the mRNA or the protein encoded by the one or more of the altered coding regions is undetectable in the genetically modified *Y. pestis*.

In one embodiment, an alteration includes a mutation in a coding region selected from lpp, msbB, pla, ypo1717, ypmt1.80c, rbsA (ypo2500), ypo0498, vasK (ypo3603), ypo3164, hxuB (ypo3248), ypo1616, ypo1119, ypo1120, and ail. In one embodiment, the mutation includes a deletion of at least one nucleotide. In one embodiment, the mutation includes a deletion of a portion of the coding region, or a deletion of the entire coding region.

Also provided is a composition that includes a genetically modified *Y. pestis* described herein and a pharmaceutically acceptable carrier. In one embodiment, composition is formulated for intramuscular administration. In one embodiment, composition is formulated for intranasal administration.

Further provided are methods for using the genetically modified *Y. pestis* described herein. In one embodiment, a method includes administering to a subject an effective amount of a composition that includes a genetically modified *Y. pestis* described herein, wherein the subject has an immune response to the genetically modified *Y. pestis*. The immune response can include a humoral immune response, a cell-mediated immune response, or a combination thereof. In one embodiment, the immune response is protective against bubonic plague. In one embodiment, the immune response is protective against septicemic plague. In one embodiment, the immune response is protective against pneumonic plague. In one embodiment, the immune response is protective against bubonic plague and pneumonic plague.

In one embodiment, the subject has or is at risk of having plague. The plague can be bubonic, septicemic, pneumonic, or a combination thereof. The subject can be, for instance, a human or a laboratory animal such as a mouse, a rat, or a non-human primate. In one embodiment, the method also includes administration of an antibiotic.

As used herein, "genetically modified" refers to a *Yersinia pestis* that has been altered through human intervention. In one embodiment, the human intervention may be the introduction of an exogenous polynucleotide into a *Y. pestis*. An example of an exogenous polynucleotide includes a polynucleotide that is inserted in the genome, such as a transposon (for instance by transposition) or a plasmid (for instance by homologous recombination). The genome of a *Y. pestis* includes chromosomal DNA and the DNA of any plasmid present in a *Y. pestis*, such as pCD1, pPCP1, and pMT1. "Genetically modified" also refers to a *Y. pestis* that has been genetically manipulated such that one or more endogenous nucleotides have been altered. For example, a microbe is a genetically modified microbe by virtue of introduction into a suitable microbe of an alteration of endogenous nucleotides. For instance, an endogenous coding region could include a mutation. Such a mutation may result in a protein having a different amino acid sequence than was encoded by the endogenous polynucleotide. Such a protein may have reduced biological activity, including no detectable biological activity. An example of a mutation resulting in no detectable biological activity is a deletion. Another example of a genetically modified *Y. pestis* is one having an altered regulatory sequence, such as a promoter, to result in increased or decreased expression of an operably linked endogenous coding region.

As used herein, "sequence similarity" refers to the amount of identity between a nucleotide sequence described herein and a second candidate nucleotide sequence. Whether a polynucleotide has sequence similarity with a polynucleotide described herein can be determined by aligning the residues of the two polynucleotides (for example, a candidate polynucleotide and any appropriate reference polynucleotide described herein, e.g., the lpp coding region of CO92) to optimize the number of identical nucleotides along the lengths of their sequences; gaps in either or both sequences are permitted in making the alignment in order to optimize the number of identical nucleotides, although the nucleotides in each sequence must nonetheless remain in their proper order. A reference polynucleotide may be a polynucleotide described herein. A candidate polynucleotide is the polynucleotide being compared to the reference polynucleotide. A candidate polynucleotide may be isolated, for example, from a plant, or can be produced using recombinant techniques, or chemically or enzymatically synthesized. A candidate polynucleotide may be present in the genome of a plant and predicted to encode a protein useful herein.

A pair-wise comparison analysis of nucleotide sequences can be carried out using the Blastn program of the BLAST search algorithm, available through the World Wide Web, for instance at the internet site maintained by the National Center for Biotechnology Information, National Institutes of Health. Preferably, the default values for all Blastn search parameters are used. Alternatively, sequence similarity may be determined, for example, using sequence techniques such as GCG FastA (Genetics Computer Group, Madison, Wis.), MacVector 4.5 (Kodak/IBI software package) or other suitable sequencing programs or methods known in the art.

Thus, as used herein, a candidate polynucleotide useful herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% nucleotide sequence identity to a reference nucleotide sequence.

As used herein, "structural similarity" refers to the amount of identity or similarity between an amino acid sequence described herein and a second amino acid sequence. Whether a protein is structurally similar to a protein described here can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. In one embodiment a reference protein is a protein described herein. A candidate protein is the protein being compared to the reference protein. A candidate protein can be isolated, for example, from a plant, or can be produced using recombinant techniques, or chemically or enzymatically synthesized.

Unless modified as otherwise described herein, a pair-wise comparison analysis of amino acid sequences can be carried out using the Blastp program of the Blastp suite-2sequences search algorithm, as described by Tatusova et al., (*FEMS Microbiol Lett,* 174, 247-250 (1999)), and available on the National Center for Biotechnology Information (NCBI) website. The default values for all blastp suite-2sequences search parameters may be used, including general parameters: expect threshold=10, word size=3, short queries=on; scoring parameters: matrix=BLOSUM62, gap costs=existence: 11 extension: 1, compositional adjustments=conditional compositional score matrix adjustment. Alternatively, proteins may be compared using other commercially available algorithms, such as the BESTFIT algorithm in the GCG package (version 10.2, Madison Wis.).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions.

Thus, as used herein, reference to an amino acid sequence disclosed herein can include a protein with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

Alternatively, as used herein, reference to an amino acid sequence disclosed herein can include a protein with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. Ail and Lpp production and transmission electron microscopy analysis. (A) *Y. pestis* cultures grown overnight (at 37° C.) were collected, and the production of Ail and Lpp in the whole-cell lysates was analyzed by immunoblotting using antibodies to Ail and Lpp. Anti-DnaK antibodies were used as a loading control for Western blots. (B) WT CO92 and its Δlpp ΔmsbB Δail triple mutant were grown to the exponential growth phase at 28° C. and subjected to transmission electron microscopy analysis. o, bacterial outer membrane; i, bacterial inner membrane; p, periplasmic space. Bar=0.5 μm.

FIG. 4. Survival analysis and antibody responses of mice infected with WT *Y. pestis* strain CO92 and its mutant strains in a pneumonic plague model. Female Swiss Webster mice (10 per group) were challenged with 1.3×10$^4$ CFU of WT *Y. pestis* strain CO92 or its various mutants by the i.n. route. (A) Survival of mice was plotted and analyzed by Kaplan-Meier survival estimates. Statistically significant P values for comparisons of various mutant- and WT CO92-infected mice are indicated under each curve. (B) Mice were bled at 14 days p.i., and the total IgG responses to F1-V antigen were determined by an ELISA. The arithmetic means±standard deviations are plotted. ** indicates statistical significance (P<0.001) compared to preimmune serum.

FIG. 6. Survival analysis and subsequent protection conferred by high doses of the Δlpp ΔmsbB Δail triple mutant of *Y. pestis* CO92 in a pneumonic plague mouse model. (A) Female Swiss Webster mice (5 to 10 per group) were infected with various doses of the Δlpp ΔmsbB Δail triple mutant or 1.3×10$^4$ CFU of WT *Y. pestis* CO92 by the i.n. route. Surviving mice with age-matched naive animals were then rechallenged on day 24 p.i. with 1.4×10$^4$ CFU of the WT CO92 luc2 strain. Statistically significant P values are for comparisons to the WT CO92-infected mice in the initial challenge or to naive control mice during the WT CO92 luc2 rechallenge. (B) Total IgG responses to the F1-V antigen or whole bacteria were examined in sera at day 14 after initial infection. The titers of antibody isotypes to F1-V antigen were further delineated by using isotype-specific secondary antibodies. *** indicates statistical significance (P<0.0001) compared to preimmune serum. (C) Animals were imaged on day 3 and/or day 7 after rechallenge for bioluminescence. The bioluminescence scale is shown on the right and ranges from most intense (red) to least intense (violet).

Figure 9:
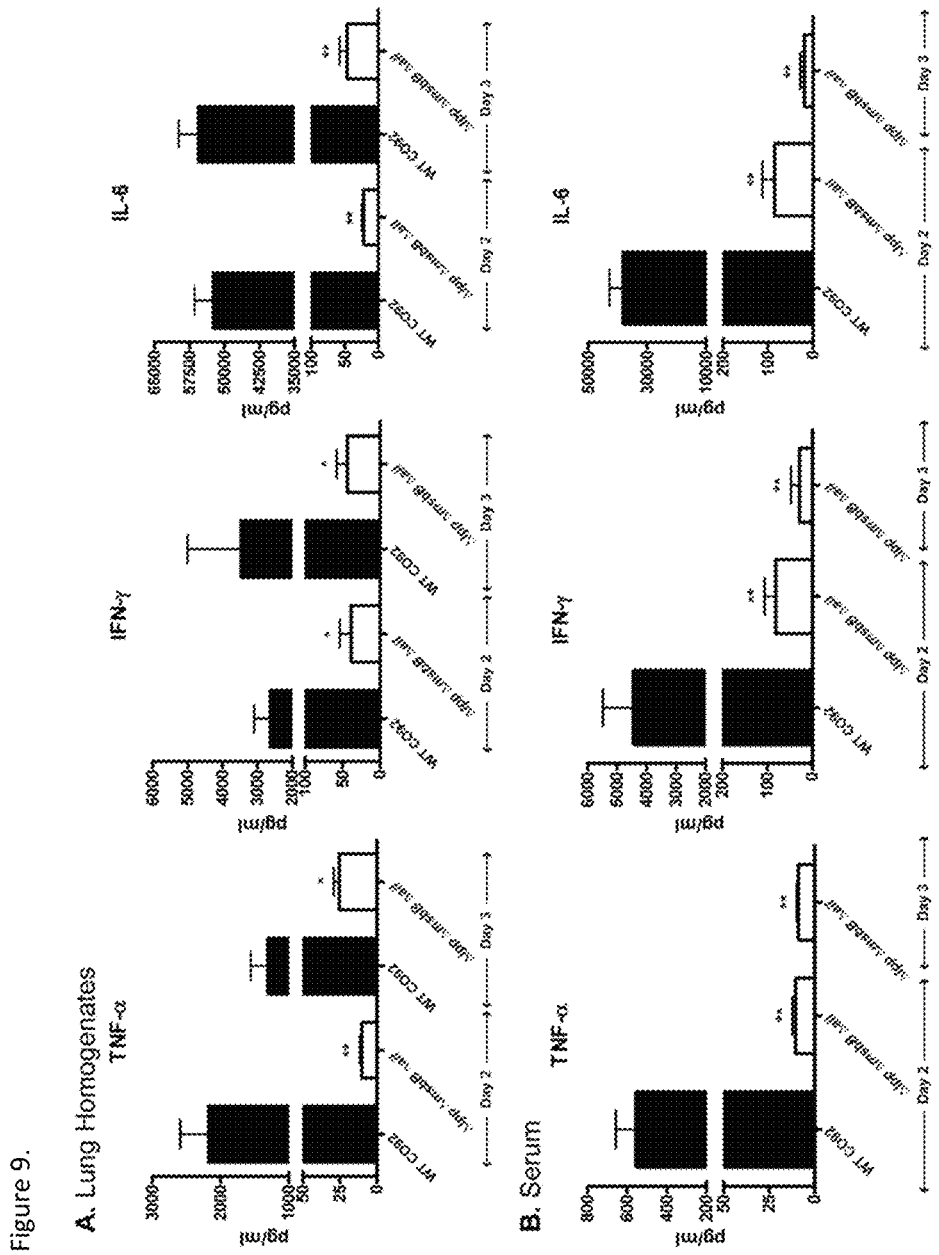

FIG. 9. Cytokine/chemokine analysis of sera (B) and lung homogenates (A) of mice in a pneumonic plague mouse model. Mice were challenged with $2.5 \times 10^6$ CFU of WT *Y. pestis* CO92 or its Δlpp ΔmsbB Δail triple mutant by the i.n. route. At 2 and 3 days p.i., 5 mice from each group (at each time point) were euthanized. The lungs were harvested and homogenized, and blood was collected via cardiac puncture. The production of various cytokines/chemokines was measured by using a multiplex assay. Only the cytokines/chemokines showing statistically significant differences in mutant-compared to WT CO92-infected mice are plotted as arithmetic means±standard deviations. * and ** indicate statistical significance ($P<0.01$ and $P<0.001$, respectively) compared to WT CO92 on each day.

Figure 10:
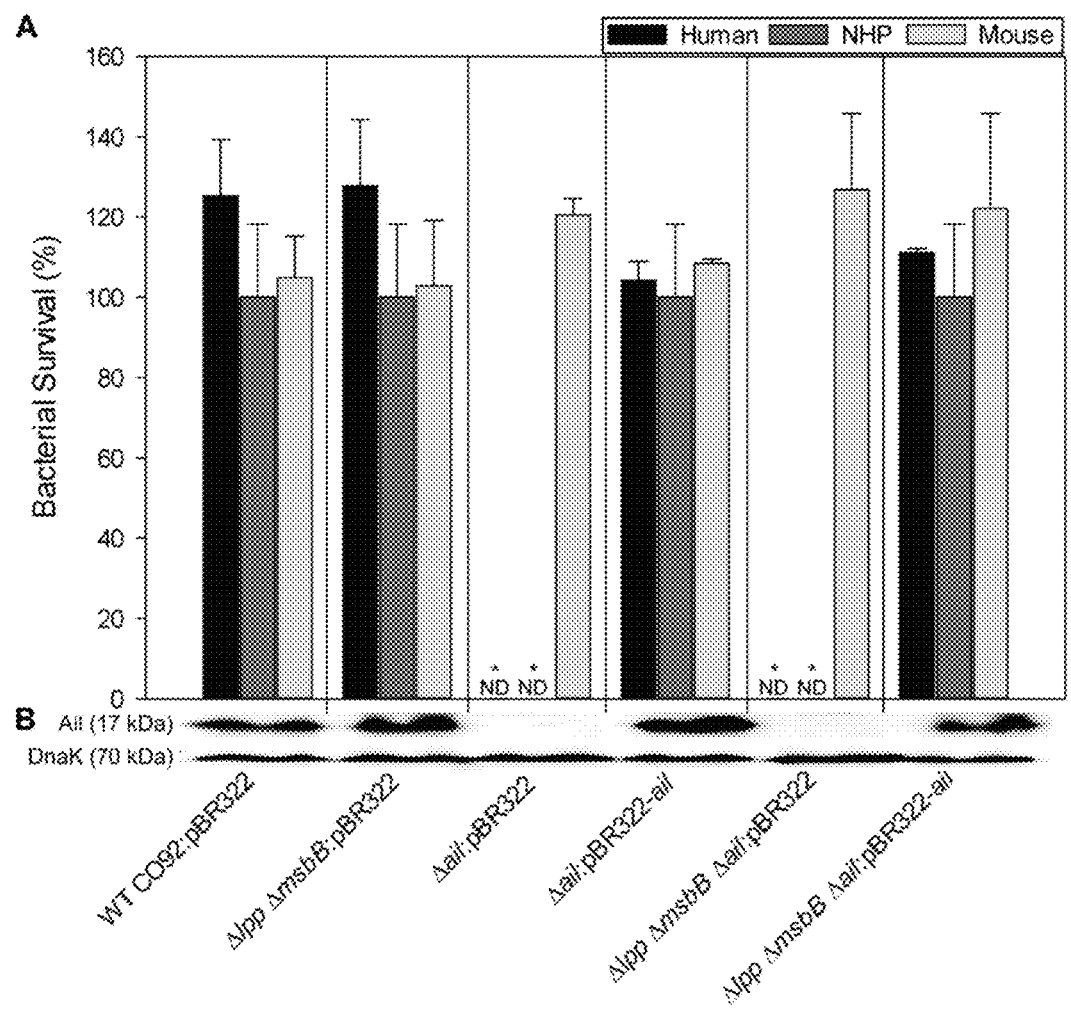

FIG. 10. Serum resistance and Ail production by various *Y. pestis* CO92 strains. Various *Y. pestis* strains (~$5 \times 10^6$ CFU) grown overnight were mixed with either unheated or heated sera from human, NHP, and mouse. (A) After incubation for 2 h at 37° C., the number of surviving bacteria (CFU) in each sample was determined. * indicates statistical significance ($P<0.01$) compared to WT CO92 for each type of serum. ND, not detectable. (B) The levels of Ail protein and DnaK in these strains were analyzed by immunoblotting using specific antibodies to Ail and DnaK.

Figure 11:
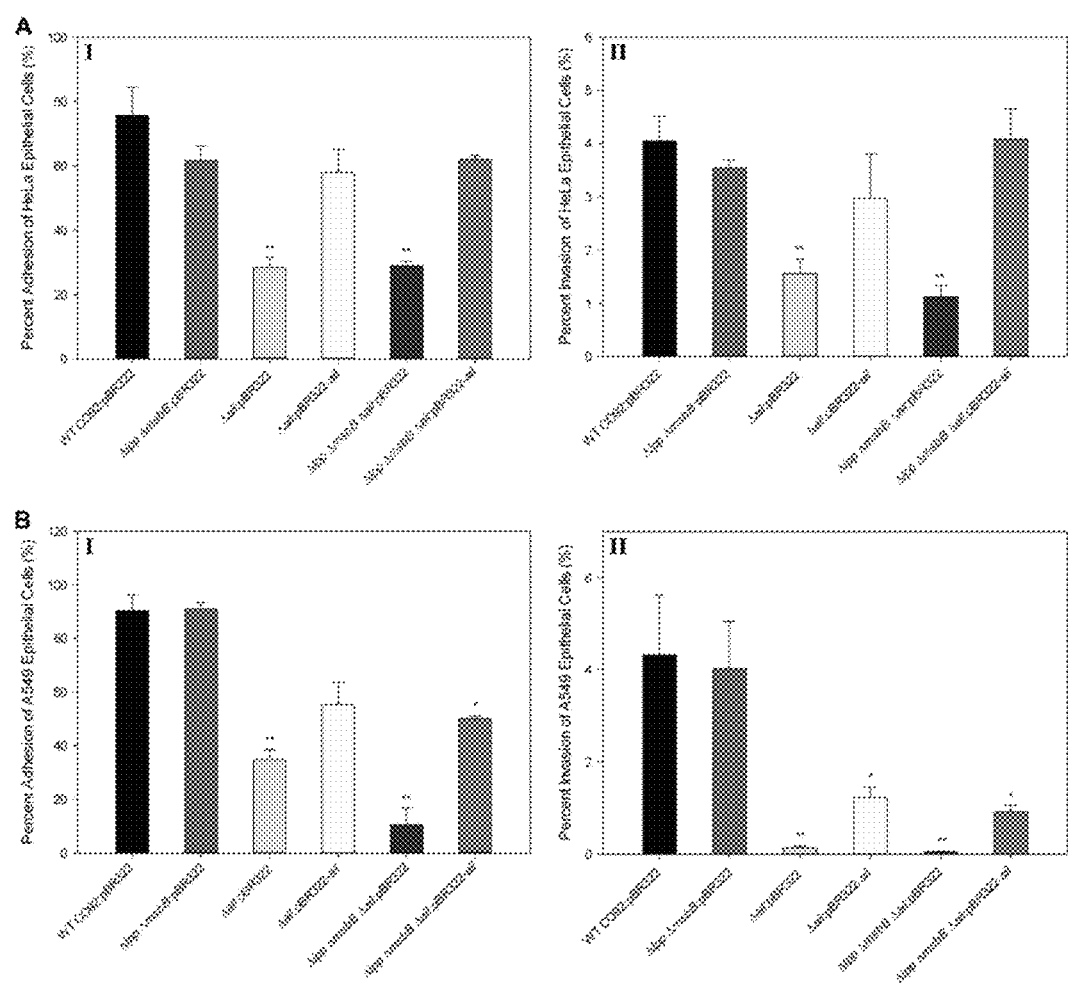

FIG. 11. Adherence and invasion of WT *Y. pestis* CO92 and its mutant strains. HeLa cells (A) and A549 cells (B) were infected with various *Y. pestis* CO92 strains at an MOI of 100 at 37° C. for 2 h. The percentages of adherent (I) and invading (II) bacteria compared to the total number of bacteria used to infect epithelial cells were calculated. The arithmetic means±standard deviations are plotted. * and ** indicate statistical significance ($P<0.05$ and $P<0.001$, respectively) compared to both WT CO92 and the Δlpp ΔmsbB mutant.

Figure 12:
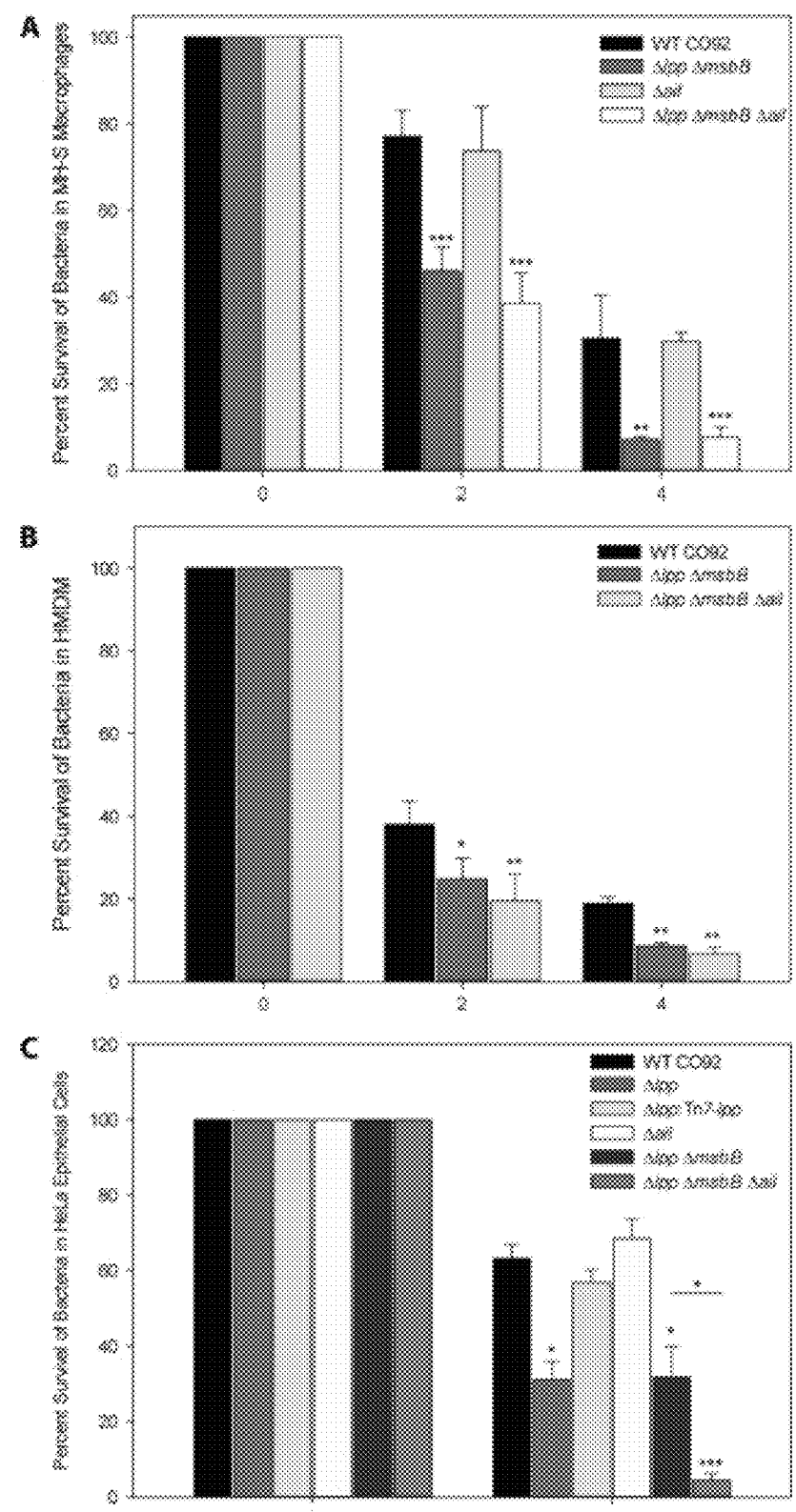
Figure 12:
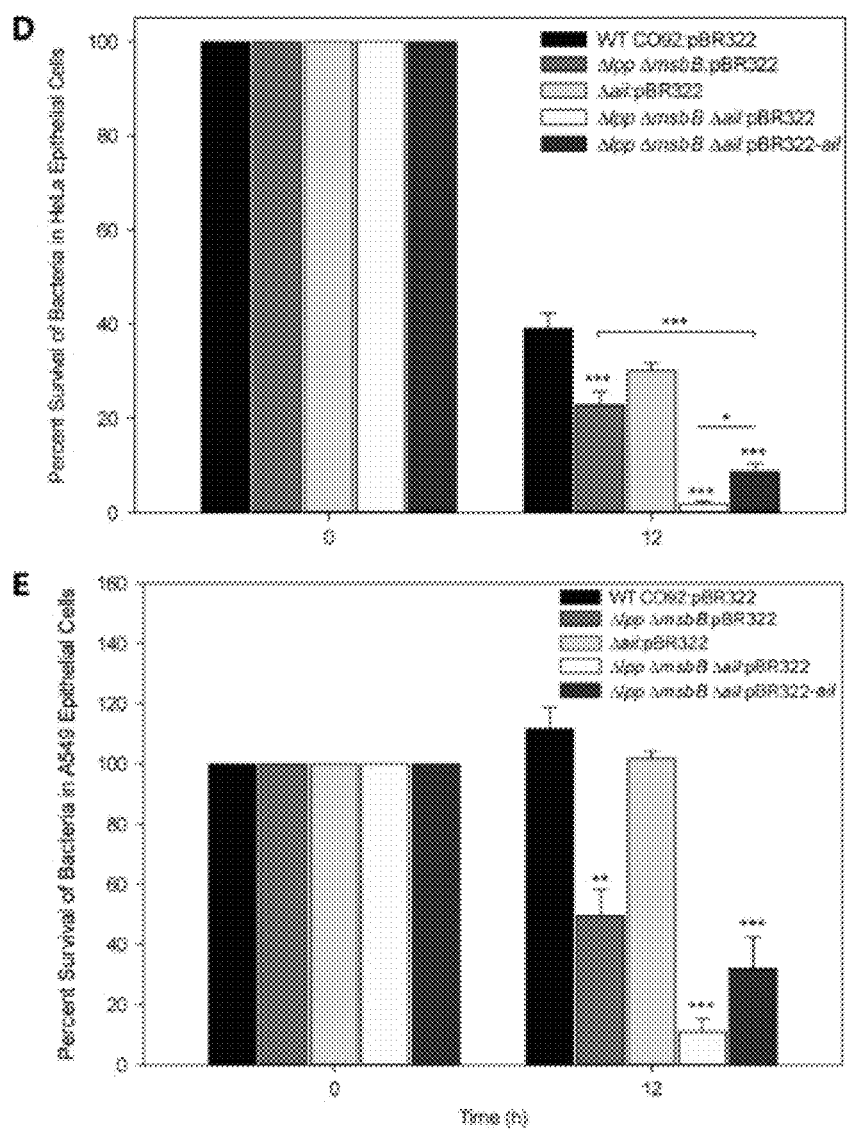

FIG. 12. Intracellular survival of various *Y. pestis* CO92 mutant strains in epithelial cells and macrophages. Murine MH-S macrophages (A), human monocyte-derived macrophages (HMDM) (B), HeLa epithelial cells (C and D), and human A549 alveolar epithelial cells (E) were infected with various *Y. pestis* CO92 strains at MOIs of 10, 1, 100, and 100, respectively. After 45 to 60 min of incubation at 37° C. and following an hour of gentamicin treatment, the cells were harvested at 2 and 4 h post-gentamicin treatment for macrophages and at 12 h for epithelial cells. The number of bacteria surviving intracellularly was assessed, and percent survival was calculated. *, , and * indicate statistical significance ($P<0.05$, $P<0.005$, and $P<0.001$, respectively) compared to WT CO92 at each time point or between two tested strains, as indicated by the horizontal bars.

FIG. 13. Inflammatory cytokine production by macrophages infected with various *Y. pestis* CO92 strains. Murine alveolar macrophages (A) and human monocyte-derived macrophages (B) were infected with various *Y. pestis* strains. Supernatants from infected macrophages were collected at 0, 2, or 4 h after gentamicin treatment. The levels of various cytokines in the supernatants were measured by using a multiplex assay. Only the cytokines/chemokines showing statistically significant differences compared to WT CO92-infected macrophages are plotted as arithmetic means±standard deviations. *, , and * indicate statistical significance ($P<0.05$, $P<0.01$, and $P<0.0001$, respectively) compared to WT CO92 on each day.

Figure 14:
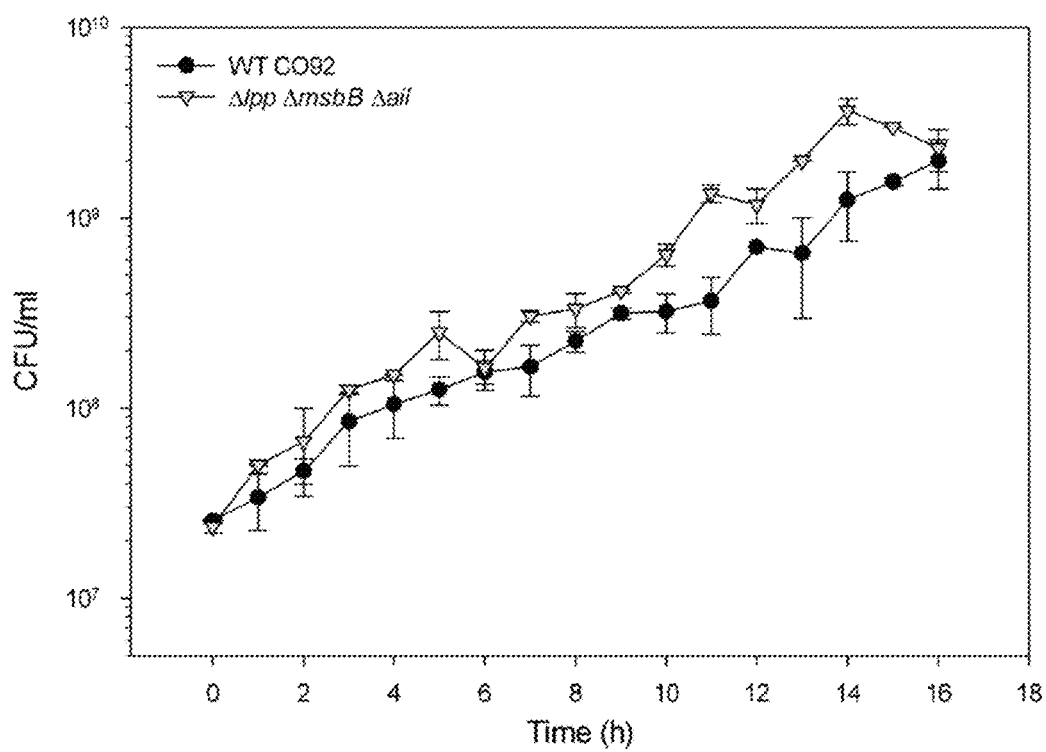

FIG. 14. Growth curve of WT *Y. pestis* CO92 and its Δlpp ΔmsbB Δail triple mutant. The organisms were grown at 28° C. in HIB medium and the samples taken at 1- to 2-h intervals until the cultures reached their saturation phases. The CFU were determined by plating on SBA plates for 48 h at 28° C. The error bars represent means±standard deviations.

Figure 15:
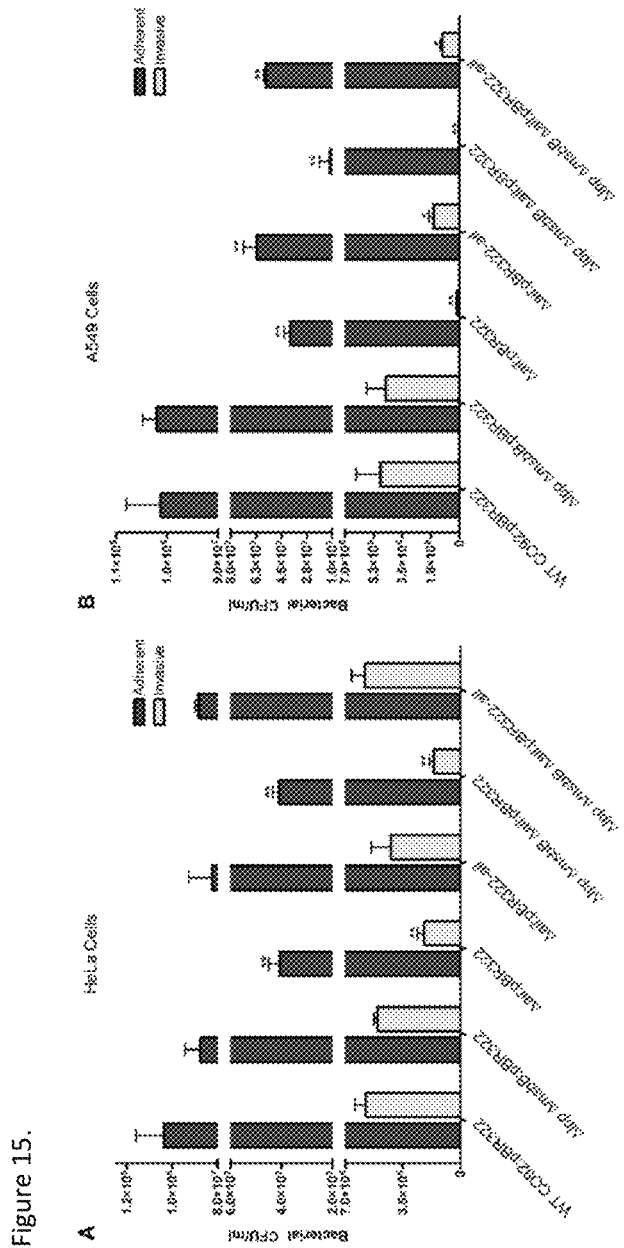

FIG. 15. Adherence and invasion of WT *Y. pestis* CO92 and its mutant strains. HeLa cells (A) and A549 (B) were infected at an MOI of 100 with various *Y. pestis* CO92 strains at 37° C. for 2 h. The total CFU of adherent and invasive bacteria is presented. The arithmetic means±standard deviations are plotted. "*" and "**" indicate statistical significance with $p<0.05$ and $p<0.001$, respectively, compared to both WT CO92 and the Δlpp ΔmsbB double mutant.

Figure 16:
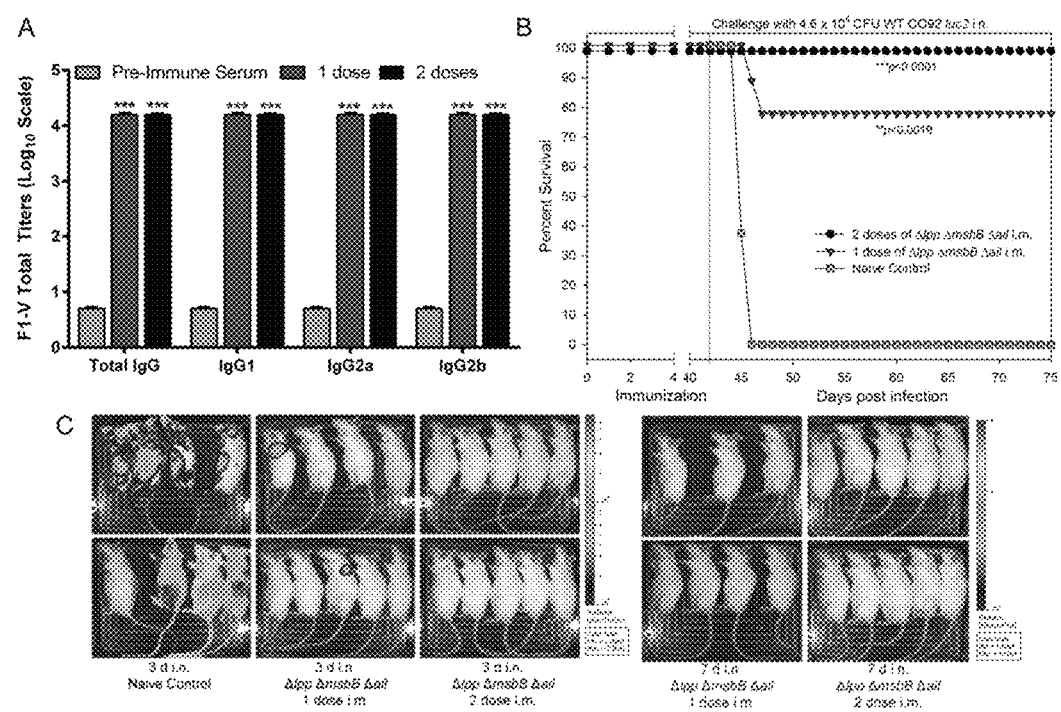

FIG. 16. Immunity conferred by the Δlpp ΔmsbB Δail triple mutant to mice via intramuscular immunization. (A) Mice (n=8-10 per group) were i.m. immunized with 1 or 2 doses of $2 \times 10^6$ CFU/100 μL of the Δlpp ΔmsbB Δail triple mutant on day 0 and/or on day 21. Mice were bled 14 days post-last immunization and an ELISA was performed to examine the antibody IgG titers and their isotypes to the F1-V antigen. P values shown are based on one-way ANOVA with a Bonferroni correction. ***$p<0.0001$ compared to their corresponding preimmune sera. (B) The above immunized mice were challenged intranasally on day 42 with $4.6 \times 10^4$ CFU (92 $LD_{50}$; 1 $LD_{50}$=~500 CFU) of the WT *Y. pestis* CO92 luc2 strain. Naive control: infected naïve mice. The P values are in comparison to naive control and are based on Kaplan-Meier Curve Analysis. (C). The exposed mice were imaged on days 3 and 7 post challenge for bioluminescence and the scale within the figure ranged from most intense (red) to least intense (violet).

Figure 17:
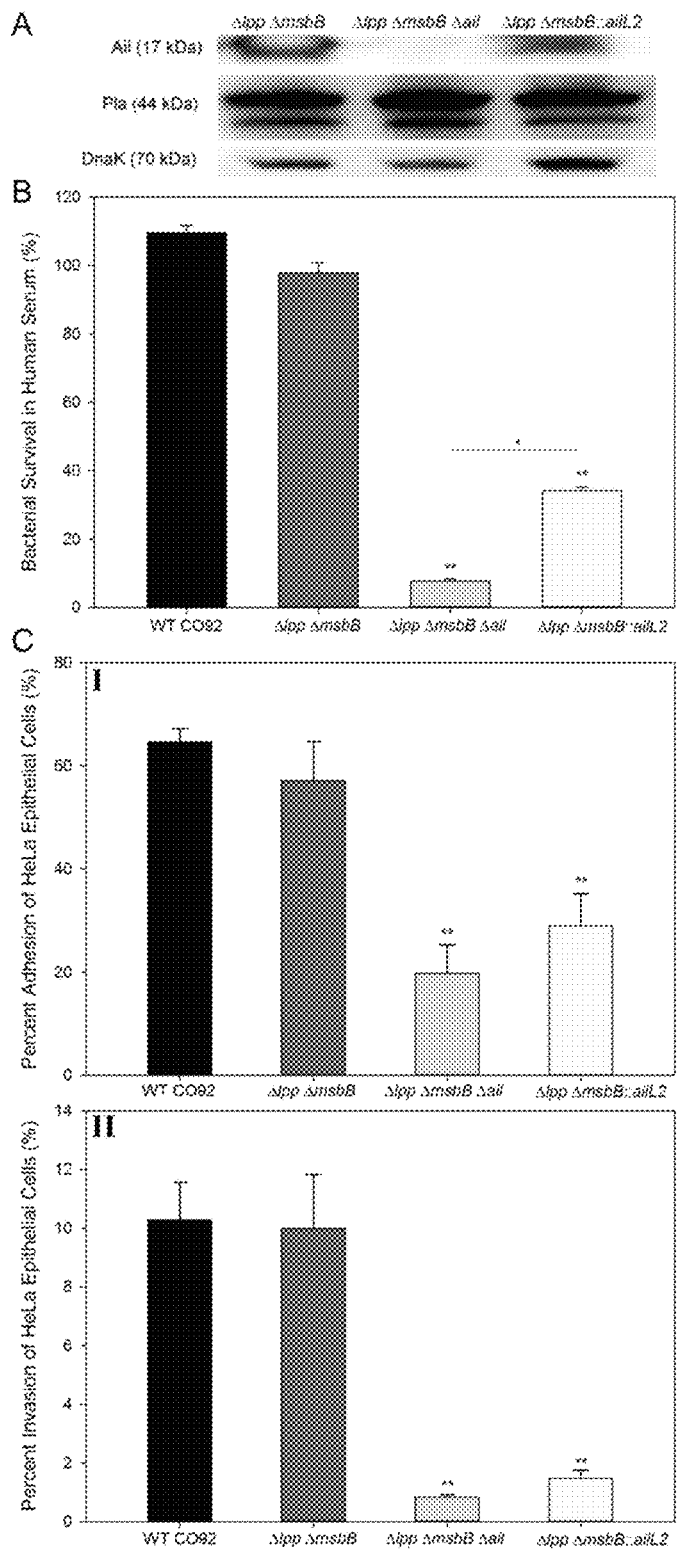

FIG. 17. Ail associated virulence activities in the Δlpp ΔmsbB::ailL2 mutant. (A) Overnight 28° C. grown *Y. pestis* cultures were collected and analyzed by immunoblotting using antibodies to Ail and Pla, respectively. Anti-DnaK antibodies were used as a loading control for the Western blots. (B) Various *Y. pestis* strains were incubated separately with the normal and heat-inactivated human sera at 37° C. for 2 h. The percent bacterial survival in normal serum over the heat-inactivated serum was plotted. P values shown are based on one-way ANOVA. **$p<0.005$ as compared to WT CO92 and the Δlpp ΔmsbB double mutant. Horizontal line with "*" indicates statistical significance ($p<0.05$) between the two indicated groups. (C). HeLa cells were infected at an MOI of 100 with various *Y. pestis* strains. After 2 h of incubation, the host cells were gently washed and the adherent bacteria were collected, and percent adhesion (I) was calculated. In another set of wells, gentamicin protection assay was followed and the percent of invasive bacteria (II) was calculated. P values shown are based on one-way ANOVA. **$p<0.001$ compared to both WT CO92 and the Δlpp ΔmsbB mutant. The arithmetic means±standard deviations are plotted.

Figure 18:
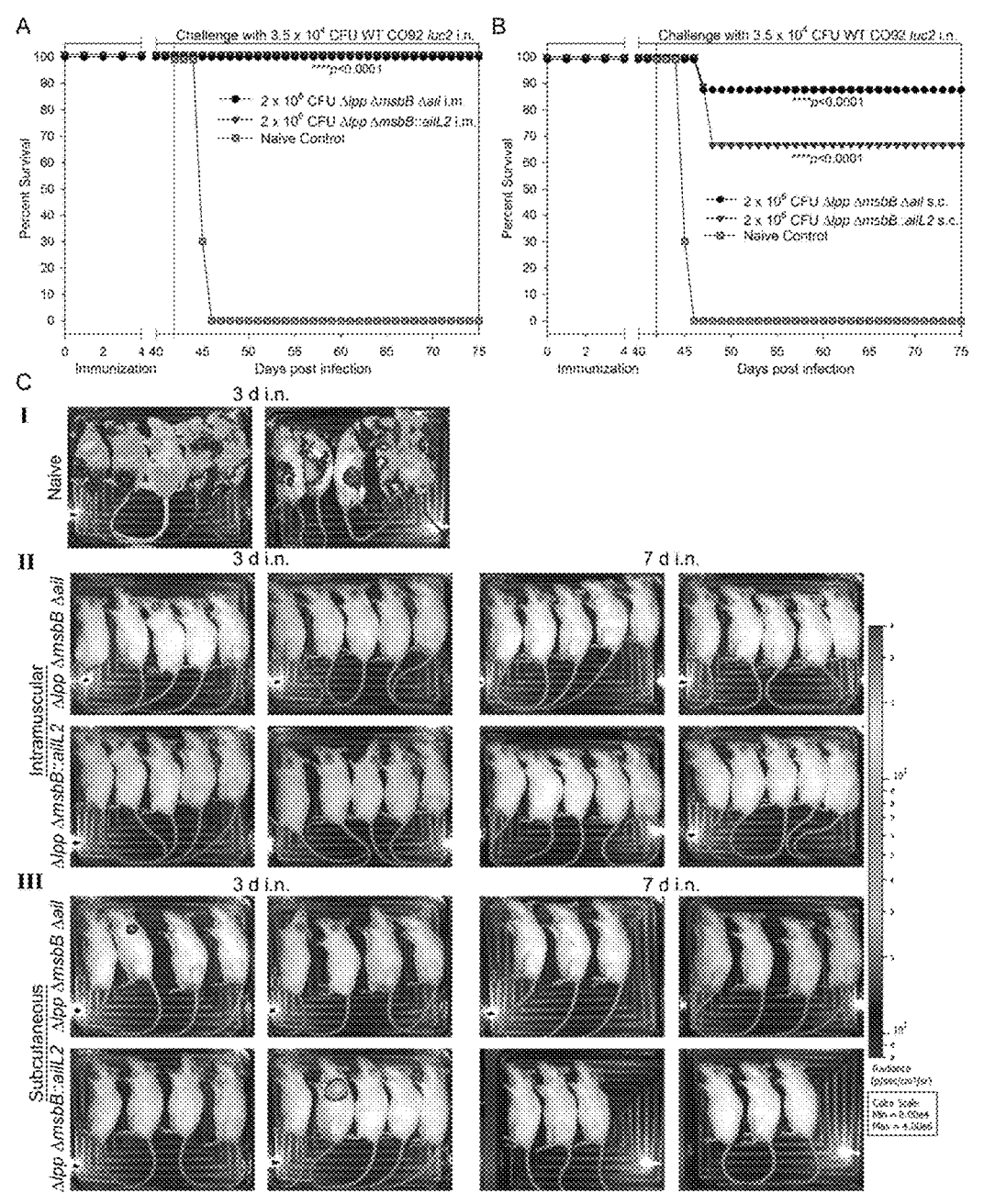
Figure 19:
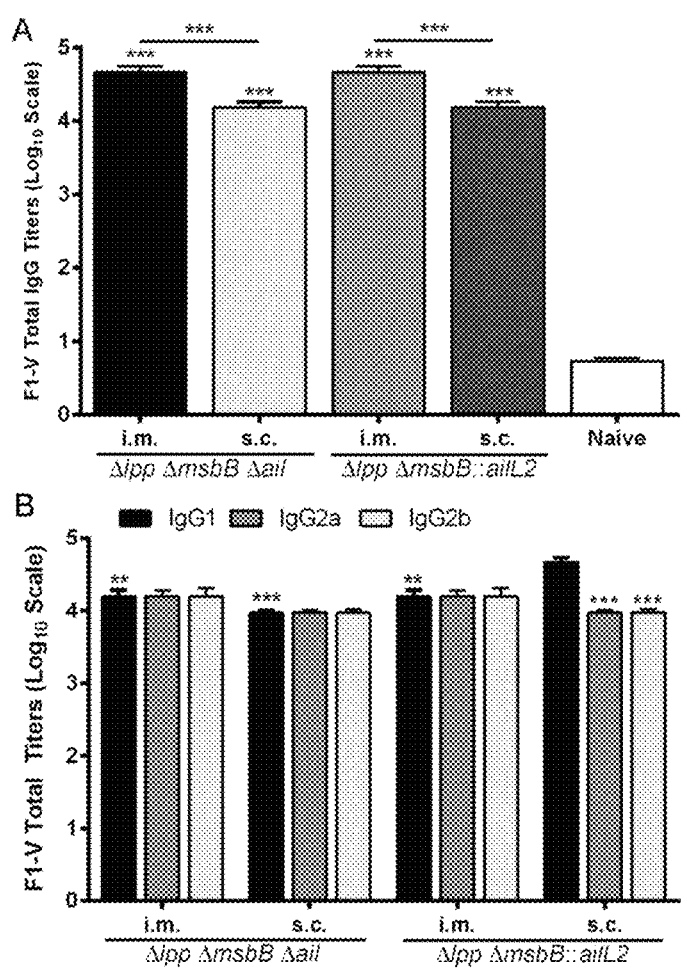

FIG. 18. Immunity conferred by the Δlpp ΔmsbB Δail and Δlpp ΔmsbB::ailL2 mutants to mice via intramuscular and subcutaneous routes of immunization. Mice (n=8-10 per group) were immunized intramuscularly (A) or subcutaneously (B) with 2 doses of $2 \times 10^6$ CFU/100 of the Δlpp ΔmsbB Δail triple mutant or the Δlpp ΔmsbB::ailL2 mutant on day 0 and 21. Mice were challenged intranasally on day 42 with $3.5 \times 10^4$ CFU (70 $LD_{50}$; 1 $LD_{50}$=~500 CFU) of the WT *Y. pestis* CO92 luc2 strain. Naive control: infected naïve mice. The P values were in comparison to naïve control and were based on Kaplan-Meier Curve Analysis. (C). The infected mice (I: naive, II: i.m-immunized and III: s.c-immunized) were imaged on days 3 and 7 post challenge for bioluminescence and the scale within the figure ranged from most intense (red) to least intense (violet).

FIG. 19. Antibody responses in mice elicited by the Δlpp ΔmsbB Δail or the Δlpp ΔmsbB::ailL2 mutant via intramuscular or subcutaneous route of immunization. Mice (n=8-10 per group) were immunized intramuscularly or subcutaneously with 2 doses of $2\times10^6$ CFU/100 μL of the Δlpp ΔmsbB Δail triple mutant or the Δlpp ΔmsbB::ailL2 mutant on days 0 and 21. Mice were bled 14 days post-last immunization and an ELISA was performed to examine the total IgG responses (A) and its isotypes (B) to the F1-V antigen. The arithmetic means±standard deviations are plotted and analyzed by one-way ANOVA with the Bonferroni correction. In (A), *p<0.001 as compared to the naïve sera. The horizontal lines with "*" indicate statistical significance within the two indicated groups. In (B), p<0.001 and *p<0.0001 as compared to that of IgG1 of subcutaneously Δlpp ΔmsbB::ailL2 mutant-immunized mice.

Figure 20:
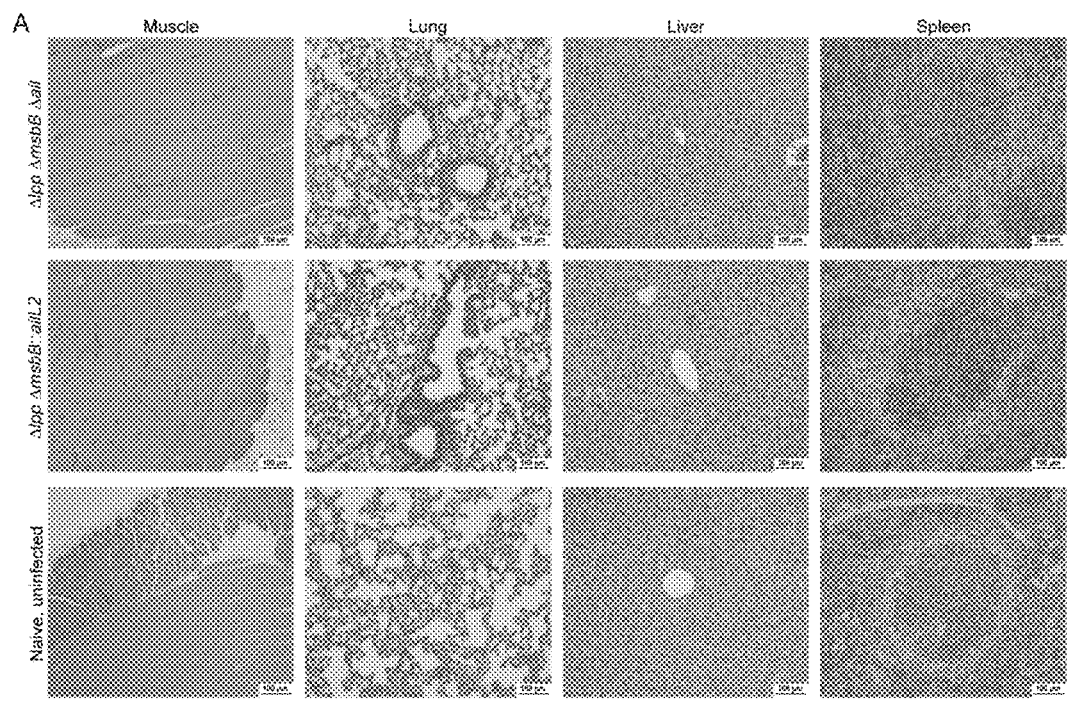

FIG. 20. Histopathological analysis of mouse organs after immunization. Mice were i.m. immunized with 2 doses of $2\times10^6$ CFU/100 μL of the Δlpp ΔmsbB Δail triple mutant or the Δlpp ΔmsbB::ailL2 mutant on days 0 and 21. Muscles, lungs, liver, and spleen were harvested from the immunized mice (n=2 per group) on day 21 after last immunization or naïve control mice for H&E staining and evaluated by light microscopy in a blinded fashion. The scale for each panel is indicated.

Figure 21:
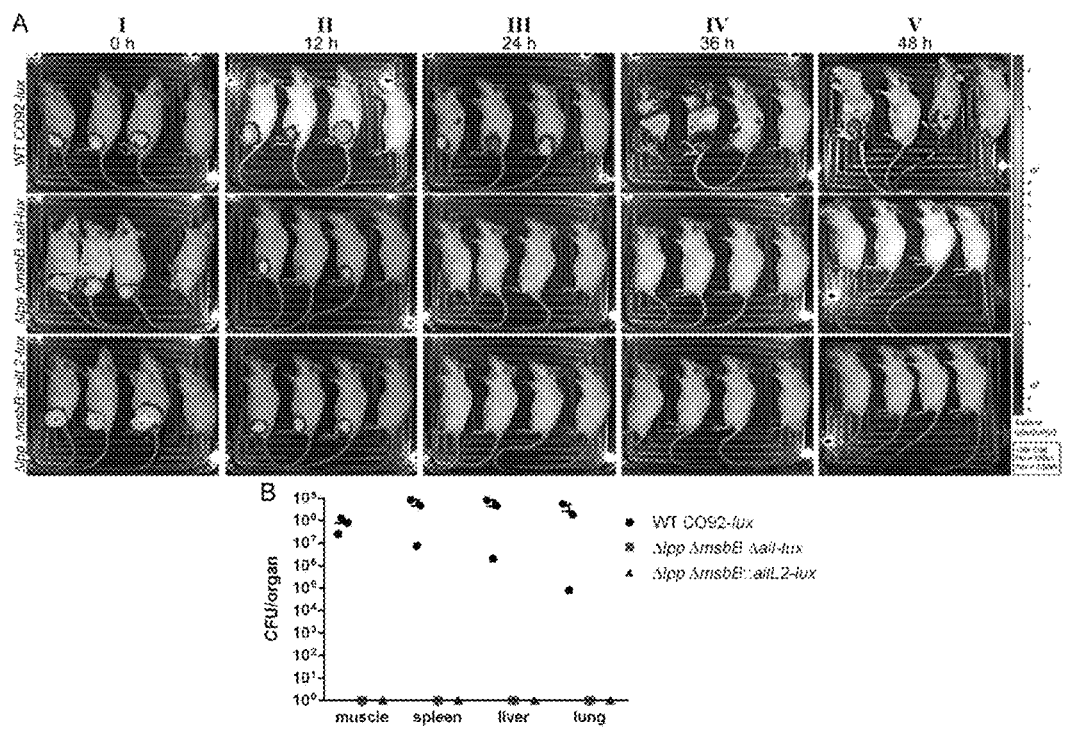

FIG. 21. Progression of infection in mice intramuscularly infected with various *Y. pestis* CO92 strains. Mice (n=3 per group) were challenged by the i.m. route with $2\times10^6$ CFU of the various Tn7-based bioluminescent *Y. pestis* strains (e.g., WT CO92-lux, Δlpp ΔmsbB Δail-lux and Δlpp ΔmsbB::ailL2-lux). Mice were imaged at 12 h intervals for bioluminescence (A) and mouse organs (muscles, lungs, liver, and spleen) were harvested to determine bacterial loads at 48 h p.i. (B). The bioluminescence within the figure ranged from most intense (red) to least intense (violet). The animal on the very right side of each panel represents a naïve, unchallenged control.

FIG. 22. T-cell proliferation. Mice were immunized by the i.m. (A) or s.c. route (B) with $1\times10^3$ CFU of *Y. pestis* KIM/D27, Δlpp ΔmsbB Δail triple mutant or the Δlpp ΔmsbB::ailL2 mutant. On day 21 p.i., T-cells were isolated separately from the spleens of 5 mice in each immunized group or 3 mice from naïve control. The isolated T-cells were co-cultured with γ-irradiated splenocytes from naïve mice (severed as antigen-presenting cells: APCs) pulsed or un-pulsed with heat-killed WT CO92. T-cell proliferation was assessed by measuring incorporation of [$^3$H] thymidine at day 3 of co-culturing with APCs. The arithmetic means±standard deviations are plotted. Data were analyzed by using the Bonferroni correction with a one-way ANOVA. The comparisons were made between the naive pulsed groups with the immunized pulsed groups or between the groups indicated by a horizontal line. *p<0.01, p<0.005, *p<0.001 and ****p<0.0001.

FIG. 23. T-cell cytokine production. Mice were immunized by the i.m. route with $1\times10^3$ CFU of *Y. pestis* KIM/D27, Δlpp ΔmsbB Δail triple mutant or Δlpp ΔmsbB::ailL2 mutant. On day 21 p.i., T-cells were isolated separately from the spleens of 5 mice in each immunized group or 3 mice from naïve control. The isolated T-cells were co-cultured with the γ-irradiated APCs pulsed or un-pulsed with heat-killed WT CO92. Culture supernatants were harvested at day 2 of the co-culturing and the production of various cytokines/chemokines was measured by using a mouse 6-plex assay kit. Data were analyzed by using the Bonferroni correction with a one-way ANOVA. The comparisons were made between the un-pulsed (−) and pulsed (+) cells within each immunization group. **p<0.0001, *p<0.001, **p<0.01 and *p<0.05.

FIG. 24. Histopathological analysis of immunized mouse organs after WT CO92 challenge. Mice were immunized by the intramuscular (i.m.) route with 2 doses of $2\times10^6$ CFU of the Δlpp ΔmsbB Δail triple mutant or the Δlpp ΔmsbB::ailL2 mutant on days 0 and 21. Mice were exposed intranasally (i.n.) on day 42 with $3.5\times10^4$ CFU (70 $LD_{50}$; 1 LD50=500 CFU) of the WT *Y. pestis* CO921uc2 strain. Lungs, liver, and spleen were harvested from mice (n=3 per group) upon death or 54 days post-infection. Portions of each organ were stained with H&E and evaluated by light microscopy in a blinded fashion. Bacteria (arrowhead), neutrophilic infiltration (arrow), depletion of the white pulp (asterisks). The scale for each panel is indicated.

FIG. 25. Histopathological alterations in mice intramuscularly infected with various *Y. pestis* CO92 strains. Mice (n=3 per group) were challenged by the i.m. route with $2\times10^6$ CFU of the various Tn7-based bioluminescent strains (e.g., WT CO92-lux, Δlpp ΔmsbB Δail-lux and Δlpp ΔmsbB::ailL2-lux. At 48 h p.i., muscles, lungs, liver, and the spleen were harvested from mice. Portions of each organ harvested at 48 h p.i. were stained with H&E and evaluated by light microscopy in a blinded fashion. Bacteria (arrowhead), neutrophilic infiltration (arrow), depletion of the white pulp (asterisks), necrosis (open arrowhead). The scale for each panel is indicated.

FIG. 26. Schematic illustration of the signature-tagged mutagenesis approach (STM). (Step 1)—Transposon mutants were generated through a mini-Tn5 transposon system with 53 unique signature tags to create a library of representative 96 *Y. pestis* (YP) mutants for each tag, totaling 5,088 mutants. (Step 2)—One mutant for each tag was combined to generate 96 pools of 53 uniquely tagged clones. (Step 3)—Each pool was used to generate an input pool of bacterial DNA and to infect mice by the i.n. route (5 $LD_{50}$). At 3 days p.i., disseminated mutant bacteria were isolated from the spleens and DNA extracted, providing the output pool of bacterial DNA. (Step 4)—Signature tag probes were generated by PCR with primer pair P2-P4 common sequences adjacent to the signature tags for input and output pools of bacterial DNA. Then, each pool of the DNA (input and out) was separately hybridized to membranes spotted with an array of the 53 unique signature tags. After hybridization, the membranes were developed and the input and output pool membranes compared for changes in corresponding signature abundance.

FIG. 27. Representative STM hybridization reactions. Bacterial DNA was isolated from input and output mutant pools, signature tags amplified, labeled with DIG, and then were used to hybridize membranes spotted with a signature tag array. Out of 56 initial signature tags, 3 were found to be cross-reactive (4, 13 and 56) and were subsequently excluded. Each array was composed of 53 signature tags that were shown to be specific. The circles highlight those mutants that show a reduction in abundance between the input and the output pools. The tag numbers (1-56) are indicated.

FIG. 28. Survival of mice after initial infection with *Y. pestis* CO92 mutants in a bubonic plague model and subsequent re-challenge to evoke pneumonic plague with WT CO92. Five adult Swiss-Webster mice were challenged with an infectious dose of 8 $LD_{50}$ by the s.c. route with the mutants and the WT CO92 strain. Surviving mice from the initial challenge with the selected mutant groups were followed for 28 days p.i. and then re-challenged with 10 $LD_{50}$ of WT CO92. Survival data were analyzed for significance by Kaplan-Meier survival estimates with Bonferonni post-hoc test. The p values are for each of the strains compared to WT CO92 or naïve control for the re-challenge study.

Figure 29:
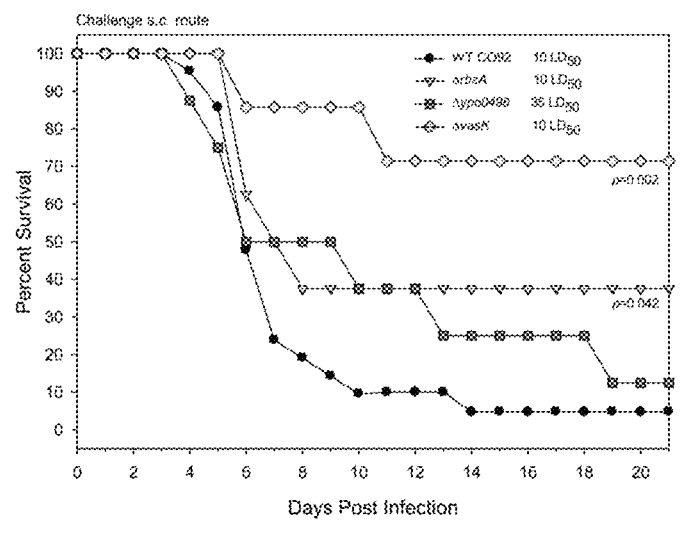

FIG. 29. Survival of mice after challenging with the indicated isogenic mutants of *Y. pestis* CO92 in a bubonic plague model. After generation of the isogenic mutants for rbsA, vasK, and ypo0498, each strain was used to challenge 10 adult Swiss-Webster mice by the s.c. route at the indicated $LD_{50}$s. The animals challenged with WT CO92 represented pool from three independent experiments, with a total number of 22 mice. Survival data were analyzed for significance by the Kaplan-Meier survival estimates with Bonferonni post-hoc test. The p values are for each of the mutant strains compared to pooled WT CO92.

Figure 30:
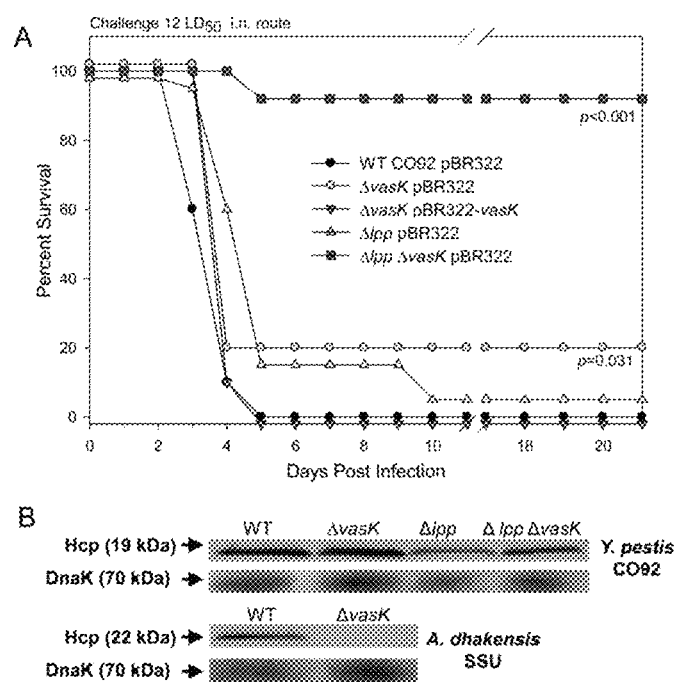

FIG. 30. Survival of mice challenged with the ΔvasK isogenic mutants of *Y. pestis* CO92 in a pneumonic plague model and secretion of Hcp through the T6SS. (A) Adult Swiss-Webster mice were challenged by i.n. route with 12 $LD_{50}$ of WT CO92 pBR322 (n=10), ΔvasK pBR322 (n=10), ΔvasK pBR322-vasK (n=10), Δlpp pBR322 (n=20), Δlpp ΔvasK pBR322 (n=10). Mice were followed for survival up to 21 days and data analyzed for significance by the Kaplan-Meier survival estimates with Bonferonni post-hoc test. The p values are for each of the mutant strains compared to WT CO92. (B) Western blot analysis was performed to detect Hcp in the supernatants of various bacterial cultures using specific anti-Hcp antibodies and the level of DnaK in bacterial pellets was examined as a loading control for samples used during Western blot analysis. The molecular weight of Hcp and DnaK are indicated.

Figure 31:
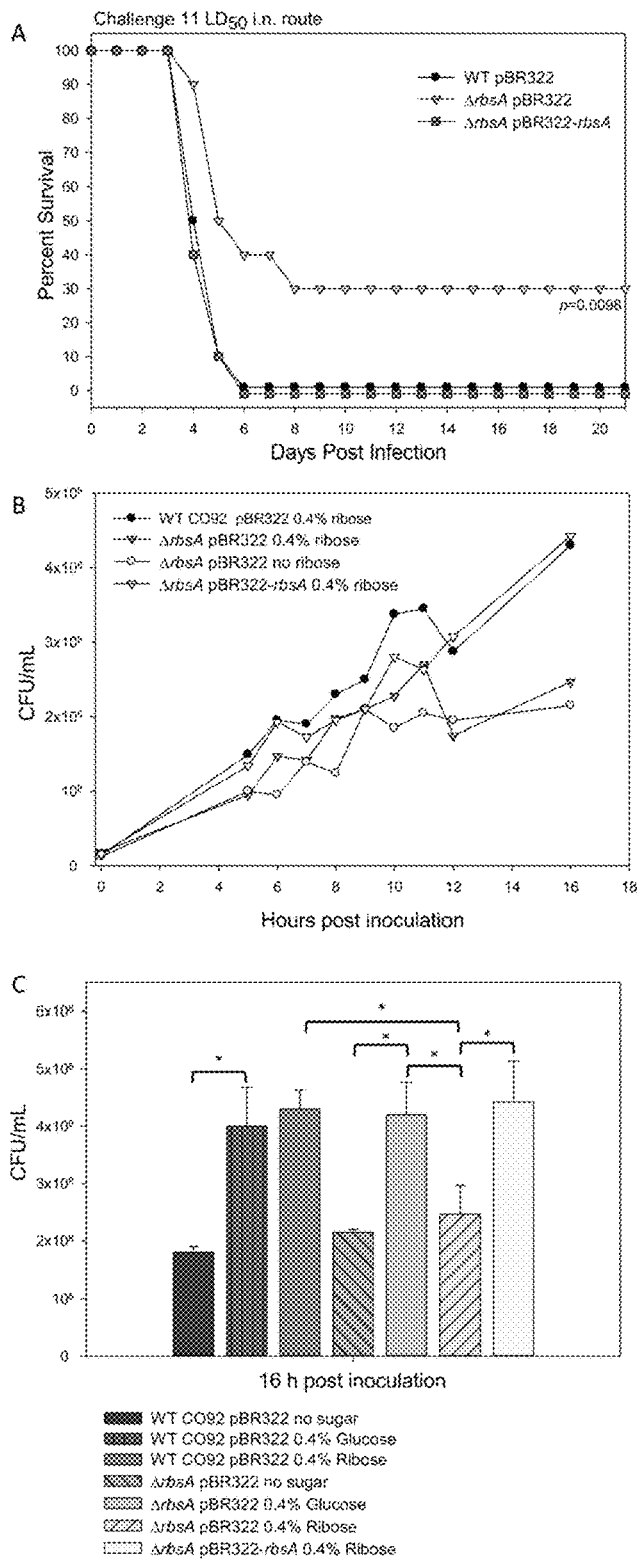

FIG. 31. Survival of mice challenged with the ΔrbsA isogenic mutant of *Y. pestis* CO92 in a pneumonic plague model and ribose utilization. (A) Ten adult Swiss-Webster mice were challenged by the i.n. route with 11 $LD_{50}$ for each of the tested strains followed by observing mortality for 21 days. Survival data were analyzed for significance by the Kaplan-Meier survival estimates with Bonferonni post-hoc test. The p values are for each of the strains compared to WT CO92. (B) Growth of mutants and WT CO92 in a modified M9 minimal medium with or without the supplementation of 0.4% ribose. Samples were taken at time points indicated and plated for CFU. (C) At 16 h post inoculation, culture titrations were determined for the WT CO92 pBR322, ΔrbsA pBR322, and ΔrbsA pBR322-rbsA grown in a modified M9 minimal medium with or without the supplementation of 0.4% glucose or 0.4% ribose. Statistical significance was analyzed by one-way ANOVA with Tukey post-hoc test. Significant comparisons are between groups indicated with (*) and brackets at a p<0.001.

Figure 32:
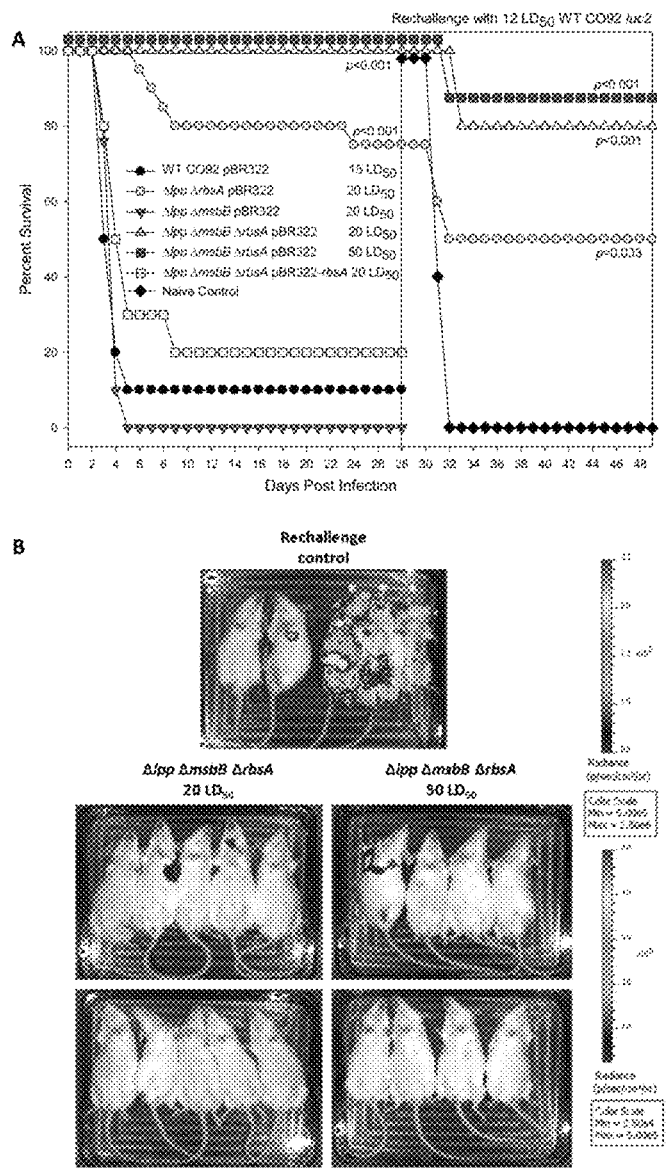

FIG. 32. Survival of mice after initial infection with the ΔrbsA isogenic mutants of *Y. pestis* CO92 in a pneumonic plague model and subsequent re-challenge with WT CO92 luc2 and evaluation of bacterial burden by IVIS. (A) Adult Swiss-Webster mice were challenged at the indicated $LD_{50}$s by the i.n. route with WT CO92 pBR322 (n=10), Δlpp ΔrbsA pBR322 (n=20), Δlpp ΔmsbB pBR322 (n=10), Δlpp ΔmsbB ΔrbsA pBR322 (20 $LD_{50}$, n=10), Δlpp ΔmsbB ΔrbsA pBR322 (50 $LD_{50}$, n=8), and Δlpp ΔmsbB ΔrbsA pBR322-rbsA (n=10) and observed for mortality over a period of 28 days. Surviving mice after the initial challenge with the mutants and the naïve control animals (n=5) were re-challenged with 12 $LD_{50}$ of WT CO92 luc2 (with luciferase gene) strain. Survival data were analyzed for significance by the Kaplan-Meier survival estimates with Bonferonni post-hoc test. The p values for each of the strains were compared to WT CO92 or naive control re-challenge with WT CO92 luc2. (B) On day 3 post re-challenge, selected groups of mice were imaged by IVIS to determine relative bacterial burden. In WT CO92, three mice indicated by asterisks were found dead before imaging.

FIG. 33. Nucleotide sequence of the intergenic region between coding regions ypo1119 and ypo1120 of *Y. pestis* CO92.

DETAILED DESCRIPTION OF ILLUSTRATIVE EMBODIMENTS

There is no FDA-approved vaccine available against *Yersinia pestis* infections. This microbe leads to different forms of plague, namely bubonic, septicemic, and pneumonic. The organism is a Tier-1 select agent and is classified by the World Health Organization as a reemerging human pathogen. Since both humoral and cell-mediated immunity are helpful in providing optimal protection to the host from plague, developing a live-attenuated vaccine(s) is a promising approach. However, developing a live-attenuated vaccine is not straightforward. Such a vaccine candidate should have minimal reactogenicity while providing protection against all forms of plague.

Identification of new virulence factors in *Y. pestis* and optionally understanding their molecular mechanisms during an infection process are helpful in designing a better vaccine or to formulate an appropriate therapeutic intervention. By using a high-throughput, signature-tagged mutagenic approach, 5,088 mutants of *Y. pestis* CO92 were created and screened them in a mouse model of pneumonic plague at a dose equivalent to 5 $LD_{50}$ of wild-type (WT) CO92. From this screen, 118 clones showing impairment in disseminating to spleen were obtained based on hybridization of input versus output DNA from mutant pools with 53 unique signature tags. In the subsequent screen, 20/118 mutants exhibited attenuation at 8 $LD_{50}$ when tested in a mouse model of bubonic plague, with 10/20 aforementioned mutants providing 40% or higher survival rates at an infectious dose of 40 $LD_{50}$. Upon sequencing, six of the attenuated mutants carried interruptions in genes encoding hypothetical proteins or proteins with putative functions. In-frame deletion mutation of two of the genes identified from the screen, namely rbsA that codes for a putative sugar transport system ATP-binding protein, and vasK, a component of the type VI secretion system, were also found to exhibit some attenuation at 11-12 $LD_{50}$ in a mouse model of pneumonic plague.

Earlier, it was found that deleting genes encoding Braun lipoprotein (Lpp) and acyltransferase (MsbB), the latter of which modifies lipopolysaccharide function, reduced virulence of the Δlpp ΔmsbB double mutant in mouse models of bubonic and pneumonic plague (Sha et al., 2013, Infect Immun 81:815-828). As described herein, deletion of ail, rbsA or vasK genes from the Δlpp ΔmsbB double mutant resulted in an unexpected synergistic increase of attenuation. The Δlpp ΔmsbB Δail triple mutant was unable to kill mice at a $LD_{50}$ dose equivalent to 6,800 $LD_{50}$s of the wild type CO92 in a mouse model of pneumonic plague. The Δlpp ΔmsbB Δrbs and Δlpp ΔmsbB ΔvasK triple mutants provided 90-100% survivability to mice in a pneumonic plague model at 20-50 $LD_{50}$s. The Δlpp ΔmsbB Δail triple mutant-infected mice at 3600-6800 $LD_{50}$s were 40% to 70% protected upon subsequent challenge with 20-28 $LD_{50}$ of WT CO92. The alteration of three genes also advantageously reduces the likelihood of reversion. These data suggest that the triple mutants described herein are useful as a live attenuated plague vaccine.

Genetically Modified *Y. pestis*

A genetically modified *Yersinia pestis* is provided herein. A genetically modified *Y. pestis* may be any strain of *Y. pestis*. In one embodiment, a genetically modified *Y. pestis* is biovar *Y.p., orientalis*, such as strain CO92 (Parkhill et al., 2001, Nature, 413(6855):523-527). In one embodiment, a genetically modified *Y. pestis* is using biovar *Y. p., medievalis*, such as strain KIM (Deng et al., J Bacteriol., 184 (16):4601-4611). In one embodiment, a genetically modified *Y. pestis* is produced using a strain that is virulent before a genetic modification described herein is made to the strain. As used herein, a *Y. pestis* is considered virulent if it causes disease in a mouse model of bubonic plague at an $LD_{50}$ of 50 colony forming units (CFUs) or less, or pneumonic plague at an $LD_{50}$ of 500 CFUs or less. In one embodiment, a genetically modified *Y. pestis* includes one, two, or three plasmids selected from pCD1, pPCP1 (also referred to as pPla or pPst) and pMT1 (also referred to as pFra). In one embodiment, a genetically modified *Y. pestis* includes all three plasmids. One or more of the plasmids may include an alteration as described herein.

A genetically modified *Y. pestis* is attenuated. An attenuated *Y. pestis* is able to replicate in an animal and induce an immune response, but has a reduced ability to cause the clinical signs and/or symptoms of disease in an animal. Whether a genetically modified *Y. pestis* is attenuated can be determined by testing using a mouse model system recognized in the art as relevant in the evaluation of putative vaccines for protection of humans from infection by *Y. pestis*. The murine model can be used to evaluate protection from bubonic, pneumonic, and/or septicemic plague caused by *Y. pestis*. In one embodiment, whether a genetically modified *Y. pestis* is attenuated can be determined as described in Example 1. Briefly, a genetically modified *Y. pestis* is administered to mice by either the intramuscular (I.M.) or intranasal (I.N.) route. The dosage of the test microbe administered is twenty 50% lethal doses, where the lethal dose is the $LD_{50}$ of the *Y. pestis* without the genetic modifications. If there is at least 90% survivability of the mice 30 days after administering the triple mutant, then the genetically modified *Y. pestis* is attenuated. In one embodiment, the genetically modified *Y. pestis* is attenuated is there is 100% survivability of the mice after 30 days.

In one embodiment, a genetically modified *Y. pestis* causes an immune response that protects the recipient from subsequent infection by a *Y. pestis*. The ability of a genetically modified *Y. pestis* to protect a recipient from challenge can be determined using the mouse model. In one embodiment, whether a genetically modified *Y. pestis* protects a recipient can be determined as described in Example 1. A population of mice are immunized I.M. or I.N. with the genetically modified *Y. pestis* at fifty 50% lethal doses, where the lethal dose is the $LD_{50}$ of the *Y. pestis* without the genetic modifications. Twenty one days later the mice are immunized again, and 21 days after the second immunization mice are challenged with 12 50% lethal doses. If at least 90% of the recipients survive, the genetically modified *Y. pestis* protects the recipient.

In one embodiment, a genetically modified *Y. pestis* includes at least three alterations compared to a control *Y. pestis*. The alteration can refer to a coding region or to an intergenic region. As used herein, a "control" *Y. pestis* is a *Y. pestis* before it is genetically modified to include the alteration. A control *Y. pestis* may be a wild-type *Y. pestis* or a *Y. pestis* that includes a genetic modification. As used herein, an "alteration" refers to a change a *Y. pestis* that attenuates virulence.

With respect to an alteration of a coding region (e.g., lpp, msbB, ail, and other coding regions described herein), the alteration can result in a reduced amount in the cell of the mRNA encoded by the coding region, a reduced amount in the cell of the protein encoded by the coding region, or a combination thereof, compared to a control *Y. pestis*. The decrease in the amount of an mRNA or a protein encoded by the coding region may be a decrease of at least 0.1%, at least 1%, at least 5%, at least 10%, at least 20%, at least 30%, at least 40%, at least 50%, at least 60%, at least 70%, at least 80%, or at least 90% compared to the amount of the mRNA or the amount of the protein in a the same *Y. pestis* that does not include the alteration. In one embodiment, the mRNA or protein encoded by an altered coding region is undetectable in the genetically modified *Y. pestis*. In one embodiment, the biological activity of a protein encoded by an altered coding region is reduced in the genetically modified *Y. pestis*, and in one embodiment the biological activity is undetectable.

With respect to an alteration of an intergenic region in the genome of a *Y. pestis*, the intergenic region is between coding regions ypo1119 and ypo1120. The intergenic region of *Y. pestis* CO92 is shown in FIG. 33. In *Y. pestis* CO92 this region is 131 nucleotides, and an insertion in this region between nucleotides 97 and 98 of SEQ ID NO:1 attenuated *Y. pestis* CO92 (see Example 3). Deletion of this region also attenuated *Y. pestis* CO92. A mutation can be in any location within the intergenic region. In one embodiment, the mutation is in the nucleotides encoding the hypothetical protein MGHPAHNYFRSILASDSKAQRSSV (SEQ ID NO:2), e.g., nucleotides 25-99 of the intergenic region. In one embodiment, the mutation is in a region of nucleotides that does not encode the hypothetical protein, e.g., nucleotides 1-24 or nucleotides 100-131 of the intergenic region. In one embodiment, the mutation, such as an insertion, is polar and affects transcription of a downstream coding region or, in the case of an operon, downstream coding regions. The ypo1120 coding region is downstream of the insertion in the intergenic region between coding regions ypo1119 and ypo1120, and is the first coding region of an operon that includes the tolQ and tolR coding regions. Examples of polynucleotides that can be used to result in an insertion include, for instance, a transposon or any polynucleotide sequence that can be inserted into this region by homologous recombination.

One of the three alterations results in decreased mRNA, decreased protein, or a combination thereof, encoded by the coding region lpp. An example of an lpp coding region of a *Y. pestis* is nucleotides 2691297-2691533 of the genomic sequence of CO92 at Genbank accession number AL590842.1 or NC 003143. The Lpp protein encoded by that lpp coding region is the amino acid sequence at Genbank accession number YP 002347360. Other lpp coding regions include those having sequence similarity to the lpp coding region of CO92. Other lpp coding regions also include those encoding a protein having structural similarity to the Lpp protein at Genbank accession number CAL21022.1 (SEQ ID NO:49).

The second of the three alterations results in decreased mRNA, decreased protein, or a combination thereof, encoded by the coding region msbB (ypo2063). An example of a msbB coding region of a *Y. pestis* is nucleotides 2341684-2342646 of the genomic sequence of CO92 at Genbank accession number AL590842.1 or NC 003143. The MsbB protein encoded by that msbB coding region is the amino acid sequence at Genbank accession number CAL20698.1. Other msbB coding regions include those having sequence similarity to the msbB coding region of CO92. Other msbB coding regions also include those encoding a protein having structural similarity to the MsbB protein at Genbank accession number CAL20698.1 (SEQ ID NO:50).

In one embodiment, the third of the three alterations results in decreased mRNA, decreased protein, or a combination thereof, encoded by coding region selected from pla, ypo1717, ypmt1.80c, rbsA (ypo2500), ypo0498, vasK (ypo3603), ypo3164, hxuB (ypo3248), ypo1616, ypo1119, ypo1120, and ail. In one embodiment, two or more of these coding regions is altered in a genetically modified Y. pestis.

An example of a pla coding region of a Y. pestis is nucleotides 6665-7603 of the pPCP1 plasmid sequence at Genbank accession number AL109969.1. The Pla protein encoded by that pla coding region is the amino acid sequence at Genbank accession number CAB53170.1 (SEQ ID NO:51). Other pla coding regions include those having sequence similarity to the pla coding region of CO92. Other pla coding regions also include those encoding a protein having structural similarity to the Pla protein at Genbank accession number CAB53170.1.

An example of a ypo1717 coding region of a Y. pestis is nucleotides 1961429-1961977 of the genomic sequence of CO92 at Genbank accession number AL590842.1 or NC_003143. The protein encoded by that ypo1717 coding region is the amino acid sequence at Genbank accession number CAL20360.1 (SEQ ID NO:52). Other ypo1717 coding regions include those having sequence similarity to the ypo1717 coding region of CO92. Other ypo1717 coding regions also include those encoding a protein having structural similarity to the protein at Genbank accession number CAL20360.1.

There are multiple copies of ypmt1.80c coding regions in Y. pestis CO92. Examples of ypmt1.80c coding regions include nucleotides 17906-19114, 1777851-1779059, 1807069-1808277, 1811445-1812653, 1842497-1843705, and 1972184-1973392 of the chromosome sequence of CO92 at Genbank accession number AL590842.1 or NC 003143 and at nucleotides 79777-80985 of the pMT1 plasmid sequence at Genbank accession number AL117211.1. The proteins encoded by that ypmt1.80c coding regions are the amino acid sequences at Genbank accession numbers CAL18701.1 (SEQ ID NO:53), CAL20207.1, CAL20228.1, CAL20234.1, CAL20266.1, and CAL20370.1 for the chromosomal coding regions, respectively, and at Genbank accession number CAB55262.1 for the plasmid coding region. Other ypmt1.80c coding regions include those having sequence similarity to a ypmt1.80c coding region of CO92. Other ypmt1.80c coding regions also include those encoding a protein having structural similarity to the protein at Genbank accession number CAL18701.1, CAL20207.1, CAL20228.1, CAL20234.1, CAL20266.1, CAL20370.1, or CAB55262.1.

An example of a rbsA (ypo2500) coding region of a Y. pestis is nucleotides 2809281-2810771 of the genomic sequence of CO92 at Genbank accession number AL590842.1 or NC_003143. The RbsA protein encoded by that rbsA coding region is the amino acid sequence at Genbank accession number CAL21128.1 (SEQ ID NO:54). Other rbsA coding regions include those having sequence similarity to the rbsA coding region of CO92. Other rbsA coding regions also include those encoding a protein having structural similarity to the RbsA protein at Genbank accession number CAL21128.1.

An example of a ypo0498 coding region of a Y. pestis is nucleotides 531628-532371 of the genomic sequence of CO92 at Genbank accession number AL590842.1 or NC_003143. The protein encoded by that ypo0498 coding region is the amino acid sequence at Genbank accession number CAL19178.1 (SEQ ID NO:55). Other ypo0498 coding regions include those having sequence similarity to the ypo0498 coding region of CO92. Other ypo0498 coding regions also include those encoding a protein having structural similarity to the protein at Genbank accession number CAL19178.1.

An example of a vasK (ypo3603) coding region of a Y. pestis is nucleotides 4012390-4015923 of the genomic sequence of CO92 at Genbank accession number AL590842.1 or NC_003143. The VasK protein encoded by that vasK coding region is the amino acid sequence at Genbank accession number CAL22191.1 (SEQ ID NO:56). Other vasK coding regions include those having sequence similarity to the vasK coding region of CO92. Other vasK coding regions also include those encoding a protein having structural similarity to the VasK protein at Genbank accession number CAL22191.1.

An example of a ypo3164 coding region of a Y. pestis is nucleotides 3527637-3528593 of the genomic sequence of CO92 at Genbank accession number AL590842.1 or NC_003143. The protein encoded by that ypo3164 coding region is the amino acid sequence at Genbank accession number CAL21759.1 (SEQ ID NO:57). Other ypo3164 coding regions include those having sequence similarity to the ypo3164 coding region of CO92. Other ypo3164 coding regions also include those encoding a protein having structural similarity to the protein at Genbank accession number CAL21759.1.

An example of a hxuB (ypo3248)coding region of a Y. pestis is nucleotides 3620645-3622435 of the genomic sequence of CO92 at Genbank accession number AL590842.1 or NC_003143. The protein encoded by that hxuB (ypo3248) coding region is the amino acid sequence at Genbank accession number CAL21842.1 (SEQ ID NO:58). Other hxuB (ypo3248) coding regions include those having sequence similarity to the hxuB (ypo3248) coding region of CO92. Other hxuB (ypo3248) coding regions also include those encoding a protein having structural similarity to the protein at Genbank accession number CAL21842.1.

An example of a ypo1616 coding region of a Y. pestis is nucleotides 1838652-1839194 of the genomic sequence of CO92 at Genbank accession number AL590842.1 or NC_003143. The protein encoded by that ypo1616 coding region is the amino acid sequence at Genbank accession number CAL20261.1 (SEQ ID NO:59). Other ypo1616 coding regions include those having sequence similarity to the ypo1616 coding region of CO92. Other ypo1616 coding regions also include those encoding a protein having structural similarity to the protein at Genbank accession number CAL20261.1.

An example of a ypo1119 coding region of a Y. pestis is nucleotides 1266799-1267131 of the genomic sequence of CO92 at Genbank accession number AL590842.1 or NC_003143. The protein encoded by that ypo1119 coding region is the amino acid sequence at Genbank accession number CAL19785.1 (SEQ ID NO:60). Other ypo1119 coding regions include those having sequence similarity to the ypo1119 coding region of CO92. Other ypo1119 coding regions also include those encoding a protein having structural similarity to the protein at Genbank accession number CAL19785.1.

An example of a ypo1120 coding region of a *Y. pestis* is nucleotides 1267263-1267664 of the genomic sequence of CO92 at Genbank accession number AL590842.1 or NC_003143. The protein encoded by that ypo1120 coding region is the amino acid sequence at Genbank accession number CAL19786.1 (SEQ ID NO:61). Other ypo1120 coding regions include those having sequence similarity to the ypo1120 coding region of CO92. Other ypo1120 coding regions also include those encoding a protein having structural similarity to the protein at Genbank accession number CAL19786.1.

An example of a ail (ypo1860) coding region of a *Y. pestis* is nucleotides 2109269-2109820 of the genomic sequence of CO92 at Genbank accession number AL590842.1 or NC_003143. The Ail protein encoded by that *ail* coding region is the amino acid sequence at Genbank accession number CAL20500.1 (SEQ ID NO:62). Other ail coding regions include those having sequence similarity to the ail coding region of CO92. Other ail coding regions also include those encoding a protein having structural similarity to the Ail protein at Genbank accession number CAL20500.1.

A genetically modified *Y. pestis* may include additional alterations. In one embodiment, a genetically modified *Y. pestis* includes an alteration in more than one ypmt1.80c coding region. In one embodiment, an additional alteration includes a mutation that attenuates the microbe. Other attenuating mutations of *Y. pestis* are known in the art.

Methods of Making

A genetically modified *Y. pestis* described herein can be made using any routine method known in the art for reducing expression of a coding region, or altering an intergenic region, in a microbe like *Y. pestis*. For instance, a coding region or an intergenic region may be deleted in whole or in part, a regulatory region of a coding region may be modified, or a protein that modulates expression of a coding region may be modified.

A genetically modified microbe can be produced using classical genetic methods, recombinant methods, or a combination thereof. Classic genetic methods include the use of transduction and conjugation to introduce mutations into a *Y. pestis*. Recombinant methods include, for instance, transformation of a *Y. pestis* with an artificial polynucleotide, such as a plasmid. For instance, DNA integration cassettes (also referred to as DNA mutagenic cassettes) can be used to replace a genomic coding region in a *Y. pestis* by homologous recombination. Such cassettes typically include the mutation to be inserted, homologous nucleotide sequences to target the mutation to the coding region, and optionally a marker sequence. The actual nucleotide sequence of a specific coding region to be altered in a *Y. pestis* may vary slightly from a publicly available sequence; however, the actual nucleotide sequence of the specific coding region can be easily determined using routine methods.

Examples of mutations that can be used in the production of a genetically modified *Y. pestis*, including a genetically modified *Y. pestis* having an alteration of a coding region or an alteration of an intergenic region, include a deletion, an insertion, and a point mutation, such as transition and/or transversion point mutations. A deletion may include deletion of part or an entire nucleotide sequence of a coding region or an intergenic region, or deletion of a regulatory region of a coding region. The genetically modified *Y. pestis* may encode a fragment of a protein encoded by the coding region, or not encode the protein. A mutation useful to produce a genetically modified *Y. pestis* described herein is stable and reverts at a low frequency. In one embodiment, a mutation useful to produce a genetically modified *Y. pestis* described herein is non-reverting.

Compositions

Provided herein are compositions that includes a genetically modified *Y. pestis*. Such a composition may include a pharmaceutically acceptable carrier. As used herein "pharmaceutically acceptable carrier" includes saline, solvents, dispersion media, coatings, antifungal agents, isotonic and absorption delaying agents, and the like, compatible with pharmaceutical administration and not deleterious to a recipient thereof. The skilled person will recognize that a pharmaceutically acceptable carrier is chosen that will not kill the genetically modified *Y. pestis* or inhibit its ability to effectively grow and cause an immune response in a subject receiving the attenuated microbe. A composition described herein may be referred to as a vaccine. The term "vaccine" as used herein refers to a composition that, upon administration to an animal, will increase the likelihood the recipient is protected against *Y. pestis*. Without intending to be limiting, administration of the composition to an animal typically produces a humoral and cellular immunological response that results in immunity.

A composition may be formulated in pharmaceutical preparations in a variety of forms adapted to the chosen route of administration, including routes suitable for stimulating an immune response. Thus, a composition described herein can be administered via known routes including, for example, parenteral (e.g., intravenous, intradermal, subcutaneous, intraperitoneal, intramuscular), enteral (e.g., oral), and topical (e.g., epicutaneous, intranasal, transmucosal) administration. In one embodiment, the route of adminstration is intramuscular. In one embodiment, the route of administration is intranasal. Appropriate dosage forms for enteral administration of the genetically modified *Y. pestis* may include tablets, capsules or liquids. Appropriate dosage forms for parenteral administration may include intramuscular administration. Appropriate dosage forms for topical administration may include nasal sprays, metered dose inhalers, dry-powder inhalers or by nebulization. It is foreseen that administration of a composition to a mucosal surface, such as by administration to the nasal or respiratory mucosa (e.g., via a spray or aerosol), may stimulate mucosal immunity, such as production of secretory IgA antibodies, throughout the subject's body.

A formulation may be conveniently presented in unit dosage form and may be prepared by methods well known in the art of pharmacy. Methods of preparing a composition with a pharmaceutically acceptable carrier include the step of bringing the active compound (e.g., a genetically modified *Y. pestis*) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations. In general, a composition can be formulated to be compatible with its intended route of administration. More specifically, the compositions described herein may be administered to any tissue of a subject, including, but not limited to, muscle (such as skeletal muscle), skin, lung tissue, intestinal tissue, and the like. A composition described herein may be administered to any internal cavity of an animal, including, but not limited to, lungs, mouth, nasal cavity, stomach, peritoneal cavity, intestine, veins, and the like.

A composition including a pharmaceutically acceptable carrier can also include an adjuvant. An "adjuvant" refers to an agent that can act in a nonspecific manner to enhance an immune response to a genetically modified *Y. pestis*, thus potentially reducing the quantity of microbe necessary in any given immunizing composition, and/or the frequency of injection necessary in order to generate an adequate immune response to the genetically modified microbe. Adjuvants may include, for example, IL-1, IL-2, emulsifiers, muramyl dipeptides, dimethyl dioctadecyl ammonium bromide (DDA), avridine, aluminum hydroxide, oils, saponins, alpha-tocopherol, polysaccharides, emulsified paraffins, ISA-70, RIBI and other substances known in the art.

In another embodiment, a composition described herein including a pharmaceutically acceptable carrier can include a biological response modifier, such as, for example, IL-2, IL-4 and/or IL-6, TNF, IFN-alpha, IFN-gamma, and other cytokines that effect immune cells.

A composition described herein may be administered in an amount sufficient to treat or prevent infection by *Y. pestis*. For instance, the amount of genetically modified microbe present in a composition can vary. For example, the dosage of genetically modified microbes can be present at a concentration of, for instance, at least $10^2$ bacteria/ml, at least $10^3$ bacteria/ml, at least $10^4$ bacteria/ml, at least $10^5$ bacteria/ml, at least $10^6$ bacteria/ml, at least $10^7$ bacteria/ml, at least $10^8$ bacteria/ml, or at least $10^9$ bacteria/ml. In one embodiment, the genetically modified microbe is present in the composition in an amount that the total volume of the composition administered is 0.5 ml to 5.0 ml, typically 1.0 to 2.0 ml. The amount administered will vary depending on various factors including, but not limited to, the specific genetically modified *Y. pestis* chosen, the weight, physical condition and age of the subject, and the route of administration. Thus, the unit dosage form can vary widely, and depends upon factors such as the species, age, weight and physical condition of the subject, as well as the method of administration. Such factors can be determined by one of skill in the art.

Methods of Use

Provided herein are methods for using the genetically modified *Y. pestis*. The method can include administering to a subject effective amount of a composition that includes a genetically modified *Y. pestis* described herein. As used herein, an "effective amount" of a composition that includes a genetically modified *Y. pestis* is the amount able to elicit the desired response in the recipient. The subject can be, for instance, a human, or a laboratory animal such as a murine (e.g., a mouse or a rat), a guinea pig, or a non-human primate. In one embodiment, a human subject is a person likely to be exposed to *Y. pestis*, such as a member of the military. In one embodiment, a subject is immunocompromised. The methods may further include additional administrations (e.g., one or more booster administrations) of the composition to the subject to enhance or stimulate a secondary immune response. A booster can be administered at a time after the first administration, for instance, 1 to 8 weeks, preferably 2 to 4 weeks, after the first administration of the composition. Subsequent boosters can be administered one, two, three, four, or more times annually.

In one embodiment, the method may be directed to making the animal cause a protective immune response to the genetically modified *Y. pestis*. As used herein, "protective" means that the immune response contributes to the lessening of any symptoms associated with infection of a subject with *Y. pestis*. For example, a genetically modified *Y. pestis* may induce an immune response that helps to reduce symptoms associated with *Y. pestis* infection or reduce the morbidity and mortality associated with infection with the microbe.

An immune response to a genetically modified *Y. pestis* described herein may include a humoral immune response, a cell-mediated immune response, or a combination thereof. In one embodiment, an immune response includes both a humoral immune response and a cell-mediated immune response. In one embodiment, the presence of a humoral immune response may be determined by measuring the increase of serum IgG to one or more antigens produced by the genetically modified *Y. pestis*. Examples of suitable antigens that can be detected include the capsular antigen F1 and the low-calcium response V antigen of the type 3 secretion system. In one embodiment, the presence of a cellular immune response can be determined by measuring T-cell proliferation, where T-cell proliferation to *Y. pestis* antigens is increased in a subject after administration of a composition described herein. Cytokine production by T-cells in response to *Y. pestis* antigens can also be measured. Increased cytokine/chemokine production, e.g., IFN-γ TNF-α, IL-6, IL-1β, and/or IL-10 can result when T-cells are stimulated with *Y. pestis* antigens after immunization with a genetically modified *Y. pestis* described herein.

In one embodiment, the method may be directed to treating an animal that has, or is at risk of having, an infection by *Y. pestis*. As used herein, the term "infection" refers to the presence of a *Y. pestis* in an subject's body, which may or may not be clinically apparent. An infection by *Y. pestis* may result in plague, such as bubonic plague, septicemic plague, pneumonic plague, or a combination thereof.

Treating an infection can be prophylactic or, alternatively, therapeutic—in this context, treatment after a subject manifests one or more indication of infection by *Y. pestis*. Generally, treatment that is prophylactic—in this context, initiated before a subject is infected by a *Y. pestis* or while an infection remains subclinical—is referred to herein as treatment of a subject that is "at risk" of infection. As used herein, the term "at risk" refers to a subject that may or may not actually possess the described risk—in this context, a subject that may or may not be infected by *Y. pestis*. Thus, typically, a subject "at risk" of infection by *Y. pestis* is a subject present in an area where individuals have been identified as infected by the *Y. pestis* and/or is likely to be exposed to the *Y. pestis* even if the subject has not yet manifested any detectable indication of infection by the *Y. pestis* and regardless of whether the subject may harbor a subclinical amount of the microbe. For example, a subject at risk includes a subject likely to be exposed to a vector of *Y. pestis*, such as a flea. Accordingly, administration of a composition can be performed before, during, or after the subject has first contact with *Y. pestis*. Treatment initiated after the animal's first contact with the microbe may result in decreasing the risk of death, increasing likelihood of survival, decreasing the severity of symptoms and/or clinical signs of infection by the microbe, completely removing the microbe, and/or decreasing the likelihood of experiencing a clinically evident infection compared either to the animal before administration of the composition or to an animal to which the composition is not administered. The method includes administering an effective amount of the composition as described herein to an animal having, or at risk of having, an infection caused by *Y. pestis*, and determining whether the infection has decreased. Methods for determining whether an infection is caused by *Y. pestis* are routine and known in the art, as are methods for determining whether the infection has decreased.

In another aspect, provided herein are methods for treating one or more symptoms or clinical signs of certain conditions in an animal that may be caused by infection by *Y. pestis*. The method includes administering an effective amount of a composition as described herein to an animal having or at risk of having a condition, or exhibiting symptoms and/or clinical signs of a condition, and determining whether at least one symptom and/or clinical sign of the condition is changed, preferably, reduced.

Treatment of symptoms and/or clinical signs associated with these conditions can be prophylactic or, alternatively, therapeutic—in this context, treatment initiated after the subject exhibits one or more symptoms or clinical signs associated with a condition caused by infection by *Y. pestis*. As used herein, the term "symptom" refers to subjective evidence of disease or condition experienced by the patient and caused by infection by a microbe. As used herein, the term "clinical sign" or, simply, "sign" refers to objective evidence of disease or condition caused by infection by *Y. pestis*. Symptoms and/or clinical signs associated with conditions referred to herein and the evaluations of such symptoms are routine and known in the art. Treatment that is prophylactic—in this context, treatment that is initiated before a subject manifests symptoms or signs of a condition caused by *Y. pestis*—is referred to herein as treatment of a subject that is "at risk" of developing the condition. Thus, typically, an animal "at risk" of developing a condition is an animal present in an area where animals having the condition have been diagnosed and/or is likely to be exposed to a *Y. pestis* causing the condition even if the animal has not yet manifested symptoms or signs of any condition caused by the microbe. For example, an animal at risk includes an animal likely to be exposed to a vector of *Y. pestis*, such as a flea. Accordingly, administration of a composition can be performed before, during, or after the occurrence of the conditions described herein. Treatment initiated after the development of a condition may result in decreasing the severity of the symptoms of one of the conditions, completely removing the symptoms, or increasing the likelihood of survival.

Kits

Also provided herein are kits for immunizing a subject. The kit includes a composition described herein in a suitable packaging material in an amount sufficient for at least one administration. Optionally, other reagents such as a buffer solution (either prepared or present in its constituent components, where one or more of the components may be premixed or all of the components may be separate), and the like, are also included. Instructions for use of the packaged composition are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the composition can be used for immunizing a subject to protect against infection by *Y. pestis*. In addition, the packaging material contains instructions indicating how the materials within the kit are employed. As used herein, the term "package" refers to a solid matrix or material such as glass, plastic, paper, foil, and the like, capable of holding within fixed limits a composition described herein. Thus, for example, a package can be a glass vial used to contain appropriate quantities of an attenuated *Y. pestis*, in an aqueous solution or dried form (e.g., lyophilized).

EXAMPLE 1

Previously, it was shown that deletion of genes encoding Braun lipoprotein (Lpp) and MsbB attenuated *Yersinia pestis* CO92 in mouse and rat models of bubonic and pneumonic plague. While Lpp activates Toll-like receptor 2, the MsbB acyltransferase modifies lipopolysaccharide. Here, we deleted the ail gene (encoding the attachment-invasion locus) from wild-type (WT) strain CO92 or its lpp single and Δlpp ΔmsbB double mutants. While the Δail single mutant was minimally attenuated compared to the WT bacterium in a mouse model of pneumonic plague, the Δlpp Δail double mutant and the Δlpp ΔmsbB Δail triple mutant were increasingly attenuated, with the latter being unable to kill mice at a 50% lethal dose ($LD_{50}$) equivalent to 6,800 $LD_{50}$s of WT CO92. The mutant-infected animals developed balanced $T_H1$- and $T_H2$-based immune responses based on antibody isotyping. The triple mutant was cleared from mouse organs rapidly, with concurrent decreases in the production of various cytokines and histopathological lesions. When surviving animals infected with increasing doses of the triple mutant were subsequently challenged on day 24 with the bioluminescent WT CO92 strain (20 to 28 $LD_{50}$s), 40 to 70% of the mice survived, with efficient clearing of the invading pathogen, as visualized in real time by in vivo imaging. The rapid clearance of the triple mutant, compared to that of WT CO92, from animals was related to the decreased adherence and invasion of human-derived HeLa and A549 alveolar epithelial cells and to its inability to survive intracellularly in these cells as well as in MH-S murine alveolar and primary human macrophages. An early burst of cytokine production in macrophages elicited by the triple mutant compared to WT CO92 and the mutant's sensitivity to the bactericidal effect of human serum would further augment bacterial clearance. Together, deletion of the ail gene from the Δlpp ΔmsbB double mutant severely attenuated *Y. pestis* CO92 to evoke pneumonic plague in a mouse model while retaining the required immunogenicity needed for subsequent protection against infection. This Example is also available as Tiner et al. 2015, Infect. Immun., 83:1318-1338.

Introduction

Pathogenic yersiniae lead to two types of diseases: yersiniosis (typified by gastroenteritis caused by *Yersinia enterocolitica* and *Y. pseudotuberculosis*) (Galindo et al., 2011, J Pathog 2011:182051) and plague (evoked by *Y. pestis*) (Perry et al., 1997, Clin Microbiol Rev 10:35-66; Prentice et al., 2007, Lancet 369:1196-1207). *Y. pestis* has evolved from *Y. pseudotuberculosis* within the last 20,000 years by acquiring additional plasmids and pathogenicity islands as well as by deactivating some genes (Achtman et al., 2004, Proc Natl Acad Sci USA 101:17837-17842; Achtman et al., 1999, Proc Natl Acad Sci USA 96:14043-14048; Skurnik et al., 2000, Mol Microbiol 37:316-330). This evolutionary adaptation allowed the plague bacterium to maintain a dual life-style in fleas and rodents/mammals and conferred the ability to survive in the blood instead of the intestine (Prentice et al., 2007, Lancet 369:1196-1207). Plague manifests itself in three forms: bubonic (acquired from an infected rodent through a flea bite), pneumonic (acquired either directly by aerosol transmission from an infected host's lungs through respiratory droplets or secondarily from bubonic plague), and septicemic (severe bacteremia either directly due to a flea bite or subsequent to bubonic or pneumonic plague) (Perry et al., 1997, Clin Microbiol Rev 10:35-66). The latter two forms of plague are almost always fatal without treatment or if the administration of antibiotics is delayed (Quenee et al., 2011, Vaccine 29:6572-6583; Centers for Disease Control and Prevention, 17 Nov. 2008, Protecting the American public by ensuring safe and secure possession, use, and transfer of select agents and toxins that pose a threat to public health. CDC Select Agent Program, Centers for Disease Control and Prevention, Atlanta, Ga.). Historically, *Y. pestis* has been credited for causing three pandemics and >200 million deaths worldwide (Perry et al., 1997, Clin Microbiol Rev 10:35-66). Currently classified as a reemerging pathogen by the World Health Organization, numbers of *Y. pestis* outbreaks are increasing with current climate changes and shifting of the rodent carrier range (World Health Organization Media Center. 6 Aug. 2009. Plague: questions and answers about plague. World Health Organization, Geneva, Switzerland). *Y. pestis* is classified as a Tier-1 select agent by the Centers for Disease Control and Prevention (CDC) due to the ease of weaponizing the organism and its associated high mortality rate in humans (Centers for Disease Control and Prevention. 17 Nov. 2008. Protecting the American public by ensuring safe and secure possession, use, and transfer of select agents and toxins that pose a threat to public health. CDC Select Agent Program, Centers for Disease Control and Prevention, Atlanta, Ga.; Inglesby et al., 2000, JAMA 283:2281-2290; Pearson et al., 1998, Biological weapons proliferation: reasons for concern, courses of action. Henry L. Stimson Center, Washington, D.C.).

Braun lipoprotein (Lpp) and lipopolysaccharide (LPS) are the most abundant components of the outer membrane of Gram-negative bacteria in the Enterobacteriaceae family, to which *Y. pestis* belongs (Glauser et al., 1991, Lancet 338: 732-736; Braun et al., 1974, Annu Rev Biochem 43:89-121). Both Lpp and LPS trigger toxic and biological responses in the hosts through the interaction of their lipid domains with Toll-like receptor 2 (TLR-2) and TLR-4, respectively, and by evoking the production of inflammatory cytokines such as tumor necrosis factor (TNF-α), interleukin 6 (IL-6), and interferon gamma (IFN-γ) (Neilsen et al., 2001, J Immunol 167:5231-5239; Aliprantis et al., 1999, Science 285:736-739). Also, the complement and coagulation cascades are activated by both Lpp and LPS, and the production of other damaging inflammatory mediators contributes to the severity of infection (Neilsen et al., 2001, J Immunol 167:5231-5239; Pernerstorfer et al., 1999, Arterioscler Thromb Vasc Biol 19:2517-2523; Jacob et al., 2007, Lab Invest 87:1186-1194; Bashir et al., 2011, Int J Biochem Res Rev 1:1-13).

While Lpp links the peptidoglycan layer to the outer membrane of *Y. pestis* (Hantke et al., 1973, Eur J Biochem 34:284-296), MsbB is an acyltransferase located in the inner membrane of the bacterial cell wall and catalyzes the addition of lauric acid ($C_{12}$) to the lipid A moiety of LPS, thus increasing its biological potency (Rebeil et al., 2006, J Bacteriol 188:1381-1388; Clementz et al., 1996, J Biol Chem 271:12095-12102; Clementz et al., 1997, J Biol Chem 272:10353-10360; Somerville et al., 1996, J Clin Invest 97:359-365). *Y. pestis* synthesizes a rough LPS devoid of the O antigen and exists in different acylated forms depending upon bacterial growth temperatures (Rebeil et al., 2006, J Bacteriol 188:1381-1388; Rebeil et al., 2004, Mol Microbiol 52:1363-1373; Anisimov et al., 2007, J Med Microbiol 56:443-453; Knirel et al., 2005, Biochemistry 44:1731-1743; Pérez-Gutiérrez et al., 2010, Infect Immun 78:2768-2781; Oyston et al., 2003, J Med Microbiol 52:289-294; Montminy et al., 2006, Nat Immunol 7:1066-1073; Kawahara et al., 2002, Infect Immun 70:4092-4098). For example, lipid A of *Y. pestis* LPS shifts from a hexa-acylated form at 21° C. to 27° C. (flea temperature) to a tetra-acylated form at 37° C. (human temperature), due in part to the inactivity of MsbB at 37° C., which prevents the activation of TLR-4 (Rebeil et al., 2006, J Bacteriol 188:1381-1388; Clementz et al., 1996, J Biol Chem 271:12095-12102; Clementz et al., 1997, J Biol Chem 272:10353-10360; Somerville et al., 1996, J Clin Invest 97:359-365).

*Y. pestis* must be able to survive in the blood to establish an infection and to increase its chances of transmission, and consequently, the organism must have evolved ways to evade and disarm the host immune system. Ail (attachment-invasion locus), also referred to as OmpX, is a major contributor to serum resistance and complement evasion in *Y. pestis* (Bartra et al., 2008, Infect Immun 76:612-622; Hinnebusch et al., 2011, Infect Immun 79:4984-4989; Kolodziejek et al., 2010, Infect Immun 78:5233-5243; Kolodziejek et al., 2007, Microbiology 153:2941-2951) and accounts for 20 to 30% of the total outer membrane proteins in yersiniae at 37° C. (Myers-Morales et al., 2007, Appl Environ Microbiol 73:5750-5759; Pieper et al., 2009, Microbiology 155:498-512; Pieper et al., 2009, Proteome Sci 7:5). Ail proteins of *Y. enterocolitica* and *Y. pestis* are ~69% homologous (Kolodziejek et al., 2007, Microbiology 153:2941-2951) and bind, as well as regulate, several mediators of the complement system, e.g., complement protein 4-binding protein (Ho et al., 2012, J Immunol 188:4450-4459; Kirjavainen et al., 2008, PLoS Pathog 4:e1000140; Ho et al., 2014, Eur J Immunol 44:742-751) and complement factor H (FH) (Ho et al., 2012, J Immunol 189:3593-3599; Biedzka-Sarek et al., 2008, Infect Immun 76:4100-4109; Biedzka-Sarek et al., 2008, Infect Immun 76:5016-5027). In addition to serum resistance, Ail of *Y. pestis* facilitates the adhesion/invasion of bacteria in host cells (Kolodziejek et al., 2010, Infect Immun 78:5233-5243; Kolodziejek et al., 2007, Microbiology 153:2941-2951; Felek et al., 2009, Infect Immun 77:825-836; Tsang et al., 2010, Infect Immun 78:3358-3368; Tsang et al., 2012, J Biol Chem 287:16759-16767), inhibits inflammatory responses (Hinnebusch et al., 2011, Infect Immun 79:4984-4989; Felek et al., 2009, Infect Immun 77:825-836), and assists in the translocation of damaging *Yersinia* outer membrane proteins (Yops) to host cells (Felek et al., 2009, Infect Immun 77:825-836; Tsang et al., 2010, Infect Immun 78:3358-3368; Yamashita et al., 2011, Structure 19:1672-1682; Felek et al., 2010, Infect Immun 78:4134-4150).

In our previous study, we investigated the effects of the deletion of the lpp and msbB genes on the pathogenesis of a highly virulent *Y. pestis* CO92 strain (Sha et al., 2013, Infect Immun 81:815-828). Both Δlpp single and Δlpp ΔmsbB double mutants exhibited significant attenuation (70 to 100%) compared to the wild-type (WT) bacterium in pneumonic and bubonic plague mouse models at a dose of 3 50% lethal doses ($LD_{50}$s) (Sha et al., 2013, Infect Immun 81:815-828). Importantly, only animals initially challenged with the double mutant in a pneumonic plague model were significantly protected (55%) upon subsequent pneumonic infection with 10 $LD_{50}$s of WT CO92 (Sha et al., 2013, Infect Immun 81:815-828). The attenuated phenotype of the Δlpp ΔmsbB double mutant in mouse models correlated with its reduced survivability in murine RAW 264.7 macrophages (Sha et al., 2013, Infect Immun 81:815-828). Furthermore, the Δlpp ΔmsbB double mutant evoked reduced levels of inflammatory cytokines compared to those induced by the WT bacterium in a pneumonic plague mouse model, which coincided with overall decreased dissemination of the mutant to the peripheral organs of mice (Sha et al., 2013, Infect Immun 81:815-828). However, it is important to mention that while the Δlpp ΔmsbB double mutant was much more impaired in its ability to disseminate than the Δlpp single mutant, substantial numbers of the double mutant bacteria were still detected at the initial infection site (lungs) in some mice at 3 days postinfection (p.i.) (Sha et al., 2013, Infect Immun 81:815-828). Similarly, the Δlpp ΔmsbB double mutant persisted in the spleen of mice by day 6 p.i. when animals were challenged by the subcutaneous route (Sha et al., 2013, Infect Immun 81:815-828), suggesting the need to delete an additional virulence factor-encoding gene(s) from this Δlpp ΔmsbB double mutant to increase attenuation.

It has been reported that the virulence potential of Ail is modulated by the LPS core saccharide length and that Ail's biological activity could be masked by LPS (Kolodziejek et al., 2010, Infect Immun 78:5233-5243). However, since the LPS of *Y. pestis* lacks 0 antigen, Ail is believed to contribute significantly to the pathogenesis of *Y. pestis* infections (Skurnik et al., 2000, Mol Microbiol 37:316-330). Indeed, a recent study by Kolodziejek et al. showed that Ail of *Y. pestis* CO92 contributed to virulence in a rat model of pneumonic plague (Kolodziejek et al., 2010, Infect Immun 78:5233-5243). Thus, we aimed to determine whether a deletion of the ail gene from WT CO92 or its Δlpp single and Δlpp ΔmsbB double mutants would further attenuate the bacterium. Our data showed that the Δlpp ΔmsbB Δail triple mutant of *Y. pestis* CO92 was severely attenuated while retaining immunogenicity.

Materials and Methods

Bacterial strains and plasmids. All bacterial strains and plasmids used in this study are listed in Table 1. *Y. pestis* was grown in heart infusion broth (HIB) (Difco, Voigt Global Distribution Inc., Lawrence, Kans.) at 28° C. with constant agitation (180 rpm). On the solid surface, *Y. pestis* was grown on either HIB agar or 5% sheep blood agar (SBA) plates (Teknova, Hollister, Calif.). Luria-Bertani (LB) medium was used for growing recombinant *Escherichia coli* at 37° C. with agitation. Strains containing plasmid pBR322 or its tetracycline-sensitive (Tc$^s$) variant were grown in media with the addition of 100 μg/ml ampicillin. All of our studies were performed in a Tier-1 select-agent facility within the Galveston National Laboratory (GNL), University of Texas Medical Branch (UTMB). Restriction endonucleases and T4 DNA ligase were obtained from Promega (Madison, Wis.). Advantage cDNA PCR kits were purchased from Clontech (Palo Alto, Calif.), and all digested plasmid DNA or DNA fragments from agarose gels were purified by using QIAquick kits (Qiagen Inc., Valencia, Calif.). All tissue culture cell lines were obtained from the American Type Culture Collection (ATCC, Manassas, Va.).

TABLE 1

Bacterial strains and plasmids used in this example

| Strain or plasmid | Genotype and/or relevant characteristic(s) | Source or reference |
|---|---|---|
| Strains | | |
| *Y. pestis* CO92 | | |
| WT | Virulent WT *Y. pestis* bv. *Orientalis* strain isolated in 1992 from a fatal pneumonic plague case and naturally resistant to polymyxin B | CDC |
| WT:pBR322 | WT *Y. pestis* CO92 transformed with pBR322 (Tc$^s$) | 1 |
| WT luc2 | WT *Y. pestis* integrated with the luciferase gene (luc), used as a reporter strain | 2 |
| Δail | ail in-frame gene deletion mutant of *Y. pestis* CO92 | This study |
| Δail:pBR322 | Δail CO92 mutant transformed with pBR322 (Tc$^s$) | This study |
| Δail:pBR322-ail | Δail CO92 mutant complemented with pBR322-ail (Tc$^s$) | This study |
| Δlpp | lpp gene deletion mutant of *Y. pestis* CO92 | 3 |
| Δlpp:Tn7-lpp | Δlpp CO92 mutant complemented with lpp in cis by using targeted Tn7 | 4 |
| Δlpp Δail | lpp and ail double gene deletion mutant of *Y. pestis* CO92 | This study |
| Δlpp ΔmsbB | lpp and msbB double gene deletion mutant of *Y. pestis* CO92 | 5 |
| Δlpp ΔmsbB:pBR322 | Δlpp ΔmsbB CO92 double mutant transformed with pBR322 (Tc$^s$) | This study |
| Δlpp ΔmsbB Δail | lpp, msbB, and ail triple gene deletion mutant of *Y. pestis* CO92 | This study |
| Δlpp ΔmsbB Δail:pBR322 | Δlpp ΔmsbB Δail CO92 triple mutant transformed with pBR322 (Tc$^s$) | This study |
| Δlpp ΔmsbB Δail:pBR322-ail | Δlpp ΔmsbB Δail CO92 triple mutant complemented with pBR322-ail (Tc$^s$) | This study |
| Δpla | pla in-frame gene deletion mutant of *Y. pestis* CO92 | 1 |
| Δcafl | caf gene deletion mutant of *Y. pestis* CO92 | 6 |
| *E. coli* K-12 DH5α λpir | Strain containing the λpir gene (lysogenized with λpir phage) designed for cloning and propagation of a plasmid with the R6K origin of replication | Invitrogen |
| Plasmids | | |
| pDMS197 | Suicide vector with a conditional R6K origin of replication (ori) and a levansucrase gene (sacB) from *Bacillus subtilis*, used for homologous recombination | 7 |
| pDMS197-Δail | Recombinant plasmid containing the upstream and downstream regions surrounding the ail gene coding region along with the Km$^r$ cassette | This study |
| pKD13 | Template plasmid for PCR amplification of the Km$^r$ gene cassette flanked by FLP recombinase recombination target sites | 8 |
| pFlp2 | Vector that produces the FLP recombinase to remove the Km$^r$ gene cassette from the mutants (Ap$^r$) | 9 |
| pBR322 (native) | Cloning vector for complementation (Tc$^r$ Ap$^r$) | GE Healthcare |

TABLE 1-continued

Bacterial strains and plasmids used in this example

| Strain or plasmid | Genotype and/or relevant characteristic(s) | Source or reference |
|---|---|---|
| pBR322 (modified) | Variant of pBR322 (Tc$^s$ Ap$^r$) | 10 |
| pBR322-ail | Recombinant plasmid containing the ail gene coding region and its putative promoter inserted into the Tc$^r$ cassette in vector pBR322, used to complement the Δail mutants of *Y. pestis* CO92 (Tc$^s$) | This study |

FLP, flippase
1. van Lier et al., 2014, Infect Immun 82: 2485-2503;
2. Sha et al. 2013 Microb Pathog 55: 39-50;
3. Sha et al., 2008, Infect Immun 76: 1390-1409;
4. Agar et al., 2009, Microbiology 155: 3247-3259;
5. Sha et al., 2013, Infect Immun 81: 815-828;
6. Sha et al., 2011, J Clin Microbiol 49: 1708-1715;
7. Edwards et al., 1998, Gene 207: 149-157;
8. Datsenko et al., 2000, Proc Natl Acad Sci USA 97: 6640-6645;
9. Choi et al., 2005, BMC Microbiol 5: 30;
10. Galindo et al., 2010, Comp Funct Genomics 2010: 342168

Deletion of the ail gene. The up- and downstream DNA sequences flanking the ail gene were PCR amplified by using primer pairs Aup5-Aup3 and Adn5-Adn3 (Table 2), respectively, with genomic DNA of *Y. pestis* CO92 as the template. Additionally, primer pair Km5-Km3 (Table 2), specific for plasmid pKD13, was used to amplify the kanamycin resistance (Km$^r$) gene cassette with flippase (FLP) recombinase recognition sites (Choi et al., 2005, BMC Microbiol 5:30; Datsenko et al., 2000, Proc Natl Acad Sci USA 97:6640-6645). The upstream DNA fragment flanking the ail gene, the Km$^r$ gene cassette, and the downstream DNA fragment flanking the ail gene were ligated in that order by using appropriate restriction enzyme sites and cloned into the pDMS197 suicide vector (Edwards et al., 1998, Gene 207:149-157). The resulting recombinant plasmid, pDMS197-Δail (Table 1), was then transformed into the WT strain, the Δlpp single mutant, and the Δlpp ΔmsbB double mutant of *Y. pestis* CO92 via electroporation (Genepulser Xcell; Bio-Rad, Hercules, Calif.). Transformants were plated onto LB agar plates containing 5% sucrose and 100 μg/ml kanamycin, and Km$^r$ colonies were screened by using PCR to ensure genomic replacement of the ail gene with the antibiotic-resistant cassette. The correct clones were retransformed with plasmid pFlp2, which contains the FLP recombinase, to remove the Km$^r$ gene cassette. Plasmid pFlp2 was eventually cured by growing colonies on 5% sucrose (Sha et al., 2013, Infect Immun 81:815-828), leading to the generation of the single (Δail), double (Δlpp Δail), and triple (Δlpp ΔmsbB Δail) mutants. Subsequent PCR analysis with primer pairs (Up5-Dn3 and Ail5-Ail3) and genomic sequencing with primer SqAil (Table 2) further confirmed the in-frame deletion of the ail gene from all three mutant strains.

TABLE 2

Sequences of primers used in this example.

| Primer pair or primer | Primer sequence (5'-3') (restriction enzyme) | Purpose |
|---|---|---|
| Aup5-Aup3 | TATGAGCTCACGACGCACAAGACTCTGGC (SacI)- (SEQ ID NO: 3)<br>AACGGATCCCCATCCAGATTGTTATAAC (BamHI) (SEQ ID NO: 4) | PCR amplification of the upstream DNA fragment flanking the ail gene of *Y. pestis* CO92 |
| Adn5-Adn3 | ATGAAGCTTCCTAACGTCCTCCTAACCATG (HindIII)- (SEQ ID NO: 5)<br>GCATCCGTCAAT GGTACCAG (KpnI) (SEQ ID NO: 6) | PCR amplification of the downstream DNA fragment flanking the ail gene of *Y. pestis* CO92 |
| Km5-Km3 | ATTCCGGGGATCCGTCGACC (BamHI)- (SEQ ID NO: 7)<br>CTTAAGCTTGTGTAGGCTGGAGCTGCTTC (HindIII) (SEQ ID NO: 8) | PCR amplification of the Km$^r$ gene cassette with FLP recombinase recognition target sites from plasmid pKD13 at both ends |
| Up5-Dn3 | ATGCCCACATCGTTACCACC- (SEQ ID NO: 9)<br>CCGTAATCCATGGTGATCTG (SEQ ID NO: 10) | ail mutant verification primers located outside the flanking DNA sequences of the ail gene on the chromosome that were used for generating the ail mutants of *Y. pestis* CO92 |
| Ail5-Ail3 | TAATGTGTATGCCGAAGGC- (SEQ ID NO: 11)<br>TTGGAGTATTCATATGAAGC (SEQ ID NO: 12) | PCR amplification of the coding region of the ail gene from *Y. pestis* CO92 |
| Apbr5-Apbr3 | CGGGATCCCGCAAGGTCAATGGGGCTATTG (BamHI)- (SEQ ID NO: 13)<br>ACGCGTCGACTTAGAACCGGTAACCCGCGC (SalI) (SEQ ID NO: 14) | PCR amplification of the ail gene of *Y. pestis* CO92 including its promoter for integration into the pBR322 vector for complementation |

TABLE 2-continued

Sequences of primers used in this example.

| Primer pair or primer | Primer sequence (5'-3') (restriction enzyme) | Purpose |
|---|---|---|
| SqAil | GGAATACTGTACGAATATCC (SEQ ID NO: 14) | Primer located 108 bp upstream of the ail gene; used to confirm the in-frame deletion of the ail gene by chromosomal DNA sequencing |

Underlining indicates restriction enzyme sites.

Complementation of the Δail mutant strains of *Y. pestis* CO92. By using primers Apbr5-Apbr3 (Table 2), the coding region of the ail gene with its promoter was PCR amplified with genomic DNA of WT CO92 as the template. The amplified DNA fragment was cloned into the pBR322 vector, creating recombinant plasmid pBR322-ail (Table 1). Through electroporation, plasmid pBR322-ail was transformed into the Δail single and Δlpp ΔmsbB Δail triple mutant strains, resulting in the creation of the complemented Δail:pBR322-ail and Δlpp ΔmsbB Δail:pBR322-ail *Y. pestis* strains (Table 1). These complemented strains were sensitive to tetracycline due to the replacement of a large portion of the tetracycline resistance (Tc$^r$) cassette from plasmid pBR322 with the ail gene. The Tc$^s$ variant of the pBR322 vector (Galindo et al., 2010, Comp Funct Genomics 2010: 342168) without the ail gene was also electroporated into WT CO92 and the Δail single, Δlpp ΔmsbB double, and Δlpp ΔmsbB Δail triple mutants for generating empty vector controls (e.g., WT:pBR322, Δail:pBR322, Δlpp ΔmsbB: pBR322, and Δlpp ΔmsbB Δail:pBR322, respectively) (Table 1).

Absence of Ail and unchanged levels of Lpp in the membranes of *Y. pestis* CO92 Δail mutants. The generated mutant strains were grown overnight in HIB medium at 28° C. with shaking at 180 rpm, and the resulting bacterial cell pellets (representing similar CFU) were dissolved by boiling in SDS-PAGE sample buffer. An aliquot of the samples was then analyzed by immunoblotting using polyclonal antibodies to Ail and monoclonal antibodies to Lpp that were available in the laboratory (Erova et al., 2013, Clin Vaccine Immunol 20:227-238; Sha et al., 2008, Infect Immun 76:1390-1409). As a loading control for the Western blots, the presence of DnaK in the bacterial pellets of the mutants and WT CO92 was assessed by using anti-DnaK monoclonal antibodies (Enzo, Farmingdale, N.Y.).

Growth kinetics and membrane alteration of the *Y. pestis* CO92 triple mutant.WT CO92 and its Δlpp ΔmsbB Δail triple mutant were grown in 100 ml of HIB medium contained in 500-ml HEPA filter Top polycarbonate Erlenmeyer culture flasks (Triforest Labware, Irvine, Calif.) at 28° C. with constant shaking (180 rpm). Samples from each flask were taken at 1- to 2-h intervals until the cultures reached their plateau phases. CFU were determined by plating (Sha et al., 2011, J Clin Microbiol 49:1708-1715). For visualization of membrane alterations, bacterial strains were grown to exponential phase at 28° C. (optical density at 600 nm [OD$_{600}$] of 0.6). The cells were washed, pelleted, fixed, and subjected to transmission electron microscopy (van Lier et al., 2014, Infect Immun 82:2485-2503).

Sensitivity of the *Y. pestis* CO92 mutants to gentamicin. The MICs of gentamicin against WT *Y. pestis* CO92: pBR322 and the Δail:pBR322, Δail::pBR322-ail, Δlpp ΔmsbB:pBR322, Δlpp ΔmsbB Δail:pBR322, and Δlpp ΔmsbB Δail:pBR322-ail mutants were determined by an E-test (bioMérieux Inc., Durham, N.C.) (Sha et al., 2013, Infect Immun 81:815-828). Briefly, the bacterial cultures were spread evenly onto 5% SBA and LB agar plates, and predefined gentamicin (range, 0.016 to 256 µg/ml) E-test strips were placed onto the plates. The plates were incubated for 48 h at 28° C., and the MICs were recorded.

Evaluation of essential *Y. pestis* virulence factors in various mutants of *Y. pestis* CO92. The intactness and functionality of the type 3 secretion system (T3SS), crucial for plague pathogenesis and immunity, were then evaluated. Through the T3 SS, the plague bacterium secretes Yops such as YopE, YopH, and LcrV (low-calcium-response V antigen) in response to a low-calcium signal. Consequently, WT CO92 and Δail single, Δlpp ΔmsbB double, and Δlpp ΔmsbB Δail triple mutant cultures grown overnight were diluted 1:20 and grown in either HIB or calcium-depleted modified M9 medium (42 mM Na$_2$HPO$_4$, 22 mM KH$_2$PO$_4$, 8.6 mM NaCl, 18.6 mM NH$_4$Cl, 0.001 mg/ml FeSO$_4$, 0.0001% thiamine, 1 mM MgSO$_4$, 0.4% dextrose, and 1% Casamino Acids) at 28° C. with shaking (180 rpm) for 3 h and then at 37° C. for 2 h.

When the bacteria were grown in HIB, 5 mM EGTA (Sigma-Aldrich, St. Louis, Mo.) was added to trigger the low-calcium response 5 min before harvesting of the cultures. Aliquots of the cultures grown in either medium (representing similar CFU) were removed, and 1 ml of the supernatants was precipitated with 55 ρl of 100% trichloroacetic acid (TCA) on ice for 2 h. The TCA precipitates were dissolved in SDS-PAGE buffer and analyzed by immunoblotting with antibodies to YopE, LcrV (Santa Cruz Biotechnology, Santa Cruz, Calif.), and YopH (Agrisera, Stockholm, Sweden) (Sha et al., 2013, Infect Immun 81:815-828; Sha et al., 2008, Infect Immun 76:1390-1409; van Lier et al., 2014, Infect Immun 82:2485-2503). The anti-DnaK monoclonal antibody (Enzo) was employed to probe bacterial pellets to ensure that the bacterial supernatants were obtained from similar numbers of bacteria across the tested strains.

To evaluate the translocation of T3SS effectors by the *Y. pestis* mutants, a digitonin extraction assay was used (Sha et al., 2008, Infect Immun 76:1390-1409). Briefly, *Y. pestis* cultures grown overnight in HIB were diluted in Dulbecco modified Eagle medium (DMEM) with 10% fetal bovine serum (FBS). The diluted bacteria were cultivated at 28° C. for 30 min and then at 37° C. for 60 min. HeLa cells (in a 12-well plate) were then infected with the above-described *Y. pestis* cultures at a multiplicity of infection (MOI) of 30. After 4 h of infection at 37° C., the cells were washed twice with phosphate-buffered saline (PBS) and lysed with 200 µl of digitonin (1% in PBS). The cells were dislodged from the surface of the plate, collected, and centrifuged at 13,000 rpm for 5 min to obtain the supernatant and the pellet fractions.

The YopE polyclonal antibodies were then used to detect YopE in both the fractions, while anti-actin (Santa Cruz Biotechnology) and anti-DnaK monoclonal antibodies were employed for the supernatant and pellet fractions, respectively, to monitor equivalent sample loading during Western blot analyses.

For examining capsular antigen (F1) production by WT CO92 and its triple mutant, bacteria grown at 37° C. were subjected to a commercially available plague detection kit, the *Yersinia pestis* (F1) Tetracore RedLine Alert kit (Tetracore, Rockville, Md.), as we previously described (Sha et al., 2011, J Clin Microbiol 49:1708-1715). A Δcaf1-negative mutant of CO92 devoid of F1 antigen was used as a control (Sha et al., 2011, J Clin Microbiol 49:1708-1715). We further analyzed F1 production by WT CO92 and its triple mutant by flow cytometry (Sha et al., 2011, J Clin Microbiol 49:1708-1715). Briefly, the above-mentioned *Y. pestis* cultures ($10^6$ CFU/sample) were fixed with 4% paraformaldehyde. After being washed with PBS, the bacteria were incubated with a primary antibody to the F1 antigen (Santa Cruz Biotechnology), followed by a secondary antibody (goat anti-mouse IgG1) conjugated with Alexa Fluor 488. The bacterial cells were then washed and resuspended in 500 μl of fluorescence-activated cell sorter (FACS) buffer (1% FBS in PBS) before analysis. Samples were read on an LSRII Fortessa instrument (UTMB Core Facility) and analyzed with FlowJo software. We also examined F1 production by WT CO92, the Δcaf1-negative mutant, and the Δlpp ΔmsbB Δail triple mutant by immunofluorescence (IF) staining using anti-F1 antibodies and microscopy (Sha et al., 2011, J Clin Microbiol 49:1708-1715).

The Pla (plasminogen activator) surface protease of *Y. pestis* is a multifunctional protein that contributes to bacterial adherence to host cells, intracellular survival, complement resistance, and bacterial dissemination by virtue of possessing fibrinolytic and coagulase activities (Felek et al., 2010, Infect Immun 78:4134-4150; van Lier et al., 2014, Infect Immun 82:2485-2503; Sebbane et al., 2006, Proc Natl Acad Sci USA 103:11766-11771; Sodeinde et al., 1992, Science 258:1004-1007; Agar et al., 2009, Microbiology 155:3247-3259; Cowan et al., 2000, Infect Immun 68:4523-4530; Korhonen et al., 2013, Front Cell Infect Microbiol 3:35; Caulfield et al., 2014, Cell Host Microbe 15:424-434). To examine whether the deletion of three membrane protein-encoding genes (lpp, msbB, and ail) from WT CO92 altered Pla levels, we performed Western blot analysis. The various *Y. pestis* strains grown overnight were diluted 1:20 in fresh HIB and grown at 28° C. with shaking (180 rpm) for 3 h and then at 37° C. for 2 h. The bacterial cell pellets were harvested and dissolved in SDS-PAGE sample buffer. An aliquot of the samples was then analyzed by immunoblotting using polyclonal antibodies to Pla that were available in the laboratory (Erova et al., 2013, Clin Vaccine Immunol 20:227-238). The anti-DnaK monoclonal antibody was also employed to monitor equivalent sample loading during Western blot analyses.

To ensure that Pla was properly displayed on the bacterial surface and enzymatically active, we measured its protease activity by using a fluorimetric assay with the Pla substrate (Agarkov et al., 2008, Bioorg Med Chem Lett 18:427-431). Briefly, all of the tested strains were plated onto HIB agar plates at 28° C. for 36 h. The strains were then replated onto fresh HIB agar plates and incubated at either 28° C. or 37° C. (representing flea and human body temperatures, respectively) for 20 to 22 h. Bacteria from each plate were suspended in PBS and adjusted to optical densities ($OD_{600}$) of 0.1 ($5\times10^7$ CFU/ml) and 0.5 ($2.5\times10^8$ CFU/ml) by using a Bio-Rad SmartSpec 300 instrument. For each strain, 50 μl of the suspension was added to the wells of a black microtiter plate (Costar Corning Inc., Corning, N.Y.) in triplicate. The hexapeptide substrate 4-{[4'-(dimethylamino)phenyl]azo}benzoic acid (DABCYL)-Arg-Arg-Ile-Asn-Arg-Glu{5-[(2'-aminoethyl)amino]naphthalene sulphonic acid (EDANS)}-$NH_2$, at a final concentration of 2.5 μg/well, was added to the bacterial cells. The kinetics of substrate cleavage by Pla displayed on the bacterial surface was measured every 15 min for 2 h by a fluorimetric assay (extinction/emission wavelength of 360 nm/460 nm) at 37° C. by using a BioTek Synergy HT spectrophotometer (BioTek Instruments Inc., Winooski, Vt.).

Animal studies with the *Y. pestis* CO92 mutant strains. Six- to eight-week-old female Swiss Webster mice (17 to 20 g) were purchased from Taconic Laboratories (Germantown, N.Y.). All of the animal studies were performed in an animal biosafety level 3 (ABSL-3) facility under an approved UTMB Institutional Animal Care and Use Committee protocol. Mice were challenged intranasally (i.n.) with $1.3\times10^4$ CFU (representing 26 50% lethal doses [$LD_{50}$s] of the WT bacterium, with 1 $LD_{50}$ corresponding to 500 CFU [van Lier et al., 2014, Infect Immun 82:2485-2503]) of WT CO92 or the Δail single, Δlpp ΔmsbB or Δlpp Δail double, or Δlpp ΔmsbB Δail triple mutant strain. Also, the animals were challenged by the i.n. route with the Δlpp ΔmsbB Δail triple mutant at higher doses of $4.0\times10^4$, $1.7\times10^5$, $5.9\times10^5$, $1.8\times10^6$, and $3.4\times10^6$ CFU (corresponding to 80, 340, 1,180, 3,600, and 6,800 $LD_{50}$s of WT CO92). Mice were assessed for morbidity and/or mortality as well as clinical symptoms over the duration of each experiment (24 to 30 days p.i.).

Survivors after initial infection with the mutants were subsequently challenged with $1\times10^4$ to $1.4\times10^4$ CFU (20 to 28 $LD_{50}$s) of the bioluminescent WT *Y. pestis* CO92 luc2 strain (Sha et al., 2013, Microb Pathog 55:39-50), which contains the luciferase (luc) gene and its substrate, allowing in vivo imaging of mice in terms of bacterial dissemination in real time. Naive mice of the same age and infected with the WT CO92 luc2 strain were used as controls. On day 3 and/or day 7 p.i., the animals were imaged by using an Ivis 200 bioluminescence and fluorescence whole-body imaging workstation (Caliper Corp., Alameda, Calif.) in the ABSL-3 facility.

Bacterial dissemination and histopathological studies of the triple mutant of *Y. pestis* CO92. Mice infected with $2.5\times10^6$ CFU (representing 5,000 $LD_{50}$s of WT CO92) of the Δlpp ΔmsbB Δail triple mutant or WT CO92 by the i.n. route were euthanized by using a mixture of ketamine and xylazine, followed by cervical dislocation on days 2, 3, and 6 p.i. For each time point, five mice per group were used, and the lungs, liver, and spleen were removed immediately following animal sacrifice. Blood was collected from these animals by cardiac puncture. The tissues were homogenized in 1 ml of PBS, and serial dilutions of the homogenates were spread onto SBA plates to assess dissemination of the bacteria to peripheral organs (Sha et al., 2013, Infect Immun 81:815-828).

Portions of each organ (lung, liver, and spleen) from 5 mice at each time point were also removed and immersion fixed in 10% neutral buffered formalin (Sha et al., 2008, Infect Immun 76:1390-1409; Agar et al., 2009, Microbiology 155:3247-3259). The tissues were processed and sectioned at 5 μm, and the samples were mounted onto slides and stained with hematoxylin and eosin (H&E). Tissue lesions were scored on the basis of a severity scale, which correlated with estimates of lesion distribution and the extent of tissue involvement (minimal, 2 to 10%; mild, >10 to 20%; moderate, >20 to 50%; severe, >50%), as previously described (Sha et al., 2008, Infect Immun 76:1390-1409; Agar et al., 2009, Microbiology 155:3247-3259). The histopathological evaluation of the tissue sections was performed in a blind fashion.

Cytokine and chemokine levels and antibody responses in mice infected with the triple mutant of *Y. pestis* CO92. Concurrently, blood was collected from infected (with WT CO92 versus the Δlpp ΔmsbB Δail triple mutant) animals on days 2, 3, and 6 p.i. (for cytokine analysis). Blood was also collected from all animals prior to infection and on day 14 p.i. to determine antibody responses. Serum samples were filtered by using Costar 0.1-μm centrifuge tube filters (Corning Inc.). The levels of cytokines/chemokines, namely, IL-12, IFN-γ, IL-4, IL-5, IL-6, and TNF-α, in sterile serum samples were analyzed by using a mouse 6-plex Bioplex assay (eBioscience, San Diego, Calif.).

Total levels of IgG and antibody isotypes in the sera of animals infected with the Δlpp ΔmsbB Δail triple mutant were determined at 14 days p.i. by an enzyme-linked immunosorbent assay (ELISA). Briefly, ELISA plates were coated with either the F1-V fusion protein (1 ng/ml; BEI Resources, Manassas, Va.) or whole bacterial cells of WT CO92 overnight at 4° C. For the whole-bacterial-cell ELISA, microtiter plates were first coated with poly-L-lysine (10 μg/ml), as we previously described (Tao et al., 2013, PLoS Pathog 9:e1003495).

The sera were serially diluted (either 1:5 or 1:10), and horseradish peroxidase (HRP)-conjugated secondary antibodies were used to determine total IgG titers and IgG isotype responses by employing goat anti-mouse IgG-HRP, IgG1-HRP, IgG2a-HRP, and IgG2b-HRP (SouthernBiotech, Birmingham, Ala.). The substrate 3,3',5,5'-tetramethylbenzidine (TMB) (ThermoScientific, Waltham, Mass.) was used for color development, and the plates were read at 450 nm by using a spectrophotometer (Tao et al., 2013, PLoS Pathog 9:e1003495).

Serum resistance of various mutants of *Y. pestis* CO92. Normal human and mouse sera were purchased from Sigma-Aldrich, and nonhuman primate (NHP) sera were collected from naive animals that were housed at the GNL. Prior to use, an aliquot of each serum sample was also heated at 56° C. for 30 min to inactivate complement and served as a control. WT CO92:pBR322, Δail:pBR322, Δlpp ΔmsbB: pBR322, Δlpp ΔmsbB Δail:pBR322, Δail:pBR322-ail, and Δlpp ΔmsbB Δail:pBR322-ail strains were grown overnight, harvested, and then diluted in PBS to an $OD_{600}$ of 0.8 ($\sim 4 \times 10^8$ CFU/ml). A 50-μl volume of the diluted bacteria ($\sim 2 \times 10^7$ CFU) was mixed with 200 μl of either normal (unheated) or heated sera. The samples were incubated at 37° C. for 2 h with shaking at 500 rpm. The number of surviving bacteria (CFU) in each sample was determined by serial dilutions and plating onto SBA plates (Sha et al., 2013, Infect Immun 81:815-828; van Lier et al., 2014, Infect Immun 82:2485-2503). Percent bacterial survival was calculated by dividing the average number of CFU in samples incubated in normal serum by the average number of CFU in samples incubated in heat-inactivated serum and multiplying by 100.

Adherence, invasion, and intracellular survival of various *Y. pestis* CO92 mutants in HeLa and A549 epithelial cells. Twelve-well tissue culture plates were seeded with either HeLa (from human cervix) or A549 (human alveolar) epithelial cells at a concentration of $4 \times 10^5$ cells in 1 ml of DMEM, 10% FBS (HeLa) or F-12K (Kaighn's) medium, and 10% FBS (A549) (Cowan et al., 2000, Infect Immun 68:4523-4530; Liu et al., 2006, Infect Immun 74:5636-5644). The cells were incubated at 37° C. in 5% $CO_2$ until a confluent monolayer was established.

Bacterial strains grown overnight were used to infect host cells at an MOI of 100. The plates were centrifuged at 1,200 rpm for 10 min to ensure bacterial contact with the host cells. After 2 h of incubation, one set of the triplicate wells was not washed, and the total numbers of bacteria used for infection that were present in the culture medium and those adhering to and/or invading the host cells were recovered by scraping and vortexing the host cells. Another set of triplicate wells was gently washed twice with 1 ml of Dulbecco phosphate-buffered saline (DPBS), and the adherent and invading bacteria in the host cells were then enumerated after lysing epithelial cells with 1 ml of ice-cold water.

The last set of the host cells was similarly washed twice with DPBS, and a gentamicin (50 μg/ml) protection assay was used to discriminate between invading and extracellular bacteria (Cowan et al., 2000, Infect Immun 68:4523-4530). After 1 h of incubation in gentamicin-containing medium to kill extracellular bacteria, the host cells were washed twice with 1 ml of DPBS, and intracellular bacteria were then enumerated after the addition of 1 ml of ice-cold water to each well (Cowan et al., 2000, Infect Immun 68:4523-4530). The percentages of invasion and adhesion were then determined.

The intracellular survival of various CO92 mutants in HeLa and A549 cells was assessed in a manner similar to that described above for the invasion assay. The 0-h samples corresponded to a time point immediately after gentamicin treatment. The intracellular bacteria in HeLa and A549 cells were then enumerated by serial dilution and plating after 12 h of incubation in medium containing 10 μg/ml gentamicin (Sha et al., 2008, Infect Immun 76:1390-1409).

Survival of WT *Y. pestis* CO92 and its mutant strains in murine alveolar macrophages and human monocyte-derived macrophages and production of cytokines. Murine MH-S alveolar macrophages were infected with WT CO92 and its mutant strains at an MOI of 10. After 30 min of infection, the host cells were treated for 45 min with 20 μg/ml gentamicin to kill extracellular bacteria. The surviving bacteria inside the macrophages were then enumerated immediately after gentamicin treatment (0-h time point) and subsequently at 2 and 4 h of incubation in medium containing 10 μg/ml gentamicin. The number of bacteria present inside the macrophages was determined by serial dilution and plating (Sha et al., 2008, Infect Immun 76:1390-1409).

Human buffy coats were obtained from three different healthy individuals in 10-ml Vacutainer tubes without additive (Becton Dickinson Labware, Franklin Lakes, N.J.) from the UTMB blood bank. The EDTA-treated blood was handled under endotoxin-free conditions and diluted 1:1 with PBS, and peripheral blood mononuclear cells (PBMCs) were purified by centrifugation over a Ficoll-sodium diatrizoate solution (Ficoll-Paque Plus; GE Healthcare Bio-Sciences AB, Uppsala, Sweden). Monocytes were then purified from PBMCs by positive selection using human CD14 microbeads and a magnetic column separation system from Miltenyi Biotec (Auburn, Calif.). Monocyte-derived macrophages were subsequently differentiated from purified $CD14^+$ monocytes.

Briefly, monocytes were cultured in RPMI 1640 medium supplemented with 10% FBS, 1-glutamine, HEPES, sodium pyruvate, penicillin-streptomycin, and granulocyte-macrophage colony-stimulating factor (GM-CSF) (100 ng/ml) (Leukine [sargramostim]; Genzyme Corp., Cambridge, Mass.). Monocytes were seeded into 24-well tissue culture plates at $10^6$ cells/ml, and adherent monocyte-derived macrophages were obtained at 6 days of culture.

These human monocyte-derived macrophages (HMDMs) were infected with WT CO92 and its mutant strains at an MOI of 1. The infected macrophages were incubated at 37° C. with 5% $CO_2$ for 45 min, followed by 1 h of treatment with 10 µg/ml gentamicin. The surviving bacteria inside the macrophages were enumerated immediately after gentamicin treatment (0-h time point) and subsequently at 2 h and 4 h (Sha et al., 2008, Infect Immun 76:1390-1409). The concentration of gentamicin used in the gentamicin protection assay was optimized for each host cell type used in this study.

Supernatants from infected macrophages during the intracellular survival assay were collected at each of the time points tested and filtered. A Bio-Rad mouse 6-plex assay kit (IL-1β, IFN-γ, IL-10, IL-17, IL-6, and TNF-α) or a Bio-Rad human 8-plex assay kit (GM-CSF, IFN-γ, IL-2, IL-4, IL-6, IL-8, IL-10, and TNF-α) was used to measure cytokine and chemokine levels.

Statistical analysis. For the majority of the experiments, one-way analysis of variance (ANOVA) was used with the Bonferroni correction, except for the intracellular survival experiments, in which Tukey's post hoc test was employed for data analysis. We used Kaplan-Meier survival estimates for animal studies, and P values of <0.05 were considered significant for all of the statistical tests used.

Results

In vitro characterization of Δail mutants of *Y. pestis* CO92. The in-frame deletion of the ail gene from WT CO92 and the Δlpp single and Δlpp ΔmsbB double mutants of *Y. pestis* CO92 was confirmed by PCR analysis using specific primers (Table 2) as well as by DNA sequencing of the flanking regions of the ail gene on the chromosome. The above-mentioned genetic manipulations resulted in the creation of authentic Δail single, Δlpp Δail double, and Δlpp ΔmsbB Δail triple mutants of *Y. pestis* CO92. As shown in FIG. 1A, Ail-specific antibodies detected the correct-sized protein in WT CO92 and its Δlpp ΔmsbB double mutant but not in the Δail single, Δlpp Δail double, and Δlpp ΔmsbB Δail triple isogenic mutants. Importantly, deletion of the ail gene from WT CO92 did not affect the production of Lpp (FIG. 1A).

Since both Ail and Lpp are outer membrane proteins and the MsbB acyltransferase modifies LPS, WT CO92 and its Δlpp ΔmsbB Δail triple mutant were subjected to transmission electron microscopy to evaluate if there were any membrane alterations. Except for finding that the Δlpp ΔmsbB Δail triple mutant had somewhat decreased periplasmic space compared to that of WT CO92 (FIG. 1B), no other abnormalities were apparent. The growth kinetics of the triple mutant was also examined, and the Δlpp ΔmsbB Δail triple mutant entered log phase at an earlier time point and grew faster initially than did WT CO92; however, both strains had similar CFU by 16 h (see FIG. 14).

Figure 2:
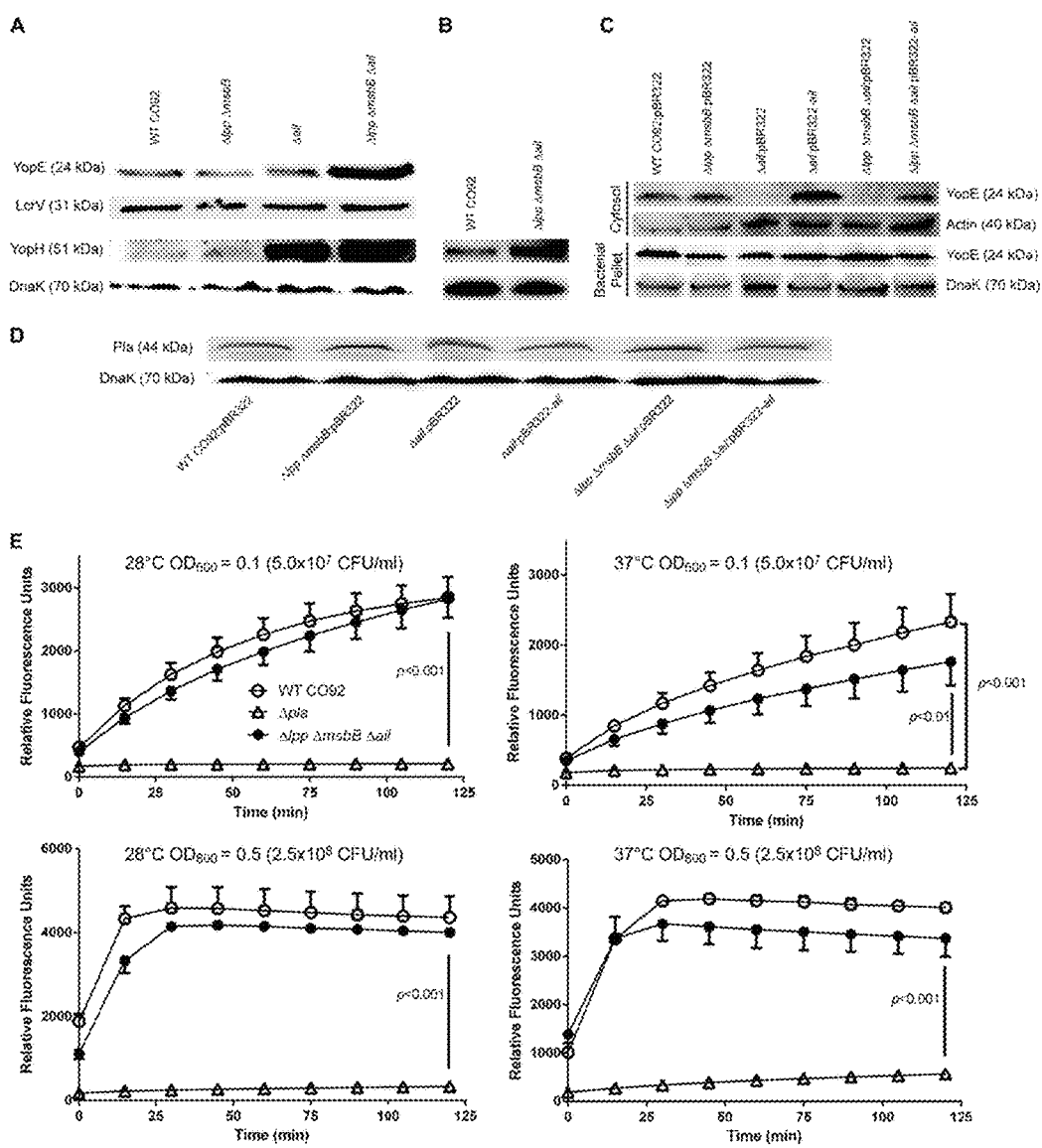
FIG. 2. Functionality of the T3SS and production/enzymatic activity of the Pla protease. Cultures of various *Y. pestis* strains grown in HIB overnight were diluted 1:20 in modified M9 medium or fresh HIB, and growth was continued at 28° C. for 3 h, followed by an additional 2 h of incubation at 37° C. (A and B) The production of YopH, LcrV, and YopE in M9 medium (A) or YopH in M9 chelated for calcium (B) was measured by Western blotting using specific antibodies. Anti-DnaK antibodies were employed to examine bacterial pellets to ensure that bacterial supernatants were obtained from similar numbers of bacteria across the tested strains. For the translocation studies, cultures of various *Y. pestis* strains grown overnight in HIB were diluted and sensitized to DMEM by growth at 28° C. for 30 min, followed by an additional 1 h of incubation at 37° C. HeLa cells were then infected with the above-mentioned cultures at an MOI of 30. (C) After 4 h of infection, the cytosolic fraction of the host cells was separated from the pellet and probed with anti-YopE antibodies. Anti-actin and anti-DnaK antibodies were also used on the supernatant and pellet fractions, respectively, to monitor equal loading of the samples during Western blot analyses. (D) Pla production in various *Y. pestis* CO92 stains was examined with specific antibodies to Pla, and anti-DnaK antibodies were used as a loading control. For measurement of Pla activity, the tested *Y. pestis* CO92 strains were mixed with the Pla substrate [DABCYL-Arg-Arg-Ile-Asn-Arg-Glu(EDANS)-NH$_2$], and the kinetics of substrate cleavage was measured. The Δpla single mutant of CO92 was employed as a negative control during the assay. (E) The kinetics of each reaction is plotted as arithmetic means±standard deviations. Statistical analysis of Pla activity data was performed by one-way ANOVA with a Bonferroni post hoc test. Statistically significant P values between the groups are indicated by a vertical line.

The Δlpp ΔmsbB Δail triple mutant of *Y. pestis* CO92 produces essential *Y. pestis* virulence and immunogenic factors. The T3 SS is an essential virulence mechanism in *Y. pestis*. Through the T3 SS, an immunoreactive antigen (LcrV) as well as other Yops such as YopE and YopH (which destroy actin monofilaments and interfere with phagocyte signal transduction machinery, respectively) are secreted. Therefore, T3 SS-dependent protein secretion in response to a low-calcium signal was measured for the generated ail mutants. This in vitro assay mimics the environment during eukaryotic host cell contact with the bacterial T3SS needles. In calcium-depleted M9 medium, the Δlpp ΔmsbB Δail triple mutant showed significantly increased levels of YopH and YopE in the culture supernatants compared to those of WT CO92 and its Δlpp ΔmsbB double mutant (FIG. 2A). While an increased level of YopH in the supernatant of the Δail single mutant was also noted, the YopE level in the culture medium was not as pronounced as those of the Δlpp ΔmsbB double mutant and WT CO92 (FIG. 2A). There was no significant difference in the levels of LcrV in the culture supernatants across the strains tested (FIG. 2A).

Figure 5:
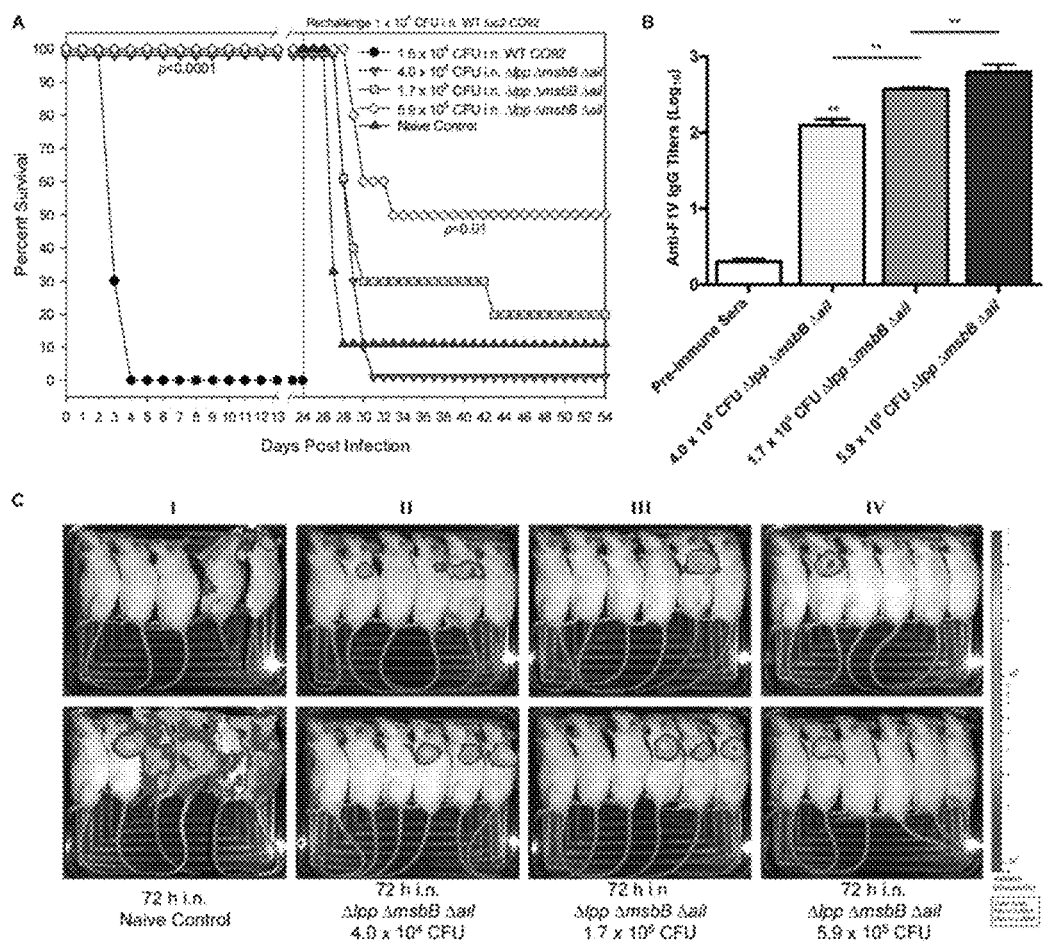
FIG. 5. Virulence potential of and subsequent protection conferred by the Δlpp ΔmsbB Δail triple mutant of *Y. pestis* CO92 in a pneumonic plague mouse model. (A) Female Swiss Webster mice (n=9 or 10/group) were challenged with the indicated doses of the Δlpp ΔmsbB Δail triple mutant or 1.6×10$^4$ CFU of WT *Y. pestis* CO92 by the i.n. route. The surviving animals and age-matched naive mice were then rechallenged on day 24 p.i. with 1×10$^4$ CFU of the WT CO92 luc2 strain. Statistically significant P values are for comparisons to WT CO92-infected mice during the initial challenge or to naive control animals during WT CO92 luc2 rechallenge. (B) Total IgG responses to the F1-V antigen were examined in sera at day 14 after initial infection. ** indicates statistical significance (P<0.001) compared to preimmune serum or between different doses of the triple mutant used for initial infection. (C) The animals after rechallenge were imaged at 72 h for bioluminescence. The bioluminescence scale is shown at the right and ranges from most intense (red) to least intense (violet). The animal on the left of each imaging panel represents an uninfected control.

To demonstrate that the higher level of the specific effector YopH observed in the culture supernatant of the Δlpp ΔmsbB Δail triple mutant (FIG. 2A) was not due to the leakiness of the bacterial cell membrane and the T3 SS itself, we examined the secretion of YopH by the triple mutant grown in HIB medium after induction of a low-calcium signal. As shown in FIG. 2B, 5 min after the addition of EGTA, YopH was detected in the supernatants of WT CO92 and its Δlpp ΔmsbB Δail triple mutant; however, no detectable level of YopH was present in uninduced culture supernatants (data not shown). Importantly, compared to the WT bacterium, there was a significant increase in the level of YopH in the supernatant of the Δlpp ΔmsbB Δail triple mutant (FIG. 2B).

To simulate in vivo conditions and to measure the translocation of Yops, HeLa cells were infected with various mutant strains of *Y. pestis*. A digitonin extraction assay was used to evaluate the translocation of YopE into the host cells. While WT CO92 and Δlpp ΔmsbB mutant bacteria had similar levels of YopE translocation, the ail deletion mutants (both Δail and Δlpp ΔmsbB Δail) had significantly decreased translocation of YopE into the cytosol of the host cells (FIG. 2C). YopE translocation was restored in the ail deletion mutants when complemented with the corresponding gene in trans (FIG. 2C). The decreased level of YopE translocation from the ail deletion mutants was not due to differential expression of the yopE gene or the number of bacteria that were used to infect HeLa cells, as all of the strains had similar levels of YopE and DnaK in the cell pellet fraction (FIG. 2C).

Pla, another important virulence factor of *Y. pestis*, is a multifunctional protein (Felek et al., 2010, Infect Immun 78:4134-4150; van Lier et al., 2014, Infect Immun 82:2485-2503; Sebbane et al., 2006, Proc Natl Acad Sci USA 103:11766-11771; Sodeinde et al., 1992, Science 258:1004-1007; Agar et al., 2009, Microbiology 155:3247-3259; Cowan et al., 2000, Infect Immun 68:4523-4530). To evaluate whether the levels of Pla remained unaltered in the Δail mutants, Western blot analysis was performed. Essentially, similar levels of the Pla protein were noted for the various mutant strains tested (Δail single, Δlpp ΔmsbB double, Δlpp ΔmsbB Δail triple, as well as ail-complemented mutant strains) compared to that of WT CO92 at 37° C., a temperature that increases Pla production and activity (Pieper et al., 2009, Microbiology 155:498-512; Chromy et al. 2005 J Bacteriol 187:8172-8180; Suomalainen et al., 2010, Infect Immun 78:2644-2652) (FIG. 2D). To confirm the Western blot data and to ensure that Pla activity was fully retained by the Δlpp ΔmsbB Δail triple mutant compared to WT CO92, the mutant bacteria were exposed to a fluorogenic hexapeptide Pla substrate. This substrate was selected from the library of fluorogenic peptides by positional screening methods (Agarkov et al. 2008 Bioorg Med Chem Lett 18:427-431). Both WT CO92 and its Δlpp ΔmsbB Δail triple mutant cleaved the substrate in a time-dependent manner following essentially similar kinetics at both 28° C. and 37° C. at the two tested bacterial concentrations (FIG. 2E). As a control, a Pla-negative mutant (Δpla) of CO92 did not cleave the substrate.

Figure 3:
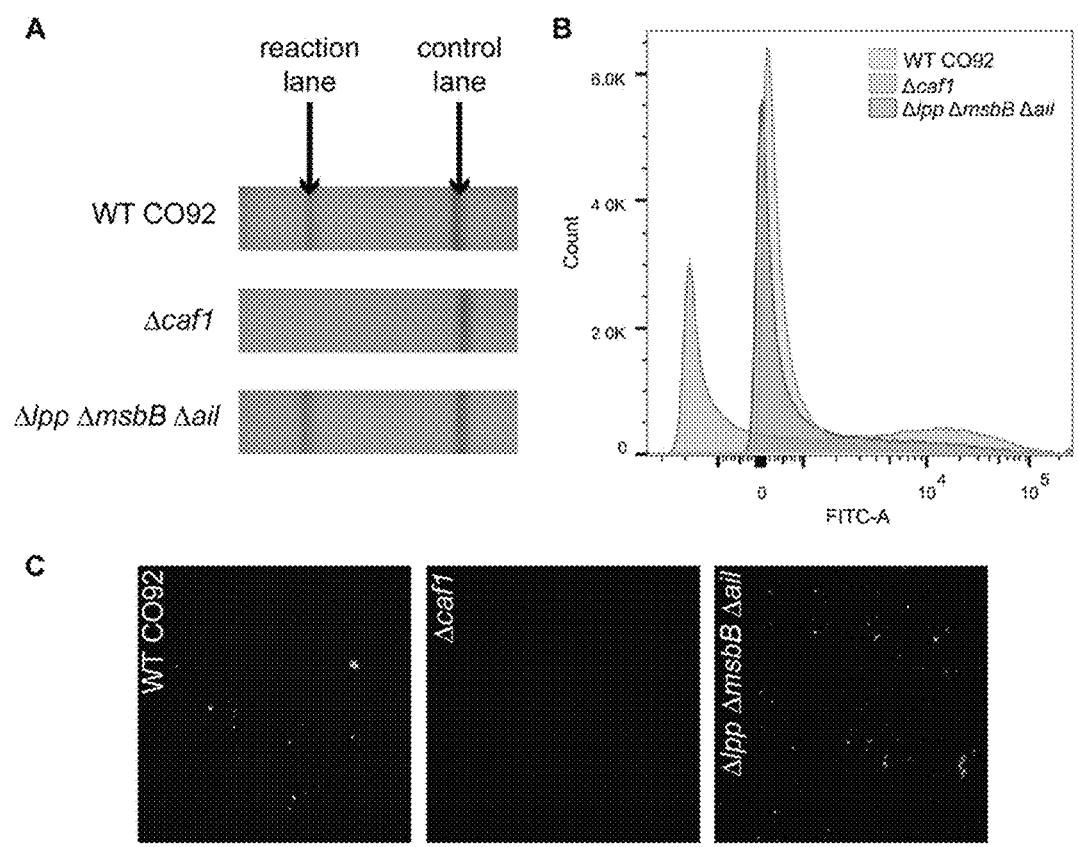
FIG. 3. Production of F1 antigen. Selected *Y. pestis* cultures grown overnight were diluted 1:20 in fresh HIB, and growth was continued at 28° C. for 3 h, followed by an additional 2 h of incubation at 37° C. F1 production was either examined by using immunochromatographic reaction dipsticks (A) or probed by immunofluorescence staining with anti-F1 antibodies followed by flow cytometric analysis (B) and microscopy (C). The Δcaf1 mutant of CO92 was employed as a negative control. Magnification, ×400 (C). FITC, fluorescein isothiocyanate.

Not only is the capsular antigen (F1) a major immunoreactive protein of Y. pestis, it also exhibits antiphagocytic properties (Du et al., 2002, Infect Immun 70:1453-1460). Thus, F1 production was verified in WT CO92 versus its triple mutant by using a commercially available plague immunochromatographic dipstick (impregnated with F1 antibodies) test, which allows rapid, in vitro qualitative identification of Y. pestis. Both WT CO92 and its Δlpp ΔmsbB Δail triple mutant produced purple bands in the reaction and control lanes of similar intensities, whereas the Δcaf1 mutant (negative control) was positive only in the control lane (FIG. 3A). To confirm these results, the presence of F1 on bacterial cells was verified by IF staining with F1-specific antibodies, followed by flow cytometry and microscopy (Sha et al., 2011, J Clin Microbiol 49:1708-1715). As shown in FIGS. 3B and C, F1 was detected on the surfaces of both WT CO92 and its Δlpp ΔmsbB Δail triple mutant, while the Δcaf1 mutant was negative for the presence of F1.

Evaluation of Y. pestis CO92 Δail mutants in a pneumonic plague mouse model. To gauge the virulence potential of the Δail mutant strains, mice (n=10/group) were infected by the i.n. route with similar doses ($1.3 \times 10^4$ CFU, representing 26 $LD_{50}$s of the WT bacterium) of the Δail single, Δlpp Δail or Δlpp ΔmsbB double, or Δlpp ΔmsbB Δail triple mutant strain as well as WT CO92. While animals inoculated with WT CO92 died by day 4 p.i., all of the mice infected with the Δail single mutant died by day 10 p.i., showing an increased mean time to death (FIG. 4A), confirming data from a previous report by Kolodziejek et al. (Kolodziejek et al., 2010, Infect Immun 78:5233-5243). Mice infected with the Δlpp Δail and Δlpp ΔmsbB double mutants and the Δlpp ΔmsbB Δail triple mutant had increased survival rates (20, 40, and 100%, respectively). Clinically, animals infected with WT CO92 or mutants that provided minimal attenuation in mice had ruffled fur, hunched back, and lethargy, and they were unable to groom and tended to huddle together.

To evaluate the specific immunity to Y. pestis that developed, sera from all of the surviving mice infected with various mutants of CO92 (FIG. 4A) were collected on day 14 p.i. Animals challenged with WT CO92 or the Δail single mutant could not be bled, since there were no survivors. Based on the ELISA data, sera from mice challenged with the Δlpp ΔmsbB and Δlpp Δail double mutants exhibited high total IgG titers (1:3,125) to the F1-V antigen (FIG. 4B), while this titer was low (1:25) when animals were infected with the Δlpp ΔmsbB Δail triple mutant (FIG. 4B).

The extent of attenuation of the virulence potential of the Δlpp ΔmsbB Δail triple mutant was then ascertained by infecting mice by the i.n. route with increasing doses ranging from $4.0 \times 10^4$ to $5.9 \times 10^5$ CFU, representing 80 to 1,180 $LD_{50}$s of the WT bacterium (FIG. 5A). A group of animals that received 32 $LD_{50}$s of WT CO92 served as a control, and all of them died by day 4 p.i. The Δlpp ΔmsbB Δail triple mutant was unable to kill mice at all of these doses and thus resulted in 100% survival rates (FIG. 5A). Importantly, the total IgG titers (on day 14 p.i.) in the sera progressively increased (up to 1:625) when the animals were challenged with increasing doses (80 to 1,180 $LD_{50}$s of WT CO92) of the Δlpp ΔmsbB Δail triple mutant (FIG. 5B).

To further assess the specific immunity induced in mice after initial infection with the Δlpp ΔmsbB Δail triple mutant strain (FIG. 5A), the surviving animals were subsequently challenged on day 24 p.i. with $1.0 \times 10^4$ CFU (20 $LD_{50}$s) of the WT CO92 luc2 strain. Age-matched naive mice were used as a control, and 90% of them died by day 4 p.i. (FIG. 5A). There was an increase in the time to death and somewhat of a dose-dependent protection, which was maximal in animals that were initially infected with $5.9 \times 10^5$ CFU (1,180 $LD_{50}$s of WT CO92) of the triple mutant (50% of the mice survived) compared to naive animals during the WT CO92 luc2 strain rechallenge (FIG. 5A).

The surviving mice were imaged on day 3 p.i. by using an in vivo imaging system, and the first animal on the left in each imaging panel was uninfected and served as a control (FIG. 5C). While the WT CO92 luc2 strain disseminated to the whole body in 6 out of 9 naive animals (FIG. 5CI), the bioluminescent strain was confined to the initial infection site (lungs) in animals that were first infected with the Δlpp ΔmsbB Δail triple mutant before being challenged with the WT CO92 luc2 strain (FIG. 5CII to IV). As the dose of the initial infection with the triple mutant was increased from $4 \times 10^4$ to $1.7 \times 10^5$ CFU, the number of animals that were positive for bioluminescence decreased from 6/10 to 4/10 animals subsequent to WT CO92 luc2 strain challenge (FIGS. 5CII and III). At the highest infection dose of the triple mutant ($5.9 \times 10^5$ CFU), only 2/10 mice were positive for bioluminescence as a result of subsequent CO92 luc2 challenge, with 80%, 60%, and 50% of the animals surviving on days 7, 8, and 10, respectively (FIG. 5A). Since half of the animals did not succumb to infection, these data indicated clearing of the WT CO92 luc2 strain (FIG. 5CIV).

Figure 6:
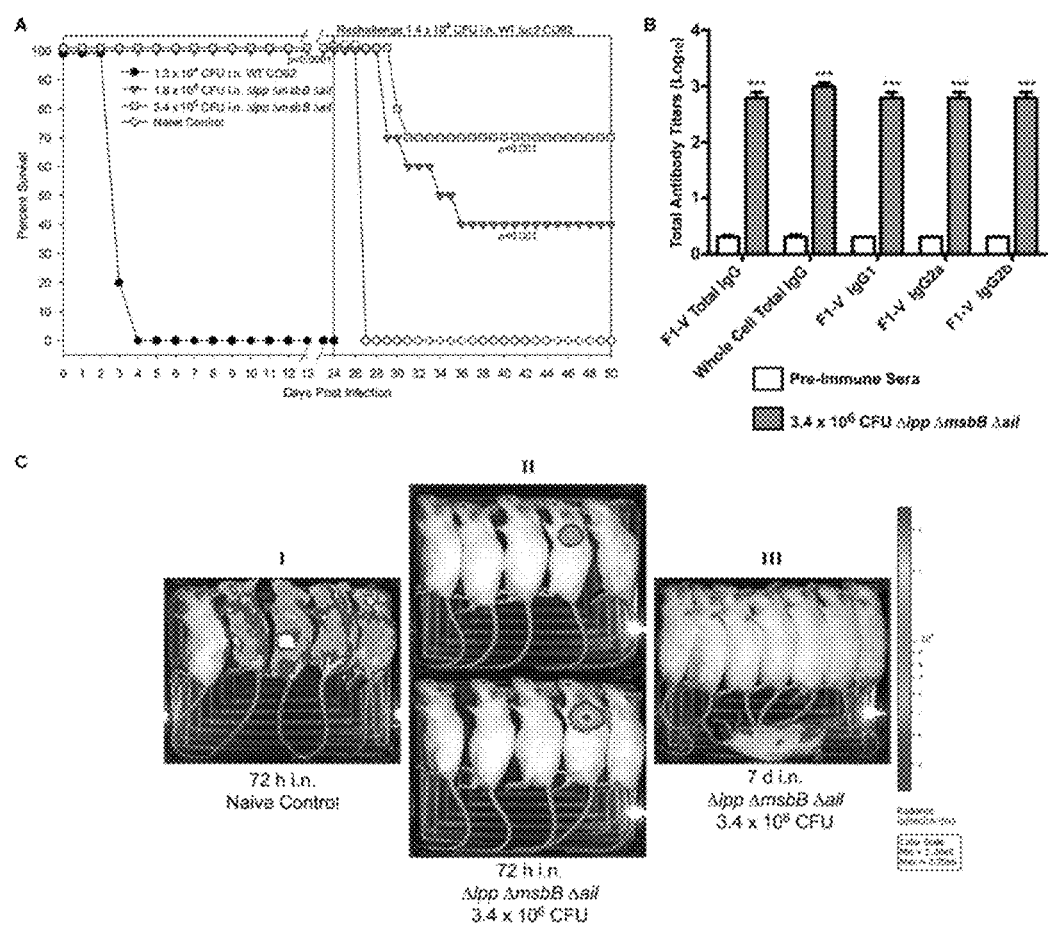

In our subsequent experiment, initial infection doses of the Δlpp ΔmsbB Δail triple mutant given to the mice i.n. were increased to $1.8 \times 10^6$ and $3.4 \times 10^6$ CFU, which corresponded to 3,600 and 6,800 $LD_{50}$s of WT CO92, respectively. As shown in FIG. 6A, even the highest dose of the triple mutant was unable to kill mice, while the control animals infected with a much lower dose of WT CO92 (26 $LD_{50}$s) died by day 4 (FIG. 6A). As expected, in the sera of mice infected with the highest challenge dose ($3.4 \times 10^6$ CFU) of the Δlpp ΔmsbB Δail triple mutant strain, the total IgG and IgG isotype (IgG1, IgG2a, and IgG2b) antibody titers to F1-V antigen were sustained at 1:625 (FIG. 6B), indicating balanced $T_H1$ and $T_H2$ responses. The total IgG titers were higher (1:1,000) when the ELISA plates were coated with whole cells and reflected the presence of antibodies to other Y. pestis antigens along with F1 and V (FIG. 6B).

As expected, protection levels increased to 70% when the animals were initially infected with the Δlpp ΔmsbB Δail triple mutant at a dose of $3.4 \times 10^6$ CFU (6,800 $LD_{50}$s of WT CO92) and then challenged i.n. on day 24 with a higher dose (28 $LD_{50}$s or $1.4 \times 10^4$ CFU) of the WT CO92 luc2 strain (FIG. 6A). Mice (n=5 to 10) were again imaged with the in vivo imaging system (FIG. 6C). On day 3 postchallenge, 5/5 naive animals were positive for bioluminescence, while the WT CO92 luc2 strain disseminated throughout the animal bodies of 4/5 mice (FIG. 6CI). Only 2 of the 10 animals that had received the triple mutant at the highest dose before being challenged with the WT CO92 luc2 strain were positive for bioluminescence (FIG. 6CII), and these animals subsequently died by day 6 (FIG. 6A). On day 7 p.i., another mouse succumbed to infection and was positive for bioluminescence (FIG. 6CIII). The low level of bioluminescence detected in the dead animal was possibly due to a lack of oxygen and a low body temperature that diminished bioluminescence (Sha et al., 2013, Microb Pathog 55:39-50). Importantly, the remaining 7 mice that were previously infected with $3.4 \times 10^6$ CFU of the Δlpp ΔmsbB Δail triple mutant were devoid of bioluminescence after subsequent challenge with the WT CO92 luc2 strain, indicating clearance of the infecting pathogen (FIG. 6CIII). Collectively, these data suggested that the increased humoral immune response generated by the triple mutant in mice seemed to correlate with the subsequent enhanced protection of animals when challenged with WT CO92.

Figure 7:
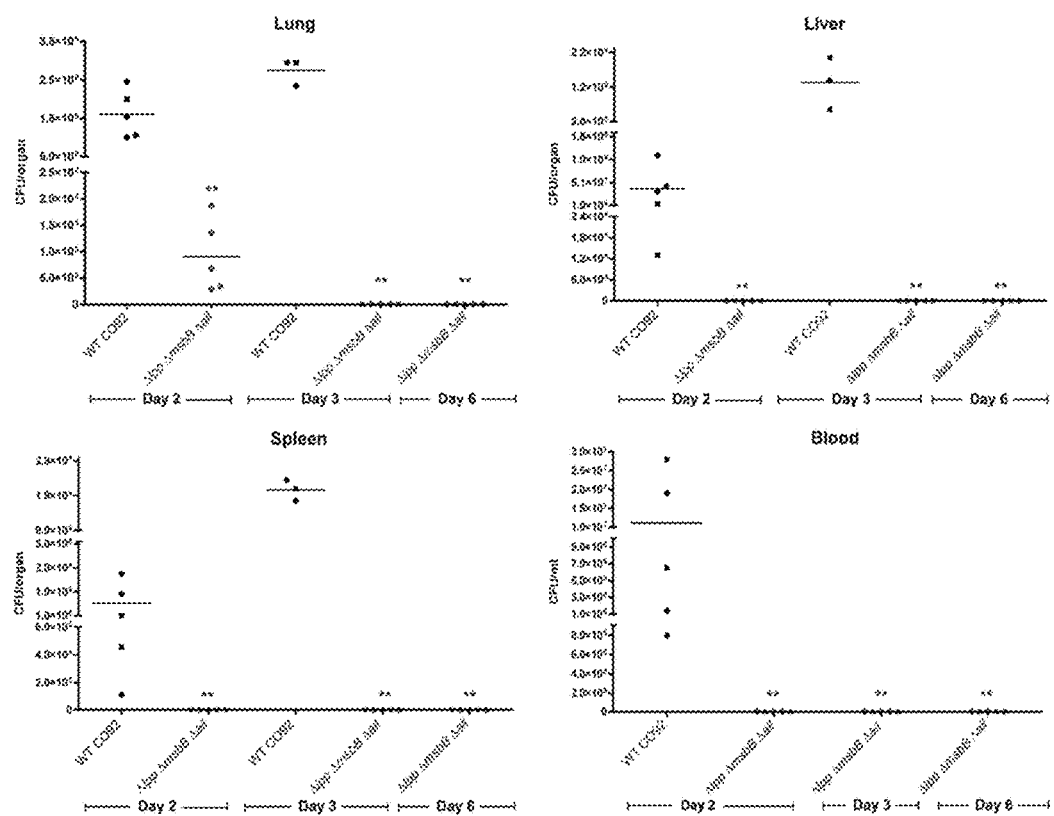
FIG. 7. Dissemination of WT CO92 and its Δlpp ΔmsbB Δail triple mutant in a mouse model of pneumonic plague. Female Swiss Webster mice were challenged with 2.5×10$^6$ CFU of WT *Y. pestis* CO92 or its Δlpp ΔmsbB Δail triple mutant by the i.n. route. Organs and blood were harvested from mice (n=5) on days 2, 3, and 6 p.i. The bacterial loads in different organs and blood from each individual mouse were plotted, and the arithmetic means are indicated by the horizontal bars. ** indicates statistical significance (P<0.001) compared to WT CO92 on each day (day 6 was compared to day 3 for WT CO92).

Bacterial dissemination and histopathological lesions in mice challenged with the Δlpp ΔmsbB Δail triple mutant of *Y. pestis* CO92 by the intranasal route. Mice were challenged with $2.5 \times 10^6$ CFU of either WT CO92 (5,000 $LD_{50}s$) or its Δlpp ΔmsbB Δail triple mutant. Animals were sacrificed on days 2, 3, and 6 p.i., and their lungs, liver, spleen, and blood were harvested and subjected to bacterial load determination. Mice challenged with WT bacteria had a high bacterial load in each of these organs on both day 2 (ranging from $1.1 \times 10^7$ to $1.7 \times 10^9$ CFU/organ) and day 3 ($1.3 \times 10^9$ to $2.8 \times 10^9$ CFU/organ). No data were collected on day 6 since all of the mice succumbed to infection within 80 h. Animals challenged with the Δlpp ΔmsbB Δail triple mutant had minimal to no bacterial load in the organs examined, except for the lungs on day 2 (ranging from $2.8 \times 10^2$ to $1.9 \times 10^3$ CFU/organ) (FIG. 7).

Figure 8:
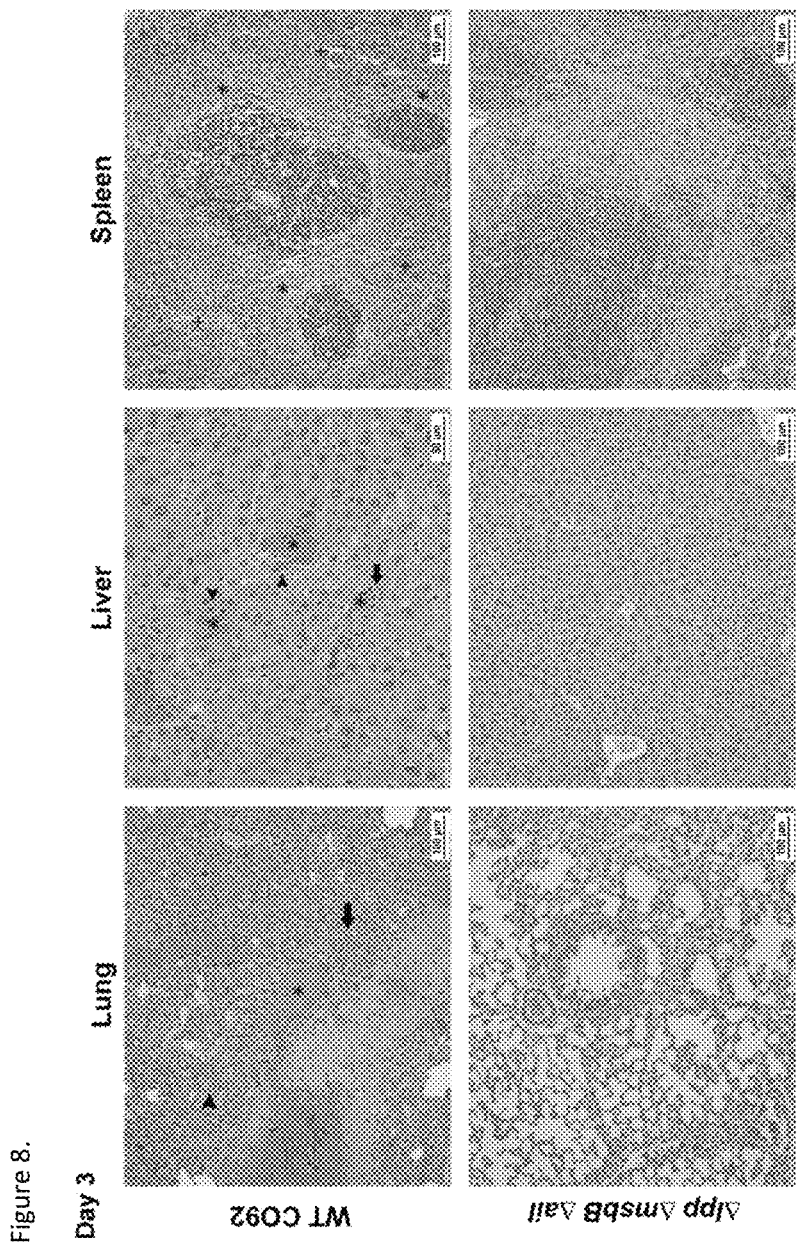
FIG. 8. Histopathology of mouse tissues following pneumonic infection with WT CO92 or its Δlpp ΔmsbB Δail triple mutant. Female Swiss Webster mice were challenged with 2.5×10$^6$ CFU of WT *Y. pestis* CO92 or the Δlpp ΔmsbB Δail triple mutant by the i.n. route. On days 2, 3, and 6 p.i., a portion of the lungs, liver, and spleen (n=3 to 5) was stained with H&E and evaluated by using light microscopy in a blind fashion. Only data for day 3 are shown. The presence of bacteria, neutrophilic infiltration, hemorrhage/ necrosis, and rarefied red pulp is indicated by asterisks, arrows, arrowheads, and plus signs, respectively.

Organs from the infected mice were also removed for histopathological analysis. At between 48 and 60 h p.i., two of the five WT bacterium-infected mice succumbed to infection, and their organs were not harvested. The remaining three mice succumbed to infection at between 60 and 72 h p.i., and their lungs had mild to moderate neutrophilic inflammation (FIG. 8, arrows). All of the animals had bacteria present in their lungs (FIG. 8, asterisks), and one had mild diffuse congestion. The alveoli of all of the lungs had a moderate level of hemorrhage (FIG. 8, arrowheads), with few alveolar spaces being observed (FIG. 8). The lungs of Δlpp ΔmsbB Δail triple mutant-infected mice appeared normal, with only one animal having minimal histiocytic infiltration of the alveolus by day 3 p.i. There were no noticeable bacteria or edema present in the lungs of triple mutant-infected mice (FIG. 8). However, the lungs of the Δlpp ΔmsbB Δail mutant-infected mice had minimal to mild neutrophilic infiltration on day 2 p.i. (data not shown). The residual lesions in the triple mutant-infected mice resolved by day 6 p.i. (data not shown).

All of the livers of WT-infected animals had bacteria (FIG. 8, asterisks), some necrosis (arrowheads), and neutrophilic infiltration (arrows). These lesions were nonexistent or minimal in the livers of Δlpp ΔmsbB Δail triple mutant-infected mice on day 3 p.i. (FIG. 8). All of the spleens of WT-infected mice had bacteria (FIG. 8, asterisks), mild lymphoid depletion of the marginal zone in the white pulp, and mild to marked diffuse rarefaction (FIG. 8, plus signs) or a loss of the normal cell population of the red pulp with fibrin present. The red pulp of these spleens also had moderate levels of hemorrhage on day 3 p.i. (FIG. 8). The spleens of the Δlpp ΔmsbB Δail triple mutant-infected mice were essentially normal, with a few animals having either minimal neutrophilic inflammation of the red pulp or mild depletion of the white pulp (FIG. 8). These changes in the spleens of animals infected with the triple mutant could be related to the generation of an immune response.

The Δlpp ΔmsbB Δail triple mutant of *Y. pestis* CO92 evokes reduced levels of inflammatory cytokines in a pneumonic plague mouse model. Samples of the lung homogenates and sera collected from the above-mentioned infected animals were assessed for cytokine production by using an eBioscience 6-plex Bioplex assay. There was a statistically significant difference in the presence of TNF-α, IFN-γ, and IL-6 in both the lungs and the sera between the WT- and the Δlpp ΔmsbB Δail triple mutant-infected animals on both days 2 and 3 p.i. (FIG. 9). In the lungs, TNF-α and IFN-γ levels from WT-infected animals were >50- to 100-fold higher than those in the triple mutant-infected animals, whereas their IL-6 levels were >1,000-fold higher (FIG. 9A). In the serum, TNF-α and IFN-γ levels from WT-infected mice were >50-fold higher than those in the triple mutant-infected animals, whereas their IL-6 levels were >300-fold higher (FIG. 9B). These reduced cytokine levels in mice infected with the mutant correlated with its rapid clearance (FIG. 7).

Δail mutants of *Y. pestis* CO92 have host-dependent serum sensitivities. Ail has been reported to function in providing serum resistance to *Y. pestis* (Bartra et al., 2008, Infect Immun 76:612-622; Hinnebusch et al., 2011, Infect Immun 79:4984-4989; Kolodziejek et al., 2010, Infect Immun 78:5233-5243; Kolodziejek et al., 2007, Microbiology 153:2941-2951). Consequently, WT CO92 and its Δail single, Δlpp ΔmsbB double, and Δlpp ΔmsbB Δail triple mutants were tested for their ability to be killed by the complement cascade. As shown in FIG. 10A, both WT CO92 and its Δlpp ΔmsbB double mutant strain showed ≥100% survival upon exposure to normal unheated mouse, NHP, or human serum. Thus, the deletion of the lpp and msbB genes did not affect the serum resistance of *Y. pestis*. In contrast, the Δail single mutant and the Δlpp ΔmsbB Δail triple mutant strains showed ≥100% bacterial survival in normal (unheated) mouse serum, with ~0% survival in NHP and human sera, indicating Ail's role in serum resistance in NHPs and humans. This serum resistance phenotype of the Δail mutants in NHP and human sera was lost when the complement was inactivated, with >100% survival.

To confirm that Ail is responsible for this phenotype, the complemented strains (Δail:pBR322-ail and Δlpp ΔmsbB Δail:pBR322-ail) were exposed to normal (unheated) NHP and human sera. Both of these strains exhibited ≥100% survival (FIG. 10A), which provided further evidence that this phenotype was indeed due to the expression of the ail gene. The survival rate of >100% indicated the ability of these bacteria to replicate in sera. Essentially, similar levels of Ail were detected in the tested strains, except for those from which the ail gene was deleted, as judged by Western blotting (FIG. 10B).

Decreased adherence and invasion of *Y. pestis* CO92 Δail mutants in epithelial cells. Since Ail functions in the adherence and subsequent invasion of bacteria in host cells, these virulence phenotypes of WT CO92 and its various mutants were first examined in HeLa cells at an MOI of 100 (FIGS. 11AI and II). Both the Δail single mutant and the Δlpp ΔmsbB Δail triple mutant had similar, significantly decreased adherence (~28%) (FIG. 11AI) and invasion (~1.1 to 1.5%) (FIG. 11AII) compared to those of WT CO92 and its Δlpp ΔmsbB double mutant (which had comparable levels, with ~60 to 75% adherence and −3 to 4% invasion) (FIGS. 11AI and II). Upon complementation with the ail gene, both the Δail:pBR322-ail and Δlpp ΔmsbB Δail:pBR322-ail strains became adherent (~60%) (FIG. 11AI) and invasive (~3 to 4%) (FIG. 11AII), at levels comparable to those seen with WT CO92 and its Δlpp ΔmsbB double mutant strain. In addition to depicting percentages of adherence and invasion, the actual CFU associated with adherence and invasion of the various tested cultures in HeLa cells are also shown (see FIG. 15). As a gentamicin protection assay was used during the experiment, the sensitivities of the various *Y. pestis* strains to this antibiotic were assessed. Our data indicated that WT CO92 and its various mutant strains exhibited similar gentamicin sensitivities, with MIC values of 0.125 µg/ml at 28° C.

Since *Y. pestis* infects the lungs during pneumonic plague, bacterial adherence to and invasion of A549 human alveolar epithelial cells were then examined to mimic a natural infection scenario. As with the HeLa cell infection model, both the Δail single mutant and the Δlpp ΔmsbB Δail triple mutant had similar significantly decreased rates of adherence (34% and 10%, respectively) (FIG. 11BI) and minimal invasion (~0.01%) (FIG. 11BII) compared to WT CO92 and its Δlpp ΔmsbB double mutant (which had comparable levels, with ~90% adherence and ~4% invasion). Upon complementation with the ail gene, both the Δail:pBR322-ail and Δlpp ΔmsbB Δail:pBR322-ail strains showed increased adherence (~50 to 55%) and invasion (~1%) (FIGS. 11BI and II). As for the HeLa cells, the actual CFU associated with the adherence and invasion of the various tested cultures in A549 cells are also shown (see FIG. 15). Thus, the decreased adherence and invasion properties of the Δail mutants were most likely due to the lack of the Ail protein.

Host-dependent survivability of *Y. pestis* CO92 Δail mutants in murine and human macrophages and epithelial cells. To determine the role of Ail in intracellular survival within macrophages, MH-S murine alveolar macrophages were infected with WT CO92 or the Δail single, Δlpp ΔmsbB double, or Δlpp ΔmsbB Δail triple mutant at an MOI of 10. The macrophages showed an increased uptake of the Δlpp ΔmsbB Δail triple mutant (29%) compared to WT CO92 and the Δail single mutant strain (12% and 13%, respectively) (data not shown). At 2 h p.i., 46% of the Δlpp ΔmsbB double mutant and 39% of the Δlpp ΔmsbB Δail triple mutant cells survived in MH-S cells, compared to 77% of WT CO92 cells (FIG. 12A), correlating with our previously reported data showing that Lpp contributes to the intracellular survival of *Y. pestis* in macrophages (Sha et al., 2013, Infect Immun 81:815-828; Sha et al., 2008, Infect Immun 76:1390-1409; van Lier et al., 2014, Infect Immun 82:2485-2503; Agar et al., 2009, Microbiology 155:3247-3259). The Δail single mutant strain had an intracellular survival rate (74%) comparable to that of WT CO92 (FIG. 12A). This trend was similar at 4 h p.i., although the percent survival of bacteria decreased further. Thus, these data suggested that Ail did not contribute to intracellular survival in murine alveolar macrophages (FIG. 12A).

To further investigate the intracellular survivability of mutant bacteria, human monocyte-derived macrophages (HMDMs) were used. The Δlpp ΔmsbB Δail triple mutant strain was most impaired in survival intracellularly (18%) in HMDMs compared to the Δlpp ΔmsbB double mutant (25%) and WT CO92 (38%) at 2 h p.i. (FIG. 12B). However, no statistical difference was noted when the Δlpp ΔmsbB double mutant and the Δlpp ΔmsbB Δail triple mutant were compared. This trend was similar at 4 h p.i., although the percent survival of bacteria decreased further (FIG. 12B).

We then infected HeLa epithelial cells with various CO92 mutants in two independent experiments (FIGS. 12C and D). In the first set of experiments, the Δlpp single mutant and its complemented strain were also tested. As shown in FIG. 12C, WT CO92 and its Δail single mutant strain had comparable intracellular survival rates (63% and 68%, respectively), whereas the Δlpp single and Δlpp ΔmsbB double mutants had decreased survival rates (31 to 32%) at 12 h p.i. On the contrary, the Δlpp ΔmsbB Δail triple mutant strain survived minimally (5%). We fully complemented the Δlpp single mutant in cis with the corresponding gene (FIG. 12C), indicating a major role of Lpp in bacterial intracellular survival. In a second HeLa cell experiment (FIG. 12D), we showed a similar pattern of the Δlpp ΔmsbB Δail triple mutant surviving minimally, while the Δail single mutant exhibited a survival pattern mimicking that of WT CO92. Furthermore, as expected, the Δlpp ΔmsbB double mutant was significantly impaired in its survival in HeLa cells compared to WT CO92 (FIG. 12D). Interestingly, we were able to partially restore the intracellular survival phenotype of the Δlpp ΔmsbB Δail triple mutant with the ail gene when provided in trans (FIG. 12D), but it did not reach the level of intracellular survival noted for the Δlpp ΔmsbB double mutant.

Finally, we infected A549 human lung epithelial cells with WT CO92 and its Δail single, Δlpp ΔmsbB double, or Δlpp ΔmsbB Δail triple mutant strain. Both the Δlpp ΔmsbB double mutant and Δlpp ΔmsbB Δail triple mutant strains had decreased survival rates (49% and 11%, respectively) at 12 h p.i. (FIG. 12E), a pattern similar to that seen in HeLa cells. Partial complementation of the Δlpp ΔmsbB Δail triple mutant in terms of intracellular survival was noted with the all gene (FIG. 12E), although the data did not reach statistical significance, unlike in HeLa cells (FIG. 12D), but reached a level comparable to that of the Δlpp ΔmsbB double mutant.

Host-dependent inflammatory cytokine secretion by *Y. pestis* CO92 Δail mutants in infected macrophages. Supernatants from the above-mentioned infected macrophages were collected and assessed for cytokine production by using either a Bio-Rad mouse 6-plex assay kit for MH-S cells or a Bio-Rad human 8-plex assay kit for HMDMs. The Δlpp ΔmsbB double mutant-infected MH-S macrophages maintained levels of TNF-α and IL-6 secretion comparable to those of WT-infected cells at 2 h p.i., both of which were significantly decreased compared to those in WT-infected MH-S macrophages at 4 h p.i. (FIG. 13A). The Δlpp ΔmsbB Δail triple mutant-infected mouse macrophages had significantly increased levels of TNF-α and IL-6 secretion at 2 h and 4 h p.i. compared to those of WT CO92- and Δlpp ΔmsbB double mutant-infected MH-S cells (FIG. 13A).

The Δlpp ΔmsbB Δail triple mutant-infected HMDMs had statistically significant increases in levels of TNF-α and IL-6 at 2 h p.i. compared to those in both the WT CO92- and Δlpp ΔmsbB double mutant-infected macrophages (FIG. 13B). The Δlpp ΔmsbB double mutant-infected HMDMs secreted levels of TNF-α to comparable to those secreted by WT CO92-infected HMDMs but exhibited a significant decrease in IL-6 secretion at 2 h p.i. (FIG. 13B). Finally, while the infected MH-S cells had extremely low levels of IFN-γ, the Δlpp ΔmsbB Δail triple mutant-infected HMDMs secreted increased amounts of IFN-γ (63 pg/ml) at 2 h p.i. compared to those in both WT CO92- and Δlpp ΔmsbB double mutant-infected HMDMs (41 and 39 pg/ml, respectively). However, the data did not reach statistical significance. Other cytokines included in the Bioplex assay were below the detection limit for the samples obtained after infection of macrophages with either WT CO92 or its mutant derivatives.

Discussion

We made an in-frame deletion of the all gene from an already existing Δlpp ΔmsbB double mutant of WT strain CO92. The Δlpp ΔmsbB double mutant was attenuated in evoking both bubonic and pneumonic plague in mouse and rat models (Sha et al., 2013, Infect Immun 81:815-828). This double mutant retained immunogenicity to partially protect rodents against pneumonic plague upon subsequent infection with lethal doses (8 to 10 $LD_{50}s$) of WT CO92 (Sha et al., 2013, Infect Immun 81:815-828). Our goal was to discern whether the deletion of the ail gene from the Δlpp ΔmsbB double mutant of WT CO92 would further attenuate the bacterium in vivo while retaining immunogenicity, to serve as a possible background strain from which additional genes could be deleted for future live-attenuated vaccine development against plague. Indeed, the triple mutant was so highly attenuated that it did not kill any mice, even at a dose as high as 3.4×10$^6$ CFU (corresponding to 6,800 LD$_{50}$s) of WT CO92 (FIG. 6A), and the animals did not exhibit any clinical symptoms of disease. Based on our data (FIG. 4), it was apparent that the Δlpp ΔmsbB Δail triple mutant was synergistically attenuated in a mouse model of pneumonic plague compared to the Δail single mutant and the Δlpp ΔmsbB double mutant.

In previous studies, the Δlpp ΔmsbB double mutant of Y. pestis CO92 and the Δail mutant of Y. pestis KIM5 were reported to have a decreased ability to disseminate to peripheral organs of mice compared to their respective parental strains; however, both of these mutant strains persisted for 3 to 7 days p.i. in mouse organs (Felek et al., 2009, Infect Immun 77:825-836; Sha et al., 2013, Infect Immun 81:815-828). On the contrary, the Δlpp ΔmsbB Δail triple mutant was more rapidly cleared from animals (by days 2 to 3 p.i.) (FIG. 7), resulting in minimal histopathological changes in the lungs, liver, and spleen (FIG. 8).

The Δlpp ΔmsbB Δail triple mutant produced levels of F1, Pla, and LcrV essentially similar to those produced by WT CO92 (FIGS. 2 and 3), and therefore, the lower total IgG titers to F1-V antigen in the triple mutant-infected mice than those in animals that were challenged with either the Δlpp ΔmsbB or the Δlpp Δail double mutant (FIG. 4B) are most likely due to the rapid clearance of the triple mutant by the immune system and not to its inability to stimulate an IgG response. This observation was substantiated by our findings that the IgG responses increased significantly when the animals were immunized with higher doses of the Δlpp ΔmsbB Δail triple mutant (FIGS. 5B and 6B).

Brown Norway rats infected with the Δail mutant of Y. pestis CO92 were recently found not only to survive pneumonic infection (Hinnebusch et al., 2011, Infect Immun 79:4984-4989), but also to have an influx of neutrophils in the draining lymph nodes when challenged by the intradermal route, leading to the development of large purulent abscesses (Hinnebusch et al., 2011, Infect Immun 79:4984-4989). In addition, Ail seemed necessary for specifically targeting neutrophils for T3SS translocation of effectors in the lungs when animals were infected intranasally with either the WT strain or the Δail mutant of Y. pseudotuberculosis (Paczosa et al., 2014, Cell Microbiol 16:247-268). In our study, the lungs of the triple mutant-infected animals had minimal to mild neutrophilic inflammation on day 2 p.i. The life span of neutrophils in mice is estimated to be up to 12.5 h (Pillay et al., 2010, Blood 116:625-627), and therefore, the influx of neutrophils and other inflammatory cells in mice at the infection site by the Δlpp ΔmsbB flail triple mutant at earlier time points clearly represents a possibility that will be investigated in the future.

In addition to neutrophils, Y. pestis preferentially infects host macrophages, probably via the recognition of specific surface-associated CCR5 molecules, and survives within these phagocytic cells during early stages of infection (Elvin et al., 2004, Nature 430:417). The intracellular survival and growth of Y. pestis in macrophages seem to play a role in the pathogenesis of the plague bacterium, as the organism acquires the ability to evade subsequent phagocytosis (e.g., by synthesizing capsule) and is protected from contact with other immune components (Pujol et al., 2003, Infect Immun 71:5892-5899). Thus, the impaired survival of the Δlpp ΔmsbB flail triple mutant in macrophages (both murine and human) (FIG. 12) seemed to contribute to its significant attenuation.

Although Y. pestis is a facultative intracellular pathogen (Perry et al., 1997, Clin Microbiol Rev 10:35-66), its ability to invade epithelial cells has been reported only recently (Kolodziejek et al., 2010, Infect Immun 78:5233-5243; Felek et al., 2009, Infect Immun 77:825-836; Cowan et al., 2000, Infect Immun 68:4523-4530; Tsang et al., 2013, PLoS One 8:e83621). Ail is a major mediator responsible for the adherence and invasion of Y. pestis KIM strains or when the ail gene is overexpressed in nonadherent and noninvasive E. coli strains in human epithelial cells of cervical origin (HeLa and Hep-2) (Kolodziejek et al., 2010, Infect Immun 78:5233-5243; Kolodziejek et al., 2007, Microbiology 153:2941-2951; Felek et al., 2009, Infect Immun 77:825-836; Tsang et al., 2010, Infect Immun 78:3358-3368). Likewise, mutated versions of the ail gene from Y. pestis, when expressed and produced in E. coli, exhibited phenotypes of decreased adherence and invasion in HeLa cells, compared to E. coli strains expressing the nonmutated ail gene (Tsang et al., 2013, PLoS One 8:e83621). We provided the first evidence that Ail of Y. pestis has a role in adherence to and invasion of the human alveolar A549 epithelial cell line (FIG. 11B), thus showing Ail's role in pneumonic plague.

In addition to Ail, Pla and pH 6 antigen (Psa) also mediate the binding of Y. pestis KIM5 to Hep-2 cells (Felek et al., 2010, Infect Immun 78:4134-4150). However, Ail is the most critical adhesion molecule, followed by Pla and then Psa (Tsang et al., 2013, PLoS One 8:e83621). We have shown that the levels of Pla and F1 as well as the enzymatic activity of Pla were not affected in the Δlpp ΔmsbB Δail triple mutant (FIGS. 2D and E and 3). The role of Psa in epithelial cell adherence and invasion is minimal at best under normal physical conditions (Felek et al., 2010, Infect Immun 78:4134-4150; Cowan et al., 2000, Infect Immun 68:4523-4530). Since we were able to restore the adherence and invasion phenotypes of the triple mutant in HeLa and A549 cells after complementation with the ail gene (FIG. 11), this finding confirmed the role of Ail as a major adhesion molecule in Y. pestis.

Our previous studies have shown that both Lpp and Pla, but not MsbB, contributed to WT CO92 survival in murine RAW 264.7 macrophages (Sha et al., 2013, Infect Immun 81:815-828; Sha et al., 2008, Infect Immun 76:1390-1409; van Lier et al., 2014, Infect Immun 82:2485-2503; Agar et al., 2009, Microbiology 155:3247-3259). In various cell types that we studied (e.g., murine alveolar macrophages and HeLa and A549 epithelial cells), the single ail gene deletion did not affect the intracellular survival of Y. pestis (FIG. 12). In contrast, deletion of the ail gene from the Δlpp ΔmsbB double mutant further decreased the survival of the triple mutant in HeLa and A549 epithelial cell lines but not in macrophages (FIG. 12A to E). This decreased survivability of the triple mutant could be fully or partially complemented in HeLa or A549 cells, respectively, when the ail gene was supplied in trans (FIGS. 12D and E), suggesting that Ail may play a role in bacterial intracellular survival. Since Ail's biological activity may possibly be masked by Lpp and LPS (Kolodziejek et al., 2010, Infect Immun 78:5233-5243), the deletion of both the lpp and msbB genes from Y. pestis might have allowed us to glean the role of Ail in intracellular survival in epithelial cells. In addition, the differential killing mechanisms employed by various host cell types could also play a crucial role in the survivability of the mutant bacteria and need to be further investigated. This decreased-survival phenotype of the triple mutant in epithelial cells was not due to the lack of production and activity of Pla (FIGS. 2D and E) and correlated with the mutant's decreased ability to disseminate and to be rapidly cleared from mouse organs (FIG. 7), compared to that of the Δlpp ΔmsbB double mutant (Sha et al., 2013, Infect Immun 81:815-828). These data emphasized the role of the epithelial barrier in host innate immunity.

We consistently detected an increased amount of YopH in culture supernatants of ail deletion mutants compared to that in WT CO92 supernatants (FIGS. 2A and B). The presence of these Yops in bacterial supernatants was not due to a leakage of the bacterial cell membrane or the T3SS needle itself, as these Yops were detected in the culture medium only after the induction of a low-calcium response by EGTA (FIG. 2B). As a key adhesion molecule, Ail docks onto the host cells to help Yop delivery, and translocation of Yops (e.g., YopE) into the host cells has been found to be decreased in ad-deficient mutants of Y. pestis KIM5 (Felek et al., 2009, Infect Immun 77:825-836; Tsang et al., 2010, Infect Immun 78:3358-3368; Yamashita et al., 2011, Structure 19:1672-1682; Felek et al., 2010, Infect Immun 78:4134-4150) as well as in Y. pestis CO92 (FIG. 2C). Therefore, the decreased translocation of Yops seen in the Δail mutant strains of Y. pestis may be due to their dysregulated release into the medium (FIGS. 2A and B) prior to the docking of the T3SS onto host cells and prior to the translocation of YopE (FIG. 2C).

Yops have been reported to be quickly degraded by proteases in the extracellular milieu, which may explain the marginally higher levels of YopE detected in the supernatant of the Δail single mutant than in WT CO92 (FIG. 2A) (Felek et al., 2010, Infect Immun 78:4134-4150). Although the production of the serine protease Pla in the Δail mutant strains was similar to that in WT CO92 (FIGS. 2D and E), the possibility of an alteration of other proteases in the Δail mutant strains cannot be ruled out. Interestingly, the level of LcrV in the culture medium of the Δlpp ΔmsbB Δail triple mutant was unaffected compared to its levels in WT CO92 (FIG. 2A), correlating with previous reports that LcrV is secreted prior to host cell contact (Cheng et al., 2000, J Bacteriol 182:3183-3190; DeBord et al., 2001, J Bacteriol 183:4588-4598; Houppert et al., 2012, PLoS One 7:e34039; Lee et al., 1998, Mol Microbiol 28:593-601). Furthermore, its extracellular location (component of the T3SS translocon) may render LcrV more resistant to Y. pestis proteases such as Pla (Felek et al., 2010, Infect Immun 78:4134-4150; Straley, 1988, Rev Infect Dis 10 (Suppl 2): S323-S326).

A recent study showed that the presence of outer membrane vesicles (OMVs) containing membrane and periplasmic components was increased in the Δlpp mutant of Y. pestis under specific conditions (Eddy et al., 2014, PLoS One 9:e107002). While our electron microscopy studies revealed no OMVs in the Δlpp ΔmsbB Δail triple mutant, an increase in the release of OMVs would not explain the increased levels of some Yops in the supernatant of the Δlpp ΔmsbB Δail triple mutant (FIG. 2A), since increased amounts of YopE and YopH were not detected in the supernatant of the Δlpp ΔmsbB double mutant.

YopE and YopH act as deterrents to bacterial phagocytosis, while YopP/YopJ inhibits inflammatory cytokine responses when injected into host cells (Boland et al., 1998, Infect Immun 66:1878-1884). Although the translocation of all the Yops by the Δlpp ΔmsbB Δail triple mutant in host cells was not assessed in this study, we observed an increased uptake of the triple mutant by MH-S murine macrophages compared to that of WT CO92 (data not shown). Importantly, this increased uptake of the triple mutant correlated with an early burst of inflammatory cytokine secretion in the triple mutant-infected murine and human macrophages compared to that in macrophages infected with WT CO92 and the Δlpp ΔmsbB double mutant (FIG. 13). The increased levels of TNF-α and IL-6 would help macrophages to combat the invading bacteria. In addition, IL-6 has been reported to enhance the polarization of alternatively activated M2 macrophages and, thus, would promote the resolution of inflammation and wound healing (Fernando et al., 2014, PLoS One 9:e94188), correlating with the minimal histopathological lesions in the organs of the Δlpp ΔmsbB Δail triple mutant-infected mice (FIG. 8).

The mutant strains of CO92 deficient in Ail production were highly sensitive to both human and NHP sera but remained resistant to mouse serum. Thus, serum sensitivity did not seem to play a role in the attenuation of these mutants in a mouse model of pneumonic plague. Differences in serum resistance of bacteria are most likely due to differences in the immune systems of the host. One obvious difference among various hosts is within the amino acid sequences of the complement proteins. For example, FH consists of 20 short consensus repeat (SCR) domains (Oyston et al., 2003, J Med Microbiol 52:289-294), and Ail is predicted to bind FH near SCR7 (Glauser et al., 1991, Lancet 338:732-736; Braun et al., 1974, Annu Rev Biochem 43:89-121; Neilsen et al., 2001, J Immunol 167:5231-5239). Mouse SCR6-8 has 55% identity and 70% homology with human SCR6-8 (Montminy et al., 2006, Nat Immunol 7:1066-1073), indicating that differences in this region of FH may influence interactions with Ail. Furthermore, other outer membrane proteins of Y. pestis may bind and recognize the mouse SCR-binding region, allowing Δail mutants to remain resistant to murine serum.

Despite the fact that the Δlpp ΔmsbB Δail triple mutant was highly attenuated and rapidly cleared from mouse tissues, animals infected with this triple mutant were still able to mount balanced $T_H1$ and $T_H2$ responses (FIG. 6B) to significantly protect them (70%) against subsequent exposure to a high challenge dose of WT CO92 in a pneumonic plague model (FIG. 6A).

Interestingly, in our previous study, Ail was also identified by mass spectrometric analysis along with several other outer membrane antigens to which antibodies were generated when rats were exposed to WT CO92 by the intranasal route to mimic pneumonic plague and then rescued by an antibiotic, levofloxacin, given 24 h postinfection for 6 days (Erova et al., 2013, Clin Vaccine Immunol 20:227-238). Importantly, immunization of rats with the recombinant Ail protein provided partial protection to animals from a lethal challenge dose of WT CO92 in a pneumonic plague model, indicating that Ail also has some immunogenic potential (Erova et al., 2013, Clin Vaccine Immunol 20:227-238). Therefore, further manipulation of the ail gene to reduce its virulence potential while retaining immunogenicity in the Δlpp ΔmsbB background strain would provide a promising strategy in our future study.

In summary, we were able to determine the mechanistic basis of attenuation of the Δlpp ΔmsbB Δail triple mutant of Y. pestis CO92. The Δlpp ΔmsbB Δail triple mutant of Y. pestis CO92 was severely attenuated, with minimal damage to the host, while retaining immunogenicity. The possibility that this mutant may provide a platform for deleting additional genes to develop a viable live-attenuated plague vaccine for immunocompetent military and health care workers is encouraging and will be pursued in future studies. Overall, our goal is to develop several highly attenuated Y. pestis mutant strains (Sha et al., 2013, Infect Immun 81:815-828; Sha et al., 2008, Infect Immun 76:1390-1409; van Lier et al., 2014, Infect Immun 82:2485-2503; Agar et al., 2009,

EXAMPLE 2

As described in Example 1, the Δlpp ΔmsbB Acid triple mutant of Yersinia pestis CO92 deleted for genes encoding Braun lipoprotein (Lpp), an acyltransferase (MsbB), and the Attachment Invasion Locus (Ail), respectively, was avirulent in a mouse model of pneumonic plague. In this study, we further evaluated the immunogenic potential of the Δlpp ΔmsbB Acid triple mutant and its derivative by different routes of vaccination. Mice were immunized via the subcutaneous (s.c.) or the intramuscular (i.m.) route with two doses ($2\times10^6$ CFU/dose) of the above-mentioned triple mutant with 100% survivability of the animals. Upon subsequent pneumonic challenge with 70-92 $LD_{50}$ of WT CO92, all of the mice survived when immunization occurred by the i.m. route. Since Ail has both virulence and immunogenic potential, a mutated version of Ail devoid of its virulence properties was created, and the genetically modified ail replaced the native ail gene on the chromosome of the Δlpp ΔmsbB double mutant, creating a Δlpp ΔmsbB::ailL2 vaccine strain. This newly generated mutant was similarly attenuated as the Δlpp ΔmsbB Δail triple mutant when administered by the i.m. route, and provided 100% protection to animals against subsequent pneumonic challenge. Not only did both of the above-mentioned mutants cleared rapidly from the initial i.m. site of injection in animals with no histopathological lesions, the immunized mice did not exhibit any disease symptoms during immunization and after subsequent exposure to WT CO92. These two mutants triggered balanced Th1- and Th2-based antibody responses and cell-mediated immunity. A substantial increase in IL-17 from T-cells of vaccinated mice, a cytokine of the Th17 cells, further augmented their vaccine potential. Thus, both Δlpp ΔmsbB Δail triple and Δlpp ΔmsbB::ailL2 mutants represent excellent vaccine candidates for plague, with the latter mutant still retaining Ail immunogenicity but much diminished virulence potential. This Example is also available as Tiner et al., 2015, Clinical Vaccine Immunol., 22:1255-1268.

Introduction

Yersinia pestis is the causative agent of plague (Perry et al., 1997, Clin Microbiol Rev 10:35-66), and there has been a rise in the number of plague cases globally in recent years due possibly to climate changes and shifting of the rodent carrier range (World Health Organization Media Center. 6 Aug. 2009, posting date. Plague: questions and answers about plague., World Health Organization, Geneva, Switzerland). The organism is classified as a Tier-1 select agent (Centers for Disease Control and Prevention. 17 Nov. 2008, posting date. Protecting the American public by ensuring safe and secure possession, use, and transfer of select agents and toxins that pose a threat to public health, CDC Select Agent Program, Centers for Disease Control and Prevention, Atlanta, Ga.; Inglesby et al., 2000, JAMA 283:2281-2290; Pearson et al., 1998, Biological Weapons Proliferation: Reasons for Concern, Courses of Action. Henry L. Stimson Center, Washington D.C.), and the progression of septicemic and pneumonic forms of plague is very rapidly fatal after first appearance of the symptoms (Inglesby et al., 2000, JAMA 283:2281-2290; Rosenzweig et al., 2011, Antimicrob Agents Chemother 55:5034-5042; Layton et al., 2011, PLoS Negl Trop Dis 5:e959; Peterson et al., 2010, Open Microbiol J 4:34-46). Alarmingly, antibiotic-resistant strains of Y. pestis have been isolated from plague patients and also engineered for bioweaponization (Inglesby et al., 2000, JAMA 283:2281-2290). Therefore, vaccination would be the optimal strategy for human protection against this deadly disease; however, there are currently no Food and Drug Administration (FDA)-licensed plague vaccines available in the United States (Smiley, 2008, Expert Rev Vaccines 7:209-221; CDC, Fed Regist 77:61083-61115; Alvarez et al., 2010, Biotechnol Adv 28:184-196).

Although a heat-killed plague vaccine composed of Y. pestis 195/P strain was in use in the United States until 1999, the production of this vaccine was discontinued because of its effectiveness only against the bubonic plague and not the pneumonic form, and it was highly reactogenic in humans (Rosenzweig et al., 2011, Appl Microbiol Biotechnol 91:265-286; Williams et al., 1980, Bull World Health Organ 58:753-756). Various live-attenuated Y. pestis EV76 vaccine strains, which lack the pigmentation locus (pgm) required for iron acquisition, provide protection against both bubonic and pneumonic plague and are being used in some parts of the world where plague is endemic (Smiley, 2008, Expert Rev Vaccines 7:209-221). However, these EV76-based vaccines are not genetically uniform and are also highly reactogenic (Cui et al., 2014, Infect Genet Evol 26:172-179), and, hence, do not meet the standards for FDA approval. In addition, the Δpgm mutants of Y. pestis (e.g., KIM/D27 strain) may not be safe because of a reported case of fatal infection in an individual with hemochromatosis (2011, Morb Mortal Wkly Rep 60:201-205; Quenee et al., 2012, J Infect Dis 206:1050-1058).

In an effort to search for a new live-attenuated plague vaccine, we recently constructed Δlpp ΔmsbB Δail triple mutant which was deleted for genes encoding Braun lipoprotein (Lpp), an acetyltransferase (MsbB), and the Attachment Invasion Locus (Ail) (Tiner et al., 2015, Infect Immun 83:1318-1338). Lpp activates Toll-like receptor-2, which leads to the production of pro-inflammatory cytokines and septic shock (Glauser et al., 1991, Lancet 338:732-736; Braun et al., 1974, Annu Rev Biochem 43:89-121; Neilsen et al., 2001, J Immunol 167:5231-5239; Aliprantis et al., 1999, Science 285:736-739). On the other hand, MsbB modifies lipopolysaccharide (LPS) by adding lauric acid to the lipid A moiety, thus, resulting in increased biological potency of LPS (Aliprantis et al., 1999, Science 285:736-739; Clementz et al., 1996, J Biol Chem 271:12095-12102; Clementz et al., 1997, J Biol Chem 272:10353-10360; Anisimov et al., 2007, J Med Microbiol 56:443-453; Oyston et al., J Med Microbiol 52:289-294; Perez-Gutierrez et al., 2010, Infect Immun 78:2768-2781; Sha et al., 2013, Infect Immun 81:815-828). Ail is a ~17 kDa outer membrane protein with four extracellular loops, and the loop 2 (L2) has been reported to be mainly responsible for Ail-mediated bacterial serum resistance and adherence/invasion of the host cells (Tiner et al., 2015, Infect Immun 83:1318-1338; Bartra et al., 2008, Infect Immun 76:612-622; Felek et al., 2009, Infect Immun 77:825-836; Felek et al., 2010, Infect Immun 78:4134-4150; Hinnebusch et al., 2011, Infect Immun 79:4984-4989; Kolodziejek et al., 2007, Microbiology 153:2941-2951; Kolodziejek et al., 2010, Infect Immun 78:5233-5243; Tsang et al., 2010, Infect Immun 78:3358-3368; Tsang et al., 2012, J Biol Chem 287:16759-16767; Yamashita et al., 2011, Structure 19:1672-1682).

In this study, to further characterize the vaccine potential of the Δlpp ΔmsbB Δail triple mutant, we evaluated its effectiveness when administered by the most common subcutaneous (s.c) or the intramuscular (i.m.) route (CDC, 2011, MMWR Recomm Rep 60:1-64). Since Ail also has immunogenic potential in addition to its role as a virulence factor (Erova et al., 2013, Clin Vaccine Immunol 20:227-238), we aimed at mutating the corresponding nucleotides in the ail gene that encodes essential amino acid (aa) residues required for virulence of L2 instead of deleting the whole ail gene from the Δlpp ΔmsbB mutant of CO92 (Yamashita et al., 2011, Structure 19:1672-1682; Miller et al., 2001, Mol Microbiol 41:1053-1062). Indeed, the generated Δlpp ΔmsbB::ailL2 mutant was severely impaired in Ail-associated virulence traits, e.g., serum resistance, host cell adhesion and invasion. Most importantly, immunization of mice with either the Δlpp ΔmsbB Δail or the Δlpp ΔmsbB::ailL2 mutant via either the i.m. or the s.c. route, elicited robust humoral and cellular immune responses, which conferred up to 100% protection in animals at high pneumonic challenge doses of 70-92 $LD_{50}$ with WT CO92. Therefore, Δlpp ΔmsbB Δail and Δlpp ΔmsbB::ailL2 mutants represent excellent plague vaccine candidates. In addition, such vaccines could be effectively administrated via different routes, providing flexibility during immunization.

Materials & Methods

Bacterial Strains and Plasmids.

All bacterial strains and plasmids used in this study are listed in Table 3. *Y. pestis* and recombinant *Escherichia coli* strains were grown as described by us previously (Tiner et al., 2015, Infect Immun 83:1318-1338; Sha et al., 2013, Infect Immun 81:815-828; Agar et al., 2009, Microbiology 155:3247-3259; van Lier et al., 2014, Infect Immun 82:2485-2503). All of our studies were performed in a Tier-1 select agent facility within the Galveston National Laboratory (GNL), UTMB. The molecular biological reagents were purchased from Promega (Madison, Wis.), Clontech (Palo Alto, Calif.), and Qiagen, Inc., Valencia, Calif.). HeLa cells were obtained from the American Type Culture Collection (ATCC, Manassas, Va.).

TABLE 3

Bacterial strains and plasmids used in this study

| Strain or plasmid | Genotype and/or relevant characteristics | Reference and Source[a] |
|---|---|---|
| Strains | | |
| *Y. pestis* CO92 | | |
| WT CO92 | Virulent WT *Y. pestis* isolated in 1992 from a fatal pneumonic plague case, biovar *Orientalis*, and naturally resistant to polymyxin B | CDC |
| WT CO92 luc2 | WT *Y. pestis* with chromosomally intergrated integrated luciferase operon via Tn5, which retains similar virulence potential as the WT CO92 and used as a bioluminescent reporter strain | (1) |
| WT CO92-lux | WT *Y. pestis* with chromosomally integrated luciferase operon downstream of the conserved glmS gene via Tn7, which retains similar virulence potential as the WT CO92 and used as a bioluminescent reporter strain | This study |
| Δlpp ΔmsbB | lpp and msbB double gene deletion mutant of *Y. pestis* CO92 | (2) |
| Δlpp ΔmsbB Δail-Km | *Y. pestis* CO92 intermediate lpp, msbB and ail triple gene deletion mutant that carried a $Km^r$ cassette in place of the ail gene | (3) |
| Δlpp ΔmsbB Δail | lpp, msbB and ail triple gene deletion mutant of *Y. pestis* CO92 | (3) |
| Δlpp ΔmsbB Δail-lux | Δlpp ΔmsbB Δail with chromosomally integrated luciferase operon downstream of the conserved glmS gene via Tn7, which was used as a bioluminescent reporter strain | This study |
| Δlpp ΔmsbB::ailL2 | lpp and msbB double gene deletion mutant with a mutated ail gene ailL2 | This study |
| Δlpp ΔmsbB::ailL2-lux | Δlpp ΔmsbB::ailL2 with chromosomally integrated luciferase operon downstream of the conserved glmS gene via Tn7, which was used as a bioluminescent reporter strain | This study |
| *E. coli* DH5α λpir | Contains the λpir gene (lysogenized with λpir phage) and it is used for the cloning and propagation of plasmid with R6K origin of replication | Laboratory stock |
| Plasmids | | |
| pDMS197 | Suicide vector with a conditional R6K origin of replication (ori) and a levansucrase gene (sacB) from *Bacillus subtilis* used for homologous recombination | (4) |
| pDMS197-ailL2 | pDMS197 vector containing the mutated ail gene [ailL2] with its flanking sequences, used to generate the Δlpp ΔmsbB::ailL2 mutant | This study |
| pUC4K | Template plasmid used as a source of the $Km^r$ cassette | Amersham Pharmacia Biotech |
| pTNS2 | Helper plasmid that expresses the transposase complex to facilitate efficient transposition | (5) |
| pUC18-mini-Tn7 T-lux-Gm | pUC18 based plasmid containing mini-Tn7 transposon, the luciferase operon (lux) and the gentamicin (Gm) resistance cassette | (5) |
| pUC18R6KT-mini-Tn7 T | pUC18 based plasmid with a conditional R6K origin of replication (ori) containing mini-Tn7 transposon | (5) |
| pUC18R6KT-mini-Tn7 T-lux | pUC18R6KT-mini-Tn7 T based plasmid containing the luciferase operon (lux) | This study |
| pUC18R6KT-mini-Tn7 T-lux-Km | pUC18R6KT-mini-Tn7 T-lux based plasmid containing the $Km^r$ cassette, used to create various bioluminescent reporter strains of *Y. pestis* | This study |

[a]CDC = Centers for Disease Control and Prevention
(1). Sha et al., 2013, Microb Pathog 55: 39-50;
(2). Sha et al., 2013, Infect Immun 81: 815-828;
(3). Tiner et al., 2015, Infect Immun 83: 1318-1338;
(4). Edwards et al., 1998, Gene 207: 149-157;
(5). Choi et al., 2005, Nat Methods 2: 443-448.

Mutation of the ail Gene.

Four aa residues (Lysine-88, Aspartate-91, Aspartate-93, and Phenylanine-94) in L2 of Ail were changed to alanine by using polymerase chain reactions (PCRs). Briefly, the primer pairs Aup5-mAup3 and mAdn5-Adn3 (Table 4) were used to introduce specific mutations within L2 region of the ail gene, as well as to amplify the mutated ail gene with its up- and down-stream DNA sequences, respectively. The mutated ail gene, designated as ailL2, with its up- and down-stream flanking DNA sequences were joined together by PCR with the primer pair Aup5-Adn3 (Table 4). The above-mentioned PCR product was subsequently cloned into the suicide vector pDMS197 (Edwards et al., 1998, Gene 207:149-157), which generated the recombinant plasmid pDMS197-ailL2 (Table 3).

Production of AilL2 and plasminogen activator (Pla) protease in the Δlpp ΔmsbB::ailL2 mutant of *Y. pestis* CO92.

The Δlpp ΔmsbB, Δlpp ΔmsbB Δail triple and the Δlpp ΔmsbB::ailL2 mutant were grown overnight in Heart Infusion Broth (HIB) at 28° C. with shaking at 180 rpm, and the resulting bacterial cells (representing similar colony forming units [CFU]) were dissolved in SDS-PAGE sample buffer. An aliquot of the samples was then resolved by SDS-PAGE and the Western blots analyzed with polyclonal antibodies to Ail and Pla (Erova et al., 2013, Clin Vaccine Immunol 20:227-238). As a loading control, the presence of DnaK in

TABLE 4

Sequences of primers used in this study

| Primer or primer pair | Primer sequences[a] (5'-3') | Purpose |
|---|---|---|
| Aup5-mAdn3 | TATgagctcACGACGCACAAGACTCTGGC (SacI), (SEQ ID NO: 16) TAGTACTTAGCAGCACCAGCAATAAGTGCGAATCCGTCAA (SEQ ID NO: 17) | PCR amplifies the upstream flanking DNA fragment to the loop 2 region of the ail gene and introduces specific muatations in the loop 2 |
| mAdn5-Adn3 | TTGACGGATTCGCACTTATTGCTGGTGCTGCTAAGTACTA, (SEQ ID NO: 18) GCATCCGTCAATggtaccAG (KpnI) (SEQ ID NO: 19) | PCR amplifies the downstream flanking DNA fragment to the loop 2 region of the ail gene and introduces specific muatations in the loop 2 |
| Aup5-Adn3 | TATgagctcACGACGCACAAGACTCTGGC (SacI), (SEQ ID NO: 20) GCATCCGTCAATggtaccAG (KpnI) (SEQ ID NO: 21) | Pimer pair used to join the ailL2 with its upstream and downstream flanking DNA fragments by PCR |
| Up5-Dn3 | ATGCCCACATCGTTACCACC, (SEQ ID NO: 22) CCGTAATCCATGGTGATCTG (SEQ ID NO: 23) | Primer pair located outside the flanking DNA sequences of the ail gene and used to verify the correct replacement of Km[r] cassette with ailL2 on the choromosome of the Δlpp ΔmsbB Δail-Km |
| P1-P2 | GGTGGCACCGAACAATGAAT, (SEQ ID NO: 24) CATTACGCTGACTTGACGGG (SEQ ID NO: 25) | PCR confirmation of the insertion of the lux operon at the ailTn7 region of *Y. pestis* CO92 |
| SqAil | GGAATACTGTACGAATATCC (SEQ ID NO: 26) | Pimer located 108 bp upstream of the ail gene; used to confirm correct integration of the ailL2 with its adjacent regions in the Δlpp ΔmsbB:ΔailL2 mutant by chormosomal DNA sequencing |

[a]Bold bases denote loop 2 region, underlined bases denote mutations and the lower case letter represent restriction enzyme sites.

Previously, we constructed an intermediate lpp, msbB, and ail triple gene deletion mutant (Δlpp ΔmsbB Δail-Km) of *Y. pestis* CO92 (Table 3) that carried a kanamycin resistance gene (Km[r]) cassette (Datsenko et al., 2000, Proc Natl Acad Sci USA 97:6640-6645) in place of the ail gene (Tiner et al., 2015, Infect Immun 83:1318-1338). Therefore, the recombinant suicide vector pDMS197-ailL2 was electroporated into the Δlpp ΔmsbB Δail-Km strain (Genepulser Xcell; Bio-Rad, Hercules, Calif.) (Tiner et al., 2015, Infect Immun 83:1318-1338). The transformants that were sensitive to kanamycin (Km[s]) and resistant to 5% sucrose were picked up and screened by PCR with the primer pair Up5-Dn3 (Table 4) (Tiner et al., 2015, Infect Immun 83:1318-1338) to ensure genomic replacement of the Km[r] cassette with the ailL2 gene. Genomic DNA sequencing with the primer SqAil (Table 4) (Tiner et al., 2015, Infect Immun 83:1318-1338) was used to further confirm replacement and to ensure no alteration in the ailL2 surrounding regions in the Δlpp ΔmsbB::ailL2 mutant, when compared to that of the native ail gene in the Δlpp ΔmsbB double mutant.

the bacterial pellets was assessed by using anti-DnaK monoclonal antibodies (Enzo, Farmingdale, N.Y.).

Serum Resistance, Adherence, and Invasion of *Y. pestis* CO92 Mutants

Various *Y. pestis* strains were grown overnight, harvested, and then diluted in phosphate-buffered saline (PBS) to an $OD_{600}$ of 0.2 (~$1\times10^8$ CFU/ml). A 50-μl volume of the diluted bacteria (~$5\times10^6$ CFU) was mixed with either 200 μl of undiluted normal (unheated) or heat-inactivated (56° C./30 min) human sera (Sigma-Aldrich, St. Louis, Mo.). After incubation at 37° C. for 2 h, the number of surviving bacteria (CFU) in each sample was determined by serial dilutions and plating on Sheep Blood Agar (SBA) plates (Tiner et al., 2015, Infect Immun 83:1318-1338; Sha et al., 2013, Infect Immun 81:815-828). Percent bacterial survival was calculated by dividing the average CFU in samples incubated in normal serum by the average CFU in samples incubated in the heat-inactivated serum and multiplying by 100.

Human HeLa cervical epithelial cells ($4\times10^5$) were seeded in 12-well plates as described previously (Tiner et al., 2015, Infect Immun 83:1318-1338) and infected with various mutants of *Y. pestis* CO92 at a multiplicity of infection (MOI) of 100. The plates were centrifuged at 1200 rpm for 10 min to facilitate bacterial contact with the HeLa cells. After 2 h of incubation, the adherence and invasion of bacteria were evaluated as we recently described (Tiner et al., 2015, Infect Immun 83:1318-1338; Cowan et al., 2000, Infect Immun 68:4523-4530).

Animal Studies

Six-to-eight-week old, female Swiss-Webster mice (17 to 20 g) were purchased from Taconic Laboratories (Germantown, N.Y.). All of the animal studies were performed in the Animal Biosafety Level (ABSL)-3 facility under an approved Institutional Animal Care and Use Committee protocol.

i) Immunization. Mice were immunized by the i.m. route with one or two doses of $2 \times 10^6$ CFU/100 microliter of the Δlpp ΔmsbB Δail triple or the Δlpp ΔmsbB::ailL2 mutant. The mutants were administered in a 50 microliter volume in each of the hind legs. When two doses of each vaccine strain were administered, they were injected twenty-one days apart (on days 0 and 21). Mice receiving only one dose were injected on the same day when the other animals received their second vaccine dose (on day 21). Another set of mice was immunized by the s.c. route with two doses of $2 \times 10^6$ CFU/100 microliter of the Δlpp ΔmsbB Δail triple or the Δlpp ΔmsbB mutai(L2) mutant strains. Subcutaneous doses were injected at one site twenty-one days apart (on days 0 and 21). Mice were assessed for morbidity and/or mortality over the duration of vaccination.

ii) Antibody responses. Blood was collected by the retro-orbital route from vaccinated mice two weeks after each immunization (on days 14 and 35). Pre-immunization blood samples served as a control. Sera were separated and filtered by using Costar 0.1-μm centrifuge tube filters (Corning Inc., Corning, N.Y.). ELISA plates were coated with the F1-V fusion protein (1 ng/microliter, BEI Resources, Manassas, Va.) (Tiner et al., 2015, Infect Immun 83:1318-1338; Sha et al., 2013, Infect Immun 81:815-828; van Lier et al., 2014, Infect Immun 82:2485-2503). Total IgG and antibody isotypes against F1-V (capsular antigen F1 and a type 3 secretion system [T3SS] component low calcium response V antigen [LcrV]) in the sera (1:5 serially diluted) of animals immunized with the Δlpp ΔmsbB Δail triple or the Δlpp ΔmsbB::ailL2 mutant were then determined as we previously described (Tao et al., 2013, PLoS Pathog 9:e1003495).

iii) Challenge. Twenty-one days after the last immunization (day 42), the immunized mice were anesthetized with a mixture of xylazine-ketamine and then exposed by the i.n. route to $3.5 \times 10^4$ to $4.6 \times 10^4$ CFU/40 microliter (70 to 92 $LD_{50}$) of the bioluminescent WT *Y. pestis* CO92 luc2 strain (WT CO92 luc2), which contains the luciferase operon (luc or lux) allowing in vivo imaging of mice for bacterial dissemination in real time (Tiner et al., 2015, Infect Immun 83:1318-1338; Sha et al., 2013, Microb Pathog 55:39-50). Naive mice of the same age were used as controls. On days 3 and 7 post infection (p.i.), the animals were imaged by using an in vivo imaging system (IVIS) 200 bioluminescent and fluorescence whole-body imaging workstation (Caliper Corp. Alameda, Calif.) in the AB SL-3 facility.

iv) Histopathological Analysis. Immunized mice (n=2) which received two doses of the vaccine by either the i.m. or the s.c. route were euthanized three weeks after the second vaccine dose (on day 42). Similarly, three mice from each of the immunized groups that survived pneumonic challenge with 70 $LD_{50}$ of WT CO92 luc2 strain were sacrificed on day 54 post challenge. Age-matched naïve uninfected mice (n=2) were also euthanized as a control. Lungs, liver, and the spleen were harvested from these mice, fixed in 10% neutral buffered formalin (Agar et al., 2009, Microbiology 155:3247-3259; Sha et al., 2008, Infect Immun 76:1390-1409), and tissues processed and sectioned at 5 The samples were mounted on slides and stained with hematoxylin and eosin (H&E). Tissue lesions were scored on the basis of a severity scale, which correlated with estimates of lesion distribution and the extent of tissue involvement (minimal, 2 to 10%; mild, >10 to 20%; moderate, >20 to 50%; severe, >50%), as previously described (Agar et al., 2009, Microbiology 155:3247-3259; Sha et al., 2008, Infect Immun 76:1390-1409). The histopathological evaluation of the tissue sections was performed in a blinded fashion.

v) Progression of Infection. To monitor progression of infection in real time, various bioluminescent stains of *Y. pestis* CO92 were constructed by using the Tn7-based system (Agar et al., 2009, Microbiology 155:3247-3259). The Tn7-based system integrates the target gene in a site-specific manner downstream of the conserved glmS (glucosamine-6-phosphate synthase) gene on the bacterial chromosome (Craig, 1996, Curr Top Microbiol Immunol 204:27-48; Peters et al., 2001, Nat Rev Mol Cell Biol 2:806-814). Briefly, the lux operon was removed from the plasmid pUC18-mini-Tn7T-lux-Gm by SpeI/KpnI restriction enzyme digestion and sub-cloned into plasmid pUC18R6KT-mini-Tn7T (Choi et al., 2005, Nat Methods 2:443-448) resulting in a derivative, designated as pUC18R6KT-mini-Tn7T-lux (Table 3).

Subsequently, the $Km^r$ cassette from the pUC4K plasmid (BamHI digestion) was inserted into pUC18R6KT-mini-Tn7T-lux, thus, resulted in the creation of the pUC18R6KT-mini-Tn7T-lux-Km plasmid (Table 3). The electrocompetent cells of WT CO92, Δlpp ΔmsbB Δail triple, and the Δlpp ΔmsbB::ailL2 mutant strains were electroporated with mixed (2 to 1) pTNS2 and pUC18R6KT-mini-Tn7T-lux-Km plasmids (Agar et al., 2009, Microbiology 155:3247-3259; Sha et al., 2013, Microb Pathog 55:39-50; Choi et al., 2005, Nat Methods 2:443-448), and selected for $Km^r$ and luminescence. The insertion of lux at the attTn7 region was confirmed by PCR using primer pair P1-P2 (Table 4) which specifically amplified the region between *Y. pestis* glmS gene and the Tn7 insertion cassette (Agar et al., 2009, Microbiology 155:3247-3259). Luminescence intensity of each strain was determined by relative luminescence unit (RLU) measurement (Spectramax M5e, Molecular Devices, Sunnyvale, Calif.) (Sha et al., 2013, Microb Pathog 55:39-50).

Mice (n=3) were then infected with $2 \times 10^6$ CFU/100 microliter of the above generated bioluminescent stains: Δlpp ΔmsbB Δail-lux, Δlpp ΔmsbB::ailL2-lux, or the WT CO92-lux (Table 3) by the i.m. route. The IVIS images were taken immediately after challenge and then every 12 h until 48 h p.i. After 48 h, mice were euthanized and the muscles, lungs, liver, and the spleen were removed immediately following animal sacrifice. The tissues were homogenized in 1 ml of PBS, and serial dilutions of the homogenates were spread on the SBA plates to assess dissemination of the bacteria to peripheral organs (Sha et al., 2013, Infect Immun 81:815-828). Portions of each organ from 3 mice at each time point were also removed for histopathological analysis (Agar et al., 2009, Microbiology 155:3247-3259; Sha et al., 2008, Infect Immun 76:1390-1409).

vi) T-cell proliferative responses and cytokine production. Mice (n=5) were infected by the i.m. or the s.c. route with *Y. pestis* KIM/D27 (pgm locus minus strain) (Table 3), the Δlpp ΔmsbB Δail triple, or the Δlpp ΔmsbB::ailL2 mutant strains of *Y. pestis* CO92 at a dose of $1\times10^3$ CFU/100 microliter. The T-cell proliferation in response to heat-killed WT CO92 antigens (pulsed) was measured on day 21 p.i., as we previously described (Sha et al., 2013, Infect Immun 81:815-828; van Lier et al., 2014, Infect Immun 82:2485-2503). T-cells from uninfected mice as well as un-pulsed T cells served as negative controls. The T-cell culture supernatants were collected at 48 h to measure cytokine/chemokine production by using a mouse 6-plex assay kit (Bio-Rad Laboratories Inc.). After 72 h of incubation, 1 µCi of [$^3$H] thymidine was added into each well, and the cells harvested 16 h later using a semi-automated sample harvester, FilterMate Harvester (PerkinElmer, Waltham, Mass.), followed by the measurement of radioactive counts (TopCount NXT, PerkinElmer).

Statistical Analysis.

For majority of the experiments, one-way analysis of variance (ANOVA) was used with the Tukey's post hoc test for data analysis except for the serum resistance assay which was examined using the Student's t-test. We used Kaplan-Meier survival estimates for animal studies, and p values of ≤0.05 were considered significant for all of the statistical tests used. The standard deviations were derived from three independently performed experiments with three replicates per experiment for in vitro assays.

Results

Evaluation of protection provided by intramuscular immunization of mice with the Δlpp ΔmsbB Δail triple mutant in a pneumonic plague model.

Mice were i.m. vaccinated with one or two doses of the Δlpp ΔmsbB Δail triple mutant at $2\times10^6$ CFU/dose. As shown in FIG. 16, similar levels of total IgG antibody titers (1:15,625) to F1-V were noted when animals were vaccinated with either one or two doses. In addition, mice developed balanced Th1- and Th2-responses based on IgG1, IgG2a, and IgG2b antibody titers to F1-V (1:15,625) despite the number of vaccine doses administered (FIG. 16A).

No disease symptoms were observed in mice during above immunizations. All of the mice immunized with two doses of the triple mutant survived the i.n. challenge with 92 LD$_{50}$ of WT CO92 luc2 strain when administered on day 21 after vaccination (FIG. 16B). While slightly lower, but still impressive level of protection (78%) was achieved when animals were vaccinated with only one dose of the triple mutant, and this protection was not statistically different when compared to the group of animals receiving two doses of the vaccine (FIG. 16B). In contrast, all naive mice succumbed to infection by day 4 p.i. and exhibited clinical symptoms such as ruffled fur, hunched back, lethargy and they were unable to groom and tended to hurdle together.

The above infected mice were also imaged on day 3 p.i. to monitor progression of infection. As shown in FIG. 16C, the WT CO92 luc2 disseminated from the lungs to the whole body in 7 out of 8 naïve animals, and they all eventually succumbed to infection. On the contrary, animals receiving one immunization dose of the Δlpp ΔmsbB Δail triple mutant, only 2/9 mice were positive for bioluminescence on day 3 post challenge (FIG. 16C). These two animals succumbed to infection resulting in an overall 78% survival rate (FIG. 16B). It was also noted that the bioluminescent strain was confined at the initial infection site (lungs) in those two bioluminescent-positive animals when compared to that of the naïve but infected controls (FIG. 16C).

In the immunized group of mice receiving two doses of the vaccine, none of the animals were positive for bioluminescence after pneumonic challenge (FIG. 16C), with 100% of the animals surviving (FIG. 16B). No clinical symptoms of the disease were apparent in mice receiving two doses of the vaccine and then subsequently challenged. Since none of the surviving animals became bioluminescent positive by day 7 (0/10), these data indicated clearing of the WT CO92 luc2 strain by day 7 (FIG. 16C). To confirm, no bacilli were detected in organs (lungs, liver, and the spleen) of the survivors on day 54 after WT CO92 luc2 challenge based on bacterial enumeration by plating (data not shown).

In Vitro Characterization of the Δlpp ΔmsbB::ailL2 Mutant of *Y. pestis* CO92.

The replacement of native ail with the ailL2 gene in the Δlpp ΔmsbB double mutant of *Y. pestis* CO92 was confirmed by PCR analysis. Further genomic DNA sequencing revealed no unexpected alterations in the ailL2 gene as well as in its adjacent regions on the chromosome when compared to that of its parental strain (data not shown). In addition, we examined expression of the ailL2 gene by Western blot analysis. As shown in FIG. 17A, Ail-specific antibodies detected the correct size protein with essentially similar intensity in all of the examined strains except for the Δlpp ΔmsbB Δail triple mutant. Importantly, the expression level of the pla gene was also similar across all strains examined, indicating that neither deletion of the native ail gene nor replacing it with the ailL2 gene in the Δlpp ΔmsbB double mutant affected production of the other tested bacterial membrane protein, i.e., Pla (FIG. 17A).

Due to Ail's ability to impart serum resistance to *Y. pestis* (Tiner et al., 2015, Infect Immun 83:1318-1338; Bartra et al., 2008, Infect Immun 76:612-622; Hinnebusch et al., 2011, Infect Immun 79:4984-4989; Kolodziejek et al., 2007, Microbiology 153:2941-2951; Kolodziejek et al., 2010, Infect Immun 78:5233-5243), the WT CO92 and its Δlpp ΔmsbB double, Δlpp ΔmsbB Δail triple, and Δlpp ΔmsbB::ailL2 mutants were evaluated for their ability to be killed by the complement cascade. Although all tested strains survived similarly in heat-inactivated sera after 2 h incubation with CFU in the range of 1.6 to $2.0\times10^4$/ml; less than 10% of the Δlpp ΔmsbB Δail triple mutant survived when exposed to the normal sera (FIG. 17B). On the other hand, both WT CO92 and its Δlpp ΔmsbB double mutant strain exhibited slightly better or similar survival rates in the normal sera when compared to that of the heat-inactivated sera. The survival rate of the Δlpp ΔmsbB::ailL2 mutant strain was ~35% in the normal sera; and as expected, it did not reach the level of the Δlpp ΔmsbB double mutant (FIG. 17B).

Since Ail also functions in adherence and subsequent invasion of bacteria in the host cells, these virulence phenotypes of WT CO92 and its various mutants were examined in HeLa cells. Both the adherence (FIG. 17C—Panel I) and invasive ability (FIG. 17C—Panel II) of the Δlpp ΔmsbB Δail triple mutant were significantly decreased when compared to those of the WT CO92 and its Δlpp ΔmsbB double mutant. The Δlpp ΔmsbB::ailL2 mutant behaved very similar to that of the Δlpp ΔmsbB Δail triple mutant in terms of its ability to adhere and invade HeLa cells.

Evaluation of protection provided by intramuscular or subcutaneous immunization of mice with the Δlpp ΔmsbB Δail triple or the Δlpp ΔmsbB::ailL2 mutant in a pneumonic plague model.

Since our data presented in FIG. 16B indicated that two doses of immunization in mice provided optimal protection against WT CO92 challenge, we used the same vaccination regimen for both i.m and s.c. routes of immunization and compared protection conferred by the Δlpp ΔmsbB::ailL2 mutant with that of the Δlpp ΔmsbB Δail triple mutant.

Irrespective of the routes of immunization with either of the two mutant strains, 100% survivability of animals was noted with no clinical symptoms. All of the mice immunized intramuscularly were protected against the lethal pneumonic challenge at the dose of 3.5×10$^4$ CFU (70 LD$_{50}$) with WT CO92 luc2 strain (FIG. 18A), while 67 to 88% protection was achieved in mice subcutaneously immunized with either the Δlpp ΔmsbB::ailL2 or the Δlpp ΔmsbB Δail mutant, respectively (FIG. 18B). Although the level of protection provided by the s.c. route of vaccination did not reach the same level as noted for the i.m. route of immunization (FIG. 18A), the difference in protection afforded by the two mutants was statistically insignificant. All naive and unimmunized mice succumbed to infection by 4 day post WT CO92 luc2 challenge (FIGS. 18A and B).

The bioluminescence images further showed that the organism disseminated from the lungs to the whole body of all naïve but infected control mice (10/10) by day 3 p.i. (FIG. 18C-I). Only one animal from the Δlpp ΔmsbB Δail i.m.-immunized group was positive for bioluminescence and the infection was confined to the throat region (FIG. 18C-II). However, the infection cleared from this animal by day 7 p.i. and hence was not fatal. In the s.c.-immunized group of mice post challenge, one animal from each of mutants'-immunized groups was positive for bioluminescence on day 3 p.i. (FIG. 18C-III), albeit only at the original infection site of lungs, and these two mice eventually succumbed to infection by day 4-5 p.i. (FIG. 18B). Surprisingly, 2 additional mice initially negative for bioluminescence on day 3 p.i. in the Δlpp ΔmsbB::ailL2 mutant s.c.-immunized group also died by day 5-6 p.i. Upon necropsy, the death of these two mice was confirmed to be due to *Y. pestis* infection, suggesting that the level of bioluminescence in these animals was below the threshold of detection when imaged on day 3 (Sha et al., 2013, Microb Pathog 55:39-50). However, by day 7 p.i., none of the remaining mice, regardless of the mutant and route used for immunization, were positive for bioluminescence, and they were healthy throughout the experiment. Importantly, 54 days after WT CO92 luc2 challenge, organs (lungs, liver, and the spleen) harvested from randomly selected three survivors of each group (immunized via either the i.m. or the s.c. route) were free of the bacilli as evaluated by plate counting (data not shown).

To gauge immunogenicity of the vaccine strains via different routes of immunization, sera were collected from all mice 14 days after each immunization. We noted a boost in antibody titers between the first and the second dose when vaccination was performed via the s.c. route. However, this phenomenon was not observed via the i.m. route of immunization, as the peak antibody titers were achieved after only one vaccine dose (data not shown). Both of the above-mentioned mutants triggered higher level of antibody responses (IgG titers of 1:46,875) to F1-V antigen when vaccination occurred via the i.m. route over the s.c. route of immunization, which showed IgG titers of 1:18,000 (FIG. 19A). Balanced Th1- and Th2-based IgG1, IgG2a, and IgG2b antibody responses to F1-V were observed irrespective of the mutant strains used for vaccination and the route of immunization employed (e.g., i.m vs s.c.) (FIG. 19B). Only exception was that the Δlpp ΔmsbB::ailL2 mutant-immunized animals by the s.c. route had significantly higher IgG1 titers over IgG2a titers, favoring a Th2 response (FIG. 19B).

Histopathological analysis of mouse tissues after intramuscular immunization with the Δlpp ΔmsbB Δail triple and the Δlpp ΔmsbB::ailL2 mutant and post exposure to WT *Y. pestis* CO92 in a pneumonic plague model.

Prior to WT CO92 challenge and after two doses of vaccination, organs (muscles, lungs, liver, and the spleen) were harvested from mice (n=2) in each group for histopathological analysis. Muscles from mice immunized with the Δlpp ΔmsbB::ailL2 mutant were within the normal limits histopathologically, similar to that for muscles obtained from naive, unimmunized mice (FIG. 20). Muscles from mice immunized with the Δlpp ΔmsbB Δail triple mutant were also within the normal limits except for mild focal inflammation (FIG. 20). Irrespective of the above two-mentioned mutants used for immunization, the lungs, livers, and spleens of animals did not exhibit any abnormal histopathology and were comparable to the organs of naive, unimmunized mice (FIG. 20).

Figure 24:
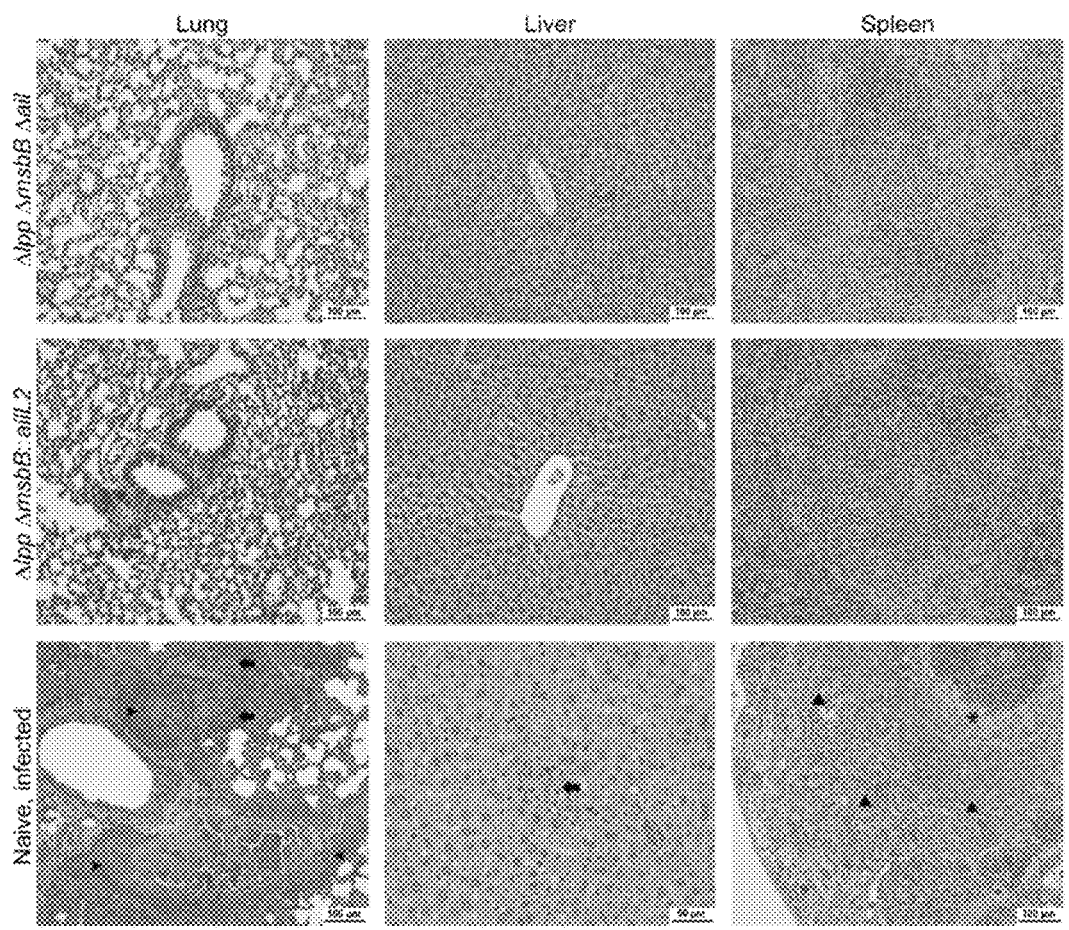

As all i.m.-immunized animals survived exposure to 70 LD$_{50}$ of WT CO92 luc2 strain (FIG. 18A), organs (lungs, liver, and the spleen) from 3 of these immunized mice were excised on day 54 p.i., to examine histopathological lesions and bacterial clearance. All of the naive mice succumbed to infection and organs from three of them were harvested at time of death. In the lungs, all of the WT CO92-infected, unimmunized control mice had mild-to-moderate neutrophilic inflammation (arrow), bacteria present (arrowhead), and mild and diffused congestion. Also, the alveoli of these mice had a moderate level of hemorrhage with few alveolar spaces observed (FIG. 24). All of the livers from WT CO92-infected, unimmunized mice had bacteria, some necrosis, and neutrophilic infiltration (arrow). All of the spleens of WT CO92-infected, unimmunized mice had bacteria (arrowhead), mild lymphoid depletion of the marginal zone in the white pulp (asterisk), and mild-to-marked diffuse rarefaction or loss of normal cell population of the red pulp with fibrin present (FIG. 24). On the contrary, all of the tissues from mice immunized with either of the two mutants (Δlpp ΔmsbB Δail triple or the Δlpp ΔmsbB::ailL2) and then challenged with WT CO92 exhibited histopathology within the normal limits (FIG. 24), similar to tissues from uninfected naive animals (FIG. 20).

When comparing histopathological changes, essentially similar data were obtained when immunization occurred via the s.c. route with either of the two mutants, and after challenge of the immunized mice by the pneumonic route with WT CO92 (data not shown).

Progression of infection and histopathological lesions in mice intramuscularly infected with the Δlpp ΔmsbB Δail triple and the Δlpp ΔmsbB::ailL2 mutant of *Y. pestis* CO92.

Mice (n=3) were either challenged with 2×10$^6$ CFU of WT CO92-lux, the Δlpp ΔmsbB Δail-lux, or the Δlpp ΔmsbB::ailL2-lux strain. Using IVIS, animals were imaged at 0, 12, 24, 36, and 48 h p.i. At 0 h, all mice were positive for bioluminescence that was localized to the injection site in the muscle (FIG. 21A—panel I). By 12 h p.i. in the muscle, all mice infected with the Δlpp ΔmsbB Δail-lux or the Δlpp ΔmsbB::ailL2-lux strain were positive but the intensity of bioluminescence had decreased compared to 0 h (FIG. 21A—panel II). From 24 to 48 h p.i., none of the mice infected with the Δlpp ΔmsbB Δail-lux or the Δlpp ΔmsbB::ailL2-lux strain were positive for bioluminescence (FIG. 21A—panels III-V).

However, mice infected with the WT CO92-lux strain had increased bioluminescence localized to the muscle at 12 h (FIG. 21A—panel II), and further dissemination of bacteria was observed in 1/3 mice at 24 h p.i. (FIG. 21A—panel III). This dissemination pattern became more prominent and was noted in the other two animals at 36 h p.i. (FIG. 21A—panel IV). At 48 h p.i., the level of bioluminescence was reduced in 1/3 mice (FIG. 21A—panels III-V). This is attributed to a death of this animal which causes bioluminescence to decrease due to diminished oxygen levels and temperature (Sha et al., 2013, Microb Pathog 55:39-50).

To further examine bacterial load in mice, after in vivo imaging at 48 h p.i., all of the animals were sacrificed, and the organs (muscles, lungs, liver, and the spleen) were harvested and subjected to bacterial count determination. As shown in FIG. 21B, mice infected with the WT CO92 had a high bacterial load in each of these organs (ranged from $8 \times 10^4$ to $8.7 \times 10^7$ CFU per organ or per gram of muscle) (FIG. 21B). The animal with a relatively lower bacterial load in various organs correspondingly exhibited weak bioluminescence at 36 and 48 h p.i. (FIG. 21A, panels IV-V), indicating bacterial counts to be below the threshold of bioluminescence detection for the WT CO92-lux strain during in vivo imaging.

Figure 25:
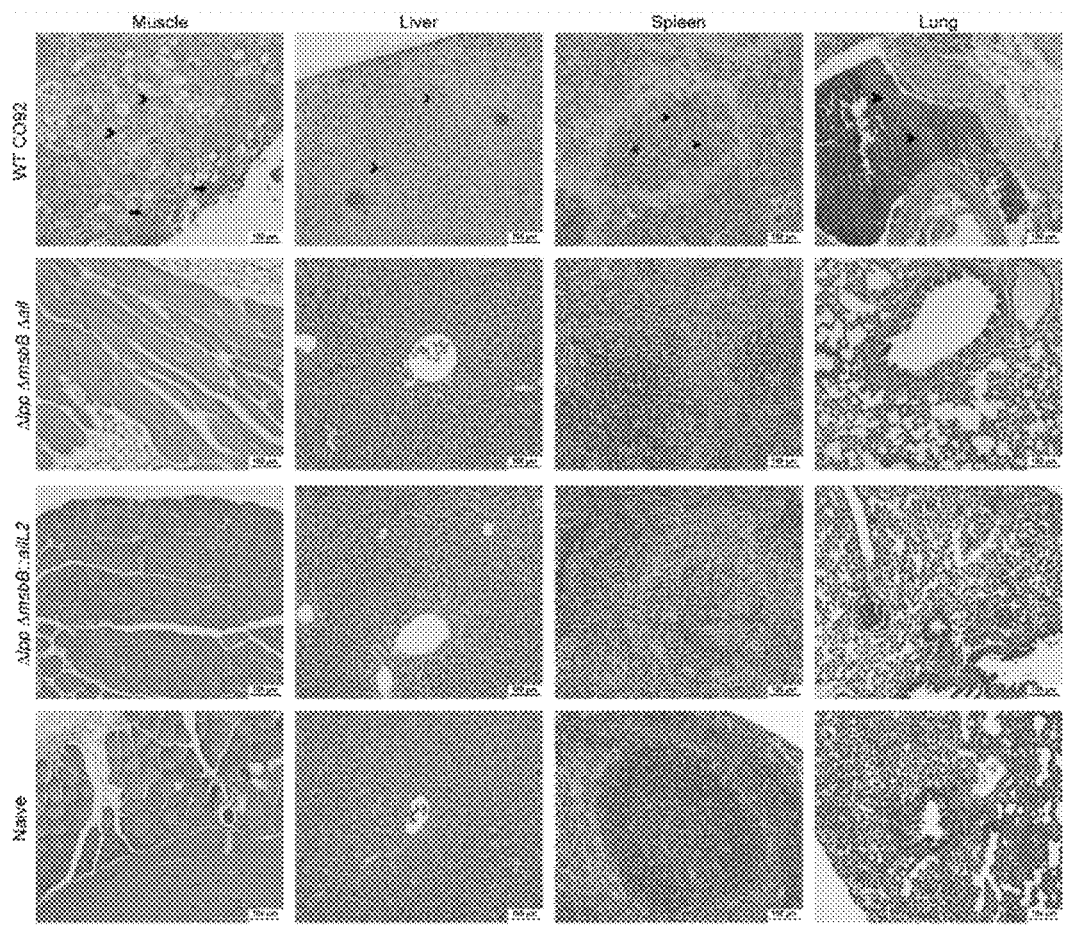

All of the animals infected with the WT CO92-lux strain had severe plague symptoms and were at the verge of death. In contrast, mice infected with either the Δlpp ΔmsbB Δail-lux triple or the Δlpp ΔmsbB::ailL2-lux mutant had minimal-to-no detectable bacterial load in any of the organs examined at 48 h p.i. (FIG. 21B). All of the tissues (muscle, liver, spleen, and lung) of WT CO92-infected animals had the presence of necrosis, hemorrhage, inflammation, edema, and bacteria (FIG. 25). However, all the tissues from mice infected with the Δlpp ΔmsbB Δail-lux triple or the Δlpp ΔmsbB::ailL2-lux mutant were within normal limits histopathologically (FIG. 25).

Activation of T cells by the Δlpp ΔmsbB Δail triple and the Δlpp ΔmsbB::ailL2 mutant of Y. pestis CO92 after intramuscular or subcutaneous immunization of mice.

To investigate T-cell responses, mice were i.m. or s.c. infected/immunized with $1 \times 10^3$ CFU dose of either KIM/D27, the Δlpp ΔmsbB Δail triple, or the Δlpp ΔmsbB::ailL2 mutant strain. Y. pestis KIM/D27 is a pgm-locus minus mutant with similar characteristics as the live-attenuated Y. pestis EV76 vaccine strain (You et al., 2012, Biomed Environ Sci 25:440-448), and, thus, served as an appropriate control. No clinical symptoms were observed in mice immunized with either the Δlpp ΔmsbB Δail triple or the Δlpp ΔmsbB::ailL2 mutant strain. Although none of KIM/D27-infected mice succumbed to infection at this low dose ($1 \times 10^3$ CFU), they all had ruffled fur and were lethargic up to 7 days post-immunization. On day 21 p.i., T-cells isolated from these mice were re-stimulated with the heat-killed WT Y. pestis CO92 ex-vivo, and T-cell proliferation (in terms of cpm) as well as cytokine production were evaluated.

Figure 22:
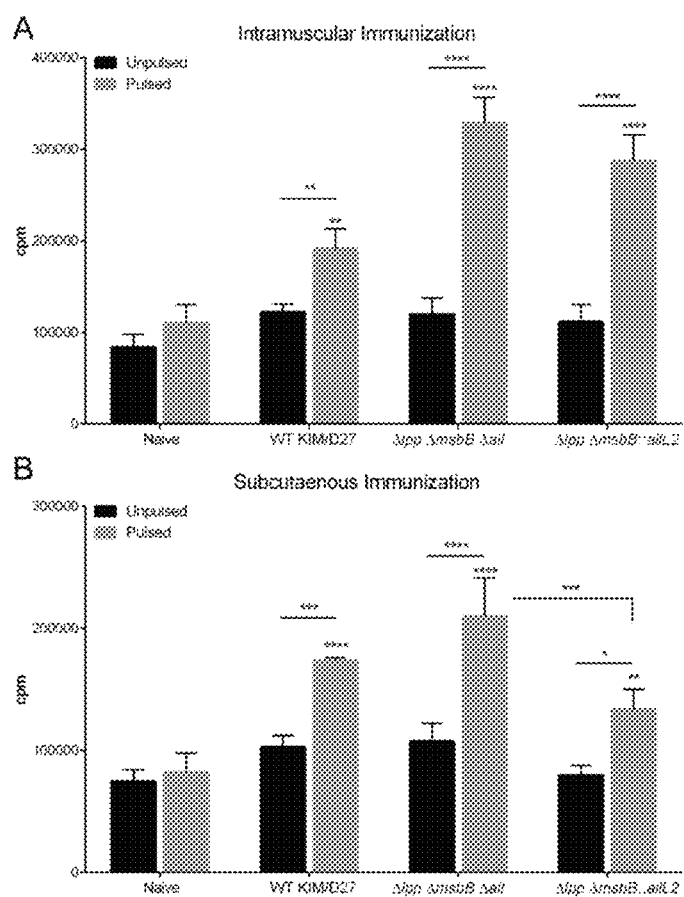

As shown in FIG. 22, all pulsed T-cells (black bars) proliferated robustly compared to their corresponding unpulsed controls (gray bars) except for the naïve group. In addition, T-cells from mice immunized by either the i.m. or the s.c. route significantly proliferated compared to T-cells isolated from naïve mice. These data indicated successful priming and re-stimulation during the experiment. Importantly, T-cells isolated from mice immunized intramuscularly by either the Δlpp ΔmsbB Δail triple or the Δlpp ΔmsbB::ailL2 mutant robustly proliferated at comparable levels which were significantly higher than T-cells isolated from the KIM/D27-immunized mice (FIG. 22A). During s.c. immunization, the T-cells from the KIM/D27-infected mice proliferated similar to that of T-cells isolated from the Δlpp ΔmsbB Δail triple or the Δlpp ΔmsbB::ailL2 mutant-infected mice (FIG. 22B). Interestingly, the T-cell proliferation was significantly higher in mice immunized (by the s.c route) with the Δlpp ΔmsbB Δail triple mutant when compared to animals vaccinated with the Δlpp ΔmsbB::ailL2 mutant strain (FIG. 22B).

Figure 23:
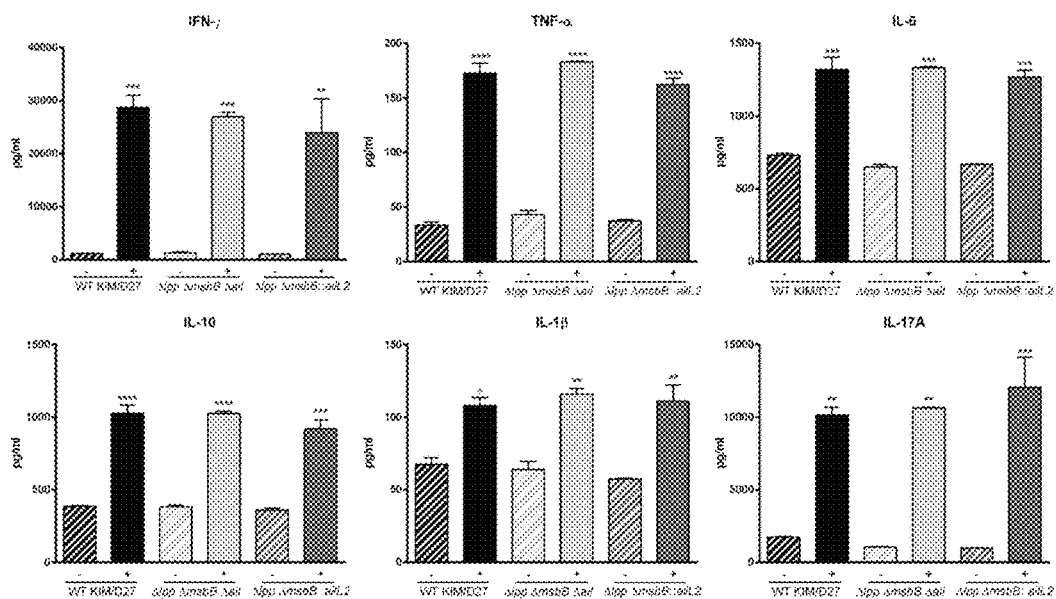

Supernatants collected from the above-mentioned T-cells were then assessed for cytokine production by using a Bio-Rad mouse 6-plex assay kit. Robust cytokine/chemokine production (i.e., IFN-γ TNF-α, IL-6, IL-1□, IL-10, and IL-17A) was observed in T-cells obtained from mice immunized intramuscularly across all the above-mentioned Y. pestis mutant strains tested in response to re-stimulation with the heat-killed Y. pestis CO92 (FIG. 23). A similar trend was noted for the production of IFN-γ, TNF-α, IL-1□, IL-6, and IL-10 in T-cells isolated from mice vaccinated subcutaneously with the above-mentioned mutant strains, except for the IL-17A production which was similar in pulsed versus un-pulsed T-cells (data not shown). Overall, cytokines were either very low or undetectable from T-cells isolated from unimmunized, naïve mice (data not shown).

Discussion

The resurgence of plague in many parts of the world, the existence of antibiotic-resistant strains naturally or generated intentionally, and the lack of a current FDA-approved plague vaccine in the United States necessitate the development of an effective vaccine.

Currently, the most promising and undergoing clinical trials are recombinant subunit vaccines consisting of F1 and LcrV antigens. These F1-V-based vaccines are efficacious against pneumonic plague in rodents and macaques (Fellows et al., 2015, Clin Vaccine Immunol 22:1070-1078; Agar et al., 2009, Microbes Infect 11:205-214; Quenee et al., 2011, Am J Pathol 178:1689-1700; Quenee et al., 2011, Vaccine 29:6572-6583; Williamson et al., 2011, Vaccine 29:4771-4777); however, protection was variable in African green monkeys (Smiley, 2008, Expert Rev Vaccines 7:209-221; Rosenzweig et al., 2011, Appl Microbiol Biotechnol 91:265-286; Quenee et al., 2011, Vaccine 29:6572-6583; Smiley, 2008, Immunol Rev 225:256-271; FDA, 2012, African Green monkey (Chlorocebus aethiops) animal model development to evaluate treatment of pneumonic plague). Further, F1 capsular antigen is dispensable for virulence (Sha et al., 2011, J Clin Microbiol 49:1708-1715; Quenee et al., 2008, Infect Immun 76:2025-2036) and the LcrV amino acid (aa) sequence has diverged among Y. pestis strains (Perry et al., 1997, Clin Microbiol Rev 10:35-66; Huang et al., 2006, Clin Med Res 4:189-199). Therefore, the F1-V-based subunit vaccines most likely will not provide optimal protection across all plague-causing strains in humans, specifically those that have been intentionally modified for possible use in terrorist attacks (Anisimov et al., 2010, Infect Genet Evol 10:137-145; Anisimov et al., 2007, Adv Exp Med Biol 603:23-27).

The live-attenuated vaccines which promote both humoral- and cell-mediated immune responses may represent a better option to overcome the above-mentioned shortcomings of the subunit vaccines (Smiley, 2008, Expert Rev Vaccines 7:209-221; Rosenzweig et al., 2011, Appl Microbiol Biotechnol 91:265-286). Recently, others and our laboratory reported development of mutant strains of Y. pestis that have shown vaccine potential (Tiner et al., 2015, Infect Immun 83:1318-1338; Sha et al., 2013, Infect Immun 81:815-828; van Lier et al., 2014, Infect Immun 82:2485-2503). For example, a single dose of our Δlpp ΔmsbB Δail triple mutant conferred dose-dependent protection in mice against developing subsequent pneumonic plague when immunization occurred by the intranasal route (Tiner et al., 2015, Infect Immun 83:1318-1338). Our data showed that up to $3.4 \times 10^6$ CFU dose of this vaccine strain was unable to kill mice, and the animals developed balanced Th1- and Th2-antibody responses which provided subsequent protection (70%) to mice when challenged with 28 $LD_{50}$ of WT CO92 (Tiner et al., 2015, Infect Immun 83:1318-1338). Although the experiments were not performed in parallel, our intramuscular immunization data with a single dose of this mutant (FIG. 16) provided comparable protection (78%) in mice but under a much stringent challenge dose of WT CO92 (92 $LD_{50}$). These data suggested that vaccination by the i.m. route might be superior to the i.n. route of immunization with this triple mutant in a mouse model.

It is generally believed that intranasal immunization has an advantage as it results in the development of both mucosal immunity and the systemic immune response. However, during mucosal immunization, the vaccine must be able to penetrate the epithelial barrier and to survive luminal host innate defenses. On the contrary, intramuscular immunization enables the vaccine to easily access blood vessels to reach blood circulation to directly stimulate the immune system (Nicolas et al., 2008, Expert Rev Vaccines 7:1201-1214). However, irrespective of the vaccination route, the Δlpp ΔmsbB Δail triple mutant (at doses of $2 \times 10^6$-$3.4 \times 10^6$ CFU) was unable to confer 100% protection to immunized mice in a single dose against developing subsequent pneumonic plague (Tiner et al., 2015, Infect Immun 83:1318-1338) (FIG. 16). Since Ail also has an immunogenic potential in addition to its role as a virulence factor (Erova et al., 2013, Clin Vaccine Immunol 20:227-238), we generated the Δlpp ΔmsbB::ailL2 mutant strain with the intention of further improving its immunogenicity.

Ail protein has eight transmembrane domains with four extracellular loops, and 8 aa residues in loops 2 and 3 of *Y. enterocolitica* being responsible for imparting serum resistance and microbe's ability to adhere/invade host cells (Miller et al., 2001, Mol Microbiol 41:1053-1062). Likewise, 3 aa residues within loop 1 have been predicted to play an important role in bacterial adherence (Yamashita et al., 2011, Structure 19:1672-1682). Loop 2 of Ail in *Y. enterocolitica* and *Y. pestis* share 70% homology, and mutations in 4 aa residues resulted in drastically altering Δlpp ΔmsbB::ailL2 mutant's ability to adhere, invade, and or to exhibit serum resistance when compared to WT CO92 and other tested mutants (FIG. 17).

A slight increase in serum resistance of the Δlpp ΔmsbB::ailL2 mutant when compared to that of the Δlpp ΔmsbB Δail triple mutant was possibly related to the contribution of other Ail loops in serum resistance that were intact in the Δlpp ΔmsbB::ailL2 mutant. Indeed loops 1 and 3 of Ail in *Y. pestis* are important for adherence and invasion, with up to 50% reduction in the above mentioned phenotypes when these two loops were mutated (Tsang et al., 2013, PLoS One 8:e83621). However, a similar adherence and invasion of Δlpp ΔmsbB::ailL2 and Δlpp ΔmsbB Δail triple mutants in HeLa cells signified an important role of loop 2 in Ail-associated virulence phenotypes and also suggested that a conformational association between various loops of Ail might be necessary for efficient adherence and invasion of bacteria to the host cells.

A comparable level of AilL2 production in the Δlpp ΔmsbB::ailL2 mutant and its parental Δlpp ΔmsbB strain (FIG. 17A), as well as diminished virulence of Ail in the Δlpp ΔmsbB::ailL2 mutant (FIGS. 17B&C) indicated successful creation of a potentially better vaccine candidate than the Δlpp ΔmsbB Δail triple mutant. In addition, a partial restoration of serum resistance of this Δlpp ΔmsbB::ailL2 mutant (FIG. 17B) might lead to a better recognition by the host immune system. However, our data indicated that both of the Δlpp ΔmsbB Δail triple and Δlpp ΔmsbB::ailL2 mutants triggered similar humoral and cell-mediated immune responses in mice immunized via the i.m. route (FIGS. 19 and 22A) and provided 100% protection to vaccinated animals when exposed to a high challenge dose of WT CO92 in a pneumonic plague model (FIG. 18).

A biased Th2 antibody response was observed in mice when vaccinated with the Δlpp ΔmsbB::ailL2 mutant by the s.c. route which provided a slightly lower protection rate in immunized mice (67%) during subsequent pneumonic challenge. In comparison, 88% protection rate with a balanced Th1 and Th2 antibody response and a higher T-cell proliferation were noticed in mice when vaccinated by the s.c. route with the Δlpp ΔmsbB Δail triple (FIGS. 18B, 19B and 22B).

The reason for this phenomenon is not clear; however, additional animal models, such as rat or nonhuman primate (NHP), may be needed to fully evaluate immunogenic potential of the Δlpp ΔmsbB::ailL2 mutant. Indeed studies have shown that Ail plays even a more important role in the pathogenesis of *Y. pestis* infection in a rat model of pneumonic plague when compared to the mouse model (Bartra et al., 2008, Infect Immun 76:612-622; Hinnebusch et al., 2011, Infect Immun 79:4984-4989; Kolodziejek et al., 2007, Microbiology 153:2941-2951; Kolodziejek et al., 2010, Infect Immun 78:5233-5243). In addition, a correlation between distinct IgG antibody subclasses and the Th1/Th2 profile seen in mice may differ in humans (Nicolas et al., 2008, Expert Rev Vaccines 7:1201-1214).

Of the two vaccination routes examined, and based on the protection rates, antibody and T-cell responses generated by the Δlpp ΔmsbB Δail triple and Δlpp ΔmsbB::ailL2 mutants in the mouse model, i.m. route was certainly optimal when compared to the s.c. route (FIGS. 18, 19, 22 and 23). Important was our observation that a robust IL-17A recall response was only observed in T-cells from mice that were immunized intramuscularly but not subcutaneously with the above-mentioned mutants (FIG. 23). A study has shown that injection of a vaccine into the layer of subcutaneous fat, where vascularization is poor, may result in slow mobilization and processing of the antigen (Poland et al., 1997, JAMA 277:1709-1711). Compared to intramuscular administration, subcutaneous injection of hepatitis B vaccine leads to significantly lower sero-conversion rates and more rapid decay of antibody response (Poland et al., 1997, JAMA 277:1709-1711; Shaw et al., 1989, Vaccine 7:425-430). A similar phenomenon was reported with the rabies and influenza vaccines (Groswasser et al., 1997, Pediatrics 100:400-403).

Recently, it was reported that intradermal inoculation of *Y. pestis* in C57BL/6J mice resulted in faster kinetics of infection when compared to subcutaneous route of inoculation due to organisms' greater ability to access the vascular and lymphatic vessels in the dermis (Gonzalez et al., 2015, Infect Immun 83:2855-2861). Studies have shown that dermis of the skin is enriched in terminal lymphatic vessels which facilitate antigen uptake as well as infiltration of immune cells to mount a stronger immune response as compared to the subcutaneous layer (Combadiere et al., 2011, Hum Vaccin 7:811-827; Shayan et al., 2006, Carcinogenesis 27:1729-1738; Teunissen et al., 2012, Curr Top Microbiol Immunol 351:25-76). Therefore, future studies examining intradermal route of immunization with our mutants will be undertaken.

IL-17A is a signature cytokine of Th17 cells which has recently been shown to provide an antibody-independent heterogonous protection and has also been implicated in protecting the host against many pathogenic bacterial infections, including *Y. pestis* (Kumar et al., 2013, Curr Opin Immunol 25:373-380; Lin et al., 2011, J Immunol 186:1675-

1684). Interestingly, production of IL-17A from T-cells was also observed in our previous study with the Δlpp ΔmsbB double mutant of WT CO92 when mice were intranasally immunized (Sha et al., 2013, Infect Immun 81:815-828). Similarly, IL-17A was induced by the intranasal immunization of mice with the *Y. pestis* strain D27-pLpxL KIM/D27 engineered to express *E. coli* LpxL (Szaba et al., 2009, Infect Immun 77:4295-4304), which contributed significantly to the cell-mediated defense against pulmonary *Y. pestis* Infection (Lin et al., 2011, J Immunol 186:1675-1684). Therefore, the induction of Th17 response in addition to the Th1 and Th2 responses provided by the Δlpp ΔmsbB Δail triple and Δlpp ΔmsbB::ailL2 mutants might be beneficial in live-attenuated plague vaccines, and need to be further studied.

The vaccine dose we used for both of our mutants ($2 \times 10^6$ CFU/dose) was considerably lower compared to $8 \times 10^8$ CFU/dose of the live-attenuated EV76 vaccine strain given to humans by the i.m. route in some countries, and $1 \times 10^7$ CFU/dose that has been used in murine studies (Zhang et al., 2014, Scand J Immunol 79:157-162; Qi et al., 2010, Vaccine 28:1655-1660; Wang et al., 2010, Clin Vaccine Immunol 17:199-201). In addition, up to $3 \times 10^9$ CFU/dose of EV76 has been used to immunize humans by the cutaneous route (Feodorova et al., 2014, Emerg Microbes Infect 3:e86). EV76 vaccine strain causes severe local and systemic reactions in both animals and human (Russell et al., 1995, Vaccine 13:1551-1556; Meyer et al., 1974, J Infect Dis 129:Suppl:S13-18; Meyer et al., 1974, J Infect Dis 129: Suppl:S85-12; Hallett et al., 1973, Infect Immun 8:876-881), and more seriously, deaths have been reported in NHPs (Meyer et al., 1974, J Infect Dis 129:Suppl:585-12). In addition, a similarpgm-minus strain of *Y. pestis* retains virulence in mice and NHPs when administered by the intranasal (i.n.) and intravenous (i.v.) routes (Smiley, 2008, Immunol Rev 225:256-271; Meyer et al., 1974, J Infect Dis 129:Suppl:585-12; Une et al., 1984, Infect Immun 43:895-900), raising serious questions about their suitability as a human vaccine (Sun et al., 2011, J Infect Dev Ctries 5:614-627). Indeed, a fatal laboratory-acquired infection with the pgm-minus KIM/D27 strain in an individual with hemochromatosis was reported recently (2011, Morb Mortal Wkly Rep 60:201-205), and mice infected intramuscularly with $10^3$ CFU of KIM/D27 in our study also showed ruffled fur and lethargy up to 7 days post infection. However, mice immunized with up to $2$-$3.4 \times 10^6$ of either the Δlpp ΔmsbB Δail triple or Δlpp ΔmsbB::ailL2 mutant via various immunization routes (i.n., i.m. and s.c.) did not display any local or systemic reactions as well as any adverse histopathological lesions (FIGS. 20 and 25) (Tiner et al., 2015, Infect Immun 83:1318-1338).

In summary, both of our Δlpp ΔmsbB Δail triple and Δlpp ΔmsbB::ailL2 mutants have rationally designed in-frame deletions, and, therefore, trigger minimal inflammatory response. Most importantly, T-cells isolated from mice immunized with either the Δlpp ΔmsbB Δail triple or the Δlpp ΔmsbB::ailL2 mutant via the i.m route displayed stronger proliferative responses than the KIM/D27-vaccinated mice (FIG. 22A). Therefore, the above-mentioned mutants might represent better plague vaccine candidates than the pgm-minus mutants for further development and testing in higher animal models.

EXAMPLE 3

Identification of new virulence factors in *Yersinia pestis* and understanding their molecular mechanisms during an infection process are necessary in designing a better vaccine or to formulate an appropriate therapeutic intervention. By using a high-throughput, signature-tagged mutagenic approach, we created 5,088 mutants of *Y. pestis* CO92 and screened them in a mouse model of pneumonic plague at a dose equivalent to 5 $LD_{50}$ of wild-type (WT) CO92. From this screen, 118 clones showing impairment in disseminating to spleen were obtained based on hybridization of input versus output DNA from mutant pools with 53 unique signature tags. In the subsequent screen, 20/118 mutants exhibited attenuation at 8 $LD_{50}$ when tested in a mouse model of bubonic plague, with 10/20 aforementioned mutants providing 40% or higher survival rates at an infectious dose of 40 $LD_{50}$. Upon sequencing, six of the attenuated mutants carried interruptions in genes encoding hypothetical proteins or proteins with putative functions. In-frame deletion mutation of two of the genes identified from the screen, namely rbsA that codes for a putative sugar transport system ATP-binding protein, and vasK, a component of the type VI secretion system, were also found to exhibit some attenuation at 11-12 $LD_{50}$ in a mouse model of pneumonic plague. Likewise, among the remaining 18 signature-tagged mutants, 9 were also attenuated (40-100%) at 12 $LD_{50}$ in a pneumonic plague mouse model. Earlier, we found that deleting genes encoding Braun lipoprotein (Lpp) and acyltransferase (MsbB), the latter of which modifies lipopolysaccharide function, reduced virulence of *Y. pestis* CO92 in mouse models of bubonic and pneumonic plague. Deletion of rbsA and vasK genes from either the Δlpp single or the Δlpp ΔmsbB double mutant augmented the attenuation to provide 90-100% survivability to mice in a pneumonic plague model at 20-50 $LD_{50}$s. The Δlpp ΔmsbB ΔrbsA triple mutant-infected mice at 50 $LD_{50}$ were 90% protected upon subsequent challenge with 12 $LD_{50}$ of WT CO92, suggesting that this mutant or others carrying combinational deletion of genes identified through our screen could potentially be further tested and developed into a live attenuated plague vaccine(s). This Example is also available as Ponnusamy et al., 2015, Infect Immun., 83:2065-2081.

Introduction

*Yersinia pestis* is a Tier-1 select agent and leads to three pathodynamic manifestations in humans, namely bubonic, septicemic, and pneumonic plague (Perry et al., 1997, Clin Microbiol Rev 10:35-66). Although the disease is endemic in certain regions of the globe (Anonymous, 1999, Wkly Epidemiol Rec 74:447), the use of this organism as a biological warfare agent is a significant worldwide concern. Particularly, aerosolized droplets charged with *Y. pestis* can lead to primary pneumonic plague and subsequent person-to-person spread, with a narrow window for antibiotic intervention (Rollins et al., 2003, Am J Clin Pathol 119 Suppl:S78-85; Kumar et al., 2011, J Bioterrorism & Biodefense 2:112; Inglesby et al., 2000, JAMA 283:2281-2290). Consequently, an ideal strategy to combat the disease is to have a vaccine offering long-lasting immunity.

Until 1999, a heat-killed plague vaccine composed of *Y. pestis* 195/P strain was available for use in the United States; however, the production of this vaccine was discontinued because of its reactinogenicity and effectiveness only against bubonic but not the pneumonic plague (Williams et al., 1980, Bull World Health Organ 58:753-756; Rosenzweig et al., 2011, Appl Microbiol Biotechnol 91:265-286). As a live-attenuated vaccine, a pigmentation locus (required for iron acquisition) minus strain, designated as EV76, of *Y. pestis* is currently used in China and the states of the former Soviet Union where plague is endemic. Although protective against both bubonic and pneumonic plague, its reactinogenicity and the possibility that EV76 could behave like a virulent wild-type (WT) strain in individuals with underlying diseases, e.g., hemochromatosis (Anonymous, 2011, MMWR Morb Mortal Wkly Rep 60:201-205), precludes Food and Drug Administration (FDA) approval of such vaccines for human use.

Consequently, significant efforts have been made in recent years to formulate recombinant subunit and DNA-based vaccines to combat *Y. pestis* infections (Rosenzweig et al., 2011, Appl Microbiol Biotechnol 91:265-286; Feodorova et al., 2012, Emerg Microbes & Infect 1: p. e36). However, a majority of these vaccines are composed of two dominant antigens of *Y. pestis*: F1 capsular antigen and V antigen (a structural component of the type 3 secretion system [T3SS]) (Rosenzweig et al., 2011, Appl Microbiol Biotechnol 91:265-286). One of the concerns associated with such vaccines is that F1 capsular antigen is dispensable for the bacterial virulence (Sha et al. 2011, J Clin Microbiol 49:1708-1715) and the gene encoding V antigen is not fully conserved among various virulent strains of *Y. pestis* (Anisimov et al., 2010, Infect Genet Evol 10:137-145). Thus, F1-V antigen-based vaccines may provide minimal cross protection. Further, both humoral and cell-mediated immune responses play roles during protection of the host from plague, and hence, subunit vaccines may not be optimal (Smiley, 2007, Adv Exp Med Biol 603:376-386; Lin et al., 2011, J Immunol 186:1675-1684). Consequently, serious consideration should be given to develop live-attenuated plague vaccines.

Identification and characterization of novel virulence factors of *Y. pestis* to rationally design a better live-attenuated vaccine and also to formulate effective new therapeutics are of significant importance. Various virulence factors of *Y. pestis* have been identified and are primarily of plasmid origin, e.g., the T3SS is carried by the pCD1 plasmid, plasminogen activator (Pla) protease and pesticin genes are harbored on the pPCP1 plasmid, and the F1 capsular antigen-encoding gene is located on the pMT1 plasmid (Deng et al., 2002, J Bacteriol 184:4601-4611; Parkhill et al., 2001, Nature 413:523-527; Cornelis, 2002, J Cell Biol 158:401-408; Sing et al., 2002, J Exp Med 196:1017-1024; van Lier et al., 2014, Infect Immun 82:2485-2503). Apart from these well-known virulence factors of *Y. pestis*, very limited information is available on other virulence factors/mechanisms that contribute to the extreme virulent phenotype of the plague bacterium. More recently, Braun lipoprotein (Lpp) and an acyltransferase (MsbB) that modifies lipid A moiety of lipopolysaccharide (LPS), were shown to contribute to *Y. pestis* virulence during both bubonic and pneumonic plague, and currently, mutants devoid of these genes are being exploited for developing live-attenuated plague vaccines (van Lier et al., 2014, Infect Immun 82:2485-2503; Sha et al., 2013, Infect Immun 81:815-828; Sha et al., 2008, Infect Immun 76:1390-1409). Similarly, an outer membrane protein Ail (Attachment Invasion Locus) which provides serum resistance to *Y. pestis* plays an important role during septicemic plague, allowing the plague bacterium to resist host complement-mediated killing (Bartra et al., 2008., Infect Immun 76:612-622). Since *Y. pestis* is a facultative intracellular pathogen, during its intracellular life cycle, the bacterium up-regulates the expression of various virulence genes, including those that code for F1 capsular antigen and pH 6-antigen (PsaA), the latter of which is an adherence factor (Li et al., 2008, Infect Immun 76:1804-1811; Du et al., 2002, Infect Immun 70:1453-1460).

Recently, a number of genome-wide functional studies have been performed, mainly utilizing array-based approaches to identify other possible virulence factors of *Y. pestis*. During mammalian host infection, *Y. pestis* increases expression of genes associated with insecticidal-toxin synthesis, iron acquisition and storage, metabolite transportation, amino acid biosynthesis, and proteins that provide *Y. pestis* a survival advantage against neutrophil generated reactive nitrogen species (Sebbane et al., 2006, Proc Natl Acad Sci USA 103:11766-11771; Vadyvaloo et al., 2010, PLoS Pathog 6:e1000783; Chauvaux et al., 2007, Microbiology 153:3112-3124; Lathem et al., 2005, Proc Natl Acad Sci USA 102:17786-17791). Although efforts have been made to further explore these targets to comprehend their underlying pathophysiological mechanisms in the disease process, the knowledge accumulated in this area is still limited (Perry et al., 1997, Clin Microbiol Rev 10:35-66; Yang et al., 2010, Front Cell Infect Microbiol 2:157). In the same vein, we performed these studies to identify novel virulence factors that are critical during infection and dissemination of *Y. pestis* in a mouse model. We employed a high-throughput signature-tagged mutagenesis (STM) approach, and subsequently screened the mutants for attenuation in vivo models of bubonic and pneumonic plague.

STM is a powerful genome manipulation technique in both prokaryotes and eukaryotes and has been successfully used to identify virulence factors of many pathogens, such as *Salmonella Typhimurium, Mycobacterium tuberculosis, Vibrio cholerae*, and *Yersinia enterocolitica* (Mazurkiewicz et al., 2006, Nat Rev Genet 7:929-939). In this approach, multiple mutants can be combined together and subjected to a screening process to determine competitive value of each of the mutants. A recent study by Palace et al., focusing on factors essential for deep tissue growth, revealed that various amino acid and sugar transporters are necessary during the deep tissue survival of *Y. pestis* (Palace et al., 2014, mBio 5:e01385-14). Notably, a branched-chain amino acid importer gene (brnQ) was identified as essential in evoking bubonic plague in a mouse model (Palace et al., 2014, mBio 5:e01385-14). The use of this approach in other *Yersinia* species helped in identifying genes related to the biosynthesis of LPS, T3SS, and other metabolic pathways as necessary virulence factors during infection of the host (Darwin et al., 1999, Mol Microbiol 32:51-62; Karlyshev et al., 2001, Infect Immun 69:7810-7819; Mecsas et al., 2001, Infect Immun 69:2779-2787).

In this study, by using STM approach with 53 unique signature tags, 5,088 mutants of *Y. pestis* CO92 were created and screened for impairment in disseminating to the spleen in a mouse model of pneumonic plague. Among 118 clones that failed to disseminate to the spleen, 15 mutants were either attenuated in a mouse model of bubonic plague at a higher infectious dose and/or in a pneumonic mouse model with an infectious dose equivalent to 12 $LD_{50}$ of WT CO92. Subsequently, the role of rbsA that codes for a putative sugar transport system ATP-binding protein; vasK, a component of the type VI secretion system; and ypo0498 (a gene within another T6SS cluster with a putative function) in the pathogenesis of *Y. pestis* infection was studied by in-frame deletion of these genes from WT- or the Δlpp single and Δlpp ΔmsbB double mutant background strains of CO92.

Materials and Methods

Bacterial strains, plasmids, and culture conditions.

Bacterial strains and plasmids used in this study are provided in Table 5. *E. coli* cultures were grown overnight at 37° C. with 180 rpm shaking in Luria-Bertani (LB) broth or grown on LB agar plates for 18-20 h. *Y. pestis* strains were cultured overnight at 28° C., unless specifically noted, with shaking at 180 rpm in heart infusion broth (HIB) (Difco, Voigt Global Distribution Inc., Lawrence, Kans.) or grown for 48 h on 5% sheep blood agar (SBA) (Teknova, Hollister, Calif.) or HIB agar plates. As appropriate, the organisms were cultivated in the presence of antibiotics such as ampicillin, kanamycin, and polymyxin B at concentrations of 100, 50, and 35 μg/ml, respectively. All of the experiments with *Y. pestis* were performed in the Centers for Disease Control and Prevention (CDC)-approved select agent laboratory in the Galveston National Laboratory (GNL), UTMB.

TABLE 5

Bacterial strains and plasmids used in this study

| Strain or Plasmid | Genotype and/or relevant characteristics | Reference or Source |
|---|---|---|
| *Y. pestis* CO92 | | |
| WT CO92 | Virulent *Y. pestis* biovar *Orientalis* strain isolated in 1992 from a fatal human pneumonic plague case and naturally resistant to polymyxin B | CDC |
| WT CO92 pBR322 | WT *Y. pestis* CO92 transformed with pBR322 (Tc$^s$) | 1 |
| WT CO92 luc2 | WT *Y. pestis* CO92 integrated with the luciferase gene (luc), used as a reporter strain | 2 |
| miniTn5Km2STM mutants | Random transposon insertion mutants of *Y. pestis* CO92 | This study |
| WT CO92 pKD46 | WT *Y. pestis* CO92 transformed with plasmid encoding λ-phage recombination system | This study |
| Δypo0498 | ypo0498 gene deletion mutant of *Y. pestis* CO92 | This study |
| ΔrbsA | rbsA gene deletion mutant of *Y. pestis* CO92 | This study |
| ΔrbsA pBR322 | ΔrbsA transformed with pBR322 (Tc$^s$) | This study |
| ΔrbsA pBR322-rbsA | ΔrbsA complemented with pBR322-rbsA (Tc$^s$) | This study |
| ΔvasK | vasK gene deletion mutant of *Y. pestis* CO92 | This study |
| ΔvasK pBR322 | ΔvasK transformed with pBR322 (Tc$^s$) | This study |
| ΔvasK pBR322-vasK | ΔvasK complemented with pBR322-vasK (Tc$^s$) | This study |
| Δlpp | lpp gene deletion mutant of *Y. pestis* CO92 | 3 |
| Δlpp pKD46 | Δlpp transformed with plasmid encoding λ-phage recombination system | This study |
| Δlpp pBR322 | Δlpp transformed with pBR322 (Tc$^s$) | This study |
| Δlpp ΔrbsA | lpp and rbsA double gene deletion mutant of *Y. pestis* CO92 | This study |
| Δlpp ΔrbsA pBR322 | Δlpp ΔrbsA double mutant transformed with pBR322 (Tc$^s$) | This study |
| Δlpp ΔrbsA pBR322-rbsA | Δlpp ΔrbsA double mutant complemented with pBR322-rbsA (Tc$^s$) | This study |
| Δlpp ΔmsbB | lpp and msbB double gene deletion mutant of *Y. pestis* CO92 | 4 |
| Δlpp ΔmsbB pKD46 | Δlpp ΔrbsA double mutant transformed with plasmid encoding λ-phage recombination system | This study |
| Δlpp ΔmsbB ΔrbsA | lpp, msbB, and rbsA triple gene deletion mutant of *Y. pestis* CO92 | This study |
| Δlpp ΔmsbB ΔrbsA pBR322 | Δlpp ΔmsbB ΔrbsA trible mutant transformed with pBR322 (Tc$^s$) | This study |
| Δlpp ΔvasK | lpp and vasK double gene deletion mutant of *Y. pestis* CO92 | This study |
| Δlpp ΔvasK pBR322 | Δlpp ΔvasK double mutant transformed with pBR322 (Tc$^s$) | This study |
| *A. hydrophila** | | |
| SSU | *Aeromonas hydrophila** human diarrheal isolate | 5 |
| ΔvasK | vasK gene deletion mutant of *A. hydrophila** SSU | 5 |
| *E. coli* | | |
| S17-1-pUTminiTn5Km2STM | *E. coli* strain S17-1, recA pro hsdR RP4-2-Tc::Mu-Km::Tn7 integrated into the chromosome, carries plasmid pUTminiTn5Km2STM | 6 |
| Plasmids | | |
| pUTminiTn5Km2STM | Mini-transposon plasmids each carrying one of 53 unique STM tags | 6 |
| pKD46 | Plasmid for λ-phage recombination system under arabinose inducible promoter | 7 |
| pKD13 | Template plasmid for PCR amplification of the Km$^r$ gene cassette flanked by FLP recombinase target sites | 7 |
| pFlp2 | Plasmid for FLP enzyme under constitutively expressing lac promoter (Ap$^r$) | 8 |
| pBR322 | A variant of pBR322 (Tc$^s$) | 9 |
| pBR322-rbsA | Plasmid containing the rbsA gene-coding region and its putative promoter inserted in the Tc$^r$ cassette of vector pBR322 | This study |

TABLE 5-continued

Bacterial strains and plasmids used in this study

| Strain or Plasmid | Genotype and/or relevant characteristics | Reference or Source |
|---|---|---|
| pBR322-vasK | Plasmid containing the vasK gene-coding region and its putative promoter inserted in the Tc$^r$ cassette of vector pBR322 | This study |

CDC = Centers for Disease Control and prevention;
Tc$^r$ = Tetracycline resistance;
Tc$^s$ = tetracycline sensitive;
Ap$^r$ = Ampicillin resistance;
FLP = flippase;
FRT = flippase recognition target;
*A. hydrophila SSU has now been reclassified as A. dhakensis SSU (40).
1. van Lier et al., 2014, Infect Immun 82: 2485-2503;
2. Sha et al., 2013, Microb Pathog 55: 39-50;
3. Sha et al., 2008, Infect Immun 76: 1390-1409;
4. Sha et al., 2013, Infect Immun 81: 815-828;
5. Suarez et al., 2008, Microb Pathog 44: 344-361;
6. Silver et al., 2007, J Bacteriol 189: 6763-6772;
7. Datsenko et al., 2000, Proc Natl Acad Sci USA 97: 6640-6645;
8. Agar et al., 2009, Microbiology 155: 3247-3259;
9. Galindo et al., 2010. Comp Funct Genomics 2010: 342168.

Construction of *Y. pestis* CO92 signature-tagged transposon mutant library.

Figure 26:
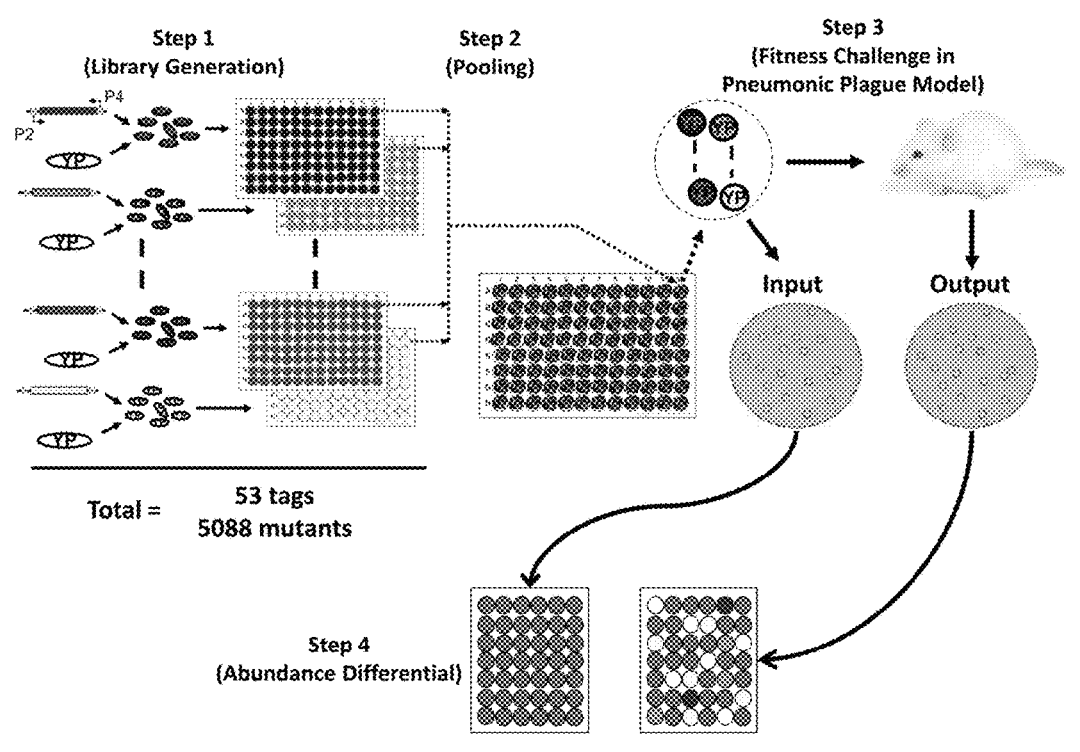

A total of 5,088 transposon mutants of WT CO92 were created, which included 96 mutants for each of the 53 unique 40 by long signature tags (Hensel et al., 1995, Science 269:400-403). As a source of the tags, 53 *E. coli* S-17 strains, each harboring the plasmid pUTminiTn5Km2STM with a unique tag, were used as donor strains and conjugated with WT CO92 (Silver et al., 2007, J Bacteriol 189:6763-6772). Initially, 56 tags were chosen as previously described (Silver et al., 2007, J Bacteriol 189:6763-6772) and were tested for their cross-hybridization. Three out of the 56 tags showed cross-reaction under our tested conditions, and, therefore, were excluded from the study. For each of the 53 signature tags, the following procedures were carried out. The *E. coli* S17-1 strain (Table 5) carrying the transposon with a unique signature tag was grown overnight, subcultured, and then further grown for 4 h ($OD_{600}$~0.6). Separately, WT CO92 was grown overnight and mixed in a 4 to 1 ratio with the above-mentioned donor *E. coli* strains. An aliquot of the mixture was spread on LB agar plates and incubated at 30° C. for 24 h. Subsequently, the cultures from the LB plates were collected in sterile phosphate-buffered saline (PBS), and a portion of the mixture was spread on HIB agar plates containing polymyxin B and kanamycin for 48 h at 28° C. Following the incubation period, separate trans-conjugant colonies were tested for resistance to polymyxin B (WT CO92 is naturally resistant to this antibiotic) (Table 5) and kanamycin, but sensitive to ampicillin. Finally, 96 trans-conjugants, which did not show any obvious growth defects, with each tag were randomly picked and individually inoculated in the wells of a 96-well microtiter plate. After 24 h of growth, the plates were stored at −80° C. after the addition of glycerol to a final concentration of 15% (FIG. 26). From the fifty three 96-well plate stocks, 96 mutant pools were prepared by combining 20 μl of stock cultures from the same respective positions of 96-well microtiter plates (FIG. 26). Thus, each mutant pool represented a collection of 53 transposon mutants, each with a unique signature tag.

Preparation of input mutant pools of *Y. pestis* CO92 and collection of corresponding output mutant pools from the spleen in a mouse model of pneumonic plague.

Each of the 96 mutant pools prepared above was individually tested in female Swiss-Webster mice (Taconic Biosciences, Inc., Hudson, N.Y.) after infecting them via the intranasal (i.n.) route. The animal experiments were conducted in accordance with the Institutional Animal Care and Use Committee (IACUC)-approved protocol in the Animal Biosafety Level (ABSL)-3 facility located in the GNL. FIG. 26 shows the schematic used for screening the mutants. For each of the mutant pools with 53 unique DNA tags, three animals were infected. Before infection of the mice, a portion of the bacterial inoculum was subjected to genomic DNA isolation using DNeasy Blood & Tissue Kit® (Qiagen, Inc., Valencia, Calif.) and was referred to as input DNA pool or input pool. The remaining inoculum was used to infect mice at a dose of 2,500 colony forming units (CFU), representing 5 $LD_{50}$ (1 $LD_{50}$=500 CFU) equivalent of WT CO92 (van Lier et al., 2014, Infect Immun 82:2485-2503). Three days post infection (p.i.), the spleens were excised to recover the output mutants. Briefly, the spleens were homogenized in sterile PBS and an aliquot of the homogenates was spread on LB agar plates containing kanamycin. After 24 h of incubation, the bacterial colonies were collected for genomic DNA isolation, which was referred to as output DNA pool or output pool.

DNA hybridization-based screening of input and output mutant pools of *Y. pestis* CO92.

The DNA hybridizations were performed for each of the input and output pools separately, as previously described (Silver et al., 2007, J Bacteriol 189:6763-6772). Briefly, 53 signature tags were polymerase chain reaction (PCR) amplified (Phusion® High-Fidelity PCR Kit, New England Biolabs, Inc., Ipswich, Mass.) using primers P2 and P4 from the respective transposon plasmids pUTminiTn5Km2STM (FIG. 26 and Tables 1&2). The PCR products were digested with the HindIII restriction enzyme (New England Biolabs, Inc.) to remove primer sequences, gel purified using QIAquick® Gel Extraction Kit (Qiagen, Inc.), and then 15 ng of the tag DNA was spotted individually on a positively charged nylon membrane (Amersham Hybond-N+, GE Healthcare Life Sciences, Pittsburgh, Pa.). The DNA probes on the membranes were sequentially subjected to denaturation in 1.5 M NaCl and 0.5 M NaOH solution for 3 min, neutralization in 1.5 M NaCl and 0.5 M Tris-HCl [pH 7.4]

solution for 5 min and again 1 min in the same but fresh solution, and washing in 2×SSC (0.3 M NaCl and 0.03 M sodium citrate [7.0]) for 2 min. Finally, DNA was UV-cross linked to the membranes.

With P2 and P4 primers (Table 6), the tag sequences from each of the input and the corresponding output DNA pools were PCR amplified and gel purified as described above, and digoxigenin (DIG) (Roche Applied Science, Indianapolis, Ind.) labeled by PCR using P2 and P4 primers as described previously (Silver et al., 2007, J Bacteriol 189:6763-6772). The labeled tags were digested with the HindIII restriction enzyme to remove the primer sequences, and denatured at 95° C. for 5 min before proceeding to hybridization. The membranes prepared as mentioned above were pre-hybridized with the DIG hybridization solution (Roche Applied Science), and finally, the labeled tags were added to the membrane in a fresh-hybridization solution and incubated overnight at 42° C.

Following hybridization, the membranes were subjected to washing, blocking, and developing at room temperature (RT), unless otherwise stated, as follow: i) twice for 5 min each in 2×SSC plus 0.1% sodium dodecyl sulfate (SDS), ii) twice for 5 min each in 0.1×SSC plus 0.1% SDS at 65° C., and once for 5 min in 0.1 M maleic acid, 0.15 M NaCl [pH 7.5], 0.3% [wt/vol] Tween 20 (MNT) buffer. Then, the membranes were placed in 1× blocking solution (Roche Applied Science) for 30 min and were probed with monoclonal anti-DIG antibody in 1× blocking solution for 30 min. The membranes were washed twice for 5 min each in MNT solution, and equilibrated for 5 min in 0.1 M Tris-HCl, 0.1 M NaCl [pH 9.5] solution. Finally, ready-to-use CDP-Star solution (Roche Applied Science) was applied to each membrane, incubated for 5 min, and the positive hybridization signals were visualized on luminescent image analyzer (Imagequant LAS4000, GE Healthcare Life Sciences). All of the hybridization steps were performed in a hybridization oven.

TABLE 6

Sequences of primers used in this study

| Primers or primer pairs | Primer sequences (5'-3') (Forward, Reverse) | Purpose |
|---|---|---|
| P2-P4 | TACCTACAACCTCAAGCT, (SEQ ID NO: 27) TACCCATTCTAACCAAGC (SEQ ID NO: 28) | PCR amplification of STM tags |
| P1-P3 | GCGCAACGGAACATTCATC, (SEQ ID NO: 29) GCAAGCTTCGGCCGCCTAGG (SEQ ID NO: 30) | Identification of Mini-Tn5 insertion sites |
| P5-P6 | AGGGTCAGCCTGAATACGCG, (SEQ ID NO: 31) CTGACTCTTATACACAAGTGC (SEQ ID NO: 32) | Identification of Mini-Tn5 insertion sites |
| Kmypo2500 | TTAGCTGGTAAGCGTGTCAATTCTCGCTCTGCTCA GGCAGAGCGATAACCGTGTAGGCTGGAGCTGCTTC (FRT sequence), (SEQ ID NO: 33) TAATGCACTCCCTGTTGCGTGAAGCATGATGTTAT TAGATTCAATTTCATATTCCGGGGATCCGTCGACC (FRT sequence) (SEQ ID NO: 34) | Construction of a DNA fragment with Km$^r$ gene cassette and FRT sequence for the rbsA gene mutation |
| ypo2500V | CGTATTGCACTGGGTATCGCGTTGG, (SEQ ID NO: 35) GTCATTTAACCCGCTCATTAAGACA (SEQ ID NO: 36) | PCR verification of the rbsA gene deletion |
| ypo2500C | CGGGATCCGGTTAGCGTAGACGGCCAACCA (BamHI), (SEQ ID NO: 37) ACGCGTCGACTCATAATGCACTCCCTGTTG (SalI) (SEQ ID NO: 38) | Cloning of the rbsA gene in plasmid pBR322 |
| Kmypo3603 | GACAACTCAAACCATGATCGCCATGGAATGCCACA GGAGCGTTAGCGCATGTGTAGGCTGGAGCTGCTTC (FRT sequence), (SEQ ID NO: 39) TGCGATCTGTCTCAATACAATCGTGTGTCTCAATA CAGAGTGTCTGGCAGATTCCGGGGATCCGTCGACC (FRT sequence) (SEQ ID NO: 40) | Construction of a DNA fragment with Km$^r$ gene cassette and FRT sequence for the vasK gene mutation |
| ypo3603V | TAAACCGGCAACCACAGCAATCCGA, (SEQ ID NO: 41) TTGACCTCTGGCCGTGCCGGGTGGT (SEQ ID NO: 42) | PCR verification of the vasK gene deletion |
| ypo3603C | CTAGCTAGCCTACAGATGATAAACCGGCAA (NheI), (SEQ ID NO: 43) ACGCGTCGACTCAATACAGAGTGTCTGGCA (SalI) (SEQ ID NO: 44) | Cloning of gene vasK into plasmid pBR322 |
| Kmypo0498 | ACCATTAGCACGATGACGTGGATGAATAGCCAAAATAAGAGGACA TAGATGTGTAGGCTGGAGCTGCTTC (FRT sequence), (SEQ ID NO: 45) TACCTCTTAATCTCCAGAGATTTTAGATCCTTTGCGTGTCAGATAG GACAATTCCGGGGATCCGTCGACC (FRT sequence) (SEQ ID NO: 46) | Construction of a DNA fragment with Km$^r$ gene cassette and FRT sequence for the ypo0498 gene mutation |
| ypo0498V | GCTATTCGCTGGTTGAGGCT, (SEQ ID NO: 47) AACGCTGGCAGAGAGATGAG (SEQ ID NO: 48) | PCR verification of the ypo0498 gene deletion |

Testing individual signature-tagged transposon mutants of *Y. pestis* CO92 in bubonic and pneumonic plague mouse models.

Mutant clones that exhibited either complete or partial loss in virulence in terms of their ability to disseminate to the spleen, as determined by the hybridization reactions, were selected for further study. Each of the mutants was individually used to infect a group of five Swiss-Webster mice via the subcutaneous (s.c.) route at a dose equivalent to 8 $LD_{50}$ of WT CO92 (1 $LD_{50}$ by the s.c. route is 50 CFU) (van Lier et al., 2014, Infect Immun 82:2485-2503). The attenuated mutants after the first screen by bubonic infection were subjected to a stringent second screen in mice (n=10 to 20) at a higher infectious dose of 40 $LD_{50}$. The animals were observed for mortality over a period of 21-28 days. The mutant clones that were attenuated to show at least 40% animal survival, were selected for genomic characterization of the transposon insertion sites.

Transposon mutants that showed promising results during the first s.c. screening were further tested for their level of attenuation in a pneumonic plague mouse model. Each selected mutant was used to infect a group of five Swiss-Webster mice at an infection dose equivalent to 12 $LD_{50}$ of WT CO92. The animals were observed for mortality over a period of 9 days.

Genomic characterization of transposon insertion sites in the signature-tagged mutants of *Y. pestis* CO92.

Inverse PCR was used to amplify DNA fragment flanking the mini-Tn5 insertion as described previously (Silver et al., 2007, J Bacteriol 189:6763-6772; Silver et al., 2007, Proc Natl Acad Sci USA 104:9481-9486). Briefly, genomic DNA from the above selected signature-tagged transposon mutants was extracted by using a DNeasy blood and tissue kit (Qiagen, Inc.). An aliquot (2 µg) of the genomic DNA was digested with the restriction enzymes BamHI, PstI, SalI or XbaI (New England Biolabs), and the resulting fragments were ligated using T4 DNA ligase (Promega, Madison, Wis.). Inverse PCR was performed using outward-facing primers P1 and P3 annealing to mini-Tn5 sequence (Table 6). Subsequently, a nested PCR amplification was carried out on each of the inverse PCR products using primers P5 and P6 (Table 6). The primers P5 and P6 annealed downstream to the primer pair P1 and P3. Then, the resulting PCR products were gel purified and sequenced using the primer P6 (Table 6). Based on the sequence information, transposon insertion sites were identified in the genome of *Y. pestis* CO92 (Parkhill et al., 2001, Nature 413:523-527).

Construction of in-frame deletion mutants and testing in mouse models of bubonic and pneumonic plague.

To construct in-frame deletion mutants of *Y. pestis* CO92, λ-phage recombination system was used (Datsenko et al., 2000, Proc Natl Acad Sci USA 97:6640-6645). Initially, the WT CO92 strain was transformed with plasmid pKD46 (Table 5) and grown in the presence of 1 mM L-arabinose to induce the expression of λ-phage recombination system. The above-mentioned *Y. pestis* culture was processed for the preparation of electroporation competent cells (Sha et al. 2011, J Clin Microbiol 49:1708-1715; Datsenko et al., 2000, Proc Natl Acad Sci USA 97:6640-6645). The latter were then transformed with 0.5 to 1.0 µg of the linear dsDNA constructs carrying the kanamycin resistance ($Km^r$) gene cassette that was immediately flanked by bacterial FRT (flippase recognition target) sequence followed by on either side by 50 by of DNA sequences homologous to the 5' and 3' ends of the gene to be deleted from WT CO92. The plasmid pKD46 from the mutants that had successful $Km^r$ gene cassette integration at the correct location was cured by growing the bacteria at 37° C. The latter mutants were transformed with plasmid pFlp2 (Table 5) to excise the $Km^r$ gene cassette (Agar et al., 2009, Microbiology 155:3247-3259). Eventually, the plasmid pFlp2 was also cured from the kanamycin sensitive ($Km^s$) clones by growing them in a medium containing 5% sucrose (Agar et al., 2009, Microbiology 155:3247-3259). To confirm the in-frame deletion, mutants showing sensitivity to kanamycin and ampicillin were tested by PCR using appropriate primer pairs (Table 6) and sequencing of the PCR products.

To construct double or triple in-frame deletion mutants of CO92, a similar procedure was followed using selected single (Δlpp) or double (Δlpp ΔmsbB) in-frame deletion mutants that existed in the laboratory (Table 5). To construct a recombinant plasmid for complementation studies, complete open reading frame of the gene of interest along with 200 by upstream DNA sequence corresponding to the promoter region of that gene from WT CO92 was PCR amplified using Phusion® High-Fidelity PCR Kit (New England Bioloabs). Then, the DNA construct was cloned in plasmid pBR322 in place of the tetracycline resistance (TO conferring gene cassette (Table 5).

Single, double, and triple isogenic mutants, and their complemented strains, were then tested in both bubonic and pneumonic plague mouse models along with the WT CO92 strain as a control. For re-challenge experiments, after 28 days p.i. with the selected mutants, the bioluminescent WT CO92 carrying luciferase gene operon, luxCDABE (Table 5), was used to infect mice as described previously (Sha et al., 2013, Microb Pathog 55:39-50). Also in vivo imaging was performed on re-challenged animals using IVIS 200 bioluminescent and fluorescence whole-body imaging workstation (Caliper Corp. Alameda, Calif.).

Western blot analysis for detecting a T6SS effector, hemolysin-coregulated protein (Hcp), in the isogenic mutants of *Y. pestis* CO92

Overnight grown cultures of various *Y. pestis* and *Aeromonas hydrophila* strains (the latter was reclassified as *A. dhakensis* (Grim et al., 2014, Appl Environ Microbiol 80:4162-4183) were harvested and the supernatants mixed with 20% trichloroacetic acid (v/v). The resulting precipitates were dissolved in the SDS-PAGE buffer by boiling and subjected to SDS 4-15% gradient polyacrylamide gel electrophoresis. The proteins from the gel were then transferred to a Hybond™-ECL™ nitrocellulose membrane (GE Healthcare) by following the standard procedure (Suarez et al., 2010, Microbiology 156:3678-3688). The membrane was blocked with 1% bovine serum albumin [BSA] or 5% skim milk, and, subsequently, incubated with anti-Hcp antibodies specific for *Y. pestis* (1:1000) followed by incubation with the secondary antibodies (Goat anti-mouse IgG [1:10000]) (Southern Biotechnology Associates, Inc., Birmingham, Ala.). The membrane was washed with TBS (Tris Buffered Saline: 20 mM Tris-base, 136 mM NaCl [pH 7.4])/0.05% Tween 20, and the blot was developed using SuperSignal® West Dura Extended Duration Substrate (Pierce, Rockford, Ill.). Finally, the positive signal was detected by using ImageQuant LAS4000 platform (GE Healthcare). Polyclonal antibodies raised in mice against Hcp of *Y. pestis* were used for immunoblot analysis. The hcp gene (YPO3708) of *Y. pestis* CO92 was over-expressed in *E. coli* using the pET30a vector system as a His-tag recombinant protein and purified by using $Ni^{2+}$ chromatography (Suarez et al., 2010, Microbiology 156:3678-3688). As a loading control for immunoblot analysis, we used monoclonal antibodies against DnaK (Enzo, Farmingdale, N.Y.), a member of conserved Hsp70 chaperone family.

Growth Kinetics of WT *Y. pestis* CO92, its ΔrbsA Mutant, and the Complemented Strain.

Overnight cultures of various *Y. pestis* strains were washed in PBS and normalized to the same absorbance by measuring optical density at 600 nm ($OD_{600}$). These bacterial cultures were then inoculated separately (with approximately $1 \times 10^7$ CFU) in 20 mL of the modified M9 medium (1×M9 salts [22 mM $KH_2PO_4$, 33.7 mM $Na_2HPO_4$, 8.55 mM NaCl, 9.35 mM $NH_4Cl$], 1 mM $MgSO_4$, 2.5 mM $CaCl_2$, 0.001 mg/mL $FeSO_4$, 0.0001% thiamine, 0.1% casamino acids) (all chemicals were obtained from Sigma-Aldrich, St. Louis, Mo.) contained in 125 mL polycarbonate Erlenmeyer flasks with HEPA-filtered tops. The medium either did not contain any sugar or supplemented with 0.4% glucose or 0.4% ribose, and the cultures were incubated at 28° C. with shaking at 180 rpm. Samples were taken by removing 100 µL of the culture from each of the flasks at the indicated time points. Each of the samples was serially diluted, plated on SBA agar plates, and incubated at 28° C. for 48 h to determine CFU/mL.

Statistical Procedures.

Animal survival rate was statistically analyzed using Kaplan-Meier survival estimates with Bonferonni post-hoc test. In vitro growth of WT CO92, its ΔrbsA mutant or the complemented strain, under different nutritional conditions was analyzed by one-way ANOVA followed by Tukey post-hoc test. Wherever applicable, the p-values were reported, and a p value of <0.05 was considered significant.

Results

*Y. pestis* CO92 signature-tagged transposon mutant library and its primary screen in a mouse model of pneumonic plague.

We generated a library of mutants with 53 unique DNA tags from WT CO92 by using a transposon Tn5-based system (FIG. 26). For each signature tag, 96 mutants potentially representing Tn5 hits at different locations on the chromosome or the plasmids of WT CO92 were randomly picked from the HIB agar plates, thus resulting in a library consisting of 5,088 mutants. During this selection process, any mutant clones that exhibited visual growth defects, such as a smaller colony size, were not included as they would be out-competed in a mixed culture infection resulting in false positives. We observed a transfer efficiency of $1.5 \times 10^{-4}$ transposon mutants per donor colony when the Tn5 harboring *E. coli* strains were mixed with the recipient WT CO92 strain at a ratio of 4:1 for the conjugation process. Finally, 96 input mutant pools, each containing a collection of 53 mutants (one clone for each one of the signature tags), were generated for screening in a mouse model of pneumonic plague for their attenuation in terms of dissemination to the internal organs, i.e., the spleen (FIG. 26).

The infectious dose of input 96 mutant pools in mice given by the i.n. route was 5 $LD_{50}$ equivalent of the wild-type (WT) CO92 (van Lier et al., 2014, Infect Immun 82:2485-2503). Three days p.i., ~60% of the animals died due to developing pneumonic plague and the remaining animals had clinical symptoms of plague, such as lethargy and ruffled fur. The excised spleens from these mice, irrespective of their survival status, had high bacterial counts in the range of $1 \times 10^7$ to $1 \times 10^8$ CFU per organ. Under the conditions of hybridization and washing optimized for the study, the nylon membranes harboring purified 53 unique signature tags hybridized with the 96 input pool DNA probes (obtained from each transposon mutant pool with 53 signature tags), and showed a clear pattern of positive reactions without any background (a representative blot is shown in FIG. 27).

Figure 27:
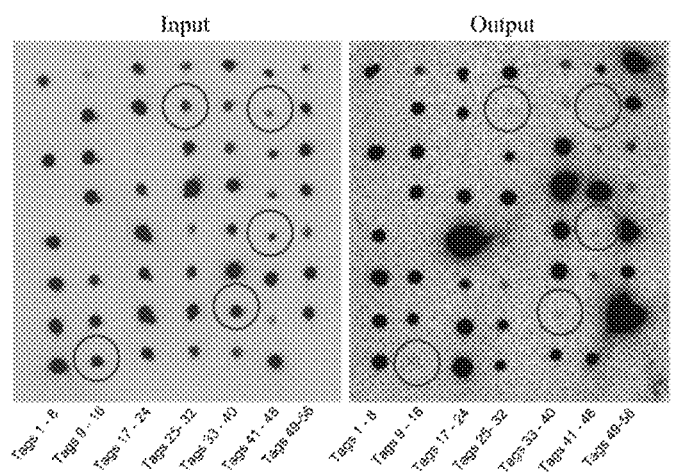

By this hybridization approach, we identified a total of 118 potential mutant candidates; among these 108 had no detectable signal on the output DNA pool membranes, and the remaining had very weak signals when compared to the corresponding input DNA pool membranes (a representative blot is shown in FIG. 27).

Second screen of selected signature-tagged transposon mutants of *Y. pestis* CO92 in a mouse model of bubonic plague.

Figure 28:
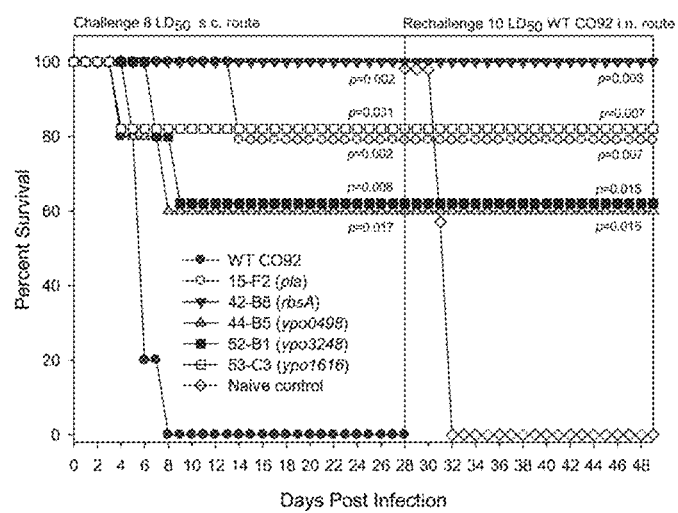

We performed a second screen with the above-generated 118 mutant clones by injecting mice with individual mutants via the s.c. route at an aimed 8 $LD_{50}$ equivalent of WT CO92 (van Lier et al., 2014, Infect Immun 82:2485-2503). Of 118 mutant clones tested, 20 of them (~17%) showed attenuation to the level of at least 20% or more animal survival (up to 100%) when compared to the WT CO92 on day 21 p.i. (Table 7). One of our long term goals is to identify candidate genes that could be deleted from the WT CO92 to develop a novel live-attenuated plague vaccine. Therefore, we also tested some of the surviving animal groups after infection with representative transposon mutants to withstand re-challenge with the WT CO92. The re-challenge occurred by a more stringent i.n. route, which evokes pneumonic plague, to gauge immunogenicity of the transposon mutant clones. As noted in FIG. 28, 100% of the animals that were initially infected with the transposon mutants (15-F2, 42-B8, 44-B5, 52-B1 and 53-C3) (Table 7) followed by re-challenge with WT CO92 strain (10 $LD_{50}$) were protected over a period of 21 days. All of the control naive mice died by day 4. These second screen mutant candidates were then subjected to a higher stringency screen in a bubonic plague mouse model by increasing the challenge dose to 40 $LD_{50}$ (Table 8). As noted from this table, 10 out of 20 mutants showed 40% or more survival rate on day 21 p.i. Following this final high stringency screen, we identified the insertion sites within the disrupted genes for each of the mutant candidate strains.

TABLE 7

Survival patterns for selected transposon mutants in mouse models of bubonic and pneumonic plague

| Clone ID | Gene Locus ID | % Survival Post ~8 $LD_{50}$ Infection (s.c.) | | | % Survival Post 12 $LD_{50}$ Infection (i.n.) | |
|---|---|---|---|---|---|---|
| | | Day 7 | Day 14 | Day 21 | Day 3 | Day 9 |
| WT CO92 | — | 40 | 0 | 0 | 0 | 0 |
| 15-F2 | YPPCP1.07 | 100 | 100 | 80 | 60 | 0 |
| 19-F7 | unconfirmed | 100 | 80 | 80 | 80 | 0 |
| 29-F7 | YPO2468 | 60 | 60 | 60 | 80 | 40 |
| 2-H3 | YPO1717 | 80 | 60 | 60 | 20 | 0 |
| 39-A7 | YPO3319 | 60 | 60 | 60 | 80 | 0 |
| 39-G4 | YPMT1.80c | 100 | 40 | 40 | 20 | 0 |
| 42-B8 | YPO2500 | 100 | 100 | 100 | NT* | NT* |
| 44-B5 | YPO0498 | 80 | 60 | 60 | 100 | 40 |
| 44-F11 | YPO3603 | 80 | 60 | 60 | NT* | NT* |
| 45-B9 | YPO2884 | 100 | 80 | 60 | 100 | 100 |
| 47-F10 | unconfirmed | 80 | 80 | 80 | 60 | 0 |
| 47-G5 | YPO3164 | 100 | 80 | 80 | 20 | 0 |
| 48-G1 | PMT1 Caf1R | 100 | 100 | 100 | 100 | 20 |
| 49-B1 | YPO1484 | 80 | 60 | 60 | 100 | 100 |
| 52-B1 | YPO3248 | 80 | 60 | 60 | 100 | 80 |
| 52-B5 | Intergenic YPO0093-0094 | 60 | 60 | 20 | 100 | 80 |
| 53-C3 | YPO1616 | 80 | 80 | 80 | 100 | 100 |
| 53-F10 | YPO1995 | 100 | 100 | 100 | 100 | 0 |

TABLE 7-continued

Survival patterns for selected transposon mutants in mouse models of bubonic and pneumonic plague

| Clone ID | Gene Locus ID | % Survival Post ~8 $LD_{50}$ Infection (s.c.) Day 7 | Day 14 | Day 21 | % Survival Post 12 $LD_{50}$ Infection (i.n.) Day 3 | Day 9 |
|---|---|---|---|---|---|---|
| 53-G5 | YPO0815 | 100 | 60 | 60 | 100 | 100 |
| 54-F6 | Intergenic YPO1119-1120 | 100 | 100 | 100 | 100 | 60 |

Note:
Clone ID represents the signature tag number and alphanumeric of individual mutants containing that signature.
s.c. = subcutaneous;
i.n = intranasal;
NT = not tested;
*prepared isogenic mutants and tested.

gene located on the pCP1 plasmid of *Y. pestis* (van Lier et al., 2014, Infect Immun 82:2485-2503; Lathem et al., 2007, Science 315:509-513). The pla protease gene was interrupted in the mutant clone (15-F2) (Table 8), adding credibility to our screening process. This mutant was highly attenuated, as 85% of the animals survived the challenge in a bubonic plague model on day 21 p.i. (Table 8).

Mutant clone 44-F11, with 60% of the mice surviving the challenge, was identified as having a disruption in a gene whose product has homology to VasK of *A. dhakensis* SSU, a key component of the T6SS (Suarez et al., 2008, Microb Pathog 44:344-361) (Table 8). Clone number 42-B8 was identified as having a transposon insertion within the gene referred to as rbsA, and 85, 70, and 60% of the animals survived after challenge on days 7, 14, and 21 p.i., respectively, in a mouse model of bubonic plague (Table 8). This gene is part of the rbs operon that codes for a putative ribose transport system and has been described in orthologous

TABLE 8

Survival patterns for selected transposon mutants over a 21 day period in a mouse model of bubonic plague at an infectious dose of 40 $LD_{50}$

| Clone ID | Gene Interrupted | % Survival Post ~40 $LD_{50}$ Infection (s.c.) Day 7 | Day 14 | Day 21 | Gene or protein description/Protein homology |
|---|---|---|---|---|---|
| WT CO92 | — | 15 | 0 | 0 | — |
| 15-F2 | pla | 85 | 85 | 85 | Plasminogen activator |
| 2-H3 | ypo1717 | 80 | 60 | 60 | Putative membrane protein |
| 39-G4 | ypmt1.80c | 100 | 40 | 40 | Putative transposase |
| 42-B8 | rbsA (ypo2500) | 85 | 70 | 60 | Putative sugar transport system, ATP-binding protein |
| 44-B5 | ypo0498 | 100 | 85 | 85 | Hypothetical protein, associated with a type 6 secretion system locus |
| 44-F11 | vasK (ypo3603) | 60 | 60 | 60 | Type-6 secretion system component-VasK |
| 47-G5 | ypo3164 | 100 | 80 | 40 | Cytochrome o ubiquinol oxidase subunit II |
| 52-B1 | hxuB (ypo3248) | 100 | 60 | 60 | HxuB (hemolysin secretion protein)/ putative surface-exposed protein |
| 53-C3 | ypo1616 | 85 | 60 | 60 | Hypothetical protein |
| 54-F6 | ypo1199-ypo1120 | 100 | 100 | 100 | Insertion in intergenic region between two conserved hypothetical protein |

Note:
Bolded mutants represent those that had transposon disruption in genes previously identified as virulence factor-encoding genes in *Y. pestis*, i.e., pla, or in *A. dhakensis* SSU, i.e., vasK. The number of animals used per group ranged from 10 to 20.

Genetic characteristics of signature-tagged transposon mutants of *Y. pestis* CO92 that are attenuated in a mouse model of bubonic plague Identification of the disrupted genes or genetic regions in the transposon mutants was accomplished using inverse PCR followed by confirmation of the mutation location by sequencing of the PCR products. Genomic characterization of 18 out of 20 attenuated mutants identified during the first screen by s.c. challenge was listed in Table 7, while genomic locations of transposon integration for mutant clones 19-F7 and 47-F10 were not confirmed. Of these confirmed 10 mutants showing attenuation under high stringency in a mouse model of bubonic plague, transposon insertion was identified in one of six uncharacterized genes (Table 8). For example, clones 52-B1 and 2-H3 encode putative surface-exposed and membrane protein, respectively. Clones 44-B5, 53-C3, 54-F6, and 39-G4 code for hypothetical or proteins with putative functions. In clone 47-G5, the transposon interruption occurred in the cytochrome o ubiquinol oxidase subunit II (Table 8). Two of the genes encoded previously characterized virulence factors and included the pla protease systems (Barroga et al., 1996, Protein Sci 5:1093-1099; Zaitseva et al., 1996, Protein Sci 5:1100-1107).

Likewise, the clone 44-B5 in which the transposition occurred in a hypothetical gene was highly attenuated, with 100, 85, and 85% survival of animals on days 7, 14, and 21 p.i., respectively (Table 8).

Pathodynamics of bubonic plague infection for the isogenic mutants of *Y. pestis* CO92 deleted for genes rbsA, vasK or Ypo0498 in a mouse model.

Transposon mutagenesis does not always provide a true estimate of bacterial attenuation during infection due partly to possible polar effects, and, therefore, we created isogenic mutants for three of the genes rbsA, vasK, and ypo0498 (Table 8). Gene rbsA was targeted as it had the most functional information available from orthologs in other bacterial species (Barroga et al., 1996, Protein Sci 5:1093-1099; Zaitseva et al., 1996, Protein Sci 5:1100-1107). Similarly, the gene ypo3603 (vasK) was targeted due to the virulence attributes associated with orthologous genes (Suarez et al., 2008, Microb Pathog 44:344-361). Another candidate gene, ypo0498, which encodes a hypothetical protein and is part of another T6SS locus, was also selected. These mutants were then used to challenge mice by the s.c. route to replicate data obtained during the transposon mutant screening.

Animals infected with the ΔrbsA or the ΔvasK isogenic mutant by the s.c. route showed a statistically significant attenuation, as 40% (p=0.042) and 70% (p=0.002), respectively, of the mice survived when challenged with 10 $LD_{50}$ equivalent of WT CO92 (FIG. 29). The control animals infected with the WT CO92 showed a survival of less than 5% in three combined independent experiments by day 14 p.i. When the Δypo0498 isogenic mutant was used to challenge mice by the s.c. route, an increase in mean time to death was noted at a much higher 35 $LD_{50}$, although the data did not reach statistical significance (FIG. 29).

Characterization of the ΔvasK mutant of Y. pestis CO92 in a mouse model of pneumonic plague.

Following evaluation by the s.c. route of the disease (bubonic plague), the ΔvasK mutant was then assessed for attenuation in a mouse model of pneumonic plague. At a dose equivalent to 12 $LD_{50}$ of WT CO92, the mice exhibited a 20 percent survival rate (p=0.031) by day 21 p.i., with no survival of animals challenged with a similar dose of WT CO92 (FIG. 30A). To further confirm that deletion of the vasK gene resulted in this attenuated phenotype, mice challenged with the complemented strain (ΔvasK pBR322-vasK) (Table 5) recapitulated the WT phenotype with no survival at an equivalent dose of the isogenic mutant. Although the attenuation of the ΔvasK mutant was not high in a stringent pneumonic plague mouse model, we obtained the first mutant which was attenuated in developing both bubonic and pneumonic plague.

In addition to generating a ΔvasK single mutant, we also deleted the vasK gene from the Δlpp background strain of CO92. Braun lipoprotein (Lpp) has previously been shown in our laboratory to provide attenuation in mouse models of pneumonic and bubonic plague through decreased intracellular survival in macrophages (Sha et al., 2013, Infect Immun 81:815-828; Sha et al., 2008, Infect Immun 76:1390-1409; Agar et al., 2009, Microbiology 155:3247-3259). The rationale for deleting the ΔvasK gene from the Δlpp background strain of CO92 was to delineate whether additive or synergistic attenuation could be achieved with the Δlpp ΔvasK double mutant in a mouse model of pneumonic plague.

Infection by the i.n. route with the Δlpp ΔvasK double mutant resulted in 90% survival (p<0.001) of mice at a dose equivalent to 12 $LD_{50}$ when compared to only 5% survival rate of animals after challenge with the Δlpp single mutant by day 21 p.i. at a comparable challenge dose (FIG. 30A). These data indicated synergistic attenuation of the Δlpp ΔvasK double mutant in a mouse model of pneumonic plague.

To determine if the attenuating effect of the vasK gene deletion from WT CO92 or its Δlpp mutant in mice was related to the inhibition of secretion of a T6SS effector, Hcp, a Western blot analysis was performed on the culture supernatants of WT CO92 and its Δlpp single, ΔvasK single, and Δlpp ΔvasK double mutants. We have shown earlier that the secretion of Hcp was blocked when the vasK gene was deleted from a diarrheal isolate SSU of A. dhakensis (Suarez et al., 2008, Microb Pathog 44:344-361). As seen in FIG. 30B, no differences in the secretion of Hcp were observed between the WT CO92 strain and the ΔvasK mutants, irrespective of whether the bacterial cultures were grown at either 28 or 37° C. As expected, while the correct size Hcp was detected in the supernatant of WT A. dhakensis SSU, the protein band was absent from its corresponding ΔvasK mutant. Since Hcp of Y. pestis and A. dhakensis exhibits high homology (81%), the same antibodies detected Hcp in both the pathogens. A higher molecular size of Hcp detected in A. dhakensis (22 kDa) when compared to that in Y. pestis (19 kDa) is likely due to post-translational modification as was also observed in the Hcp from Vibrio cholerae (Williams et al., 1996, Infect Immun 64:283-289).

The gene rbsA is required for the full virulence of Y. pestis CO92 in a pneumonic plague mouse model and in the utilization of ribose.

In a pneumonic plague model, the ΔrbsA mutant was attenuated with 30% of the mice (p=0.0098) having survived the challenge, while the animals infected with the WT CO92 or those infected with the rbsA complemented strain died by day 6 at a similar infectious dose of 11 $LD_{50}$ (FIG. 31A).

Earlier studies suggested that domains with sequence homology to the RbsA protein function as a ribose transport system (Barroga et al., 1996, Protein Sci 5:1093-1099; Zaitseva et al., 1996, Protein Sci 5:1100-1107). To explore the role of ribose utilization, the ΔrbsA mutant was grown in a modified minimal medium that was restricted for the carbon source. In a minimal medium supplemented with 0.4% ribose, the ΔrbsA mutant displayed a delayed growth pattern similar to when no ribose was added to the medium (FIG. 31B). However, the WT CO92 and the ΔrbsA pBR322-rbsA complemented strain exhibited normal and similar growth kinetics in a ribose-containing medium (FIG. 31B).

In a minimal medium, WT CO92 without any carbon source grew poorly after 16 h of incubation; however, the addition of either 0.4% glucose or ribose resulted in luxuriant bacterial mass (p<0.001) (FIG. 31C). As mentioned in FIG. 31B, the ΔrbsA mutant grew poorly in the minimal medium supplemented with ribose after 16 h of incubation and had a bacterial mass similar to when no carbon source was added to the medium (FIG. 31C). However, the ΔrbsA mutant exhibited similar growth as noted for the WT CO92 when the medium was supplemented with glucose (FIG. 31C). The complemented ΔrbsA mutant strain restored the ability to utilize ribose and allowed the bacteria to grow to a density twice that of the non-complemented strain (p<0.001) (FIG. 31C) and similar to the WT CO92 strain when grown in the ribose or glucose supplemented medium.

To assess the potential of rbsA deletion as a component of the live attenuated vaccine and to further characterize its attenuating characteristics, we constructed double and triple isogenic mutants in which the rbsA gene was deleted from the Δlpp and Δlpp ΔmsbB background strains of CO92. The msbB gene encodes an acylytansferase that attaches lauric acid to the lipid A moiety to increase biological potency of LPS (Karow et al., 1992, J Bacteriol 174:702-710). The Δlpp ΔmsbB double mutant exhibited increased attenuation compared to respective single mutants alone (Sha et al., 2013, Infect Immun 81:815-828). The resulting double (Δlpp ΔrbsA) or the triple (Δlpp ΔmsbB ΔrbsA) isogenic mutant showed a synergistic reduction in virulence (FIG. 32A).

While none of the Δlpp ΔmsbB double mutant-infected mice survived day 5 p.i. at 20 $LD_{50}$, 90% of the mice challenged with 15 $LD_{50}$ of the WT CO92 died (FIG. 32A). Animals infected with the Δlpp ΔrbsA double mutant showed 75% survival (p<0.001) at a dose of 20 $LD_{50}$. Challenge with 20-50 $LD_{50}$ of the Δlpp ΔmsbB ΔrbsA triple mutant in mice by the i.n. route provided 100% survival over 28 days p.i. (p<0.001) (FIG. 32A). As was observed with the ΔrbsA single mutant strain (FIG. 31A), when the Δlpp ΔmsbB ΔrbsA triple mutant was complemented with the rbsA gene and used to infect mice, 80% of the animals succumbed to infection with no significant difference in the survival pattern when compared to mice infected with the Δlpp ΔmsbB double mutant (FIG. 32A).

As part of the evaluation for its inclusion as a component in a live-attenuated vaccine candidate, we were interested in testing the immune-protective potential of this strain. To accomplish this, we re-challenged the groups of mice that received a 20 $LD_{50}$ of the Δlpp ΔrbsA double mutant or the Δlpp ΔmsbB ΔrbsA triple mutant strain with a fully virulent bioluminescent Y. pestis CO92 strain on day 28 post initial challenge. Likewise, the group receiving a 50 $LD_{50}$ of Δlpp ΔmsbB ΔrbsA triple mutant strain was subsequently challenged with bioluminescent Y. pestis CO92 strain (FIG. 32B). This bioluminescent strain allowed us to evaluate progression of the disease as well as survival data from the same groups of mice. By day 3 p.i., 60% of naive mice succumbed to the disease while 1 of the remaining 2 showed heavy infection in the lungs (FIG. 32B) and died on the following day. The remaining naive mouse succumbed 2 days following imaging.

Only 2 of the 10 mice (20%) from the initial 20 $LD_{50}$ challenge group with the Δlpp ΔmsbB ΔrbsA triple mutant strain showed bacterial burden and later succumbed to infection due to WT CO92 (FIGS. 32A&B). Only 1 out of the 8 mice (13%) from the initial 50 $LD_{50}$ challenge group of the Δlpp ΔmsbB ΔrbsA triple mutant strain showed bacterial burden and succumbed to infection during re-challenge with WT CO92 (FIGS. 32A&B).

Interestingly, animals initially challenged with the Δlpp ΔrbsA double mutant strain (75% protected) showed only a 50% survival after re-challenge (FIG. 32A), indicating that the Δlpp ΔmsbB ΔrbsA triple mutant strain was better attenuated than the Δlpp ΔrbsA double mutant and developed superior immunity in mice to subsequently protect animals from re-challenge with the WT CO92.

Third screen of selected signature-tagged transposon mutants of Y. pestis CO92 in a mouse model of pneumonic plague.

During the initial stage of pneumonic plague, Y. pestis suppresses the host immune system to down-regulate the inflammatory response, and, thereby, creating a highly permissive niche for the bacterium to multiply in an unrestrictive manner (Bubeck et al., 2007, Infect Immun 75:697-705; Price et al., 2012, Proc Natl Acad Sci USA 109: 3083-3088). Subsequently, this accumulation of proliferating bacteria leads to the induction of a massive inflammatory reaction and that causes lung edema and death of the infected animals (Bubeck et al., 2007, Infect Immun 75:697-705; Price et al., 2012, Proc Natl Acad Sci USA 109: 3083-3088; Agar et al., 2008, Microbiology 154:1939-1948). Taken these findings together, it is likely that a Y. pestis mutant which is attenuated for dissemination to the peripheral organs after intra-nasal infection could still cause inflammatory changes in the lung tissue. Consequently, infected animals would succumb to infection due to pneumonia rather than the septicemic dissemination as noted during bubonic plague. Therefore, we further evaluated the extent of attenuation in causing pneumonic plague by the remaining 18 (ΔvasK and ΔrbsA isogenic mutants were already characterized) signature-tagged mutants (Table 7) identified during the screening process, and the animals were infected by the i.n. route at a dose equivalent to 12 $LD_{50}$ of WT CO92 (Table 7).

In general, a delayed pattern of death was noted for all the mutants on day 3 after infection (Table 7). Nine out of 18 mutants exhibited between 40-100% survivals on day 9. The mutants 45-B9, 49-B1, 53-C3, and 53-G5 were unable to kill any mice, while 80% of mice survived challenge with mutants 52-B1, and 52-B5. These data implied that some mutants identified during the initial bubonic plague screen were attenuated in causing primary pneumonic plague as well and will be further characterized.

Discussion

Knowledge on the virulence factors of Y. pestis is crucial to developing a new plague vaccine or to design a better therapeutic intervention. As no FDA approved plague vaccine is available for humans and the antibiotics have limited role when the disease progresses to a clinical stage, search for novel virulence factors of the organism becomes a compulsive need to combat plague in the future. Here, we chose high-throughput STM approach, because this technique offers a power of analyzing multiple mutants simultaneously for attenuation in virulence either in vitro or in vivo assays (Mazurkiewicz et al., 2006, Nat Rev Genet 7:929-939; Hensel et al., 1995, Science 269:400-403).

In this study, more than 5,000 transposon mutants of Y. pestis CO92, an isolate originally from a human case of pneumonic plague in the United States (Williamson et al., 2011, Vaccine 29:4771-4777), were screened for impairment to disseminate to internal organs (e.g., spleen) in a mouse model of pneumonic plague (FIG. 26). Among these mutants, 118 were unable to reach in detectable numbers in the spleen as identified by comparing the presence or absence of signature tags between the input and output pools. The detection rate of such mutants (~2.4%) was close to that obtained in other studies using similar types of STM techniques (Silver et al., 2007, J Bacteriol 189:6763-6772; Mei et al., 1997, Mol Microbiol 26:399-407). We preferred to use pneumonic plague mouse model for our initial screening of the mutants for the following reasons: 1) pneumonic plague is the deadliest form with a high fatality rate compared to the bubonic form of plague, and 2) majority of the mice die due to pneumonic infection by day 3 p.i., with approximately $10^7$ to $10^9$ cfu of the plague bacterium in the peripheral organs (Agar et al., 2008, Microbiology 154: 1939-1948). A high bacterial burden in the peripheral organs of mice is needed to obtain an adequate tag representation in the output pools during STM, and $10^4$ cfu of bacteria is recommended as a threshold for obtaining authentic data (Flashner et al., 2004, Infect Immun 72:908-915). When animals are infected by the s.c. route to evoke bubonic plague, gauging consistent disease progression is somewhat challenging and the bacterial load in peripheral organs is relatively lower compared to that in the pneumonic plague mouse model (Bonacorsi et al., 1994, Antimicrob Agents Chemother 38:481-486; Walker et al., 1953, J Immunol 70:245-252).

The complexity of the mutant pools during STM is a crucial parameter and has to be carefully considered for obtaining a high quality screen in the animal models (Hensel et al., 1995, Science 269:400-403). Although an increased pool complexity would enable more mutants to be screened simultaneously, one might also enhance the probability that some virulent mutants would not be present in sufficient numbers in the organs of an infected animal, and, thus, leading to false positive data. In addition, the quantity of a labeled tag for each transposon is inversely proportional to the complexity of the tag pool during hybridization analysis (Hensel et al., 1995, Science 269:400-403). In our study, the number of signature tags was reduced from 56 to 53 due to cross-reaction noted for three tags during the prescreening step (Silver et al., 2007, J Bacteriol 189:6763-6772). The elimination of such tags is a pre-requisite in performing STM-based screens (Mazurkiewicz et al., 2006, Nat Rev Genet 7:929-939). At a challenge dose of 5 LD$_{50}$ (used in our study), the inocula for the mutant pools with a complexity of 53 tags would provide ~50 cfu of the each tested mutant to ensure adequate bacterial number at the initial infection site, i.e., the lungs.

Unlike in other STM studies, we neither opted for a second round of animal infection-hybridization screening process nor used an in vitro assay to narrow down the number of selected mutants for further studies (Silver et al., 2007, J Bacteriol 189:6763-6772; Flashner et al., 2004, Infect Immun 72:908-915). We rather chose bubonic plague mouse model and tested each of the 118 mutants individually and animals examined for mortality. While 20/118 mutants exhibited an attenuated phenotype at 8 LD$_{50}$, only 10 showed promising level of attenuation at an infectious dose of 40 LD$_{50}$ (Tables 3&4). The false positive clones appeared in our initial screen were most likely due to technical artifacts associated with the STM technique. Indeed, hybridization signals for 3 tags (2, 9 and 19) were consistently missing from the blots of our input pools (FIG. 27), suggesting that these three tags were insufficiently PCR amplified and labeled from the complex DNA pools. These data correlated with an earlier report that STM mutants were frequently found to contain un-amplifiable tags or no tags at all (Zhao et al., 1999, Microbiology 145:185-195). However, the genetic nature of the pathogen being studied may also play a role as the same 56 signature tags were successfully used in *Salmonella Typhimurium* and *A. veronii* (Hensel et al., 1995, Science 269:400-403; Silver et al., 2007, J Bacteriol 189:6763-6772). Nevertheless, further reduction in the complexity of the pools should be highly recommended to improve specificity of the STM approach.

Our genomic characterization of the 10 mutants showed transposon insertion largely in uncharacterized genes (in 6 mutants) encoding hypothetical or putative proteins (Table 4). In the remaining four mutants (15-F2, 42-B8, 44-F11, and 52-B1), the interrupted genes encoded or were assigned some functions. In clone 15-F2, the interruption occurred in a well-known virulence gene pla located on the pPCP1 plasmid of the plague bacterium. Pla plays an important role during bubonic plague, particularly in facilitating *Y. pestis* to disseminate systemically (van Lier et al., 2014, Infect Immun 82:2485-2503; Lathem et al., 2007, Science 315: 509-513), thus validating our screening process.

STM technique has previously been used to identify virulence factors in several pathogenic bacteria, including *Y. pestis* (Flashner et al., 2004, Infect Immun 72:908-915; Leigh et al., 2005, Microb Pathog 38:259-266). These studies employed either *Y. pestis* C099-3015 strain lacking the pCD1 plasmid with a cell culture-based in vitro screen or *Y. pestis* Kimberley53 strain in a bubonic plague mouse model (infection dose of 100 cfu) as the initial screen (Flashner et al., 2004, Infect Immun 72:908-915; Leigh et al., 2005, Microb Pathog 38:259-266). Strain Kimberley53 was obtained by infecting mice by the s.c. route with *Y. pestis* Kimberley (Flashner et al., 2004, Infect Immun 72:908-915; Ben-Gurion et al., 1958, J Gen Microbiol 19:289-297). More recently, a laboratory reconstructed version of *Y. pestis* KIM10 strain, KIM1001, was used for transposon mutagenesis with a high-throughput sequencing (Tn-seq) to systematically probe the *Y. pestis* genome for elements contributing to fitness during infection. An intravenous route with an infection dose of $2.3\times10^7$ cfu of KIM1001 was used in order to preserve the diversity of the mutant pools (Palace et al., 2014, mBio 5:e01385-14). Although all of the above-mentioned studies yielded a set of genes associated with the virulence of *Y. pestis*, several of them belonged to the category of uncharacterized genes. Importantly, none of these genes were shared when compared with the interrupted genes identified in our mutant clones. This could be attributed to different strains and infection routes used as well as stringency of the screening procedures, and the threshold for accepting attenuated clones.

Two attenuated mutant clones were identified during our screens (44-B5 and 44-F11, Table 4) in which transposition occurred in the T6SS. Although the role of T6SS has been demonstrated in some pathogenic bacteria (Boyer et al., 2009, BMC Genomics 10:104; Pukatzki et al., 2009, Curr Opin Microbiol 12:11-17), its involvement in the pathogenesis of *Y. pestis* infections has not been elucidated. Based on in silico analysis, six T6SS clusters have been predicated in the *Y. pestis* genome (Boyer et al., 2009, BMC Genomics 10:104). Mutant 44-B5 was interrupted in an uncharacterized gene ypo0498 and it is within the ypo0495-ypo0518 locus, one of the six T6SS clusters found in *Y. pestis* CO92 (Boyer et al., 2009, BMC Genomics 10:104; Robinson et al., 2009, Microb Pathog 47:243-251). Interestingly, the expression of the genes (ypo0499-ypo0516) in this T6SS locus was found to be up regulated at 26° C. compared to that at 37° C., and, therefore, its role in bacterial lifecycle in fleas has been speculated (Robinson et al., 2009, Microb Pathog 47:243-251). However, deleting a portion (ypo0499-ypo0516) of this T6SS locus from WT CO92 did not affect the ability of the bacterium to infect the oriental rat flea, *Xenopsylla cheopis*, as well as its associated disease dynamics in both bubonic and pneumonic plague mouse models, although a decreased uptake by murine macrophage-like J774.A1 cells was noticed for the deletion mutant (Boyer et al., 2009, BMC Genomics 10:104; Robinson et al., 2009, Microb Pathog 47:243-251).

Similarly, the expression of the ypo0498 gene was up regulated approximately 3.7 folds when *Y. pestis* CO92 strain was exposed to human plasma, and was 14 folds higher at the mid-phase of the exponential growth compared to that at the stationary phase of bacterial growth. Interestingly, switching the growth temperature from 28° C. to 37° C. down-regulated the expression of the ypo0498 gene to approximately 9 folds (Chauvaux et al., 2007, Microbiology 153:3112-3124). Further, during infection in mice, the expression of the Δypo0498 gene was down regulated (2-fold) in the lung tissues when compared to bacterial growth in the BHI broth at 37° C. (Lathem et al., 2005, Proc Natl Acad Sci USA 102:17786-17791). Although we have shown a delayed time to death in mice infected with the Δypo0498 isogenic mutant in a bubonic plague model, it is as virulent as the WT CO92 in a pneumonic plague mouse model (data not shown). Therefore, the role of YP00498 and its associated T6SS locus in the pathogenesis of *Y. pestis* infections is still uncertain and needs further investigation.

In mutant 44-F11, the transposition occurred in the ypo3603 gene which is homologous to the vasK gene and encodes a key component of the T6SS (Suarez et al., 2008, Microb Pathog 44:344-361). The ypo3603 gene belongs to another T6SS locus (ypo3588-ypo3615) in *Y. pestis* CO92 (Boyer et al., 2009, BMC Genomics 10:104). Our earlier study showed that VasK mediated the secretion of T6SS effectors (e.g., Hcp) in *A. dhakensis* SSU, as the deletion of this gene led to a failure of the mutant to secrete Hcp to the extracellular medium and the mutant was attenuated in a speticemic mouse model of infection (Suarez et al., 2008, Microb Pathog 44:344-361). Although six possible T6SS gene clusters have been predicted, BLAST search of the hcp gene sequence against the other predicted protein-encoding genes on *Y. pestis* CO92 genome revealed only one copy of the hcp gene. Amino acid sequence of this *Y. pestis* hcp gene shares 82% and 81% homology with the Hcp of *Vibrio cholerae* and *A. dhakensis* strain SSU, respectively (http://blast.ncbi.nlm.nih.gov/Blast.cgi). Surprisingly, deletion of the ypo3603 gene (ΔvasK) from *Y. pestis* CO92 did not prevent secretion of Hcp (FIG. 30B), suggesting that the secretion of Hcp might operate through other T6SS channels in *Y. pestis* CO92 and needs further studies. Nevertheless, our data demonstrated that the ΔvasK mutant of *Y. pestis* CO92 was attenuated in inducing both bubonic and pneumonic plague in mouse models. Importantly, the attenuated phenotype of the mutant ΔvasK could be fully complemented. To the best of our knowledge, this is the first report demonstrating a role of T6SS in the pathogenesis of *Y. pestis* infection.

In our screen, we did not identify so far any genes related to the T3 SS which is an important virulence mechanism for *Y. pestis* (Cornelis, 2002, J Cell Biol 158:401-408). We would like to emphasize that our screening process for identifying *Y. pestis* mutants defective for dissemination to peripheral mouse organs in a pneumonic plague mouse model has not been completed as yet, and, thus far, only 50% of the total output pools have been successfully screened for this study. We expect that further screening of the remaining output pools would likely identify mutant clones related to the T3SS and its effectors as well as other known virulence factors of *Y. pestis*.

In addition to the above T6SS related mutants, clone 42-B8 was identified as having transposon insertion in the putative sugar transport system, ATP-binding protein, which is referred to as the rbsA gene. This gene is a part of the ribose transport (rbs) operon encoding ribose transport and modification system. The rbs operon consists of genes rbsDACBK, in which genes rbsD and rbsK are involved in phosphorylation of the ribose sugar. Based on the genomic composition, the rbsACB genes are organized in a polycistronic transcript and form the ribose transportation channel (Horazdovsky et al., 1987, J Mol Biol 197:27-35; Park et al., 1999, Embo J 18:4149-4156). RbsA carries an ATP binding domain and possesses nucleotide-binding property, while RbsB is a ribose-binding protein in the periplasmic space, and RbsC is a hydrophobic transmembrane protein (Barroga et al., 1996, Protein Sci 5:1093-1099; Zaitseva et al., 1996, Protein Sci 5:1100-1107; Park et al., 1999, J Bacteriol 181:1039-1042).

In addition to transport ribose, RbsA was shown to mediate chemotaxis of ribose sugar for *E. coli*, and when this gene was mutated, the chemotactic activity as well as the ribose transportation across the bacterial membrane was significantly affected (Barroga et al., 1996, Protein Sci 5:1093-1099). We have shown for the first time that deletion of the rbsA gene attenuated the bacterium in both bubonic and pneumonic plague mouse models and clearly demonstrated the role of RbsA in the pathogenesis of *Y. pestis* infection. Although the underlying mechanism of attenuation is currently not clear, however, considering the primary role of RbsA in sugar transportation, it is most likely that failure to utilize ribose by the ΔrbsA mutant would have a negative effect on bacterial fitness and survival inside the hostile environment of the host.

Interestingly, the rbs operon has been reported to be regulated by quorum sensing (QS) AI-2 system, and RbsB shares structural resemblance with the sensor protein LuxP (Pukatzki et al., 2009, Curr Opin Microbiol 12:11-17; Bladergroen et al., 2003, Mol Plant Microbe Interact 16:53-64). Therefore, RbsA may regulate bacterial virulence through QS. In addition, RbsB has been reported as a putative effector of T6SS in *Rhizobium leguminosarum* (Pukatzki et al., 2009, Curr Opin Microbiol 12:11-17). In line with this finding, it is possible that the secretion of RbsB may be affected by the deletion of the ypo3603 gene, a homolog of vasK. There could possibly be an interplay between RbsA and VasK which would constitute part of our future studies. Similar to RbsA, a glucose importer (PtsG) from *Y. pestis* strain KIM1001 was recently reported as required for in vivo growth in mouse spleen tissues, although deletion of this gene did not change the pathodynamics of bubonic plague from its parental strain (Palace et al., 2014, mBio 5:e01385-14). Likewise, the chvE-gguAB operon in *Agrobacterium tumefaciens* encodes a glucose and galactose importer. Sugar binding to ChvE triggers a signaling response that results in virulence gene expression (Davidson et al., 2008, Microbiol Mol Biol Rev 72:317-364). These studies highlighted the importance of sugar transporter in bacterial pathogenesis.

We noted that the level of attenuation of the isogenic mutants (FIG. 29) in a mouse model of bubonic plague was on the lower side when compared to their respective transposon mutants (Tables 3 and 4). Likewise, Δypo0498 mutant did not show any attenuation in a mouse pneumonic model (data not shown) while its corresponding STM mutant (44-B5) showed 60% survival of animals (Table 3). It is plausible that the presence of a kanamycin-resistant cassette in transposon mutants could contribute to the organism becoming more sensitive to host antibacterial defense mechanisms (Leigh et al., 2005, Microb Pathog 38:259-266). For example, expression of the neomycin phosphotransferase-II (kanamycin resistant cassette) interferes with bacterial signaling pathways that would be detrimental for *Y. pestis* survivability during host infections. When the antibiotic cassette was removed while creating isogenic mutants, the mutant strains reflected their actual level of attenuation. It is also possible that the transposon mutant clones corresponding to the isogenic mutants carried more than one transposon insertions.

Although the transposon DNA constructs used in this study did not carry any known prokaryotic transcription termination sites, the level of mRNA transcription from the neighboring genes or from other genes of an operon (e.g., rbs operon) and their stability and secondary structure could be altered when the transposon insertion occurred. However, these transcriptional alternations would be minimal in isogenic mutants, and thus such mutants showed less attenuation than the corresponding transposon mutants.

Despite the reduced level of attenuation observed with each of the single isogenic mutants, they would be invaluable in the construction of a live-attenuated plague vaccine strain carrying deletion for multiple virulence genes. Evidently, when the rbsA gene was deleted from the Δlpp mutant of CO92 strain, the level of attenuation increased synergistically in a mouse model of pneumonic plague (FIG. 31A). Similar synergistic attenuation for developing pneumonic plague was also noticed for the Δlpp ΔvasK double mutant of CO92 (FIG. 30A). In agreement with these results, we have shown earlier that deletion of the msbB gene, encoding an acetyltransferase to modify lipid A portion of LPS, from the Δlpp background strain of CO92 further attenuated the Δlpp ΔmsbB double mutant in both models of plague (Sha et al., 2013, Infect Immun 81:815-828). However, this synergistic augmentation of virulence attenuation was not noticed in the Δlpp Δypo0498 double mutant of CO92 in a mouse model of pneumonic plague (data not shown).

Lipoproteins play varying roles in different bacterial species such as their involvement in host cell colonization and adhesion, bacterial cell division, protein folding and signal transduction (Kovacs-Simon et al., 2011, Infect Immun 79:548-561). In *Y. pestis* KIM/D27 strain (deleted for the pigmentation [pgin] locus), we reported that deletion of the lpp gene led to increased production of cytokines, such as interferon (IFN)-γ and interleukin (IL)-2 from mouse splenic T-cells, and IL-12 from macrophages. Further, this mutant caused less apoptotic changes and increased NF-kappa B signaling in both mouse splenocytes and macrophages (Liu et al., 2010, Microb Pathog 48:42-52). Similarly, we showed that the splenic T-cells from mice infected with the Δlpp Δpla double mutant of CO92 showed increased tumor necrosis factor (TNF)-α production when such immune cells were exposed ex vivo to heat-killed WT CO92 antigens (van Lier et al., 2014, Infect Immun 82:2485-2503). Further, the Δlpp mutant of CO92 was defective in intracellular survival in RAW 264.7 murine macrophages, and it was attenuated in evoking both bubonic and pneumonic plague in a mouse model (Sha et al., 2013, Infect Immun 81:815-828).

Therefore, it is likely that the deletion of rbsA and vasK genes from the Δlpp background strain of CO92, or the deletion of the rbsA gene from the Δlpp ΔmsbB background strain would augment the host immune system to increase cytokine production. Both IFN-γ and TNF-α contribute to host survival by inhibiting bacterial multiplication in vivo and increasing bacterial clearance by macrophages (Nakajima et al., 1993, Infect Immun 61:23-31). However, further detailed studies are needed to fully understand this cytokine interplay in synergistic attenuation of virulence by the double (Δlpp ΔvasK, Δlpp ΔrbsA) or triple (Δlpp ΔmsbB ΔrbsA) isogenic mutants during mouse models of plague infection.

In summary, we have identified 20 potential targets that could be associated with the full virulence of *Y. pestis* CO92 strain by using the STM approach. Among them, 15 mutants were either attenuated in a mouse model of bubonic plague at a higher infectious dose of 40 $LD_{50}$ and/or in a pneumonic mouse model with an infectious dose equivalent to 12 $LD_{50}$ of WT CO92. For the first time, we have demonstrated the role of VasK and RbsA in the pathogenesis of *Y. pestis* infections. The generated double mutants, Δlpp ΔvasK and Δlpp ΔrbsA, as well as the triple mutant Δlpp ΔmsbB ΔrbsA showed promising potential in their further development as live-attenuated vaccines. Our future study will continue to characterize the remaining genes that have been identified during this study and their roles in causing plague.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

---

What is claimed is:

1. A genetically modified *Y. pestis*, comprising three alterations compared to a control *Y. pestis*,
    wherein the first alteration comprises a mutation in a first coding region encoding a first protein having at least 80% identity to the amino acid sequence of SEQ ID NO:49, wherein the first protein is undetectable in the genetically modified *Y. pestis*,
    wherein the second alteration comprises a mutation in a second coding region encoding a second protein having at least 80% identity to the amino acid sequence of SEQ ID NO:50, wherein the second protein is undetectable in the genetically modified *Y. pestis*,
    wherein the third alteration comprises a mutation in either a third coding region or a deletion of an intergenic region, wherein the third coding region encodes a third protein having at least 80% identity to the amino acid sequence of SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, or SEQ ID NO:62, and wherein the intergenic region has at least 80% identity to SEQ ID NO:2, wherein the third protein is undetectable in the genetically modified *Y. pestis*, and
    wherein the genetically modified *Y. pestis*, is attenuated.

2. The genetically modified *Y. pestis* of claim 1 wherein the mutation comprises a deletion of the coding region encoding the first protein, the coding region encoding the second protein, and the coding region encoding the third protein.

3. A composition comprising the genetically modified *Y. pestis* of claim 1 and a pharmaceutically acceptable carrier.

4. The composition of claim 3 formulated for intramuscular or intranasal administration.

5. A method of using a genetically modified *Yersinia pestis* to produce an immune response to the genetically modified *Y. pestis* in a subject, comprising:
    administering to a subject an effective amount of the composition of claim 3, wherein the subject has an immune response to the genetically modified *Y. pestis*.

6. The method of claim 5 wherein the immune response comprises a humoral immune response, a cell-mediated immune response, or a combination thereof.

7. The method of claim 6 wherein the immune response is protective against bubonic, septicemic, or pneumonic plague.

8. The method of claim 6 wherein the immune response is protective against bubonic and pneumonic plague.

9. The method of claim 6 wherein the subject has or is at risk of having plague.

10. The method of claim 9 wherein the plague is bubonic, septicemic, pneumonic, or a combination thereof.

11. The method of claim 6 wherein the subject is a human.

12. The method of claim 6 wherein the subject is a laboratory animal.

13. The method of claim 12 wherein the laboratory animal is a mouse, a rat, or a non-human primate.

14. The method of claim 6 wherein the method further comprises administration of an antibiotic.

15. The genetically modified *Y. pestis* of claim 1 wherein mutation of the first coding region, the second coding region, the third coding region, or a combination thereof, comprises an insertion or an in-frame deletion.

16. A genetically modified *Y. pestis* comprising three alterations compared to a control *Y. pestis*,
    wherein the first alteration comprises a mutation in a first coding region encoding a first protein having at least 80% identity to SEQ ID NO:49, wherein the first protein is undetectable in the genetically modified *Y. pestis*,
    wherein the second alteration comprises a mutation in a second coding region encoding a second protein having at least 80% identity to SEQ ID NO:50, wherein the second protein is undetectable in the genetically modified *Y. pestis*,
    wherein the third alteration comprises a mutation in a third coding region encoding a third protein having at least 80% identity to the amino acid sequence of SEQ ID NO:62, SEQ ID NO:54, or SEQ ID NO:56, wherein the third protein is undetectable in the genetically modified *Y. pestis*,
    wherein the genetically modified *Y. pestis* is attenuated.

17. The method of claim 5 wherein the method further comprises administering a booster administration of the composition to the subject.

18. The method of claim 5 wherein the method further comprises administering at least one booster administration of the composition to the subject.

19. The method of claim 18 wherein one, two, or three booster administrations of the composition are administered to the subject.

* * * * *

UNITED STATES PATENT AND TRADEMARK OFFICE
CERTIFICATE OF CORRECTION

| | |
|---|---|
| PATENT NO. | : 10,328,139 B2 |
| APPLICATION NO. | : 14/995743 |
| DATED | : June 25, 2019 |
| INVENTOR(S) | : Ahsok K. Chopra and Jian Sha |

It is certified that error appears in the above-identified patent and that said Letters Patent is hereby corrected as shown below:

In the Specification

In Column 29, Table 2, delete "(SEQ ID NO: 14)" and replace with --(SEQ ID NO: 15)--

In the Claims

In Claim 1, Column 129, Line 17, delete "A genetically modified Y. pestis, comprising" and replace with --A genetically modified Y. pestis comprising--

Signed and Sealed this
Fourteenth Day of January, 2020

Andrei Iancu
*Director of the United States Patent and Trademark Office*